US010017811B2

(12) United States Patent
Leamon et al.

(10) Patent No.: US 10,017,811 B2
(45) Date of Patent: *Jul. 10, 2018

(54) METHODS AND COMPOSITIONS FOR MULTIPLEX PCR

(71) Applicant: LIFE TECHNOLOGIES CORPORATION, Carlsbad, CA (US)

(72) Inventors: John Leamon, Stonington, CT (US); Mark Andersen, Carlsbad, CA (US); Michael Thornton, San Francisco, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/518,904

(22) Filed: Oct. 20, 2014

(65) Prior Publication Data

US 2015/0038375 A1    Feb. 5, 2015

Related U.S. Application Data

(63) Continuation of application No. 13/458,739, filed on Apr. 27, 2012.

(60) Provisional application No. 61/479,952, filed on Apr. 28, 2011, provisional application No. 61/531,583, filed on Sep. 6, 2011, provisional application No. 61/531,574, filed on Sep. 6, 2011, provisional application No. 61/538,079, filed on Sep. 22, 2011, provisional application No. 61/564,763, filed on Nov. 29, 2011, provisional application No. 61/578,192, filed on Dec. 20, 2011, provisional application No. 61/594,160, filed on Feb. 2, 2012, provisional application No. 61/598,881, filed on Feb. 14, 2012, provisional application No. 61/598,892, filed on Feb. 14, 2012, provisional application No. 61/625,596, filed on Apr. 17, 2012, provisional application No. 61/639,017, filed on Apr. 26, 2012.

(51) Int. Cl.
| | |
|---|---|
| *C07H 21/04* | (2006.01) |
| *C07H 21/02* | (2006.01) |
| *C12Q 1/686* | (2018.01) |
| *C12Q 1/6806* | (2018.01) |
| *C12Q 1/6855* | (2018.01) |
| *C12N 15/10* | (2006.01) |
| *C12Q 1/6886* | (2018.01) |
| *C12Q 1/6874* | (2018.01) |
| *C12Q 1/68* | (2018.01) |

(52) U.S. Cl.
CPC ......... *C12Q 1/686* (2013.01); *C12N 15/1065* (2013.01); *C12Q 1/6806* (2013.01); *C12Q 1/6855* (2013.01); *C12Q 1/6874* (2013.01); *C12Q 1/6886* (2013.01); *C12Q 2600/16* (2013.01)

(58) Field of Classification Search
CPC ............ C12Q 1/6855; C12Q 2521/307; C12Q 2525/101; C12Q 2525/191; C12Q 2537/143; C12Q 1/6806; C12Q 1/686; C12Q 1/6874; C12Q 1/6886; C12Q 2600/16

See application file for complete search history.

(56) References Cited

U.S. PATENT DOCUMENTS

| | | |
|---|---|---|
| 5,582,989 A | 12/1996 | Caskey et al. |
| 5,814,491 A | 9/1998 | Vijg et al. |
| 5,882,856 A | 3/1999 | Shuber et al. |
| 6,207,372 B1 | 3/2001 | Shuber |
| 6,251,588 B1 | 6/2001 | Shannon et al. |
| 7,101,663 B2 | 9/2006 | Godfrey et al. |
| 7,118,867 B2 | 10/2006 | Tabiti et al. |
| 7,217,515 B2 | 5/2007 | Chiu et al. |
| 7,670,774 B2 | 3/2010 | Moon et al. |
| 7,687,247 B1 | 3/2010 | Hartley et al. |
| 8,323,897 B2 | 12/2012 | Andersen et al. |
| 2007/0172839 A1 | 7/2007 | Smith et al. |
| 2007/0231823 A1 | 10/2007 | McKernan et al. |
| 2008/0131937 A1 | 6/2008 | Schroeder |
| 2008/0228589 A1 | 9/2008 | Koehler et al. |
| 2008/0293589 A1 | 11/2008 | Shapero |
| 2010/0129874 A1 | 5/2010 | Mitra et al. |

(Continued)

FOREIGN PATENT DOCUMENTS

| | | |
|---|---|---|
| EP | 2702170 | 12/2015 |
| WO | WO-2007/140417 | 12/2007 |

(Continued)

OTHER PUBLICATIONS

Puck, T.T. et al. (PNAS, vol. 41, pp. 432-437, 1955).*

(Continued)

*Primary Examiner* — Teresa E Strzelecka

(57) ABSTRACT

The present invention provides methods, compositions, kits, systems and apparatus that are useful for multiplex PCR of one or more nucleic acids present in a sample. In particular, various target-specific primers are provided that allow for the selective amplification of one or more target sequences. In one aspect, the invention relates to target-specific primers useful for the selective amplification of one or more target sequences associated with cancer or inherited disease. In some aspects, amplified target sequences obtained using the disclosed methods, kits, systems and apparatuses can be used in various downstream processes including nucleic acid sequencing and used to detect the presence of genetic variants.

20 Claims, 55 Drawing Sheets

(56) References Cited

U.S. PATENT DOCUMENTS

| | | | |
|---|---|---|---|
| 2011/0105364 A1* | 5/2011 | Kurn | C12Q 1/6811 |
| | | | 506/16 |
| 2011/0177517 A1 | 7/2011 | Rava et al. | |
| 2011/0201507 A1 | 8/2011 | Rava et al. | |
| 2011/0212490 A1 | 9/2011 | Fredriksson et al. | |
| 2011/0319290 A1 | 12/2011 | Raymond et al. | |
| 2012/0295819 A1 | 11/2012 | Leamon et al. | |
| 2013/0059738 A1 | 3/2013 | Leamon et al. | |

FOREIGN PATENT DOCUMENTS

| | | |
|---|---|---|
| WO | WO-2007/147079 | 12/2007 |
| WO | WO-2012/149438 | 11/2012 |
| WO | WO-2014/012107 | 1/2014 |

OTHER PUBLICATIONS

Ellenberger, T. et al., Ann. Rev. Biochem., vol. 77, pp. 313-338 (2008).*

Visnes, T. et al., Phil. Trans. R. Soc. B, vol. 364, pp. 563-568 (2008).*

Integated DNA Technologies "Molecular Facts and Figures" (pp. 1-9, 2005 & 2011).*

Loeb, L.A. et al., Nature Rev. Genet., vol. 9, pp. 594-604 (2008).*

Rittie, L. et al., J. Cell Commun. Signal., vol. 2, pp. 25-45 (2008).*

Wong, K.M. et al., Ann. Rev. Genomics Hum. Genet., vol. 12, pp. 407-430 (Jun. 2011).*

Borneman, A. et al., "Whole-Genome Comparison Reveals Novel Genetic Elements That Characterize the Genome of Industrial Strains of *Saccharomyces cerevisiae*", PLoS Genetics, vol. 7 (2), Feb. 3, 2011, 10 Pages.

PCT/US2015/045209, International Search Report and Written Opinion dated Oct. 26, 2015, 11 pages.

EP15170140, Extended European Search Report dated Oct. 12, 2015, 5 pages.

Ho, Antoine et al., "Sequencing by ligation variation with endonuclease V digestion and deoxyinosine-containing query oligonucleotides", BMC Genomics, vol. 12:598, 2011, 1-8.

Shendure, Jay et al., "Next-generation DNA sequencing", Nature Biotechnology, vol. 26, No. 10, Oct. 2008, 1135-1145.

Tabor, Stanley, "DNA Ligases", Curr. Prot. Mol. Biol., 3.14.1-3.14. 4, 1987, 4 pages.

Varley, Katherine et al., "Nested Patch PCR enables highly multiplexed mutation discovery in candidate genes", Genome Res., vol. 18, and Supplement pp. 1-9, 2008, 1844-1850.

Buck, et al., "Design strategies and performance of custom sequencing primers", BioTechniques, 27, vol. 27, No. 3, Sep. 1999, 528-536.

Cross, Deanna et al., "Development of a fingerprinting panel using medically relevant polymorphisms", BMC Medical Genomics, 2:17, http://www.biomedcentral.com/1755-8794/2/17, 2009.

Dieffenbach, C. W. et al., "General concepts for PCR primer design", Genome Res., 3:, 1993, S30-S37.

Longo, M et al., "Use of uracil DNA glycosylase to control carry-over contamination in polymerase chain reactions", Gene, vol. 93, 1990, 125-128.

Meyer, Matthias et al., "Illumina Sequencing Library Preparation for Highly Multiplexed Target Capture and Sequencing", Cold Spring Harbor Protocols, vol. 2010, protocol 5448, 2010, 1-10.

PCT/US2012/035612, International Search Report and Written Opinion dated Jul. 25, 2012, 2012.

PCT/US2012/062494, International Preliminary Report on Patentability dated Jun. 12, 2014, 5 pages.

PCT/US2012/062494, International Search Report and Written Opinion dated Jan. 17, 2013, 1-11.

PCT/US2012/065650, International Preliminary Report on Patentability dated Jun. 12, 2014, 6 pages.

PCT/US2012/065650, International Search Report and Written Opinion dated Jan. 23, 2013, 1-12.

Stiller, Mathias et al., "Direct multiplex sequencing (DMPS)—a novel method for targeted highly degraded DNA", Genome Research, Supplemental Material, 2009, 1-15.

Stiller, Mathias et al., "Direct multiplex sequencing (DMPS)—a novel method for targeted highly degraded DNA", Genome Research, vol. 19, 2009, 1843-1848.

Varley, Katherine Elena et al., "Nested Patch PCR enables highly multiplexed mutation discovery in candidate genes", Genome Res., 18:, 2008, 1844-1850.

EP15200283-8, Extended EP Search Report dated Aug. 30, 2016, 1-6.

Qiagen, "Multiplex PCR Handbook", 2010, 1-48.

Hu, Gouhong, et al., "A highly sensitive and specific system for large-scale gene expression profiling", BMC Genomics, vol. 9:9, 2008, 1-14.

Tang, F., et al., "mRNA-Seq whole-transcriptome analysis of a single cell", Nat Methods, vol. 6(5), 2009, pp. 377-382 and supplemental content—online methods, pp. 1-2.

* cited by examiner

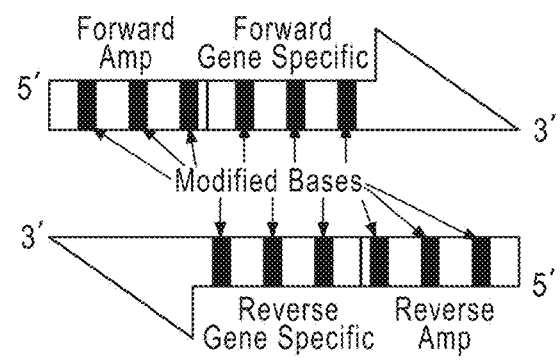
FIG. 1A
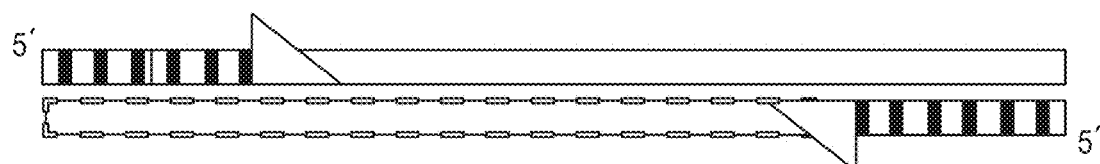
FIG. 1B₁
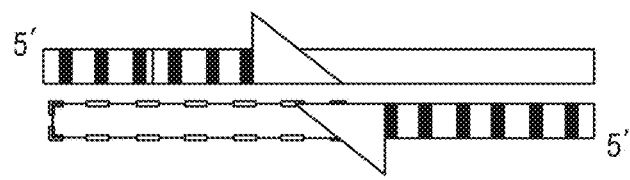
FIG. 1B₂
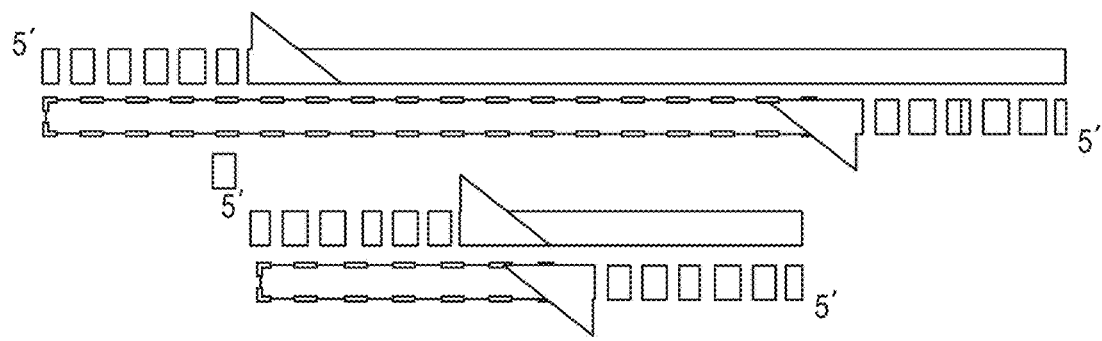
FIG. 1C₁

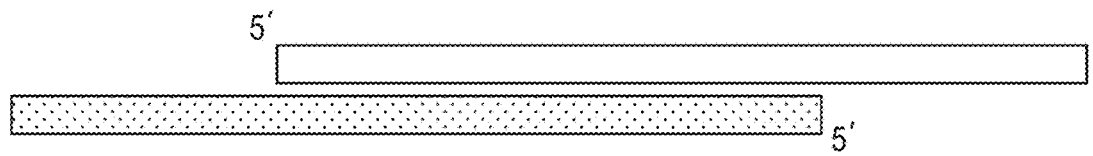
FIG. 1D₁
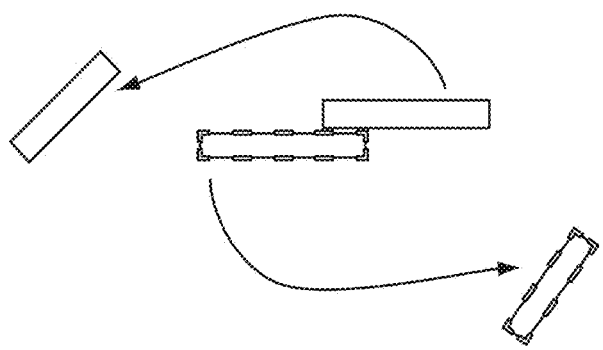
FIG. 1D₂
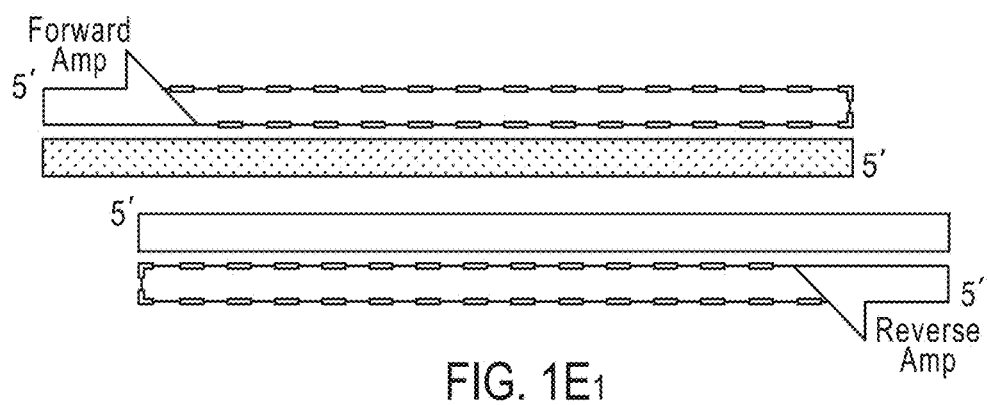
FIG. 1E₁

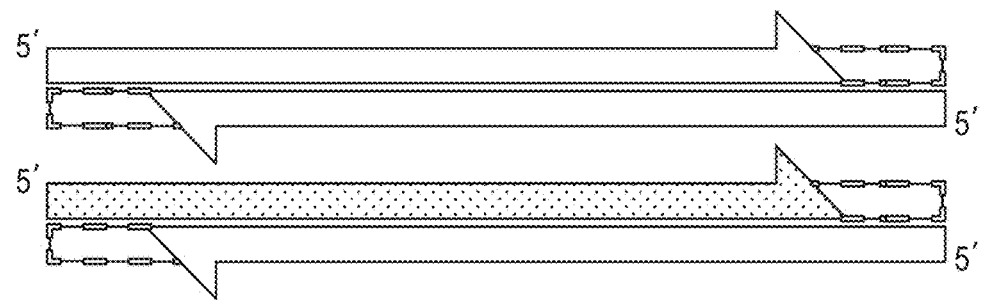
FIG. 1E_{1i}
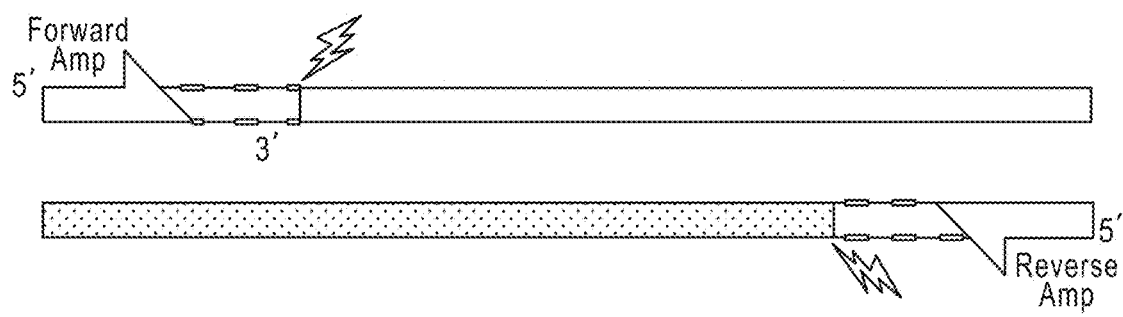
FIG. 1E_2

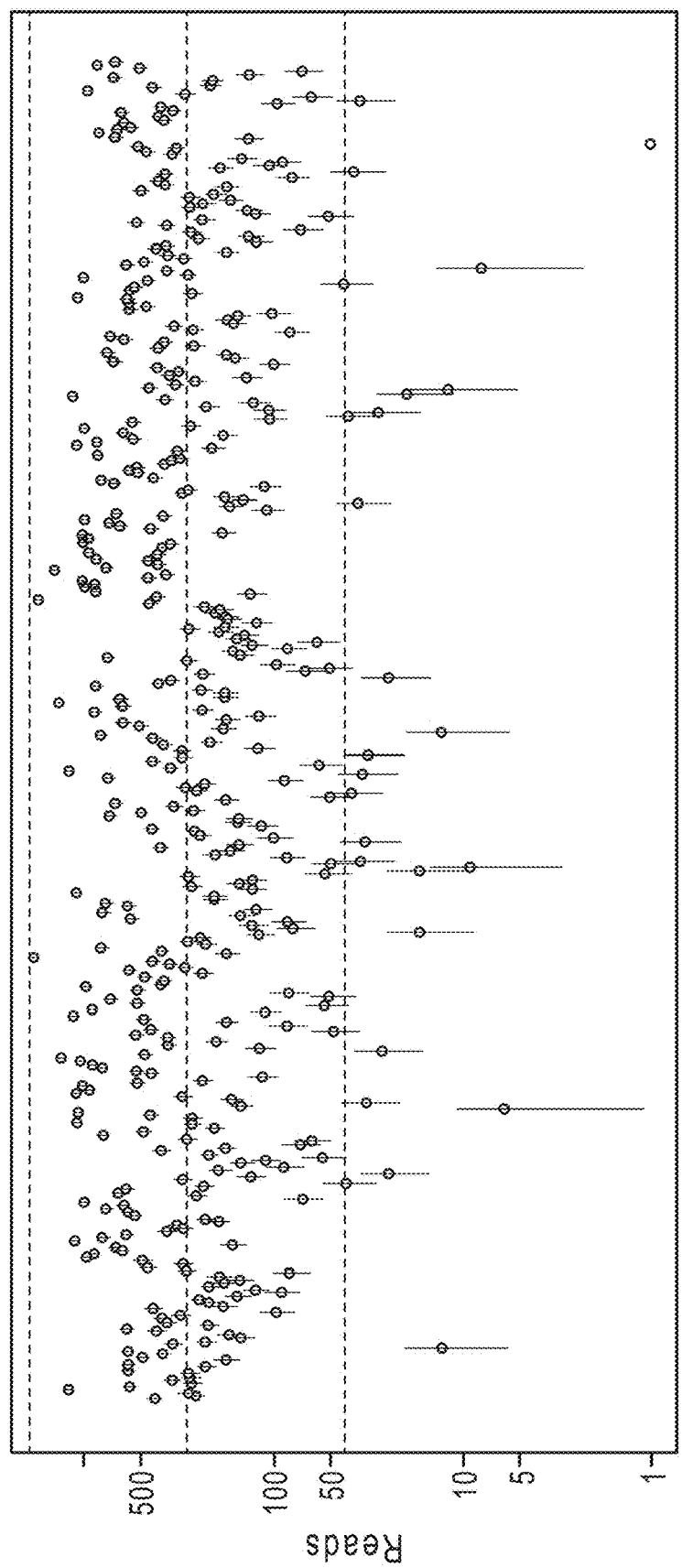

c.869+11C>T                                              SEQ ID NO.
[ TAAGACAGTAAGTTGTTCCAATAATTTCAATAT                      103144
[ TAAGACAGTAAGTTGTTCCAATAATTTCAATAT                      103144

[ TAA|

[ TAAGACAGT|
[ TAAGACAGTAAGT▶                                         103145
[ TAAGACAGTAAGTTGTTTCAATAA▶                              103146
[ TAAGACAGTAAGTTGTTTCAATA▶                               103147
[ TAAGACAGTAAGTTGTT▶                                     103148
[ TAAGACAGTAAGTTGTTCCAATAATTTC|                          103149
[ TAAGACAGTAAGTTGTTTCAATAA▶                              103146
[ TAAGACAGTAAGTTGTTCCAATAATTTCAATAT                      103144
[ ————◀CAGTAAGTTGTTCCAATAATTTCAATAT                      103150
[ ———————————————◀TTTCAATAATTTCAATAT                     103151
[ ——————————————————⊦AATAATTTCAATAT                      103152
[ ——————————————————⊦AATAATTTCAATAT                      103152
[ ———————————————————◀ATAATTTCAATAT                      103153
[ ——————————————————————◀ATTTCAATAT                      103154
[ ————————————————————————◀TTCAATAT
[ ————————————————————————◀TTCAATAT
[ ——————————————————————————————◀ATAT
[ ————————————————————————————————
[ ————————————————————————————————
[ ————————————————————————————————

FIG. 13A

| c.4389G>A | SEQ ID NO. |
|---|---|
| GTCTAAGCCCAGATTGCTGCTCTGAA | 103155 |
| GTCTAAGCCCAGATTGCTGCTCTGAA | 103155 |

```
GTC|
GTCTAAGCCC▶                        103156
GTCTA|
GTCTAAGCCCAGATTGC▶                 103157
GTCTAAGCCCAGATTGCTG|               103158
GTCTAAGCCCAGATTGCTGCTC|            103159
GTCTAAGCCC▶                        103156
GTCTAAGCCCAAATTGCTGCTCTG|          103160
GTCTAAGCCCAGATTGCTGCTCT▶           103161
GTCTAAGCCCAGATTGCTGCTCTG|          103162
GTCTAAGCCCAAATTGCTGCTCTGAA         103163
◀TCTAAGCCCAAATTGCTGCTCTGAA         103164
       ◀CCCAGATTGCTGCTCTGAA        103165
       |AAATTGCTGCTCTGAA           103166
         |TTGCTGCTCTGAA            103167
        ◀TTGCTGCTCTGAA             103167
         ◀TGCTGCTCTGAA             103168
           |CTGCTCTGAA             103169
           |CTGCTCTGAA             103169
             ◀GCTCTGAA
                |GAA
```

FIG. 13B

| ΔF508 | SEQ ID NO. |
|---|---|
| CACCATTAAAGAAAATATCATCTTTGGTGTTTCCTATGATGAAT | 103170 |
| CACCATTAAAGAAAATATCATCTTTGGTGTTTCCTATGATGAAT | 103170 |

| | |
|---|---|
| CACC▶ | |
| CAC▶ | |
| CACCATTAAAGAAAATAT⎯ | 103171 |
| CACCATTAAAGAAAATATCAT⎯ | 103172 |
| CACCATTAAAGAAAATATCATCTTTGGT⎯ | 103173 |
| CACCATTAAAGAAAATATCAT---TGGTGTTTCCT▶ | 103174 |
| CACCATTAAAGAAAATATCAT---TG▶ | 103175 |
| CACCATTAAAGAAAATATCAT---TGGTGTTTCCTATGAT▶ | 103176 |
| CACCATTAAAGAAAATATCATCTTTGGT⎯ | 103173 |
| ---⎯CATTAAAGAAAATATCAT---TGGTGTTTCCTATGATGAA▶ | 103177 |
| ----⎯TTAAAGAAAATATCATCTTTGGTGTTTCCTATGATGAA▶ | 103178 |
| -----------◀AAATATCAT---TGGTGTTTCCTATGATGAAT | 103179 |
| -----------◀AAATATCAT---TGGTGTTTCCTATGATGAAT | 103179 |
| -------------◀TATCATCTTTGGTGTTTCCTATGATGAAT | 103180 |
| -------------◀TATCATCTTTGGTGTTTCCTATGATGAAT | 103180 |
| ---------------◀TATCAT---TGGTGTTTCCTATGATGAAT | 103181 |
| ----------------◀ATCATCTTTGGTGTTTCCTATGATGAAT | 103182 |
| ----------------------------◀TTCCTATGATGAAT | 103183 |

FIG. 13C c.2562T>G
CGATATATTACTGTCCACAAGAGCTTA     SEQ ID NO.
CGATATATTACTGTCCACAAGAGCTTA     103184
CGATATATTACTGTCCACAAGAGCTTA     103184 c|

| Sequence | SEQ ID NO. |
|---|---|
| CGATATATTACTGTC▶ | 103185 |
| CGATATATTA| | 103186 |
| CGATATATTACTGTCCACAA▶ | 103187 |
| CGATATATTACGGTCCACA▶ | 103188 |
| CGATATATTACTG| | 103189 |
| CGATATATTACGGTCCACAAGAG▶ | 103190 |
| CGATATATTACTGTCC| | 103191 |
| CGATATATTACTGTCCACAAGAGCT▶ | 103192 |
| CGATATATTACGGTC| | 103193 |
| CGATATATTACGGTCCACAAGAGCTTA | 103194 |
| CGATATATTACTGTCCACAAGC| | 103195 |
| --------◀TACTGTCCACAAGAGCTTA | 103196 |

FIG. 13D c.1408G>A

| | SEQ ID NO. |
|---|---|
| [ TCACTTCTAATGGTGATTATGGGAGA | 103197 |
| [ TCACTTCTAATGGTGATTATGGGAGA | 103197 |
| | |
| [ TC▶ | |
| [ TCACTTCTAATGATGAT▶ | 103198 |
| [ TCACTTCTAATGAGATTATGGGAGA | 103199 |
| [ TCACTTCTAATGATGAT▶ | 103198 |
| [ TCACTTCTAATGATGATTATGGGAGA | 103200 |
| [ TCACTTCTAATG▶ | 103201 |
| —◀CACTTCTAATGATGATTATGGGAGA | 103202 |
| ———◀CTTCTAATGATGATTATGGGAGA | 103203 |
| —————◀TCTAATGATGATTATGGGAGA | 103204 |
| ——————————◀GATGATTATGGGAGA | 103205 |
| ————————————◀TGATTATGGGAGA | 103206 |
| —————————————◀ATTATGGGAGA | 103207 |
| ———————————————◀TATGGGAGA | |
| ———————————————◀TATGGGAGA | |
| ————————————————◀TATGGGAGA | |
| ——————————————————┤AGA | | c.1-8G>C

| | |
|---|---|
| GGACCCCAGCGCCCGAGAGACCATGCAGAGGTCC | 103208 |
| GGACCCCAGCGCCCGAGAGACCATGCAGAGGTCC | 103208 |
| | |
| GGACCCCAGCGCCCGAGAGACCAT❘ | 103209 |
| GGACCCCAGCGCCCGAGA❘ | 103210 |
| GGACCCCAGCGCCCAGAGACC❘ | 103211 |
|        ❘CCCAGAGACCA❘TGCAGAGGTCC | 103212 |
|                 ❘ATGCAGAGGTCC | 103213 |
|                       ❘AGAGGTCC | |

FIG. 13E

METHODS AND COMPOSITIONS FOR MULTIPLEX PCR

CROSS REFERENCE TO RELATED APPLICATIONS

This application is a continuation of U.S. Nonprovisional application Ser. No. 13/458,739, filed Apr. 27, 2012, which claims benefit of priority under 35 U.S.C. § 119(e) to U.S. Provisional Application No. 61/479,952, filed Apr. 28, 2011, U.S. Provisional Application No. 61/531,583, filed Sep. 6, 2011, U.S. Provisional Application No. 61/531,574, filed Sep. 6, 2011, U.S. Provisional Application No. 61/538,079, filed Sep. 22, 2011, U.S. Provisional Application No. 61/564,763, filed Nov. 29, 2011, U.S. Provisional Application No. 61/578,192, filed Dec. 20, 2011, U.S. Provisional Application No. 61/594,160 filed Feb. 2, 2012, U.S. Provisional Application No. 61/598,881 filed Feb. 14, 2012, U.S. Provisional Application No. 61/598,892 filed Feb. 14, 2012, U.S. Provisional Application No. 61/625,596 filed Apr. 17, 2012, and U.S. Provisional Application No. 61/639,017 filed Apr. 26, 2012 entitled "METHODS AND COMPOSITIONS FOR MULTIPLEX PCR", the disclosures of which are incorporated herein by reference in their entireties.

SEQUENCE LISTING

This application hereby incorporates by reference the material of the electronic Sequence Listing filed concurrently herewith. The material in the electronic Sequence Listing is submitted as a text (.txt) file entitled "2013-08-29_LT00503_CON_6_ST25.txt" created on Aug. 29, 2013, which has a file size of 18957 KB, and is herein incorporated by reference in its entirety.

TECHNICAL FIELD

In some embodiments, the disclosure relates generally to methods, compositions, systems, apparatuses and kits for amplifying one or more target sequences within a sample containing a plurality of target sequences. Optionally, a plurality of target sequences, for example at least 10, 50, 100, 500, 1000, 2500, 5000, 7500, 10000, 25000, 50000 or 100000, are amplified within a single amplification reaction. In some embodiments, the disclosure relates generally to methods, compositions, systems, apparatuses and kits for amplifying one or more target sequences from a single source, such as genomic DNA or formalin-fixed paraffin-embedded (FFPE) DNA. In particular, methods, kits, systems apparatuses and compositions useful for amplifying one or more target sequences using primers having a cleavable group are disclosed.

BACKGROUND

Several biological applications involve the selective amplification of nucleic acid molecules within a population. For example, next-generation sequencing methods can involve the analysis of selected targets within a large population of nucleic acid molecules. For such applications, it can be useful to increase the total number of targets that can be selectively amplified from a population within a single amplification reaction. Such selective amplification is typically achieved through use of one or more primers that can selectively hybridize to, or selectively promote the amplification of, a particular target nucleic acid molecule. Such selective amplification can be complicated by the formation of amplification artifacts, such as primer-dimers and the like. The formation of such amplification artifacts (also referred to herein as nonspecific amplification products) can consume critical amplification reagents, e.g., nucleotides, polymerase, primers, etc. Furthermore, such artifacts can frequently have shorter length relative to the intended product and in such situations can amplify more efficiently than the intended products and dominate the reaction output. Selective amplification can also be complicated by the formation of 'superamplicons', i.e., the formation of a extended amplicon, which can occur when extension of a first primer is extended through an adjacent target nucleic acid sequence, thereby creating a long non-specific amplification product, which can act as a template for extension with a second primer. The formation of such artifacts in amplification reactions, even when only a single pair of primers is employed, can complicate downstream applications such as qPCR, cloning, gene expression analysis and sample preparation for next-generation sequencing. In some downstream applications, including several next-generation sequencing methods, this problem can be compounded by the requirement to practice a secondary amplification step, since the artifacts can be further amplified during the secondary amplification. For example, downstream sequencing applications can involve the generation of clonally amplified nucleic acid populations that are individually attached to separate supports, such as beads, using emulsion PCR ("emPCR") and enrichment for clonal amplicons performed via positive selection. In such applications, the artifacts can be carried all the way through the library generation process to the emPCR stage, producing DNA capture beads that include non-specific amplification products. These artifact-containing beads can be selected for during the enrichment process with the template containing beads but are genetically non-informative.

Nucleic acid molecules amplified in a multiplex PCR reaction can be used in many downstream analysis or assays with, or without, further purification or manipulation. For example, the products of a multiplex PCR reaction (amplicons) when obtained in sufficient yield can be used for single nucleotide polymorphism (SNP) analysis, genotyping, copy number variation analysis, epigenetic analysis, gene expression analysis, hybridization arrays, analysis of gene mutations including but not limited to detection, prognosis and/or diagnosis of disease states, detection and analysis of rare or low frequency allele mutations, nucleic acid sequencing including but not limited to de novo sequencing or targeted resequencing, and the like.

Exemplary next-generation sequencing systems include the Ion Torrent PGM™ sequencer (Life Technologies) and the Ion Torrent Proton™ Sequencer (Life Technologies), which are ion-based sequencing systems that sequence nucleic acid templates by detecting ions produced as a byproduct of nucleotide incorporation. Typically, hydrogen ions are released as byproducts of nucleotide incorporations occurring during template-dependent nucleic acid synthesis by a polymerase. The Ion Torrent PGM™ sequencer and Ion Proton™ Sequencer detect the nucleotide incorporations by detecting the hydrogen ion byproducts of the nucleotide incorporations. The Ion Torrent PGM™ sequencer and Ion Torrent Proton™ sequencer include a plurality of nucleic acid templates to be sequenced, each template disposed within a respective sequencing reaction well in an array. The wells of the array are each coupled to at least one ion sensor that can detect the release of $H^+$ ions or changes in solution pH produced as a byproduct of nucleotide incorporation. The ion sensor comprises a field effect transistor (FET)

coupled to an ion-sensitive detection layer that can sense the presence of $H^+$ ions or changes in solution pH. The ion sensor provides output signals indicative of nucleotide incorporation which can be represented as voltage changes whose magnitude correlates with the $H^+$ ion concentration in a respective well or reaction chamber. Different nucleotide types are flowed serially into the reaction chamber, and are incorporated by the polymerase into an extending primer (or polymerization site) in an order determined by the sequence of the template. Each nucleotide incorporation is accompanied by the release of $H^+$ ions in the reaction well, along with a concomitant change in the localized pH. The release of $H^+$ ions is registered by the FET of the sensor, which produces signals indicating the occurrence of the nucleotide incorporation. Nucleotides that are not incorporated during a particular nucleotide flow will not produce signals. The amplitude of the signals from the FET may also be correlated with the number of nucleotides of a particular type incorporated into the extending nucleic acid molecule thereby permitting homopolymer regions to be resolved. Thus, during a run of the sequencer multiple nucleotide flows into the reaction chamber along with incorporation monitoring across a multiplicity of wells or reaction chambers permit the instrument to resolve the sequence of many nucleic acid templates simultaneously. Further details regarding the compositions, design and operation of the Ion Torrent PGM™ sequencer can be found, for example, in U.S. patent application Ser. No. 12/002,781, now published as U.S. Patent Publication No. 2009/0026082; U.S. patent application Ser. No. 12/474,897, now published as U.S. Patent Publication No. 2010/0137143; and U.S. patent application Ser. No. 12/492,844, now published as U.S. Patent Publication No. 2010/0282617, all of which applications are incorporated by reference herein in their entireties. In some embodiments, amplicons can be manipulated or amplified through bridge amplification or emPCR to generate a plurality of clonal templates that are suitable for a variety of downstream processes including nucleic acid sequencing. In one embodiment, nucleic acid templates to be sequenced using the Ion Torrent PGM™ or Ion Torrent Proton™ system can be prepared from a population of nucleic acid molecules using one or more of the target-specific amplification techniques outlined herein. Optionally, following target-specific amplification a secondary and/or tertiary amplification process including, but not limited to a library amplification step and/or a clonal amplification step such as emPCR can be performed.

As the number of nucleic acid targets desired to be amplified within a sample nucleic acid population increases, the challenge of selectively amplifying these targets while avoiding the formation of undesirable amplification artifacts can correspondingly increase. For example, the formation of artifacts including primer-dimers and superamplicons can be a greater issue in multiplex PCR reactions where PCR primer pairs for multiple targets are combined in a single reaction tube and co-amplified. In multiplex PCR, the presence of additional primer pairs at elevated concentrations relative to the template DNA makes primer-primer interactions, and the formation of primer-dimers and other artifacts, more likely.

Current methods for avoiding or reducing the formation of artifacts, such as primer-dimers, during nucleic acid amplification center around the primer design process and often utilize dedicated software packages (e.g., DNAsoftwares's Visual OMP, MultiPLX, ABI's Primer Express, etc.) to design primer pairs that are predicted to exhibit minimal interaction between the other primers in the pool during amplification. Through the use of such software, primers can be designed to be as target-specific or amplicon-specific as possible, and often are grouped into subsets to minimize primer-primer interactions, primer-dimer formation and superamplicons. Stringent design parameters, however, limit the number of amplicons that can be co-amplified simultaneously and in some cases may prevent the amplification of some amplicons altogether. Other current methods require the use of multiple PCR primer pools to segregate primers into non-overlapping pools to minimize or prevent primer artifacts during the amplification step. Other methods include the use of multiple primer pools or single plex reactions to enhance the overall yield of amplification product per reaction. In a multiplex PCR reaction, each primer pair competes in the amplification reaction with additional primer pairs for a finite amount of dNTPs, polymerase and other reagents. There is therefore a need for improved methods, compositions, systems, apparatuses and kits that allow for the selective amplification of multiple target nucleic acid molecules within a population of nucleic acid molecules while avoiding, or minimizing, the formation of artifacts (also referred to as non-specific amplification products), including primer dimers. There is also a need for improved methods, compositions, systems, apparatuses and kits that allow for the selective amplification of multiple target nucleic acid molecules from a single nucleic acid sample, such as genomic DNA and/or formalin-fixed paraffin embedded (FFPE) DNA while avoiding, or minimizing, the formation of artifacts. There is also a need in the art for improved methods, compositions, systems and kits that allow for the simultaneous amplification of thousands of target-specific nucleic acid molecules in a single reaction, which can be used in any applicable downstream assay or analysis.

The practice of the present subject matter may employ, unless otherwise indicated, conventional techniques and descriptions of organic chemistry, molecular biology (including recombinant techniques), cell biology, and biochemistry, which are within the skill of the art. Such conventional techniques include, but are not limited to, preparation of synthetic polynucleotides, polymerization techniques, chemical and physical analysis of polymer particles, preparation of nucleic acid libraries, nucleic acid sequencing and analysis, and the like. Specific illustrations of suitable techniques can be used by reference to the examples provided herein. Other equivalent conventional procedures can also be used. Such conventional techniques and descriptions can be found in standard laboratory manuals such as *Genome Analysis: A Laboratory Manual Series* (Vols. I-IV), *PCR Primer: A Laboratory Manual, and Molecular Cloning: A Laboratory Manual* (all from Cold Spring Harbor Laboratory Press), 1-ermanson, Bioconjugate Techniques, Second Edition (Academic Press, 2008); Merkus, Particle Size Measurements (Springer, 2009); Rubinstein and Colby, Polymer Physics (Oxford University Press, 2003); and the like.

Unless defined otherwise, all technical and scientific terms used herein have the same meaning as is commonly understood by one of ordinary skill in the art to which these inventions belong. All patents, patent applications, published applications, treatises and other publications referred to herein, both supra and infra, are incorporated by reference in their entirety. If a definition and/or description is set forth herein that is contrary to or otherwise inconsistent with any definition set forth in the patents, patent applications, published applications, and other publications that are herein incorporated by reference, the definition and/or description set forth herein prevails over the definition that is incorporated by reference.

As used herein, the terms "comprises," "comprising," "includes," "including," "has," "having" or any other variation thereof, are intended to cover a non-exclusive inclusion. For example, a process, method, article, or apparatus that comprises a list of features is not necessarily limited only to those features but may include other features not expressly listed or inherent to such process, method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

BRIEF DESCRIPTION OF THE DRAWINGS

The accompanying drawings, which are incorporated into and form a part of the specification, illustrate one or more exemplary embodiments and serve to explain the principles of various exemplary embodiments. The drawings are exemplary and explanatory only and are not to be construed as limiting or restrictive in any way.

FIG. 1A-FIG. 1E2 are schematic outlining an exemplary embodiment of a method utilizing degradable amplification primers according to the disclosure.

FIG. 2 is a schematic outlining an exemplary embodiment of a method obtaining a target-specific amplicon library according to the disclosure.

FIG. 3A shows a significant and predominant production of primer-dimers when using an exemplary set of standard multiplex primers. FIG. 3B shows a decrease in primer-dimers and an overall increase in expected amplicon product (104 bp) when using an exemplary set of modified multiplex primers as exemplified by the application.

FIG. 6A-6B show quantification of the abundance and reproducibility of an exemplary multiplex reaction on genomic DNA when analyzed using an Ion Torrent PGM™ Sequencer (Life Technologies). The data shows the number of reads per amplicon for both the forward (FIG. 6A) and reverse primers (FIG. 6B) in the primer pool.

FIG. 13A-FIG. 13E show sequencing alignment data identifying 6 mutations of the cystic fibrosis (CFTR) gene in a sample when using exemplary modified multiplex primers and exemplary library amplification process according to the disclosure.

SUMMARY

Figure 2:
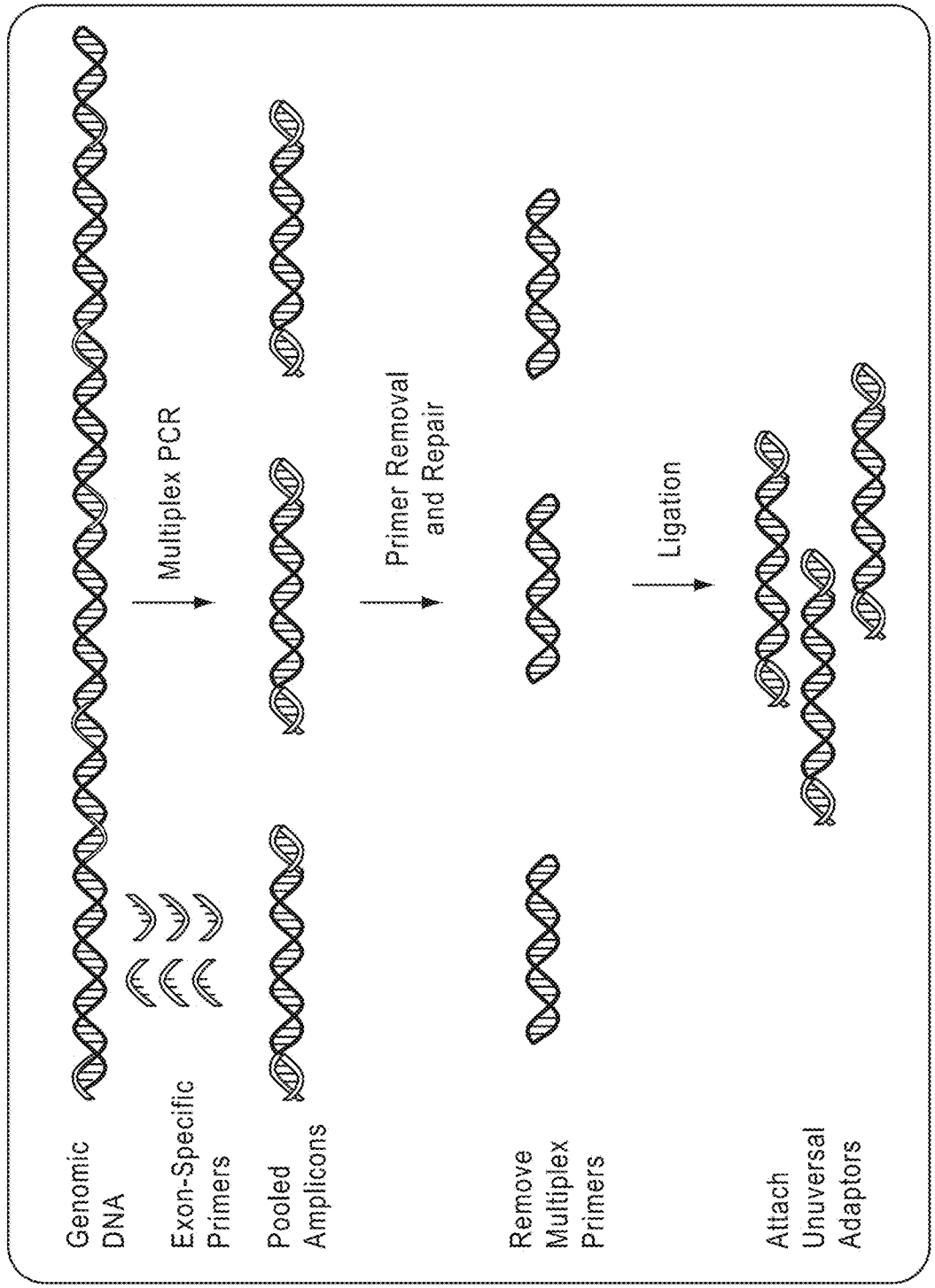

In some embodiments, the disclosure relates generally to methods, compositions, systems, apparatuses and kits for performing multiplex amplification of nucleic acids. In some embodiments, the method includes amplifying a plurality of target sequences within a sample including two or more target sequences. Optionally, multiple target sequences of interest from a sample can be amplified using one or more target-specific primers in the presence of a polymerase under amplification conditions to produce a plurality of amplified target sequences. The amplifying optionally includes contacting a nucleic acid molecule including at least one target sequence with one or more target-specific primers and at least one polymerase under amplification conditions. The contacting can produce one or more amplified target sequences.

In some embodiments, the disclosed methods (and related compositions, systems, apparatuses and kits) can include ligating at least one adapter to at least one of the amplified target sequences to produce one or more adapter-ligated amplified target sequences. The adapter can include at least one sequence that is substantially non-complementary to the target sequence, to the amplified target sequence, and/or to the nucleic acid molecule.

In some embodiments, the amplifying can produce least two amplified target sequences that are less than 50% complementary to each other. In some embodiments, at least one amplified target sequence is substantially non-complementary to another target sequence in the sample. In some embodiments, an amplified target sequence can be substantially noncomplementary to any one or more nucleic acid molecules in the sample that does not include the target sequence.

In some embodiments, the disclosed methods (as well as related compositions, systems, apparatuses and kits) can involve reamplifying at least one of the amplified target sequences c. For example, an adapter-ligated amplified target sequence can be reamplified to produce at least one reamplified adapter-ligated amplified target sequence. In some embodiments, at least one of the adapter-ligated amplified target sequences can be contacted with one or more adapters or their complement, and a polymerase under amplification conditions to produce at least one reamplified adapter-ligated amplified target sequence. In some embodiments, at least one adapter or its complement is substantially non-complementary to at least one amplified target sequence.

In some embodiments, the disclosure relates generally to compositions (as well as related methods, kits, apparatuses and systems using such compositions) comprising one or more target-specific primers useful for hybridizing to, and optionally amplifying, at least one target sequence in a sample. In some embodiments, the composition can include a plurality of target-specific primers useful for amplifying one, two or more target sequences in a sample. The compositions can further include one or more adapters.

In some embodiments, a target sequence includes one or more mutational hotspots, single nucleotide polymorphisms (SNPs), short tandem repeats (STRs), coding regions, exons and genes. In some embodiments, the number of target sequences amplified by one or more of the methods using the compositions (and related kits, apparatuses and systems) disclosed herein can be dozens, hundreds or thousands of target sequences in a single reaction. In some embodiments, the number of different targets amplified in a single multiplex amplification can be at least 100, 300, 500, 750, 1000, 2500, 5000, 7500, 10000, 12500, 15000 or greater.

In some embodiments, a target-specific primer, adapter, amplified target sequence or nucleic acid molecule can include one or more cleavable moieties, also referred to herein as cleavable groups. Optionally, the methods can further include cleaving at least one cleavable group of the target-specific primer, adapter, amplified target sequence or nucleic acid molecule. The cleaving can be performed before or after any of the other steps of the disclosed methods. In some embodiments, the cleavage step occurs after the amplifying and prior to the ligating. In one embodiment, the cleaving includes cleaving at least one amplified target sequence prior to the ligating. The cleavable moiety can be present in a modified nucleotide, nucleoside or nucleobase. In some embodiments, the cleavable moiety can include a nucleobase not naturally occurring in the target sequence of interest. In some embodiments, uracil or uridine can be incorporated into a DNA-based nucleic acid as a cleavable group. In one exemplary embodiment, a uracil DNA glycosylase can be used to cleave the cleavable group from the nucleic acid. In another embodiment, inosine can be incorporated into a DNA-based nucleic acid as a cleavable group. In one exemplary embodiment, EndoV can be used to cleave near the inosine residue and a further enzyme such as Klenow can be used to create blunt-ended fragments capable of blunt-ended ligation. In another exemplary embodiment, the enzyme hAAG can be used to cleave inosine residues from a nucleic acid creating abasic sites that can be further processed by one or more enzymes such as Klenow to create blunt-ended fragments capable of blunt-ended ligation.

In some embodiments, the methods disclosed herein (as well as related kits, compositions, apparatuses and systems) can include amplifying at least two target sequences of the sample (e.g., a first target sequence and a second target sequence) that are different from each other. In some embodiments, the methods disclosed herein (as well as related kits, compositions, apparatuses and systems) include simultaneously amplifying a first target sequence and a second target sequence that are less than 50% complementary to each other. In some embodiments, the first target sequence and a second target sequence are substantially non-complementary to each other.

In some embodiments, the methods disclosed herein (as well as related kits, compositions, apparatuses and systems) can include amplifying using at least two target-specific primers (e.g., a first target-specific primer and a second target-specific primer) that are different from each other. In some embodiments, a first target-specific primer can be at least 50% complementary to at least some portion of a first target sequence. In some embodiments, the first target-specific primer can be substantially noncomplementary to another target sequence in the sample. For example, the first target-specific primer can be substantially noncomplementary to a second target sequence. Optionally, the first target-specific primer can be substantially complementary to a first target sequence within a sample and can be substantially noncomplementary to any portion of any other nucleic acid molecule within the sample other than the first target sequence.

Optionally, methods of multiplex amplification disclosed herein include amplifying at least a portion of a target sequence in a sample using at least one target-specific primer that is substantially complementary to at least some portion of a nucleic acid molecule that includes a corresponding target sequence. In some embodiments, the at least one target-specific primer is substantially complementary to at least some portion of the corresponding target sequence. In some embodiments, the amplifying can include using a primer pair including a target-specific forward primer and a target-specific reverse primer. In some embodiments, the target-specific primer can include at least one sequence that is substantially complementary or substantially identical to at least some portion of a nucleic acid molecule that includes the corresponding target sequence or its complement. Optionally, the target-specific primer is not substantially complementary to any other nucleic acid molecule present in the sample. In some embodiments, the target-specific primer can include at least one sequence that is substantially complementary or substantially identical to at least some portion of a corresponding target sequence or its complement. In some embodiments, the target-specific primer can include at least one sequence that is complementary or identical to at least some portion of a corresponding target sequence or its complement. In some embodiments, a target-specific primer does not include any nucleic acid sequence that is at least 5 contiguous nucleotides, 8 nucleotides, 10 contiguous nucleotides, or 15 contiguous nucleotides in length, and that is substantially noncomplementary to at least some portion of its corresponding target sequence. In some embodiments, a target-specific primer can hybridize under stringent conditions to at least some portion of a corresponding target sequence in the sample. In some embodiments, at least one of the target-specific primers is not substantially complementary to any nucleic acid sequence present in the sample other than its corresponding target sequence.

In some embodiments, one or more target-specific primers can be designed to exclude one or more sequence motifs. For example, at least one of the target-specific primers may be designed to not include a triplet nucleotide motif that is repeated 5 or more times in the target-specific primer. Optionally, at least one of the target-specific primers may be designed to not include the nucleotide sequence "ACA", repeated 3 or more times. Further, at least one of the target-specific primers may be designed to not include a homopolymer greater than 8 nucleotides in length. Optionally, at least one of the target-specific primers of the methods disclosed herein may be designed to possess a GC content of less than 85%.

In some embodiments, one or more of the methods of amplifying disclosed herein includes performing a target-specific amplification. Performing the target-specific amplification can include amplifying one or more target sequences using one or more exclusively target-specific primers, i.e., primers that do not include any shared or universal sequence motifs. Typically, one or more of the target-specific primers are substantially complementary to at least some portion of their corresponding target sequence, or to some portion of the nucleic acid molecule including the corresponding target sequence. In some embodiments, one, some or all of the target-specific primers are substantially complementary to at least some portion of their corresponding target sequence, or to some portion of the nucleic acid molecule including the corresponding target sequence, across their (i.e., the primers') entire length.

In some embodiments, a nucleic acid molecule in a sample, an amplified target sequence, an adapter or a target-specific primer includes a 5' end and a 3' end. The 5' end can include a free 5' phosphate group or its equivalent; the 3' end can include a free 3' hydroxyl group or its equivalent. Optionally, the ends of an amplified target sequence can be substantially non-complementary to the ends of another amplified target sequence. In some embodiments, the 3' end can include about 30 nucleotides, or about 15 nucleotides from the 3' hydroxyl group. In some embodiments, the 5' end can include about 30 nucleotides, or about 15 nucleotides, from the 5' phosphate group. In some embodiments, any one amplified target sequence having a 3' end and 5'end can be substantially non-complementary to any portion of any other amplified target sequence.

Optionally, the disclosed methods can further include ligating one or more adapters including a universal priming sequence to the amplified product formed as a result of such target-specific amplification. For example, in some embodiments, one or more adapters can be ligated to an amplified target sequence. Optionally, an adapter that is ligated to an amplified target sequence is susceptible to exonuclease digestion. In some embodiments, an adapter susceptible to exonuclease digestion can be ligated to the 3' end of an amplified target sequence. In some embodiments, an adapter ligated to an amplified target sequence does not include a protecting group. In some embodiments, the adapter does not include a protecting group that can prevent nucleic acid degradation or digestion under degrading or digesting conditions. Subsequent enzymatic digestion of the adapter-ligated amplified target sequence in the presence of nucleic acids that do not include a protecting group, offers a means for selective digestion of the unprotected nucleic acids. In some embodiments, an adapter can include a DNA barcode or tagging sequence.

In some embodiments, the methods disclosed herein (as well as related kits, systems, apparatuses and compositions) can include contacting an amplified target sequence having a 3' end and a 5'end with a ligation reaction mixture. In some embodiments, a ligation reaction mixture can include one or more adapters and a ligase to produce at least one adapter-ligated amplified target sequence. In some embodiments, none of the adapters in a ligation mixture, prior to the ligating, includes a target-specific sequence. In some embodiments, none of the adapters in the ligation mixture, prior to ligating, includes a sequence that is substantially complementary to a 3' end or a 5' end of an amplified target sequence. Optionally, the 3' end or the 5' end of an amplified target sequence includes about 30 nucleotides, and in some instances refers to about 15 nucleotides from the 3' end or the 5' end of an amplified target sequence. In some embodiments, none of the adapters in a ligation mixture, prior to ligating, can hybridize under high stringency, to some portion of an amplified target sequence. In some embodiments, ligating can include direct ligation of one or more adapters to one or more amplified target sequences. In one embodiment, ligating can include performing a blunt-ended ligation. For example, the process of blunt-ended ligation can include ligating a substantially blunt-end double-stranded amplified target sequence to a substantially blunt-ended double-stranded adapter. In some embodiments, ligating does not include one or more additional oligonucleotide adapters prior to ligating an adapter to an amplified target sequence.

In some embodiments, the disclosure relates generally to methods for performing amplification of a target sequence (as well as related compositions, systems, apparatuses and kits using the disclosed methods) and can include a digestion step. In some embodiments, the methods also include a ligating step, and the digestion step is performed prior to a ligating step. In some embodiments, an amplified target sequence can be partially digested prior to performing a ligation step. For example, an amplified target sequence can be digested by enzymatic, thermal or chemical means. In some embodiments, an amplified target sequence can be digested prior to ligating to produce a blunt-end amplified target sequence. In some embodiments, a blunt-ended amplified target sequence can include a 5' phosphate group at the 5' end of the digested amplified target sequence.

In some embodiments, the disclosure relates generally to methods, compositions, systems, apparatuses and kits for performing multiplex nucleic acid amplification. In some embodiments, the methods (as well as related compositions, kits, apparatuses and systems using such methods) include amplifying one or more target sequences using one or more target-specific primers in the presence of polymerase under amplification conditions to produce an amplified target sequence and, ligating an adapter to the amplified target sequence. Further, the method can include reamplifying an adapter-ligated amplified target sequence to form a reamplified adapter-ligated amplified target sequence. In some embodiments, a reamplified adapter-ligated amplified target sequence can be produced using no more than two rounds of target-specific selection.

In some embodiments, one or more target-specific primers, target sequences or adapters can include a cleavable group. Furthermore, a cleavable group can be located at a nucleotide position at, or near, the terminus of a target-specific primer, target sequence or adapter. In some embodiments, a cleavable group can be located within 15 nucleotides of the 3' end or 5' end of the nucleic acid having the cleavable group. In some embodiments, a cleavable group can be located at or near a central nucleotide in a target-specific primer. In some embodiments, one or more cleavable groups can be present in a target-specific primer or adapter. In some embodiments, cleavage of one or more cleavable groups in a target-specific primer or an adapter can generate a plurality of nucleic acid fragments with differing melting temperatures. In one embodiment, the placement of one or more cleavable groups in a target-specific primer or adapter can be regulated or manipulated by determining a comparable maximal minimum melting temperature for each nucleic acid fragment, after cleavage of the cleavable group. In some embodiments the cleavable group can be a uracil or uridine moiety. In some embodiments the cleavable group can be an inosine moiety. In some embodiments, at least 50% of the target-specific primers can include at least one cleavable group. In some embodiments, each target-specific primer includes at least one cleavable group.

In one embodiment, a multiplex nucleic acid amplification method is disclosed herein that includes a) amplifying one or more target sequences using one or more target-specific primers in the presence of polymerase to produce an amplified target sequence, and b) ligating an adapter to the amplified target sequence to form an adapter-ligated amplified target sequence. In some embodiments, amplifying can be performed in solution such that an amplified target sequence or a target-specific primer is not linked to a solid support or surface. In some embodiments, ligating can be performed in solution such that an amplified target sequence or an adapter is not linked to a solid support or surface. In another embodiment, amplifying and ligating can be performed in solution such that an amplified target sequence, a target-specific primer or an adapter is not linked to a solid support or surface.

In some embodiments, the disclosure relates generally to methods, compositions, systems, apparatuses and kits for synthesizing two or more target sequences within a sample. In one embodiment, the synthesizing method includes a) synthesizing two or more target sequences using a plurality of target-specific primers in the presence of polymerase under polymerizing conditions to produce a plurality of synthesized target sequences. In some embodiments, the method further includes ligating one or more adapters to the synthesized target sequences. In some embodiments, a target sequence of interest includes one or more mutational hotspots, single nucleotide polymorphisms (SNPs), short tandem repeats (STRs), coding regions, exons and genes. In some embodiments, the number of target sequences that can be synthesized in a multiplex reaction using the compositions (and related methods, kits, apparatuses and systems) disclosed herein can be dozens, hundreds or thousands of target sequences in a single sample. Optionally, multiple target sequences of interest from a sample can be synthesized using one or more target-specific primers in the presence of a polymerase under polymerizing conditions to produce a plurality of synthesized target sequences. In some embodiments, a synthesized target sequence can be less than 50% complementary to another synthesized target sequence. In some embodiments, a synthesized target sequence can be substantially non-complementary to another target sequence in the sample. In some embodiments, a synthesized target sequence can be substantially noncomplementary to any one or more nucleic acid molecules in the sample that is not a target sequence of interest. In some embodiments, synthesizing a target sequence can include ligating an adapter to a synthesized target sequence, thereby producing an adapter-ligated synthesized target sequence.

In some embodiments, the disclosure relates generally to synthesizing a target sequence from a plurality of target sequences. For example, a method of synthesizing can include synthesizing a target sequence using a plurality of target-specific primers in the presence of polymerase under polymerizing conditions to produce a plurality of synthesized target sequences. Synthesizing can further include resynthesizing at least one adapter-ligated synthesized target sequence. In some embodiments, resynthesizing can include contacting at least one adapter-ligated synthesized target sequence with at least one adapter or its complement and a polymerase under polymerizing conditions to produce a plurality of resynthesized adapter-ligated synthesized target sequences. In some embodiments, a resynthesized adapter-ligated synthesized target sequence can be produced using no more than two rounds of target-specific selection.

In some embodiments, a method for synthesizing target sequences can include a synthesizing and a ligating step. In some embodiments, ligating does not include an adapter that is substantially complementary to a portion of a synthesized target sequence. In some embodiments, an adapter is not substantially complementary to about 30 contiguous nucleotides, or about 20 contiguous nucleotides, from a 3' end or a 5' end of a synthesized target sequence. In some embodiments, an adapter can include at least one sequence that is substantially complementary, or substantially identical, to at least a portion of a universal primer.

In some embodiments, the disclosure relates generally to methods, compositions, systems, apparatuses and kits for performing multiplex nucleic acid amplification. In one embodiment, the method includes amplifying one or more target sequences using one or more target-specific primers in the presence of polymerase under amplification conditions to produce an amplified target sequence; ligating an adapter to the amplified target sequence; and reamplifying at least one adapter-ligated amplified target sequence. In some embodiments, reamplifying includes contacting an adapter-ligated amplified target sequence with one or more adapters (or their complements) and a polymerase under amplification conditions to produce at least one reamplified adapter-ligated amplified target sequence. In some embodiments, an amplified target sequence can be less than 50% complementary to another amplified target sequence. In some embodiments, an amplified target sequence can be substantially non-complementary to another target sequence in the sample. In some embodiments, an amplified target sequence can be substantially noncomplementary to any one or more nucleic acid molecules in the sample that is not a target sequence of interest. In some embodiments, an amplified target sequence can be ligated to at least one adapter, or their complement, to produce one or more adapter-ligated amplified target sequences. In some embodiments, an adapter-ligated amplified target sequence can be reamplified to produce at least one reamplified adapter-ligated amplified target sequence. In some embodiments, an adapter or their complement is not substantially complementary to any portion of any other nucleic acid molecule within the sample. In some embodiments, an adapter or their complement is not substantially complementary to at least one amplified target sequence. In one embodiment, one or more of the adapters or their complement during the reamplifying step can be a universal primer. In one embodiment, the ligating step can further include ligating a DNA barcode or DNA tagging sequence to an amplified target sequence prior to ligating an adapter to an amplified target sequence.

In some embodiments, amplifying and synthesizing methods of the disclosure can be performed as "addition-only" processes. In some embodiments, an addition-only process excludes the removal of all, or a portion of a first reaction mixture including the amplifying or synthesizing compositions, for further manipulation during the amplification or synthesizing steps. In some embodiments, an addition-only process can be automated for example for use in high-throughput processing.

In some embodiments, the disclosure generally relates to compositions (as well as related kits, methods, systems and apparatuses using the disclosed compositions) for performing nucleic acid amplification and nucleic acid synthesis. In some embodiments, one or more of the compositions disclosed herein (as well as related methods, kits, systems and apparatuses) can include at least one target-specific primer and/or at least one adapter. In some embodiments, the compositions include a plurality of target-specific primers or adapters that are about 15 to about 40 nucleotides in length. In some embodiments, the compositions include one or more target-specific primers or adapters that include one or more cleavable groups. In some embodiments, one or more types of cleavable groups can be incorporated into a target-specific primer or adapter. In some embodiments, a cleavable group can be located at, or near, the 3' end of a target-specific primer or adapter. In some embodiments, a cleavable group can be located at a terminal nucleotide, a penultimate nucleotide, or any location that corresponds to less than 50% of the nucleotide length of the target-specific primer or adapter. In some embodiments, a cleavable group can be incorporated at, or near, the nucleotide that is central to the target-specific primer or the adapter. For example, a target specific primer of 40 bases can include a cleavage group at nucleotide positions 15-25. Accordingly, a target-specific primer or an adapter can include a plurality of cleavable groups within its 3' end, its 5' end or at a central location. In some embodiments, the 5' end of a target-specific primer includes only non-cleavable nucleotides. In some embodiments, the cleavable group can include a modified nucleobase or modified nucleotide. In some embodiments, the cleavable group can include a nucleotide or nucleobase that is not naturally occurring in the corresponding nucleic acid. For example, a DNA nucleic acid can include a RNA nucleotide or nucleobase. In one example, a DNA based nucleic acid can include uracil or uridine. In another example, a DNA based nucleic acid can include inosine. In some embodiments, the cleavable group can include a moiety that can be cleaved from the target-specific primer or adapter by enzymatic, chemical or thermal means. In some embodiments, a uracil or uridine moiety can be cleaved from a target-specific primer or adapter using a uracil DNA glycosylase. In some embodiments, a inosine moiety can be cleaved from a target-specific primer or adapter using hAAG or EndoV.

In some embodiments, the disclosure relates generally to compositions including a target-specific primer of about 15 to about 40 nucleotides in length having a cleavable group located near the terminus of the target-specific primer, hybridized to a first strand of a double-stranded target sequence. In some embodiments, the primer is substantially complementary to the first strand of the double-stranded target sequence. In some embodiments, the disclosure relates generally to compositions including a target-specific primer of about 15 to about 40 nucleotides in length having a cleavable group located near the terminus of the target-specific primer, hybridized to a first strand of a double-stranded target sequence, and a second target-specific primer of about 15 to about 40 nucleotides in length having a cleavable group located near the terminus of the second target-specific primer, hybridized to a second strand of the double-stranded target sequence. In some embodiments, the second target-specific primer is substantially complementary to the second strand of the double-stranded target sequence.

In some embodiments, the disclosure generally relates to compositions (as well as related kits, methods, systems and apparatuses using the disclosed compositions) for performing nucleic acid amplification and nucleic acid synthesis. In some embodiments, the compositions include a target-specific primer of about 15 to about 40 nucleotides in length having a uracil nucleotide located near the terminus of the target-specific primer and a second uracil nucleotide located near the central nucleotide of the target-specific primer. In some embodiments, the disclosure generally relates to compositions (as well as related kits, methods, systems and apparatuses using the disclosed compositions) for performing nucleic acid amplification and nucleic acid synthesis. In some embodiments, the compositions include a target-specific primer of about 15 to about 40 nucleotides in length having an inosine nucleotide located near the 3' terminus of the target-specific primer and at least a second inosine nucleotide located near the central nucleotide of the target-specific primer.

In some embodiments, the disclosure relates generally to a composition comprising at least one target-specific primer or at least one target-specific primer pair. In some embodiments, the disclosure relates generally to a composition comprising a plurality of target-specific primers. Optionally, the composition can include at least 100, 200, 300, 500, 750, 1000, 1250, 1500, 1750, 2000, 2500, 3000, 4000, 5000, 7500 or 10,000 target-specific primers or target-specific primer pairs. In some embodiments, the composition comprising a plurality of target-specific primers includes at least one of the target-specific primers disclosed herein. In some embodiments, the composition comprising a plurality of target-specific primers includes at least one target-specific primer that is at least 90% identical to any one of the nucleic acid sequences provided herein or in the concurrently filed sequencing listing. In some embodiments, the composition comprising a plurality of target-specific primers includes one or more target-specific primer pairs disclosed herein or one or more primer pairs having at least 90% identity to any one of the primer pair nucleic acid sequences provided herein. In some embodiments, the composition comprising a plurality of target-specific primers can include a percentage identity of at least 91%, 92%, 93%, 94%, 95%, 96%, 97%, 98% or 99% identity to any one or more of the nucleic acid sequences disclosed herein or in the concurrently filed sequence listing. In some embodiments, the composition comprising a plurality of target-specific primers can include any one or more target-specific primers selected from Tables 2, 3, 13, 14, 15, 17 and 19 from U.S. Ser. No. 13/458,739, filed Apr. 27, 2012, hereby incorporated by reference in its entirety. In some embodiments, the composition comprising a plurality of target-specific primers can include any one or more target-specific primer pairs selected from Tables 2, 3, 13, 14, 15, 17 and 19 from U.S. Ser. No. 13/458,739, filed Apr. 27, 2012, hereby incorporated by reference in its entirety. In some embodiments, the composition comprising a plurality of target-specific primers generally relates to any one or more nucleic acid sequences selected from SEQ ID NOs: 1-103,143 or includes at least 15 contiguous nucleotides from any one nucleic acid sequence selected from SEQ ID NOs: 1-103,143. In some embodiments, the composition is generally directed to an isolated nucleic acid sequence consisting of any one or more of the nucleic acid sequences set forth in SEQ ID NOs: 1-103,143.

In some embodiments, the disclosure relates generally to a composition comprising a target-specific primer of about 15 nucleotides to about 40 nucleotides in length. In some embodiments, the disclosure relates generally to a composition comprising a plurality of at least 2 target-specific primers of about 15 nucleotides to about 40 nucleotides in length. In some embodiments, the composition comprises a plurality of target-specific primer pairs of about 15 nucleotides to about 40 nucleotides in length designed using the primer selection criteria or primer selection methods outlined herein.

In some embodiments, the composition includes at least one target-specific primer that is substantially complementary across its entire length to at least one target sequence in a sample. In some embodiments, the composition includes a plurality of target-specific primers, where substantially all of the plurality of target-specific primers include a complementary nucleic acid sequence across their entire primer lengths to one or more target sequences in a sample. In some embodiments, the composition includes at least one target-specific primer that is complementary across its entire length to at least one target sequence in a sample. In some embodiments, the composition includes a plurality of target-specific primers, where substantially all of the plurality of target-specific primers include a complementary nucleic acid sequence across their entire primer lengths to one or more target sequences in a sample.

In some embodiments, the disclosure relates generally to a composition comprising a plurality of target-specific primers having a cleavable group located at a 3' end of at least one of the plurality of the target-specific primers. In some embodiments, the composition includes a cleavable group located at a 3' end of substantially all of the plurality of target-specific primers. In some embodiments, the cleavable group can include a uracil nucleobase, an inosine nucleoside or an analog thereof. In some embodiments, the 3' end of one or more target-specific primers can include more than one cleavable group and/or more than one species of cleavable group. For example, a composition having a cleavable group at the 3' end of one target-specific primer can include one uracil moiety and an inosine moiety in the 3' end of the same target-specific primer. In some embodiments, the composition can include at least one target-specific primer that includes a non-cleavable at the 3' terminal nucleotide. For example, a target-specific primer can include a cleavable group at the 3' end of the target-specific primer except for the terminal nucleotide at the 3' end of the target-specific primer. In some embodiments, the composition can include a plurality of target-specific primers where substantially all of the target-specific primers include a cleavable group at the 3' end except for the terminal nucleotide location.

In some embodiments, the disclosure relates generally to a composition comprising a plurality of target-specific primers having a cleavable group located near or about a central nucleotide of at least one of the target-specific primers. In some embodiments, the composition includes a cleavable group located near or about a central nucleotide of substantially all of the plurality of the target-specific primers. For example, in a target-specific primer of 40 nucleotides, a cleavable group can be located near the central nucleotide, for example at the 15th nucleotide through the 25th nucleotide. In some instances, 'near' a central nucleotide can refer to a percentage of the length of the entire target-specific primer. For example in a 40 nucleotide target-specific primer, the location of a central cleavable group can include any location from about 40% to about 60% of the length of the target-specific primer. In some embodiments, a central nucleotide of an odd numbered target-specific primer includes the central nucleotide of the target-specific primer. In an even numbered target-specific primer a central nucleotide can include one nucleotide either side of the central nucleotide location. For example, in a 20 nucleotide target-specific primer, the central nucleotide can include nucleotide position 10, nucleotide position 11, or both.

In some embodiments, the disclosure relates generally to a composition comprising a plurality of target-specific primers having at a 5' end only non-cleavable nucleotides. In some embodiments, the composition can include substantially all of the plurality of target-specific primers having only non-cleavable nucleotides at the 5' end. In some embodiments, the 5' end of the plurality of target-specific primers having only non-cleavable nucleotides can include fewer than 10 nucleotides from the 5' end. In some embodiments, the 5' end can include fewer than 8, 7, 6, 5, 4, 3 or 2 nucleotides from the 5' end. In some embodiments, the 5' end having non-cleavable nucleotides can include less than 50% of the length of the target specific primer, less than 40% of the length of the target specific primer, less than 30% of the length of the target specific primer, less than 20% of the length of the target specific primer, or less than 10% of the length of the target-specific primer from the 5' end.

In some embodiments, the disclosure relates generally to a composition comprising a plurality of target-specific primers where at least one of the target-specific primers includes less than 20% of the nucleotides across the primer's entire length containing a cleavable group. In some embodiments, the composition comprises a plurality of target-specific primers where substantially all of the target-specific primers include less than 20% of the nucleotides across each primer's entire length containing a cleavable group. For example, a target-specific primer of 20 nucleotides in length can include 4 or fewer cleavage groups. In some embodiments, the disclosure relates generally to a composition comprising a plurality of target-specific primers where at least one of the target-specific primers includes less than 10% of the nucleotides across the primer's entire length containing a cleavable group. In some embodiments, the composition comprises a plurality of target-specific primers where substantially all of the target-specific primers include less than 10% of the nucleotides across each primer's entire length containing a cleavable group. For example, a target-specific primer of 20 nucleotides in length can include 2 or fewer cleavage groups.

In some embodiments, the disclosure relates generally to a composition comprising a plurality of target-specific primers having minimal cross-hybridization to at least one of the target-specific primers in the plurality of primers. In some embodiments, the disclosure relates generally to a composition comprising a plurality of target-specific primers having minimal cross-hybridization to substantially all of the target-specific primers in the plurality of primers. In some embodiments, minimal cross-hybridization to one or more target-specific primers in the plurality of primers can be evaluated by the formation of primer-dimers or dimer-dimers. In some embodiments, the composition can include fewer primer-dimers in a multiplex PCR amplification reaction as compared to a multiplex PCR amplification reaction of the prior art under corresponding amplification conditions.

In some embodiments, the disclosure relates generally to a composition comprising a plurality of target-specific primers, where at least one of the target-specific primers includes minimal cross-hybridization to non-specific sequences present in a sample. In some embodiments, the composition comprises a plurality of target-specific primers where substantially all of the target-specific primers include minimal cross-hybridization to non-specific sequences present in a sample. In some embodiments, minimal cross-hybridization to non-specific sequences present in a sample can be evaluated by the presence of 'percent of reads off-target' or a decrease in 'percent of reads on target'. In some embodiments, the compositions as disclosed herein can provide fewer 'percent of reads off-target' or an increase in 'percent of reads on target' in multiplex PCR amplification reactions as compared to multiplex PCR amplification reactions of the prior art under corresponding amplification conditions. The "plex" of a given multiplex amplification refers generally to the number of different target-specific sequences that are amplified during a single multiplex amplification according to the disclosure. In some embodiments, the plex can be about 12-plex, 24-plex, 48-plex, 96-plex, 192-plex, 384-plex, 768-plex, 1536-plex, 3072-plex, 6144-plex or higher. In some embodiments, minimal cross-hybridization to non-specific sequences present in a sample can include less than 15%, less than 12%, or fewer than 10% reads off target. In some embodiments, the percent of reads on target per multiplex amplification can be greater than 85%, 88%, 90%, 92%, 94%, 95%, 96%, 97%, 98%, or more.

In some embodiments, the disclosure relates generally to a composition comprising a plurality of target-specific primers having minimal self-complementarity. In some embodiments, the composition includes at least one target-specific primer that does not form a secondary structure, such as loops or hairpins. In some embodiments, the composition includes a plurality of target-specific primers where a majority (i.e., greater than 50%), or substantially all of the plurality of target-specific primers fail to form a secondary structure. The "plex" of a given multiplex amplification refers generally to the number of different target-specific sequences that are amplified during a single multiplex amplification according to the disclosure. In some embodiments, the plex can be about 12-plex, 24-plex, 48-plex, 96-plex, 192-plex, 384-plex, 768-plex, 1536-plex, 3072-plex, 6144-plex or higher. In some embodiments, minimal self-complementarity can include less than 10%, less than 8%, less than 5% or less than 3% of the plurality of target-specific primers possessing self-complementarity that allows a target-specific primer to form a secondary structure.

In some embodiments, the disclosure relates generally to a composition comprising a plurality of target-specific primers having minimal nucleotide sequence overlap at a 3' end or a 5' end. In some embodiments, the composition can include minimal overlap of nucleotide sequence in the 3' end of at least one target-specific primer. In some embodiments, the composition can include minimal overlap of nucleotide sequence in the 3' end of substantially all of the plurality of target-specific primers. In some embodiments, the composition can include minimal overlap of nucleotide sequence in the 5' end of at least one target-specific primer. In some embodiments, the composition can include minimal overlap of nucleotide sequence in the 5' end of substantially all of the plurality of target-specific primers. In some embodiments, the composition can include minimal overlap of nucleotide sequence in the 3' end and the 5' end of at least one target-specific primer. In some embodiments, the composition can include minimal overlap of nucleotide sequence in the 3' end and the 5' end of substantially all of the plurality of target-specific primers. In some embodiments, the amount of nucleotide sequence overlap between one or more target-specific primers is less than 8 nucleotides. In some embodiments, the amount of nucleotide sequence overlap between one or more target-specific primers is less than 5 nucleotides. In some embodiments, the amount of nucleotide sequence between one or more target-specific primers of the plurality of primers is less than 8, 7, 6, 5, 4, 3, 2 or 1 nucleotide. In some embodiments, the composition can include a plurality of target-specific primers including a nucleotide sequence gap of one or more nucleotides. In some embodiments, the composition can include a nucleotide sequence gap of 1, 2, 3, 4, 5, 10, 15, 20 or more nucleotides between two or more of the plurality of target-specific primers. In some embodiments, the composition can include a nucleotide sequence gap of about 50 nucleotides between two or more target-specific primers in the plurality of target-specific primers. In some embodiments, the composition can include a nucleotide sequence gap of about 10, 20, 30, 40, or 50 nucleotides between substantially all of the target-specific primers in the plurality of target-specific primers.

In some embodiments, the disclosure relates generally to a composition comprising a plurality of target-specific primers of about 15 nucleotides to about 40 nucleotides in length having at least two or more following criteria, a cleavable group located at a 3' end of substantially all of the plurality of primers, a cleavable group located near or about a central nucleotide of substantially all of the plurality of primers, substantially all of the plurality of primers at a 5' end including only non-cleavable nucleotides, minimal cross-hybridization to substantially all of the primers in the plurality of primers, minimal cross-hybridization to non-specific sequences present in a sample, minimal self-complementarity, and minimal nucleotide sequence overlap at a 3' end or a 5' end of substantially all of the primers in the plurality of primers. In some embodiments, the composition can include any 3, 4, 5, 6 or 7 of the above criteria.

In some embodiments, the disclosure relates generally to a composition comprising a plurality of at least 2 target-specific primers of about 15 nucleotides to about 40 nucleotides in length having two or more of the following criteria, a cleavable group located near or about a central nucleotide of substantially all of the plurality of primers, substantially all of the plurality of primers at a 5' end including only non-cleavable nucleotides, substantially all of the plurality of primers having less than 20% of the nucleotides across the primer's entire length containing a cleavable group, at least one primer having a complementary nucleic acid sequence across its entire length to a target sequence present in a sample, minimal cross-hybridization to substantially all of the primers in the plurality of primers, minimal cross-hybridization to non-specific sequences present in a sample, and minimal nucleotide sequence overlap at a 3' end or a 5' end of substantially all of the primers in the plurality of primers. In some embodiments, the composition can include any 3, 4, 5, 6 or 7 of the above criteria.

In some embodiments, the disclosure relates generally to a composition comprising a plurality of target-specific primers designed according to the criteria disclosed here or including any one or more of the target-specific primers disclosed herein, where at least one of the plurality of target-specific primers is substantially complementary across its entire length to at last a portion of one or more genes selected from ABI1; ABL1; ABL2; ACSL3; ACSL6; AFF1; AFF3; AFF4; AKAP9; AKT1; AKT2; ALK; APC; ARHGAP26; ARHGEF12; ARID1A; ARNT; ASPSCR1; ASXL1; ATF1; ATIC; ATM; AXIN2; BAP1; BARD1; BCAR3; BCL10; BCL11A; BCL11B; BCL2; BCL3; BCL6; BCL7A; BCL9; BCR; BIRC3; BLM; BMPR1A; BRAF; BRCA1; BRCA2; BRD3; BRD4; BRIP1; BUB1B; CARD11; CARS; CASC5; CBFA2T3; CBFB; CBL; CBLB; CBLC; CCDC6; CCNB1IP1; CCND1; CCND2; CD74; CD79A; CDC73; CDH1; CDH11; CDK4; CDK6; CDKN2A; CDKN2B; CDKN2C; CDX2; CEBPA; CEP110; CHEK1; CHEK2; CHIC2; CHN1; CIC; CIITA; CLP1; CLTC; CLTCL1; COL1A1; CREB1; CREB3L2; CREBBP; CRTC1; CRTC3; CSF1R; CTNNB1; CXCR7; CYLD; CYTSB; DCLK3; DDB2; DDIT3; DDR2; DDX10; DDX5; DDX6; DEK; DGKG; DICER1; DNMT3A; EGFR; EIF4A2; ELF4; ELL; ELN; EML4; EP300; EPS15; ERBB2; ERBB4; ERC1; ERCC2; ERCC3; ERCC4; ERCC5; ERG; ETV1; ETV4; ETV5; ETV6; EWSR1; EXT1; EXT2; EZH2; FAM123B; FANCA; FANCC; FANCD2; FANCE; FANCF; FANCG; FAS; FBXW7; FCRL4; FGFR1; FGFR1OP; FGFR2; FGFR3; FH; FIP1L1; FLCN; FLI1; FLT1; FLT3; FNBP1; FOXL2; FOXO1; FOXO3; FOXO4; FOXP1; FUS; GAS7; GATA1; GATA2; GATA3; GMPS; GNAQ; GNAS; GOLGA5; GOPC; GPC3; GPHNGPR124; HIP1; HIST1H4I; HLF; HNF1A; HNRNPA2B1; HOOK3; HOXA11; HOXA13; HOXA9; HOXC11; HOXC13; HOXD13; HRAS; HSP90AA1; HSP90AB1; IDH1; IDH2; IKZF1; IL2; IL21R; IL6ST; IRF4; ITGA10; ITGA9; ITK; JAK1; JAK2; JAK3; KDM5A; KDM5C; KDM6A; KDR; KDSR; KIAA1549; KIT; KLF6; KLK2; KRAS; KTN1; LASP1; LCK; LCP1; LHFP; LIFR; LMO2; LPP; MAF; MALT1; MAML2; MAP2K1; MAP2K4; MDM2; MDM4; MECOM; MEN1; MET; MITF; MKL1; MLH1; MLL; MLLT1; MLLT10; MLLT3; MLLT4; MLLT6; MN1; MPL; MRE11A; MSH2; MSH6; MSI2; MSN; MTCP1; MTOR; MUC1; MYB; MYC; MYCL1; MYCN; MYH11; MYH9; MYST3; MYST4; NACA; NBN; NCOA1; NCOA2; NCOA4; NEK9; NF1; NF2; NFE2L2; NFKB2; NIN; NKX2-1; NLRP1; NONO; NOTCH1; NOTCH2; NPM1; NR4A3; NRAS; NSD1; NTRK1; NTRK3; NUMA1; NUP214; NUP98; OLIG2; OMD; PAFAH1B2; PALB2; PATZ1; PAX3; PAX5; PAX7; PAX8; PBRM1; PBX1; PCM1; PDE4DIP; PDGFB; PDGFRA; PDGFRB; PER1; PHOX2B; PICALM; PIK3CA; PIK3R1; PIM1; PLAG1; PML; PMS1; PMS2; POU2AF1; POU5F1; PPARG; PPP2R1A; PRCC; PRDM16; PRF1; PRKAR1A; PRRX1; PSIP1; PTCH1; PTEN; PTPN11; RABEP1; RAD50; RAD51L1; RAF1; RANBP17; RAP1GDS1; RARA; RB1; RBM15; RECQL4; REL; RET; RHOH; RNF213; ROS1; RPN1; RPS6KA2; RUNX1; RUNX1T1; SBDS; SDHAF2; SDHB; SETD2; SFPQ; SFRS3; SH3GL1; SLC45A3; SMAD4; SMARCA4; SMARCB1; SMO; SOCS1; SRC; SRGAP3; SS18; SS18L1; STIL; STK11; STK36; SUFU; SYK; TAF15; TAF1L; TAL1; TAL2; TCF12; TCF3; TCL1A; TET1; TET2; TEX14; TFE3; TFEB; TFG; TFRC; THRAP3; TLX1; TLX3; TMPRSS2; TNFAIP3; TOP1; TP53; TPM3; TPM4; TPR; TRIM27; TRIM33; TRIP11; TSC1; TSC2; TSHR; USP6; VHL; WAS; WHSC1L1; WRN; WT1; XPA; XPC; ZBTB16; ZMYM2; ZNF331; ZNF384; and ZNF521.

In some embodiments, the disclosure relates generally to a composition comprising a plurality of target-specific primers designed according to the criteria disclosed here or including any one or more of the target-specific primers disclosed herein, where at least one of the plurality of target-specific primers is substantially complementary across its entire length to at last a portion of one or more genes selected from ABL1; AKT1; ALK; APC; ATM; BRAF; CDH1; CDKN2A; CSF1R; CTNNB1; EGFR; ERBB2; ERBB4; FBXW7; FGFR1; FGFR2; FGFR3; FLT3; GNAS; HNF1A; HRAS; IDH1; JAK2; JAK3; KDR; KIT; KRAS; MET; MLH1; MPL; NOTCH1; NPM1; NRAS; PDGFRA; PIK3CA; PTEN; PTPN11; RB1; RET; SMAD4; SMARCB1; SMO; SRC; STK11; TP53; and VHL.

In some embodiments, the disclosure relates generally to a composition comprising a plurality of target-specific primers designed according to the criteria disclosed here or including any one or more of the target-specific primers disclosed herein, where at least one of the plurality of target-specific primers is substantially complementary across its entire length to at last a portion of one or more genes selected from ABCA4; ABCC8; ABCD1; ACADVL; ACTA2; ACTC; ACTC1; ACVRL1; ADA; AIPL1; AIRE; ALK1; ALPL; AMT; APC; APP; APTX; AR; ARL6; ARSA; ASL; ASPA; ASS; ASS1; ATL; ATM; ATP2A2; ATP7A; ATP7B; ATXN1; ATXN2; ATXN3; ATXN7; BBS6; BCK-DHA; BCKDHB; BEST1; BMPR1A; BRCA1; BRCA2; BRIP1; BTD; BTK; C2orf25; CA4; CALR3; CAPN3; CAV3; CCDC39; CCDC40; CDH23; CEP290; CERKL; CFTR; CHAT; CHD7; CHEK2; CHM; CHRNA1; CHRNB1; CHRND; CHRNE; CLCN1; CNBP; CNGB1; COH1; COL11A1; COL11A2; COL1A1; COL1A2; COL2A1; COL3A1; COL4A5; COL5A1; COL5A2; COL7A1; COL9A1; CRB1; CRX; CTDP1; CTNS; CYP21A2; CYP27A1; DAX1; DBT; DCX; DES; DHCR7; DJ1; DKC1; DLD; DMD; DMPK; DNAAF1; DNAAF2; DNAH11; DNAH5; DNAI1; DNAI2; DNAL1; DNM2; DOK7; DSC2; DSG2; DSP; DYSF; DYT1; EMD; ENG; EYA1; EYS; F8; F9; FANCA; FANCC; FANCF; FANCG; FANCJ; FANDC2; FBN1; FBXO7; FGFR1; FGFR3; FMO3; FMR1; FOXL2; FRG1; FRMD7; FSCN2; FXN; GAA; GALT; GBA; GBE1; GCSH; GDF5; GJB2; GJB3; GJB6; GLA; GLDC; GNE; GNPTAB; GPC3; GPR143; GUCY2D; HBA1; HBA2; HBB; HD; HERG; HEXA; HFE; HHF; HIBCH; HLA-B27; HMBS; HPLH1; HPRP3; HR; HTNB; HTT; IKBKAP; IKBKG; IL2RG; IMPDH1; ITGB4; JAG1; JPH3; KCNE1; KCNE2; KCNH2; KCNQ1; KCNQ4; KIAA0196; KLHL7; KRAS; KRT14; KRT5; L1CAM; LAMB3; LAMP2; LDB3; LMNA; LMX18; LRAT; LRRK2; MAPT; MC1R; MECP2; MED12; MEN1; MERTK; MFN2; MKKS; MLH1; MMAA; MMAB; MMACHC; MMADHC; MPZ; MSH2; MTM1; MTND5; MTTG; MTTI; MTTK; MTTL1; MTTQ; MUT; MYBPC3; MYH11; MYH6; MYH7; MYL2; MYL3; MYLK2; MYO7A; ND5; ND6; NEMO; NF1; NF2; NIPBL; NROB1; NR2E3; NRAS; NSD1; OCA2; OCRL; OPA1; OTC; PABPN1; PAFAH1B1; PAH; PARK2; PARK7; PARKIN; PAX3; PAX6; PCDH15; PEX1; PEX2; PEX10; PEX13; PEX14; PEX19; PEX26; PEX3; PEX5; PINK1; PKD1; PKD2; PKD3; PKHD1; PKP2; PLEC1; PLOD1; PMM2; PMP22; POLG; PPT1; PRCD; PRKAG2; PRNP; PROM1; PRPF3; PRPF8; PRPH2; PRPN; PSEN1; PSEN2; PTCH1; PTPN11; RAB7A; RAF1; RAI1; RAPSN; RB1; RDH12; RDS; RECQL3; RET; RHO; ROR2; RP1; RP2; RP9; RPE65; RPGR; RPGRIP1; RPL11; RPL35A; RPS10; RPS17; RPS19; RPS24; RPS26; RPS6KA3; RPS7; RPSL5; RS1; RSPH4A; RSPH9; RYR1; RYR2; SALL4; SCA3; SCN5A; SCN9A; SEMA4A; SERPINA1; SERPINGi; SGCD; SH3BP2; SHOX; SIX1; SIX5; SLC25A13; SLC25A4; SLC26A4; SMAD4; SMN1; SNCA; SNRNP200; SOD1; SOS1; SOX9; SP110; SPAST; SPATA7; SPG3A; SPG4; SPG7; TAF1; TBX5; TCOF1; TGFBR1; TGFBR2; TNFRSC13C; TNNC1; TNNI3; TNNT1; TNNT2; TNXB; TOPORS; TOR1A; TP53; TPM1; TRNG; TRNI; TRNK; TRNL1; TRNQ; TSC1; TSC2; TTN; TTPA; TTR; TULP1; TWIST1; TXNDC3; TYR; USH1C; USH1H; USH2A; VCL; VHL; VPS13B; WAS; WRN; WT1; and ZNF9.

In some embodiments, the disclosure relates generally to a composition comprising a plurality of target-specific primers designed according to the criteria disclosed here or including any one or more of the target-specific primers disclosed herein, where at least one of the plurality of target-specific primers is substantially complementary across its entire length to at last a portion of one or more genes associated with breast cancer selected from AIM1, AR, ATM, BARD1, BCAS1, BRIP1, CCND1, CCND2, CCNE1, CDH1, CDK3, CDK4, CDKN2A, CDKN2B, CAMK1D, CHEK2, DIRAS3, EGFR, ERBB2, EPHA3, ERBB4, ETV6, GNRH1, KCTD9, CDCA2, EBF2, EMSY, BNIP3L, PNMA2, DPYSL2, ADRA1A, STMN4, TRIM35, PAK1, AQP11, CLSN1A, RSF1, KCTD14, THRSP, NDUFC2, ALG8, KCTD21, USP35, GAB2, DNAH9, ZNF18, MYOCD, STK11, TP53, JAK1, JAK2, MET, PDG-FRA, PML, PTEN, RET, TMPRSS2, WNK1, FGFR1, IGF1R, PPP1R12B, PTPRT, GSTM1, IP08, MYC, ZNF703, MDM1, MDM2, MDM4, MKK4, P14 KB, NCOR1, NBN, PALB2, RAD50, RAD51, PAK1, RSF1, INTS4, ZMIZ1, SEPHS1, FOXM1, SDCCAG1, IGF1R, TSHZ2, RPSK6K1, PPP2R2A, MTAP, MAP2K4, AURKB, BCL2, BUB1, CDCA3, CDCA4, CDC20, CDC45, CHEK1, FOXM1, HDAC2, IGF1R, KIF2C, KIFC1, KRAS, RB1, SMAD4, NCOR1, UTX, MTHDFD1L, RAD51AP1, TTK and UBE2C.

In some embodiments, the disclosure is generally related to a combination of polynucleotides, where the combination of polynucleotides includes at least one polynucleotide selected from Tables 2, 3, 13, 14, 15, 17 and 19 (from U.S. Ser. No. 13/458,739, filed Apr. 27, 2012, hereby incorporated by reference in its entirety), and one or more additional polynucleotides independent of the polynucleotides disclosed herein. In some embodiments, the disclosure is generally related to a combination of polynucleotides, where the combination of polynucleotides includes a polynucleotide having at least 90% identity to one or more polynucleotides selected from Tables 2, 3, 13, 14, 15, 17 and 19 (from U.S. Ser. No. 13/458,739, filed Apr. 27, 2012, hereby incorporated by reference in its entirety). In some embodiments, the disclosure relates to 2, 3, 4, 5, 6, 7, 8, 9, 10, 20, 30, 40, 50, 60, 70, 80, 90, 100, 200, 500, 1000, 2000, 3000, 4000, 5000, 6000, 7000, 8000, 9000, 10,000 or more polynucleotides selected from Tables 2, 3, 13, 14, 15, 17 and 19 from U.S. Ser. No. 13/458,739, filed Apr. 27, 2012, hereby incorporated by reference in its entirety.

In some embodiments, the disclosure is generally related to a combination of polynucleotides, where the combination of polynucleotides includes at least one polynucleotide selected from Tables 2, 3, 13, 14, 15, 17 and 19 (from U.S. Ser. No. 13/458,739, filed Apr. 27, 2012, hereby incorporated by reference in its entirety), and one or more additional polynucleotides independent of the polynucleotides disclosed herein. In some embodiments, the disclosure is generally related to a combination of polynucleotides, where the combination of polynucleotides includes at least one polynucleotide having at least 90% identity to one or more polynucleotides selected from Tables 2, 3, 13, 14, 15, 17 and 19 from U.S. Ser. No. 13/458,739, filed Apr. 27, 2012, hereby incorporated by reference in its entirety. In some embodiments, the disclosure relates to 2, 3, 4, 5, 6, 7, 8, 9, 10, 20, 30, 40, 50, 60, 70, 80, 90, 100, 200, 500, 1000, 2000, 3000, 4000, 5000, 6000, 7000, 8000, 9000, 10,000 or more polynucleotides selected from Tables 2, 3, 13, 14, 15, 17 and 19 (from U.S. Ser. No. 13/458,739, filed Apr. 27, 2012, hereby incorporated by reference in its entirety) or one or more polynucleotides having at least 90% identity thereto.

In some embodiments, the disclosure is generally related to a pair of polynucleotides that specifically anneal to a portion of at least one gene selected from EGFR, BRAF or KRAS. In one embodiment, a pair of polynucleotides that specifically anneal to a portion of the EGFR gene includes any one or more of the following Amplicon IDs: 229910389, 227801665, 229055506, 230397881, 230175199, 230195609, 228630698, 230632980, 227722022, 232978808, 231616816, 230481741, 231198336, 229919273, 227816834, 228030652, 230679876, 229747025, 228741519, 228636601, 230635054, 230738160, 232984355, 228941652, 230495367, 231212482, 229608278, 230461276, 228035285, 230683371, 230173849, 330137554, 228857751, 230742871, 232237229, 228956984, 228732632, 231222418, 231493149, 229630617, 229052979, 230392156, 230683680, 230187475, 228709018, 230628101, 227716821, 227830783, 232260099, 230075336, 231314233, and 231239581. In one embodiment, a pair of polynucleotides that specifically anneal to a portion of the BRAF gene includes any one or more of the following Amplicon IDs: 222636793, 223460541, 223967627, 326913823, 223739184, 223944056, 224404546, 222922922, 224119138, 223519358, 223465859, 223971374, 222680486, 223741661, 223950351, 224410546, 222935598, 224119999, 222629880, 223175118, 223719489, 225222024, 222684242, 223700378, 222258987, 222895407, 223103332, 222635553, 223177865, 223960162, 326889377, 223588249, 223708886, 222259284, 222903910, and 223104608. In one embodiment, a pair of polynucleotides that specifically anneal to a portion of the KRAS gene includes any one or more of the following Amplicon IDs: 233361228, 234355242, 234355242, 233466735, 233466735, 231132733, 231132733, 234764991, 234764991, 233467720, 233467720, 231133990, 231133990, 233356818, 326772204, and 326772204.

In some embodiments, the disclosure is generally related to kits (as well as related compositions, methods, apparatuses and systems using such kits) for amplifying one or more target sequences in a sample. In some embodiments, the kits for amplifying one or more target sequences in a sample include at least one target-specific primer that can amplify the at least one target sequence in the sample. In some embodiments, the kit can include at least two target-specific primers that can amplify at least one target sequence in the sample. In another embodiment, the kit can include a plurality of target-specific primers for amplifying at least two target sequences in a sample, where the kit includes a) a first target-specific primer having at least 90% identity to a nucleic acid sequence selected from SEQ ID NOs: 1-103, 143 being substantially complementary to the first target sequence in a sense direction; b) a second target-specific primer having at least 90% identity to a nucleic acid sequence selected from SEQ ID NOs: 1-103,143 being substantially complementary to the first target sequence in a antisense direction; c) a third target-specific primer having at least 90% identity to a nucleic acid sequence selected from SEQ ID NOs: 1-103,143 being substantially complementary to the second target sequence in a sense direction; and, d) a fourth target-specific primer having at least 90% identity to a nucleic acid sequence selected from SEQ ID NOs: 1-103, 143 being substantially complementary to the second target sequence in a antisense direction. In some embodiments, the sample can be an environmental, aquatic, microbiological, entomological, plant, fungi, animal or mammalian nucleic acid containing sample. In some embodiments, the sample can include a clinical, surgical, physician, forensic or laboratory obtained nucleic acid sample.

In some embodiments, the disclosure relates generally to a method for amplifying a plurality of target sequences in a sample comprising contacting at least some portion of the sample with at least one target-specific primer as disclosed herein, or designed using the primer selection criteria disclosed herein, and a polymerase under amplification conditions thereby producing at least one amplified target sequence. In some embodiments, the method further includes ligating at least one adapter to at least one amplified target sequence, thereby producing at least one adapter-ligated amplified target sequence. In some embodiments, the method includes any one or more of the target-specific primers provided in Tables 2, 3, 13, 14, 15, 17 and 19 (from U.S. Ser. No. 13/458,739, filed Apr. 27, 2012, hereby incorporated by reference in its entirety) or any nucleic acid sequence having at least 90% identity to any one or more of the target-specific primers provided in Tables 2, 3, 13, 14, 15, 17 and 19 (from U.S. Ser. No. 13/458,739, filed Apr. 27, 2012, hereby incorporated by reference in its entirety).

In some embodiments, the disclosure is generally related to an amplification product generated by amplifying at least one target sequence present in a sample with one or more target-specific primers disclosed herein or one or more target-specific primers designed using the primer selection criteria disclosed herein. In some embodiments, the disclosure is generally related to an amplification product generated by contacting at least one target sequence in a sample with one or more target-specific primers disclosed herein or one or more target-specific primers designed using the primer selection criteria disclosed herein under amplification conditions. In some embodiments, the amplification product can include one or more mutations associated with cancer or inherited disease. For example, a sample suspected of containing one or more mutations associated with at least one cancer can be subjected to any one of the amplification methods disclosed herein. The amplification products obtained from the selected amplification method can optionally be compared to a normal or matched sample known to be noncancerous with respect to the at least one cancer, and can therefore be used as a reference sample. In some embodiments, the amplification products obtained by the methods disclosed herein can be optionally sequenced using any suitable nucleic acid sequencing platform to determine the nucleic acid sequence of the amplification products, and optionally compared to sequencing information from the normal or non-cancerous sample. In some embodiments, amplification products can include one or more markers associated with antibiotic resistance, pathogenicity or genetic modification. In some embodiments, nucleic acid sequences of one or more amplification products obtained by contacting at least one target sequence with at least one target-specific primer under amplification conditions can be used to determine the presence or absence of a genetic variant within the one or more amplification products.

In some embodiments, the disclosure generally relates to compositions (as well as related kits, methods, systems and apparatuses using the disclosed compositions) for performing nucleic acid amplification and nucleic acid synthesis. In some embodiments, the composition includes a plurality of target-specific primer pairs, at least one target-specific primer pair including a target-specific forward primer and a target-specific reverse primer. In some embodiments, the composition includes at least 100, 200, 500, 750, 1000, 2500, 5000, 7500, 10000, 12000, 15000, 17500, 20000 or 50000 different primer pairs, some or all of which can be target-specific. Optionally at least two of the different target-specific primer pairs are directed to (i.e., are specific for) different target sequences.

In some embodiments, the composition includes at least one target-specific primer pair that can be specific for at least one amplified target sequence. In some embodiments, the composition includes a plurality of target-specific primer pairs, at least two target-specific primer pairs being specific for at different amplified target sequences. In some embodiments, the composition includes a target-specific primer pair, which each member of the primer pair includes a target-specific primer that can hybridize to at least a portion of a first amplified sequence or its complement, and that is substantially non-complementary to the 3' end or the 5' end of any other amplified sequence in the sample. In some embodiments, the composition includes at least one target-specific primer pair that can be substantially non-complementary to a portion of any other nucleic acid molecule in the sample. In some embodiments, the compositions include a plurality of target-specific primer pairs that include one or more cleavable groups at one or more locations within the target-specific primer pair.

In some embodiments, the composition includes one or more target-specific primer pairs that can amplify a short tandem repeat, single nucleotide polymorphism, gene, exon, coding region, exome, or portion thereof. For example, a plurality of target-specific primer pairs can uniformly amplify one gene, exon, coding region, exome or portion thereof. In some embodiments, the compositions include target-specific primer pairs designed to minimize overlap of nucleotide sequences amplified using the one or more target-specific primer pairs. In some embodiments, the nucleotide sequence overlap between one or more target-specific primers can be minimized at the 3' end, the 5' end, or both. In some embodiments, at least one primer in a plurality of target-specific primers includes less than 5 nucleotides of nucleotide sequence overlap at the 3' end, 5' end or both. In some embodiments, at least one target-specific primer of a plurality of target-specific primers includes a nucleotide sequence gap of at least one nucleotide, as compared to the plurality of target-specific primers. In some embodiments, the compositions include one or more target-specific primer pairs designed to comprehensively amplify one or more genes or exons. For example, a plurality of target-specific primer pairs can be designed to uniformly amplify (i.e., provide 100% representation of all nucleotides) in a single gene or exon.

In some embodiments, at least two pairs of target-specific primers are capable of hybridizing to locations on a template nucleic acid and serving as substrates for template-dependent primer extension by a polymerase. In some embodiments, the template-dependent primer extension can include amplification of the region of template located between the sites of hybridization of the primers of the at least two pairs of primers, resulting in formation of an amplified region or "amplicon". Typically, the sequence of the amplicon includes the sequence of the template located between the sites of hybridization of the primers, as well as at least part of the sequence of the primers themselves. In some embodiments, the amplification reaction can include at least about 5, 10, 25, 50, 100, 150, 200, 250, 400, 500, 750, 1000, 1200, 1250, 1500, 1750, 2000, 2250, 2500, 2750, 3000, 5000, 7500 or 10,000 different primer pairs. In some embodiments, the amplification reaction can result in the generation of at least about 5, 10, 25, 50, 100, 150, 200, 250, 400, 500, 750, 1000, 1200, 1250, 1500, 1750, 2000, 2250, 2500, 2750, 3000, 5000, 7500 or 10,000 different amplicons. In some embodiments, at least about 75%, 80%, 90%, 95%, 97% or 99% of the amplicons generated during the amplification reaction are similarly sized, for example, the amplicons differ in size from each other by no more than 5, 10, 25, 50, 75, 100, 500, 1000 or 2000 nucleotides. In some embodiments, the difference in length between any two amplicons is no greater than 1%, 5%, or 10% of average amplicon length in the amplification reaction mixture. Optionally, the average amplicon length is about 50, 60, 70, 80, 90, 100, 110, 120, 130, 140, 150, 200, 250, 500, 1000, 2000, 10,000 nucleotides or greater. In some embodiments, the standard deviation in length among amplicons in a mixture is no greater than 0.1, 0.25, 0.4, 0.5, 0.75, 1, 1.5, 2.0, 2.4 or 3.0.

In some embodiments, the compositions include target-specific primer pairs designed to generate amplified target sequences that overlap with an adjacent amplified target sequence by a single nucleotide. In some embodiments, the compositions include target-specific primer pairs designed to generate an amplified target sequence that does not overlap with an adjacent amplified target sequence. For example, target-specific primer pairs can be designed to generate amplified target sequences that are separated by one or more nucleotides. In some embodiments, the composition includes target-specific primer pairs designed to separate amplified target sequences by about 50 nucleotides.

In some embodiments, the composition includes a plurality of exon- or gene-specific, target-specific primer pairs that can be substantially complementary to an individual exon or gene. In some embodiments, the composition includes a plurality of exon- or gene-specific, target-specific primer pairs that can be substantially complementary to one or more exons or genes. In some embodiments, the composition includes a plurality of substantially complementary exon- or gene-specific, target-specific primer pairs and that no two primer pairs amplify greater than 10% of the same target sequence. In some embodiments, no two target-specific primer pairs amplify the same exon or gene. In some embodiments, the target-specific primer pairs amplify about 100 to about 600 nucleotides of a target sequence. In some embodiments, the target-specific primer pairs can be used to amplify about 25% to 100% of an exon, gene or coding region. In some embodiments, the compositions includes a plurality of target-specific primer pairs to generate a plurality of amplified target sequences and that no individual amplified target sequence is overexpressed by more than 50% as compared to the other amplified target sequences. In some embodiments, the compositions includes a plurality of target-specific primer pairs designed to generate a plurality of amplified target sequences that are substantially homogenous (i.e., homogenous with respect to GC content, melting temperature, or amplified target sequence length). In some embodiments, the plurality of target-specific primer pairs overlap in sequence by no more than five nucleotides.

In some embodiments, the disclosure generally relates to a method for preventing or eliminating non-specific amplification products in a multiplex PCR reaction. In some embodiments, the method includes (as well as related compositions, kits, systems and apparatuses used using the disclosed methods) hybridizing one or more target-specific primer pairs to a target sequence in a sample having a plurality of target sequences, extending the hybridized target-specific primers to form a plurality of amplified target sequences, denaturing and annealing the amplified target sequences to form a plurality of double-stranded amplified target sequences and performing a digesting step on the sample containing the double-stranded amplified target sequences to eliminate non-specific amplification products. In some embodiments, the method includes one or more cleavable groups at one or more locations in one or more target-specific primer pairs. In some embodiments, each target-specific primer pair includes at least one cleavable group. In some embodiments, each target-specific primer of the primer pairs includes a cleavable group. In some embodiments, the digestion is an enzymatic or chemical digestion. In some embodiments, the digestion step includes partial digestion of a target-specific primer of an amplified target sequence. In some embodiments, the method includes a thermostable polymerase. In some embodiments, the thermostable polymerase can be optionally reactivated by heat or chemical treatment.

In some embodiments, the composition includes a plurality of target-specific primer pairs directed to one or more diseases or disorders. In some embodiments, a target-specific primer pair can be substantially complementary to a target sequence correlated or associated with one or more cancers. In some embodiments, a target-specific primer pair can be substantially complementary to a target sequence correlated with or associated with one or more congenital or inherited disorders. In some embodiments, one or more target-specific primer pairs can be associated with one or more neurological, metabolic, neuromuscular, developmental, cardiovascular or autoimmune disorders. In some embodiments, one or more target-specific primer pairs can be associated with one or more genes or exons associated with one or more neurological, metabolic, neuromuscular, developmental, cardiovascular or autoimmune disorders. In some embodiments, the plurality of target-specific primers can include a gene or gene fragment associated with neoplastic development in mammals.

In some embodiments, the disclosure relates generally to compositions (as well as related kits, methods, systems and apparatuses using the disclosed compositions) comprising any, some or all of the primers disclosed herein, including in the Examples and in the related appendices, supplements and sequence listings attached hereto and including all the tables in U.S. Ser. No. 13/458,739, filed Apr. 27, 2012, hereby incorporated by reference in its entirety. In some embodiments, the disclosure relates generally to compositions (as well as related kits, methods, systems and apparatuses using the disclosed compositions) comprising any of the primer pools used in the Examples, or any subset thereof. For example, in some embodiments the disclosure relates generally to compositions including one or more target-specific primers selected from the primers listed in Tables 2, 3, 13, 14, 15, 17 and 19 (from U.S. Ser. No. 13/458,739, filed Apr. 27, 2012, hereby incorporated by reference in its entirety), which include sets of primers designed and selected using the design methods and selection criteria of the disclosure, and which have been used to perform highly multiplex amplification according to the methods disclosed herein. It will be readily appreciated by one of ordinary skill in the art that any subsets of each of the primer sets set forth in Tables 2, 3, 13, 14, 15, 17 and 19 (from U.S. Ser. No. 13/458,739, filed Apr. 27, 2012, hereby incorporated by reference in its entirety) can also be expected to support multiplex amplification, since the entire set of primers of each table (e.g., tables found in U.S. Ser. No. 13/458,739, filed Apr. 27, 2012, hereby incorporated by reference in its entirety) has been demonstrated to support such multiplex amplification and removal of particular primer pairs from the pool will not be expected to significantly alter the performance of the remaining primers for purposes of multiplex amplification. In some embodiments, the disclosure relates generally to compositions including any 1, 2, 5, 10, 25, 50, 100, 250, 500, 750, 1000, 2500, 5000, 7500, 10000, 12500, 50000, 100000 or more different target-specific primer pairs set forth in Tables 2, 3, 13, 14, 15, 17 and 19 (from U.S. Ser. No. 13/458,739, filed Apr. 27, 2012, hereby incorporated by reference in its entirety). In some embodiments, the disclosure relates to a composition including at least 1, 2, 5, 10, 25, 50, 100, 250, 500, 750, 1000, 2500, 5000, 7500, 10000, 12500, 50000, 100000 or more primers selected from Tables 2, 3, 13, 14, 15, 17 and 19 (from U.S. Ser. No. 13/458,739, filed Apr. 27, 2012, hereby incorporated by reference in its entirety), or their complements. In some embodiments, the disclosure relates to a composition including at least 1, 2, 5, 10, 25, 50, 100, 250, 500, 750, 1000, 2500, 5000, 7500, 10000, 12500, 50000, 100000 or more primers that are at least 85% identical or complementary to any primer of Tables 2, 3, 13, 14, 15, 17 and 19 (from U.S. Ser. No. 13/458,739, filed Apr. 27, 2012, hereby incorporated by reference in its entirety). In some embodiments, the composition includes at least one 1, 2, 5, 10, 25, 50, 100, 250, 500, 750, 1000, 2500, 5000, 7500, 10000, 12500, 50000, 100000 or more primers selected from Tables 2, 3, 13, 14, 15, 17 and 19 (from U.S. Ser. No. 13/458,739, filed Apr. 27, 2012, hereby incorporated by reference in its entirety), or their complements, wherein at least one primer includes at least one nucleotide substitution. A nucleotide substitution includes replacement of any nucleotide residue or nucleobase of any primer with any other nucleotide or nucleobase, and can include, for example, purine to purine substitutions, pyrimidine to pyrimidine substitutions, purine to pyrimidine substitutions, and pyrimidine to purine substitutions. In some embodiments, the at least one primer of the composition can include any one, two, three, four or more nucleotide substitutions. In some embodiments, the at least one primer of the composition includes at least one primer in which any one, some or all of the uracil-containing nucleotide residues or nucleobases of the primer are replaced with a thymine-containing nucleotide residue or nucleobase. In some embodiments, the at least one primer of the composition includes at least one primer in which any one, two, three, four, five or more uracil-containing nucleotide residues or nucleobases of the primer are replaced with a thymine-containing nucleotide residue or nucleobase.

In some embodiments, a target-specific primer pair can include a nucleic acid sequence including a somatic or germline mutation. In some embodiments, the germline or somatic mutation can be found in any one or more of the genes provided in Tables 1, 4, 16 or 18 (from U.S. Ser. No. 13/458,739, filed Apr. 27, 2012, hereby incorporated by reference in its entirety). In some embodiments, the target-specific primer pairs can be used to amplify a target sequence that can be used to detect the presence of mutations at less than 5% allele frequency. In some embodiments, the plurality of target-specific primers includes at least 500, at least 1000, at least 3000, at least 6000, at least 10000, at least 12000, or more target-specific primer pairs.

In some embodiments, the disclosure relates generally to a kit for performing multiplex nucleic acid amplification or multiplex nucleic acid synthesis. In some embodiments, the kit comprises a plurality of target-specific primers. In some embodiments, the kit can further include a polymerase, at least one adapter and/or a cleaving reagent. In some embodiments, the kit can also include dATP, dCTP, dGTP, dTTP and/or an antibody. In some embodiments, the cleaving reagent is any reagent that can cleave one or more cleaving groups present in one or more target-specific primers. In some embodiments the cleaving reagent can include an enzyme or chemical reagent. In some embodiments, the cleaving reagent can include an enzyme with an affinity for apurinic bases. In some embodiments, the cleaving reagent can include a first enzyme with an affinity for a first cleavable group and can further include a second enzyme with an affinity for a second cleavable group. In some embodiments, the kit can further include an enzyme with an affinity for abasic sites. In some embodiments, the polymerase is a thermostable polymerase. In some embodiments, the kits can include one or more preservatives, adjuvants or nucleic acid sequencing barcodes.

In some embodiments, the disclosure relates generally to methods (as well as related compositions, systems, kits and apparatuses) for determining copy number variation comprising performing any of the amplification methods disclosed herein.

DETAILED DESCRIPTION

The following description of various exemplary embodiments is exemplary and explanatory only and is not to be construed as limiting or restrictive in any way. Other embodiments, features, objects, and advantages of the present teachings will be apparent from the description and accompanying drawings, and from the claims.

As used herein, "amplify" "amplifying" or "amplification reaction" and their derivatives, refer generally to any action or process whereby at least a portion of a nucleic acid molecule (referred to as a template nucleic acid molecule) is replicated or copied into at least one additional nucleic acid molecule. The additional nucleic acid molecule optionally includes sequence that is substantially identical or substantially complementary to at least some portion of the template nucleic acid molecule. The template nucleic acid molecule can be single-stranded or double-stranded and the additional nucleic acid molecule can independently be single-stranded or double-stranded. In some embodiments, amplification includes a template-dependent in vitro enzyme-catalyzed reaction for the production of at least one copy of at least some portion of the nucleic acid molecule or the production of at least one copy of a nucleic acid sequence that is complementary to at least some portion of the nucleic acid molecule. Amplification optionally includes linear or exponential replication of a nucleic acid molecule. In some embodiments, such amplification is performed using isothermal conditions; in other embodiments, such amplification can include thermocycling. In some embodiments, the amplification is a multiplex amplification that includes the simultaneous amplification of a plurality of target sequences in a single amplification reaction. At least some of the target sequences can be situated on the same nucleic acid molecule or on different target nucleic acid molecules included in the single amplification reaction. In some embodiments, "amplification" includes amplification of at least some portion of DNA- and RNA-based nucleic acids alone, or in combination. The amplification reaction can include single or double-stranded nucleic acid substrates and can further including any of the amplification processes known to one of ordinary skill in the art. In some embodiments, the amplification reaction includes polymerase chain reaction (PCR).

As used herein, "amplification conditions" and its derivatives, generally refers to conditions suitable for amplifying one or more nucleic acid sequences. Such amplification can be linear or exponential. In some embodiments, the amplification conditions can include isothermal conditions or alternatively can include thermocyling conditions, or a combination of isothermal and themocycling conditions. In some embodiments, the conditions suitable for amplifying one or more nucleic acid sequences includes polymerase chain reaction (PCR) conditions. Typically, the amplification conditions refer to a reaction mixture that is sufficient to amplify nucleic acids such as one or more target sequences, or to amplify an amplified target sequence ligated to one or more adapters, e.g., an adapter-ligated amplified target sequence. Generally, the amplification conditions include a catalyst for amplification or for nucleic acid synthesis, for example a polymerase; a primer that possesses some degree of complementarity to the nucleic acid to be amplified; and nucleotides, such as deoxyribonucleotide triphosphates (dNTPs) to promote extension of the primer once hybridized to the nucleic acid. The amplification conditions can require hybridization or annealing of a primer to a nucleic acid, extension of the primer and a denaturing step in which the extended primer is separated from the nucleic acid sequence undergoing amplification. Typically, but not necessarily, amplification conditions can include thermocycling; in some embodiments, amplification conditions include a plurality of cycles where the steps of annealing, extending and separating are repeated. Typically, the amplification conditions include cations such as $Mg^{++}$ or $Mn^{++}$ (e.g., $MgCl_2$, etc) and can also include various modifiers of ionic strength.

As used herein, "target sequence" or "target sequence of interest" and its derivatives, refers generally to any single or double-stranded nucleic acid sequence that can be amplified or synthesized according to the disclosure, including any nucleic acid sequence suspected or expected to be present in a sample. In some embodiments, the target sequence is present in double-stranded form and includes at least a portion of the particular nucleotide sequence to be amplified or synthesized, or its complement, prior to the addition of target-specific primers or appended adapters. Target sequences can include the nucleic acids to which primers useful in the amplification or synthesis reaction can hybridize prior to extension by a polymerase. In some embodiments, the term refers to a nucleic acid sequence whose sequence identity, ordering or location of nucleotides is determined by one or more of the methods of the disclosure.

As defined herein, "sample" and its derivatives, is used in its broadest sense and includes any specimen, culture and the like that is suspected of including a target. In some embodiments, the sample comprises DNA, RNA, PNA, LNA, chimeric, hybrid, or multiplex-forms of nucleic acids. The sample can include any biological, clinical, surgical, agricultural, atmospheric or aquatic-based specimen containing one or more nucleic acids. The term also includes any isolated nucleic acid sample such a genomic DNA, fresh-frozen or formalin-fixed paraffin-embedded nucleic acid specimen.

As used herein, "contacting" and its derivatives, when used in reference to two or more components, refers generally to any process whereby the approach, proximity, mixture or commingling of the referenced components is promoted or achieved without necessarily requiring physical contact of such components, and includes mixing of solutions containing any one or more of the referenced components with each other. The referenced components may be contacted in any particular order or combination and the particular order of recitation of components is not limiting. For example, "contacting A with B and C" encompasses embodiments where A is first contacted with B then C, as well as embodiments where C is contacted with A then B, as well as embodiments where a mixture of A and C is contacted with B, and the like. Furthermore, such contacting does not necessarily require that the end result of the contacting process be a mixture including all of the referenced components, as long as at some point during the contacting process all of the referenced components are simultaneously present or simultaneously included in the same mixture or solution. For example, "contacting A with B and C" can include embodiments wherein C is first contacted with A to form a first mixture, which first mixture is then contacted with B to form a second mixture, following which C is removed from the second mixture; optionally A can then also be removed, leaving only B. Where one or more of the referenced components to be contacted includes a plurality (e.g, "contacting a target sequence with a plurality of target-specific primers and a polymerase"), then each member of the plurality can be viewed as an individual component of the contacting process, such that the contacting can include contacting of any one or more members of the plurality with any other member of the plurality and/or with any other referenced component (e.g., some but not all of the plurality of target specific primers can be contacted with a target sequence, then a polymerase, and then with other members of the plurality of target-specific primers) in any order or combination.

As used herein, the term "primer" and its derivatives refer generally to any polynucleotide that can hybridize to a target sequence of interest. In some embodiments, the primer can also serve to prime nucleic acid synthesis. Typically, the primer functions as a substrate onto which nucleotides can be polymerized by a polymerase; in some embodiments, however, the primer can become incorporated into the synthesized nucleic acid strand and provide a site to which another primer can hybridize to prime synthesis of a new strand that is complementary to the synthesized nucleic acid molecule. The primer may be comprised of any combination of nucleotides or analogs thereof, which may be optionally linked to form a linear polymer of any suitable length. In some embodiments, the primer is a single-stranded oligonucleotide or polynucleotide. (For purposes of this disclosure, the terms 'polynucleotide" and "oligonucleotide" are used interchangeably herein and do not necessarily indicate any difference in length between the two). In some embodiments, the primer is single-stranded but it can also be double-stranded. The primer optionally occurs naturally, as in a purified restriction digest, or can be produced synthetically. In some embodiments, the primer acts as a point of initiation for amplification or synthesis when exposed to amplification or synthesis conditions; such amplification or synthesis can occur in a template-dependent fashion and optionally results in formation of a primer extension product that is complementary to at least a portion of the target sequence. Exemplary amplification or synthesis conditions can include contacting the primer with a polynucleotide template (e.g., a template including a target sequence), nucleotides and an inducing agent such as a polymerase at a suitable temperature and pH to induce polymerization of nucleotides onto an end of the target-specific primer. If double-stranded, the primer can optionally be treated to separate its strands before being used to prepare primer extension products. In some embodiments, the primer is an oligodeoxyribonucleotide or an oligoribonucleotide. In some embodiments, the primer can include one or more nucleotide analogs. The exact length and/or composition, including sequence, of the target-specific primer can influence many properties, including melting temperature (Tm), GC content, formation of secondary structures, repeat nucleotide motifs, length of predicted primer extension products, extent of coverage across a nucleic acid molecule of interest, number of primers present in a single amplification or synthesis reaction, presence of nucleotide analogs or modified nucleotides within the primers, and the like. In some embodiments, a primer can be paired with a compatible primer within an amplification or synthesis reaction to form a primer pair consisting or a forward primer and a reverse primer. In some embodiments, the forward primer of the primer pair includes a sequence that is substantially complementary to at least a portion of a strand of a nucleic acid molecule, and the reverse primer of the primer of the primer pair includes a sequence that is substantially identical to at least of portion of the strand. In some embodiments, the forward primer and the reverse primer are capable of hybridizing to opposite strands of a nucleic acid duplex. Optionally, the forward primer primes synthesis of a first nucleic acid strand, and the reverse primer primes synthesis of a second nucleic acid strand, wherein the first and second strands are substantially complementary to each other, or can hybridize to form a double-stranded nucleic acid molecule. In some embodiments, one end of an amplification or synthesis product is defined by the forward primer and the other end of the amplification or synthesis product is defined by the reverse primer. In some embodiments, where the amplification or synthesis of lengthy primer extension products is required, such as amplifying an exon, coding region, or gene, several primer pairs can be created than span the desired length to enable sufficient amplification of the region. In some embodiments, a primer can include one or more cleavable groups. In some embodiments, primer lengths are in the range of about 10 to about 60 nucleotides, about 12 to about 50 nucleotides and about 15 to about 40 nucleotides in length. Typically, a primer is capable of hybridizing to a corresponding target sequence and undergoing primer extension when exposed to amplification conditions in the presence of dNTPS and a polymerase. In some instances, the particular nucleotide sequence or a portion of the primer is known at the outset of the amplification reaction or can be determined by one or more of the methods disclosed herein. In some embodiments, the primer includes one or more cleavable groups at one or more locations within the primer.

As used herein, "target-specific primer" and its derivatives, refers generally to a single stranded or double-stranded polynucleotide, typically an oligonucleotide, that includes at least one sequence that is at least 50% complementary, typically at least 75% complementary or at least 85% complementary, more typically at least 90% complementary, more typically at least 95% complementary, more typically at least 98% or at least 99% complementary, or identical, to at least a portion of a nucleic acid molecule that includes a target sequence. In such instances, the target-specific primer and target sequence are described as "corresponding" to each other. In some embodiments, the target-specific primer is capable of hybridizing to at least a portion of its corresponding target sequence (or to a complement of the target sequence); such hybridization can optionally be performed under standard hybridization conditions or under stringent hybridization conditions. In some embodiments, the target-specific primer is not capable of hybridizing to the target sequence, or to its complement, but is capable of hybridizing to a portion of a nucleic acid strand including the target sequence, or to its complement. In some embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the target sequence itself; in other embodiments, the target-specific primer includes at least one sequence that is at least 75% complementary, typically at least 85% complementary, more typically at least 90% complementary, more typically at least 95% complementary, more typically at least 98% complementary, or more typically at least 99% complementary, to at least a portion of the nucleic acid molecule other than the target sequence. In some embodiments, the target-specific primer is substantially non-complementary to other target sequences present in the sample; optionally, the target-specific primer is substantially non-complementary to other nucleic acid molecules present in the sample. In some embodiments, nucleic acid molecules present in the sample that do not include or correspond to a target sequence (or to a complement of the target sequence) are referred to as "non-specific" sequences or "non-specific nucleic acids". In some embodiments, the target-specific primer is designed to include a nucleotide sequence that is substantially complementary to at least a portion of its corresponding target sequence. In some embodiments, a target-specific primer is at least 95% complementary, or at least 99% complementary, or identical, across its entire length to at least a portion of a nucleic acid molecule that includes its corresponding target sequence. In some embodiments, a target-specific primer can be at least 90%, at least 95% complementary, at least 98% complementary or at least 99% complementary, or identical, across its entire length to at least a portion of its corresponding target sequence. In some embodiments, a forward target-specific primer and a reverse target-specific primer define a target-specific primer pair that can be used to amplify the target sequence via template-dependent primer extension. Typically, each primer of a target-specific primer pair includes at least one sequence that is substantially complementary to at least a portion of a nucleic acid molecule including a corresponding target sequence but that is less than 50% complementary to at least one other target sequence in the sample. In some embodiments, amplification can be performed using multiple target-specific primer pairs in a single amplification reaction, wherein each primer pair includes a forward target-specific primer and a reverse target-specific primer, each including at least one sequence that substantially complementary or substantially identical to a corresponding target sequence in the sample, and each primer pair having a different corresponding target sequence. In some embodiments, the target-specific primer can be substantially non-complementary at its 3' end or its 5' end to any other target-specific primer present in an amplification reaction. In some embodiments, the target-specific primer can include minimal cross hybridization to other target-specific primers in the amplification reaction. In some embodiments, target-specific primers include minimal cross-hybridization to non-specific sequences in the amplification reaction mixture. In some embodiments, the target-specific primers include minimal self-complementarity. In some embodiments, the target-specific primers can include one or more cleavable groups located at the 3' end. In some embodiments, the target-specific primers can include one or more cleavable groups located near or about a central nucleotide of the target-specific primer. In some embodiments, one of more targets-specific primers includes only non-cleavable nucleotides at the 5' end of the target-specific primer. In some embodiments, a target specific primer includes minimal nucleotide sequence overlap at the 3'end or the 5' end of the primer as compared to one or more different target-specific primers, optionally in the same amplification reaction. In some embodiments 1, 2, 3, 4, 5, 6, 7, 8, 9, 10 or more, target-specific primers in a single reaction mixture include one or more of the above embodiments. In some embodiments, substantially all of the plurality of target-specific primers in a single reaction mixture includes one or more of the above embodiments.

As used herein, "polymerase" and its derivatives, generally refers to any enzyme that can catalyze the polymerization of nucleotides (including analogs thereof) into a nucleic acid strand. Typically but not necessarily, such nucleotide polymerization can occur in a template-dependent fashion. Such polymerases can include without limitation naturally occurring polymerases and any subunits and truncations thereof, mutant polymerases, variant polymerases, recombinant, fusion or otherwise engineered polymerases, chemically modified polymerases, synthetic molecules or assemblies, and any analogs, derivatives or fragments thereof that retain the ability to catalyze such polymerization. Optionally, the polymerase can be a mutant polymerase comprising one or more mutations involving the replacement of one or more amino acids with other amino acids, the insertion or deletion of one or more amino acids from the polymerase, or the linkage of parts of two or more polymerases. Typically, the polymerase comprises one or more active sites at which nucleotide binding and/or catalysis of nucleotide polymerization can occur. Some exemplary polymerases include without limitation DNA polymerases and RNA polymerases. The term "polymerase" and its variants, as used herein, also refers to fusion proteins comprising at least two portions linked to each other, where the first portion comprises a peptide that can catalyze the polymerization of nucleotides into a nucleic acid strand and is linked to a second portion that comprises a second polypeptide. In some embodiments, the second polypeptide can include a reporter enzyme or a processivity-enhancing domain. Optionally, the polymerase can possess 5' exonuclease activity or terminal transferase activity. In some embodiments, the polymerase can be optionally reactivated, for example through the use of heat, chemicals or re-addition of new amounts of polymerase into a reaction mixture. In some embodiments, the polymerase can include a hot-start polymerase or an aptamer based polymerase that optionally can be reactivated.

As used herein, the term "nucleotide" and its variants comprises any compound, including without limitation any naturally occurring nucleotide or analog thereof, which can bind selectively to, or can be polymerized by, a polymerase. Typically, but not necessarily, selective binding of the nucleotide to the polymerase is followed by polymerization of the nucleotide into a nucleic acid strand by the polymerase; occasionally however the nucleotide may dissociate from the polymerase without becoming incorporated into the nucleic acid strand, an event referred to herein as a "non-productive" event. Such nucleotides include not only naturally occurring nucleotides but also any analogs, regardless of their structure, that can bind selectively to, or can be polymerized by, a polymerase. While naturally occurring nucleotides typically comprise base, sugar and phosphate moieties, the nucleotides of the present disclosure can include compounds lacking any one, some or all of such moieties. In some embodiments, the nucleotide can optionally include a chain of phosphorus atoms comprising three, four, five, six, seven, eight, nine, ten or more phosphorus atoms. In some embodiments, the phosphorus chain can be attached to any carbon of a sugar ring, such as the 5' carbon. The phosphorus chain can be linked to the sugar with an intervening O or S. In one embodiment, one or more phosphorus atoms in the chain can be part of a phosphate group having P and O. In another embodiment, the phosphorus atoms in the chain can be linked together with intervening O, NH, S, methylene, substituted methylene, ethylene, substituted ethylene, $CNH_2$, $C(O)$, $C(CH_2)$, $CH_2CH_2$, or $C(OH)CH_2R$ (where R can be a 4-pyridine or 1-imidazole). In one embodiment, the phosphorus atoms in the chain can have side groups having O, $BH_3$, or S. In the phosphorus chain, a phosphorus atom with a side group other than O can be a substituted phosphate group. In the phosphorus chain, phosphorus atoms with an intervening atom other than O can be a substituted phosphate group. Some examples of nucleotide analogs are described in Xu, U.S. Pat. No. 7,405,281. In some embodiments, the nucleotide comprises a label and referred to herein as a "labeled nucleotide"; the label of the labeled nucleotide is referred to herein as a "nucleotide label". In some embodiments, the label can be in the form of a fluorescent dye attached to the terminal phosphate group, i.e., the phosphate group most distal from the sugar. Some examples of nucleotides that can be used in the disclosed methods and compositions include, but are not limited to, ribonucleotides, deoxyribonucleotides, modified ribonucleotides, modified deoxyribonucleotides, ribonucleotide polyphosphates, deoxyribonucleotide polyphosphates, modified ribonucleotide polyphosphates, modified deoxyribonucleotide polyphosphates, peptide nucleotides, modified peptide nucleotides, metallonucleosides, phosphonate nucleosides, and modified phosphate-sugar backbone nucleotides, analogs, derivatives, or variants of the foregoing compounds, and the like. In some embodiments, the nucleotide can comprise non-oxygen moieties such as, for example, thio- or borano-moieties, in place of the oxygen moiety bridging the alpha phosphate and the sugar of the nucleotide, or the alpha and beta phosphates of the nucleotide, or the beta and gamma phosphates of the nucleotide, or between any other two phosphates of the nucleotide, or any combination thereof. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group can include sulfur substitutions for the various oxygens, e.g. .alpha.-thio-nucleotide 5'-triphosphates. For a review of nucleic acid chemistry, see: Shabarova, Z. and Bogdanov, A. Advanced Organic Chemistry of Nucleic Acids, VCH, New York, 1994.

The term "extension" and its variants, as used herein, when used in reference to a given primer, comprises any in vivo or in vitro enzymatic activity characteristic of a given polymerase that relates to polymerization of one or more nucleotides onto an end of an existing nucleic acid molecule. Typically but not necessarily such primer extension occurs in a template-dependent fashion; during template-dependent extension, the order and selection of bases is driven by established base pairing rules, which can include Watson-Crick type base pairing rules or alternatively (and especially in the case of extension reactions involving nucleotide analogs) by some other type of base pairing paradigm. In one non-limiting example, extension occurs via polymerization of nucleotides on the 3' OH end of the nucleic acid molecule by the polymerase.

The term "portion" and its variants, as used herein, when used in reference to a given nucleic acid molecule, for example a primer or a template nucleic acid molecule, comprises any number of contiguous nucleotides within the length of the nucleic acid molecule, including the partial or entire length of the nucleic acid molecule.

The terms "identity" and "identical" and their variants, as used herein, when used in reference to two or more nucleic acid sequences, refer to similarity in sequence of the two or more sequences (e.g., nucleotide or polypeptide sequences). In the context of two or more homologous sequences, the percent identity or homology of the sequences or subsequences thereof indicates the percentage of all monomeric units (e.g., nucleotides or amino acids) that are the same (i.e., about 70% identity, preferably 75%, 80%, 85%, 90%, 95%, 98% or 99% identity). The percent identity can be over a specified region, when compared and aligned for maximum correspondence over a comparison window, or designated region as measured using a BLAST or BLAST 2.0 sequence comparison algorithms with default parameters described below, or by manual alignment and visual inspection. Sequences are said to be "substantially identical" when there is at least 85% identity at the amino acid level or at the nucleotide level. Preferably, the identity exists over a region that is at least about 25, 50, or 100 residues in length, or across the entire length of at least one compared sequence. A typical algorithm for determining percent sequence identity and sequence similarity are the BLAST and BLAST 2.0 algorithms, which are described in Altschul et al, Nuc. Acids Res. 25:3389-3402 (1977). Other methods include the algorithms of Smith & Waterman, Adv. Appl. Math. 2:482 (1981), and Needleman & Wunsch, J. Mol. Biol. 48:443 (1970), etc. Another indication that two nucleic acid sequences are substantially identical is that the two molecules or their complements hybridize to each other under stringent hybridization conditions.

The terms "complementary" and "complement" and their variants, as used herein, refer to any two or more nucleic acid sequences (e.g., portions or entireties of template nucleic acid molecules, target sequences and/or primers) that can undergo cumulative base pairing at two or more individual corresponding positions in antiparallel orientation, as in a hybridized duplex. Such base pairing can proceed according to any set of established rules, for example according to Watson-Crick base pairing rules or according to some other base pairing paradigm. Optionally there can be "complete" or "total" complementarity between a first and second nucleic acid sequence where each nucleotide in the first nucleic acid sequence can undergo a stabilizing base pairing interaction with a nucleotide in the corresponding antiparallel position on the second nucleic acid sequence. "Partial" complementarity describes nucleic acid sequences in which at least 20%, but less than 100%, of the residues of one nucleic acid sequence are complementary to residues in the other nucleic acid sequence. In some embodiments, at least 50%, but less than 100%, of the residues of one nucleic acid sequence are complementary to residues in the other nucleic acid sequence. In some embodiments, at least 70%, 80%, 90%, 95% or 98%, but less than 100%, of the residues of one nucleic acid sequence are complementary to residues in the other nucleic acid sequence. Sequences are said to be "substantially complementary" when at least 85% of the residues of one nucleic acid sequence are complementary to residues in the other nucleic acid sequence. In some embodiments, two complementary or substantially complementary sequences are capable of hybridizing to each other under standard or stringent hybridization conditions. "Non-complementary" describes nucleic acid sequences in which less than 20% of the residues of one nucleic acid sequence are complementary to residues in the other nucleic acid sequence. Sequences are said to be "substantially non-complementary" when less than 15% of the residues of one nucleic acid sequence are complementary to residues in the other nucleic acid sequence. In some embodiments, two non-complementary or substantially non-complementary sequences cannot hybridize to each other under standard or stringent hybridization conditions. A "mismatch" is present at any position in the two opposed nucleotides are not complementary. Complementary nucleotides include nucleotides that are efficiently incorporated by DNA polymerases opposite each other during DNA replication under physiological conditions. In a typical embodiment, complementary nucleotides can form base pairs with each other, such as the A-T/U and G-C base pairs formed through specific Watson-Crick type hydrogen bonding, or base pairs formed through some other type of base pairing paradigm, between the nucleobases of nucleotides and/or polynucleotides in positions antiparallel to each other. The complementarity of other artificial base pairs can be based on other types of hydrogen bonding and/or hydrophobicity of bases and/or shape complementarity between bases.

As used herein, "amplified target sequences" and its derivatives, refers generally to a nucleic acid sequence produced by the amplification of/amplifying the target sequences using target-specific primers and the methods provided herein. The amplified target sequences may be either of the same sense (the positive strand produced in the second round and subsequent even-numbered rounds of amplification) or antisense (i.e., the negative strand produced during the first and subsequent odd-numbered rounds of amplification) with respect to the target sequences. For the purposes of this disclosure. Ihe amplified target sequences are typically less than 50% complementary to any portion of another amplified target sequence in the reaction.

As used herein, the terms "ligating", "ligation" and their derivatives refer generally to the act or process for covalently linking two or more molecules together, for example, covalently linking two or more nucleic acid molecules to each other. In some embodiments, ligation includes joining nicks between adjacent nucleotides of nucleic acids. In some embodiments, ligation includes forming a covalent bond between an end of a first and an end of a second nucleic acid molecule. In some embodiments, for example embodiments wherein the nucleic acid molecules to be ligated include conventional nucleotide residues, the litgation can include forming a covalent bond between a 5' phosphate group of one nucleic acid and a 3' hydroxyl group of a second nucleic acid thereby forming a ligated nucleic acid molecule. In some embodiments, any means for joining nicks or bonding a 5'phosphate to a 3' hydroxyl between adjacent nucleotides can be employed. In an exemplary embodiment, an enzyme such as a ligase can be used. Generally for the purposes of this disclosure, an amplified target sequence can be ligated to an adapter to generate an adapter-ligated amplified target sequence.

As used herein, "ligase" and its derivatives, refers generally to any agent capable of catalyzing the ligation of two substrate molecules. In some embodiments, the ligase includes an enzyme capable of catalyzing the joining of nicks between adjacent nucleotides of a nucleic acid. In some embodiments, the ligase includes an enzyme capable of catalyzing the formation of a covalent bond between a 5' phosphate of one nucleic acid molecule to a 3' hydroxyl of another nucleic acid molecule thereby forming a ligated nucleic acid molecule. Suitable ligases may include, but not limited to, T4 DNA ligase, T4 RNA ligase, and *E. coli* DNA ligase.

As used herein, "ligation conditions" and its derivatives, generally refers to conditions suitable for ligating two molecules to each other. In some embodiments, the ligation conditions are suitable for sealing nicks or gaps between nucleic acids. As defined herein, a "nick" or "gap" refers to a nucleic acid molecule that lacks a directly bound 5' phosphate of a mononucleotide pentose ring to a 3' hydroxyl of a neighboring mononucleotide pentose ring within internal nucleotides of a nucleic acid sequence. As used herein, the term nick or gap is consistent with the use of the term in the art. Typically, a nick or gap can be ligated in the presence of an enzyme, such as ligase at an appropriate temperature and pH. In some embodiments, T4 DNA ligase can join a nick between nucleic acids at a temperature of about 70-72° C.

As used herein, "blunt-end ligation" and its derivatives, refers generally to ligation of two blunt-end double-stranded nucleic acid molecules to each other. A "blunt end" refers to an end of a double-stranded nucleic acid molecule wherein substantially all of the nucleotides in the end of one strand of the nucleic acid molecule are base paired with opposing nucleotides in the other strand of the same nucleic acid molecule. A nucleic acid molecule is not blunt ended if it has an end that includes a single-stranded portion greater than two nucleotides in length, referred to herein as an "overhang". In some embodiments, the end of nucleic acid molecule does not include any single stranded portion, such that every nucleotide in one strand of the end is based paired with opposing nucleotides in the other strand of the same nucleic acid molecule. In some embodiments, the ends of the two blunt ended nucleic acid molecules that become ligated to each other do not include any overlapping, shared or complementary sequence. Typically, blunted-end ligation excludes the use of additional oligonucleotide adapters to assist in the ligation of the double-stranded amplified target sequence to the double-stranded adapter, such as patch oligonucleotides as described in Mitra and Varley, US2010/0129874, published May 27, 2010. In some embodiments, blunt-ended ligation includes a nick translation reaction to seal a nick created during the ligation process.

As used herein, the terms "adapter" or "adapter and its complements" and their derivatives, refers generally to any linear oligonucleotide which can be ligated to a nucleic acid molecule of the disclosure. Optionally, the adapter includes a nucleic acid sequence that is not substantially complementary to the 3' end or the 5' end of at least one target sequences within the sample. In some embodiments, the adapter is substantially non-complementary to the 3' end or the 5' end of any target sequence present in the sample. In some embodiments, the adapter includes any single stranded or double-stranded linear oligonucleotide that is not substantially complementary to an amplified target sequence. In some embodiments, the adapter is substantially non-complementary to at least one, some or all of the nucleic acid molecules of the sample. In some embodiments, suitable adapter lengths are in the range of about 10-100 nucleotides, about 12-60 nucleotides and about 15-50 nucleotides in length. Generally, the adapter can include any combination of nucleotides and/or nucleic acids. In some aspects, the adapter can include one or more cleavable groups at one or more locations. In another aspect, the adapter can include a sequence that is substantially identical, or substantially complementary, to at least a portion of a primer, for example a universal primer. In some embodiments, the adapter can include a barcode or tag to assist with downstream cataloguing, identification or sequencing. In some embodiments, a single-stranded adapter can act as a substrate for amplification when ligated to an amplified target sequence, particularly in the presence of a polymerase and dNTPs under suitable temperature and pH.

As used herein, "reamplifying" or "reamplification" and their derivatives refer generally to any process whereby at least a portion of an amplified nucleic acid molecule is further amplified via any suitable amplification process (referred to in some embodiments as a "secondary" amplification or "reamplification", thereby producing a reamplified nucleic acid molecule. The secondary amplification need not be identical to the original amplification process whereby the amplified nucleic acid molecule was produced; nor need the reamplified nucleic acid molecule be completely identical or completely complementary to the amplified nucleic acid molecule; all that is required is that the reamplified nucleic acid molecule include at least a portion of the amplified nucleic acid molecule or its complement. For example, the reamplification can involve the use of different amplification conditions and/or different primers, including different target-specific primers than the primary amplification.

As defined herein, a "cleavable group" generally refers to any moiety that once incorporated into a nucleic acid can be cleaved under appropriate conditions. For example, a cleavable group can be incorporated into a target-specific primer, an amplified sequence, an adapter or a nucleic acid molecule of the sample. In an exemplary embodiment, a target-specific primer can include a cleavable group that becomes incorporated into the amplified product and is subsequently cleaved after amplification, thereby removing a portion, or all, of the target-specific primer from the amplified product. The cleavable group can be cleaved or otherwise removed from a target-specific primer, an amplified sequence, an adapter or a nucleic acid molecule of the sample by any acceptable means. For example, a cleavable group can be removed from a target-specific primer, an amplified sequence, an adapter or a nucleic acid molecule of the sample by enzymatic, thermal, photo-oxidative or chemical treatment. In one aspect, a cleavable group can include a nucleobase that is not naturally occurring. For example, an oligodeoxyribonucleotide can include one or more RNA nucleobases, such as uracil that can be removed by a uracil glycosylase. In some embodiments, a cleavable group can include one or more modified nucleobases (such as 7-methylguanine, 8-oxo-guanine, xanthine, hypoxanthine, 5,6-dihydrouracil or 5-methylcytosine) or one or more modified nucleosides (i.e., 7-methylguanosine, 8-oxo-deoxyguanosine, xanthosine, inosine, dihydrouridine or 5-methylcytidine). The modified nucleobases or nucleotides can be removed from the nucleic acid by enzymatic, chemical or thermal means. In one embodiment, a cleavable group can include a moiety that can be removed from a primer after amplification (or synthesis) upon exposure to ultraviolet light (i.e., bromodeoxyuridine). In another embodiment, a cleavable group can include methylated cytosine. Typically, methylated cytosine can be cleaved from a primer for example, after induction of amplification (or synthesis), upon sodium bisulfite treatment. In some embodiments, a cleavable moiety can include a restriction site. For example, a primer or target sequence can include a nucleic acid sequence that is specific to one or more restriction enzymes, and following amplification (or synthesis), the primer or target sequence can be treated with the one or more restriction enzymes such that the cleavable group is removed. Typically, one or more cleavable groups can be included at one or more locations with a target-specific primer, an amplified sequence, an adapter or a nucleic acid molecule of the sample.

As used herein, "cleavage step" and its derivatives, generally refers to any process by which a cleavable group is cleaved or otherwise removed from a target-specific primer, an amplified sequence, an adapter or a nucleic acid molecule of the sample. In some embodiments, the cleavage steps involves a chemical, thermal, photo-oxidative or digestive process.

As used herein, the term "hybridization" is consistent with its use in the art, and generally refers to the process whereby two nucleic acid molecules undergo base pairing interactions. Two nucleic acid molecule molecules are said to be hybridized when any portion of one nucleic acid molecule is base paired with any portion of the other nucleic acid molecule; it is not necessarily required that the two nucleic acid molecules be hybridized across their entire respective lengths and in some embodiments, at least one of the nucleic acid molecules can include portions that are not hybridized to the other nucleic acid molecule. The phrase "hybridizing under stringent conditions" and its variants refers generally to conditions under which hybridization of a target-specific primer to a target sequence occurs in the presence of high hybridization temperature and low ionic strength. In one exemplary embodiment, stringent hybridization conditions include an aqueous environment containing about 30 mM magnesium sulfate, about 300 mM Tris-sulfate at pH 8.9, and about 90 mM ammonium sulfate at about 60-68° C., or equivalents thereof. As used herein, the phrase "standard hybridization conditions" and its variants refers generally to conditions under which hybridization of a primer to an oligonucleotide (i.e., a target sequence), occurs in the presence of low hybridization temperature and high ionic strength. In one exemplary embodiment, standard hybridization conditions include an aqueous environment containing about 100 mM magnesium sulfate, about 500 mM Tris-sulfate at pH 8.9, and about 200 mM ammonium sulfate at about 50-55° C., or equivalents thereof.

As used herein, "triple nucleotide motif" and its derivatives, refers generally to any nucleotide sequence that is repeated contiguously over three nucleotides e.g., AAA or CCC. Generally, a triple nucleotide motif is not repeated more than five times in a target-specific primer (or adapter) of the disclosure.

As used herein, "an ACA nucleotide motif" and its derivatives, refers generally to the nucleotide sequence "ACA". Generally, this motif is not repeated three or more times in a target-specific primer (or adapter) of the disclosure.

As used herein, "homopolymer" and its derivatives, refers generally to any repeating nucleotide sequence that is eight nucleotides or greater in length e.g., AAAAAAAA or CCCCCCCC. Generally, a homopolymer as defined herein is not present in a target-specific primer (or adapter) of the disclosure.

As used herein, "GC content" and its derivatives, refers generally to the cytosine and guanine content of a nucleic acid molecule. Generally, the GC content of a target-specific primer (or adapter) of the disclosure is 85% or lower. More typically, the GC content of a target-specific primer or adapter of the disclosure is between 15-85%.

As used herein, the term "end" and its variants, when used in reference to a nucleic acid molecule, for example a target sequence or amplified target sequence, can include the terminal 30 nucleotides, the terminal 20 and even more typically the terminal 15 nucleotides of the nucleic acid molecule. A linear nucleic acid molecule comprised of linked series of contiguous nucleotides typically includes at least two ends. In some embodiments, one end of the nucleic acid molecule can include a 3' hydroxyl group or its equivalent, and can be referred to as the "3' end" and its derivatives. Optionally, the 3' end includes a 3' hydroxyl group that is not linked to a 5' phosphate group of a mononucleotide pentose ring. Typically, the 3' end includes one or more 5' linked nucleotides located adjacent to the nucleotide including the unlinked 3' hydroxyl group, typically the 30 nucleotides located adjacent to the 3' hydroxyl, typically the terminal 20 and even more typically the terminal 15 nucleotides. Generally, the one or more linked nucleotides can be represented as a percentage of the nucleotides present in the oligonucleotide or can be provided as a number of linked nucleotides adjacent to the unlinked 3' hydroxyl. For example, the 3' end can include less than 50% of the nucleotide length of the oligonucleotide. In some embodiments, the 3' end does not include any unlinked 3' hydroxyl group but can include any moiety capable of serving as a site for attachment of nucleotides via primer extension and/or nucleotide polymerization. In some embodiments, the term "3' end" for example when referring to a target-specific primer, can include the terminal 10 nucleotides, the terminal 5 nucleotides, the terminal 4, 3, 2 or fewer nucleotides at the 3'end. In some embodiments, the term "3' end" when referring to a target-specific primer can include nucleotides located at nucleotide positions 10 or fewer from the 3' terminus.

As used herein, "5' end", and its derivatives, generally refers to an end of a nucleic acid molecule, for example a target sequence or amplified target sequence, which includes a free 5' phosphate group or its equivalent. In some embodiments, the 5' end includes a 5' phosphate group that is not linked to a 3' hydroxyl of a neighboring mononucleotide pentose ring. Typically, the 5' end includes to one or more linked nucleotides located adjacent to the 5' phosphate, typically the 30 nucleotides located adjacent to the nucleotide including the 5' phosphate group, typically the terminal 20 and even more typically the terminal 15 nucleotides. Generally, the one or more linked nucleotides can be represented as a percentage of the nucleotides present in the oligonucleotide or can be provided as a number of linked nucleotides adjacent to the 5' phosphate. For example, the 5' end can be less than 50% of the nucleotide length of an oligonucleotide. In another exemplary embodiment, the 5' end can include about 15 nucleotides adjacent to the nucleotide including the terminal 5' phosphate. In some embodiments, the 5' end does not include any unlinked 5' phosphate group but can include any moiety capable of serving as a site of attachment to a a 3' hydroxyl group, or to the 3'end of another nucleic acid molecule. In some embodiments, the term "5' end" for example when referring to a target-specific primer, can include the terminal 10 nucleotides, the terminal 5 nucleotides, the terminal 4, 3, 2 or fewer nucleotides at the 5'end. In some embodiments, the term "5' end" when referring to a target-specific primer can include nucleotides located at positions 10 or fewer from the 5' terminus. In some embodiments, the 5' end of a target-specific primer can include only non-cleavable nucleotides, for example nucleotides that do not contain one or more cleavable groups as disclosed herein, or a cleavable nucleotide as would be readily determined by one of ordinary skill in the art.

As used herein, "protecting group" and its derivatives, refers generally to any moiety that can be incorporated into an adapter or target-specific primer that imparts chemical selectivity or protects the target-specific primer or adapter from digestion or chemical degradation. Typically, but not necessarily, a protecting group can include modification of an existing functional group in the target-specific primer r adapter to achieve chemical selectivity. Suitable types of protecting groups include alcohol, amine, phosphate, carbonyl, or carboxylic acid protecting groups. In an exemplary embodiment, the protecting group can include a spacer compound having a chain of carbon atoms.

As used herein, "DNA barcode" or "DNA tagging sequence" and its derivatives, refers generally to a unique short (6-14 nucleotide) nucleic acid sequence within an adapter that can act as a 'key' to distinguish or separate a plurality of amplified target sequences in a sample. For the purposes of this disclosure, a DNA barcode or DNA tagging sequence can be incorporated into the nucleotide sequence of an adapter.

As used herein, the phrases "two rounds of target-specific hybridization" or "two rounds of target-specific selection" and their derivatives refers generally to any process whereby the same target sequence is subjected to two consecutive rounds of hybridization-based target-specific selection, wherein a target sequence is hybridized to a target-specific sequence. Each round of hybridization based target-specific selection can include multiple target-specific hybridizations to at least some portion of a target-specific sequence. In one exemplary embodiment, a round of target-specific selection includes a first target-specific hybridization involving a first region of the target sequence and a second target-specific hybridization involving a second region of the target sequence. The first and second regions can be the same or different. In some embodiments, each round of hybridization-based target-specific selection can include use of two target specific oligonucleotides (e.g., a forward target-specific primer and a reverse target-specific primer), such that each round of selection includes two target-specific hybridizations.

As used herein, "comparable maximal minimum melting temperatures" and its derivatives, refers generally to the melting temperature (Tm) of each nucleic acid fragment for a single adapter or target-specific primer after cleavage of the cleavable groups. The hybridization temperature of each nucleic acid fragment generated by a single adapter or target-specific primer is compared to determine the maximal minimum temperature required preventing hybridization of any nucleic acid fragment from the target-specific primer or adapter to the target sequence. Once the maximal hybridization temperature is known, it is possible to manipulate the adapter or target-specific primer, for example by moving the location of the cleavable group along the length of the primer, to achieve a comparable maximal minimum melting temperature with respect to each nucleic acid fragment.

As used herein, "addition only" and its derivatives, refers generally to a series of steps in which reagents and components are added to a first or single reaction mixture. Typically, the series of steps excludes the removal of the reaction mixture from a first vessel to a second vessel in order to complete the series of steps. Generally, an addition only process excludes the manipulation of the reaction mixture outside the vessel containing the reaction mixture. Typically, an addition-only process is amenable to automation and high-throughput.

As used herein, "synthesizing" and its derivatives, refers generally to a reaction involving nucleotide polymerization by a polymerase, optionally in a template-dependent fashion. Polymerases synthesize an oligonucleotide via transfer of a nucleoside monophosphate from a nucleoside triphosphate (NTP), deoxynucleoside triphosphate (dNTP) or dideoxynucleoside triphosphate (ddNTP) to the 3' hydroxyl of an extending oligonucleotide chain. For the purposes of this disclosure, synthesizing includes to the serial extension of a hybridized adapter or a target-specific primer via transfer of a nucleoside monophosphate from a deoxynucleoside triphosphate.

As used herein, "polymerizing conditions" and its derivatives, refers generally to conditions suitable for nucleotide polymerization. In typical embodiments, such nucleotide polymerization is catalyzed by a polymerase. In some embodiments, polymerizing conditions include conditions for primer extension, optionally in a template-dependent manner, resulting in the generation of a synthesized nucleic acid sequence. In some embodiments, the polymerizing conditions include polymerase chain reaction (PCR). Typically, the polymerizing conditions include use of a reaction mixture that is sufficient to synthesize nucleic acids and includes a polymerase and nucleotides. The polymerizing conditions can include conditions for annealing of a target-specific primer to a target sequence and extension of the primer in a template dependent manner in the presence of a polymerase. In some embodiments, polymerizing conditions can be practiced using thermocycling. Additionally, polymerizing conditions can include a plurality of cycles where the steps of annealing, extending, and separating the two nucleic strands are repeated. Typically, the polymerizing conditions include a cation such as $MgCl_2$. Generally, polymerization of one or more nucleotides to form a nucleic acid strand includes that the nucleotides be linked to each other via phosphodiester bonds, however, alternative linkages may be possible in the context of particular nucleotide analogs.

As used herein, the term "nucleic acid" refers to natural nucleic acids, artificial nucleic acids, analogs thereof, or combinations thereof, including polynucleotides and oligonucleotides. As used herein, the terms "polynucleotide" and "oligonucleotide" are used interchangeably and mean single-stranded and double-stranded polymers of nucleotides including, but not limited to, 2'-deoxyribonucleotides (nucleic acid) and ribonucleotides (RNA) linked by internucleotide phosphodiester bond linkages, e.g. 3'-5' and 2'-5', inverted linkages, e.g. 3'-3' and 5'-5', branched structures, or analog nucleic acids. Polynucleotides have associated counter ions, such as $H^+$, $NH_4^+$, trialkylammonium, $Mg^{2+}$, $Na^+$ and the like. An oligonucleotide can be composed entirely of deoxyribonucleotides, entirely of ribonucleotides, or chimeric mixtures thereof. Oligonucleotides can be comprised of nucleobase and sugar analogs. Polynucleotides typically range in size from a few monomeric units, e.g. 5-40, when they are more commonly frequently referred to in the art as oligonucleotides, to several thousands of monomeric nucleotide units, when they are more commonly referred to in the art as polynucleotides; for purposes of this disclosure, however, both oligonucleotides and polynucleotides may be of any suitable length. Unless denoted otherwise, whenever a oligonucleotide sequence is represented, it will be understood that the nucleotides are in 5' to 3' order from left to right and that "A" denotes deoxyadenosine, "C" denotes deoxycytidine, "G" denotes deoxyguanosine, "T" denotes thymidine, and "U" denotes deoxyuridine. Oligonucleotides are said to have "5' ends" and "3' ends" because mononucleotides are typically reacted to form oligonucleotides via attachment of the 5' phosphate or equivalent group of one nucleotide to the 3' hydroxyl or equivalent group of its neighboring nucleotide, optionally via a phosphodiester or other suitable linkage.

As defined herein, the term "nick translation" and its variants comprise the translocation of one or more nicks or gaps within a nucleic acid strand to a new position along the nucleic acid strand. In some embodiments, a nick can be formed when a double stranded adapter is ligated to a double stranded amplified target sequence. In one example, the primer can include at its 5' end, a phosphate group that can ligate to the double stranded amplified target sequence, leaving a nick between the adapter and the amplified target sequence in the complementary strand. In some embodiments, nick translation results in the movement of the nick to the 3' end of the nucleic acid strand. In some embodiments, moving the nick can include performing a nick translation reaction on the adapter-ligated amplified target sequence. In some embodiments, the nick translation reaction can be a coupled 5' to 3' DNA polymerization/degradation reaction, or coupled to a 5' to 3' DNA polymerization/strand displacement reaction. In some embodiments, moving the nick can include performing a DNA strand extension reaction at the nick site. In some embodiments, moving the nick can include performing a single strand exonuclease reaction on the nick to form a single stranded portion of the adapter-ligated amplified target sequence and performing a DNA strand extension reaction on the single stranded portion of the adapter-ligated amplified target sequence to a new position. In some embodiments, a nick is formed in the nucleic acid strand opposite the site of ligation.

As used herein, the term "polymerase chain reaction" ("PCR") refers to the method of K. B. Mullis U.S. Pat. Nos. 4,683,195 and 4,683,202, hereby incorporated by reference, which describe a method for increasing the concentration of a segment of a polynucleotide of interest in a mixture of genomic DNA without cloning or purification. This process for amplifying the polynucleotide of interest consists of introducing a large excess of two oligonucleotide primers to the DNA mixture containing the desired polynucleotide of interest, followed by a precise sequence of thermal cycling in the presence of a DNA polymerase. The two primers are complementary to their respective strands of the double stranded polynucleotide of interest. To effect amplification, the mixture is denatured and the primers then annealed to their complementary sequences within the polynucleotide of interest molecule. Following annealing, the primers are extended with a polymerase to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired polynucleotide of interest. The length of the amplified segment of the desired polynucleotide of interest (amplicon) is determined by the relative positions of the primers with respect to each other, and therefore, this length is a controllable parameter. By virtue of repeating the process, the method is referred to as the "polymerase chain reaction" (hereinafter "PCR"). Because the desired amplified segments of the polynucleotide of interest become the predominant nucleic acid sequences (in terms of concentration) in the mixture, they are said to be "PCR amplified". As defined herein, target nucleic acid molecules within a sample including a plurality of target nucleic acid molecules are amplified via PCR. In a modification to the method discussed above, the target nucleic acid molecules can be PCR amplified using a plurality of different primer pairs, in some cases, one or more primer pairs per target nucleic acid molecule of interest, thereby forming a multiplex PCR reaction. Using multiplex PCR, it is possible to simultaneously amplify multiple nucleic acid molecules of interest from a sample to form amplified target sequences. It is also possible to detect the amplified target sequences by several different methodologies (e.g., quantitation with a bioanalyzer or qPCR, hybridization with a labeled probe; incorporation of biotinylated primers followed by avidin-enzyme conjugate detection; incorporation of $^{32}$P-labeled deoxynucleotide triphosphates, such as dCTP or dATP, into the amplified target sequence). Any oligonucleotide sequence can be amplified with the appropriate set of primers, thereby allowing for the amplification of target nucleic acid molecules from genomic DNA, cDNA, formalin-fixed paraffin-embedded DNA, fine-needle biopsies and various other sources. In particular, the amplified target sequences created by the multiplex PCR process as disclosed herein, are themselves efficient substrates for subsequent PCR amplification or various downstream assays or manipulations.

As defined herein "multiplex amplification" refers to selective and non-random amplification of two or more target sequences within a sample using at least one target-specific primer. In some embodiments, multiplex amplification is performed such that some or all of the target sequences are amplified within a single reaction vessel. The "plexy" or "plex" of a given multiplex amplification refers generally to the number of different target-specific sequences that are amplified during that single multiplex amplification. In some embodiments, the plexy can be about 12-plex, 24-plex, 48-plex, 96-plex, 192-plex, 384-plex, 768-plex, 1536-plex, 3072-plex, 6144-plex or higher.

In some embodiments, the disclosure relates generally to methods, compositions, systems, apparatuses and kits for avoiding or reducing the formation of amplification artifacts (for example primer-dimers) during selective amplification of one or more target nucleic acid molecules in a population of nucleic acid molecules.

In some embodiments, the disclosure relates generally to the amplification of multiple target-specific sequences from a population of nucleic acid molecules. In some embodiments, the method comprises hybridizing one or more target-specific primer pairs to the target sequence, extending a first primer of the primer pair, denaturing the extended first primer product from the population of nucleic acid molecules, hybridizing to the extended first primer product the second primer of the primer pair, extending the second primer to form a double stranded product, and digesting the target-specific primer pair away from the double stranded product to generate a plurality of amplified target sequences. In some embodiments, the digesting includes partial digesting of one or more of the target-specific primers from the amplified target sequence. In some embodiments, the amplified target sequences can be ligated to one or more adapters. In some embodiments, the adapters can include one or more DNA barcodes or tagging sequences. In some embodiments, the amplified target sequences once ligated to an adapter can undergo a nick translation reaction and/or further amplification to generate a library of adapter-ligated amplified target sequences.

In some embodiments, the disclosure relates generally to the preparation and formation of multiple target-specific amplicons. In some embodiments, the method comprises hybridizing one or more target-specific primer pairs to a nucleic acid molecule, extending a first primer of the primer pair, denaturing the extended first primer from the nucleic acid molecule, hybridizing to the extended first primer product, a second primer of the primer pair and extending the second primer, digesting the target-specific primer pairs to generate a plurality of target-specific amplicons. In some embodiments, adapters can be ligated to the ends of the target-specific amplicons prior to performing a nick translation reaction to generate a plurality of target-specific amplicons suitable for nucleic acid sequencing. In some embodiments, the one or more target specific amplicons can be amplified using bridge amplification or emPCR to generate a plurality of clonal templates suitable for nucleic acid sequencing. In some embodiments, the disclosure generally relates to methods for preparing a target-specific amplicon library, for use in a variety of downstream processes or assays such as nucleic acid sequencing or clonal amplification. In one embodiment, the disclosure relates to a method of performing target-specific multiplex PCR on a nucleic acid sample having a plurality of target sequences using primers having a cleavable group.

In one embodiment, nucleic acid templates to be sequenced using the Ion Torrent PGM™ or Ion Torrent Proton™ system can be prepared from a population of nucleic acid molecules using the target-specific amplification techniques as outlined herein. Optionally, following target-specific amplification a secondary and/or tertiary amplification process including, but not limited to, a library amplification step and/or a clonal amplification step such as emPCR can be performed.

In some embodiments, the disclosure relates to a composition comprising a plurality of target-specific primer pairs, each containing a forward primer and a reverse primer having at least one cleavable group located at either a) the 3' end or the 5' end, and/or b) at about the central nucleotide position of the target-specific primer, and wherein the target-specific primer pairs can be substantially non-complementary to other primer pairs in the composition. In some embodiments, the composition comprises at least 1000, 2000, 3000, 4000, 6000, 9000, 12000, or more target-specific primer pairs. In some embodiments, the target-specific primer pairs comprise about 15 nucleotides to about 40 nucleotides in length, wherein at least one nucleotide is replaced with a cleavable group. In some embodiments the cleavable group can be a uridine nucleotide. In some embodiments, the target-specific primer sets are designed to amplify an exon, gene, exome or region of the genome associated with a clinical or pathological condition, e.g., the amplification of one or more single nucleotide mutations (SNPs) associated with cancer, such as colon cancer, or the amplification of mutations associated with an inherited disease such as cystic fibrosis. In some embodiments, the target-specific primer pairs when hybridized to a target sequence and amplified as outlined herein can generate a library of adapter-ligated amplified target sequences that are about 100 to about 500 base pairs in length. In some embodiments, no one adapter-ligated amplified target sequence is overexpressed in the library by more than 30% as compared to the remainder of the adapter-ligated amplified target sequences in the library. In some embodiments, the adapter-ligated amplified target sequence library is substantially homogenous with respect to GC content, amplified target sequence length or melting temperature (Tm).

In some embodiments, the disclosure relates generally to a kit for performing multiplex PCR comprising a plurality of target-specific primers having a cleavable group, a DNA polymerase, an adapter, dATP, dCTP, dGTP and dTTP. In some embodiments, the cleavable group can be a uracil nucleotide. The kit can further include one or more antibodies, nucleic acid barcodes, purification solutions or columns.

In some embodiments, the disclosure relates to a kit for generating a target-specific amplicon library comprising a plurality of target-specific primers having a cleavable group, a DNA polymerase, an adapter, dATP, dCTP, dGTP, dTTP, and a cleaving reagent. In some embodiments, the kit further comprises one or more antibodies, nucleic acid barcodes, purification solutions or columns.

In one embodiment, the disclosure generally relates to the amplification of multiple target-specific sequences from a single nucleic acid source or sample. In another embodiment, the disclosure relates generally to the target-specific amplification of two or more target sequences from two or more nucleic acid sources, samples or species. For example, it is envisioned by the disclosure that a single nucleic acid sample can include genomic DNA or fixed-formalin paraffin-embedded (FFPE) DNA. It is also envisioned that the sample can be from a single individual, a collection of nucleic acid samples from genetically related members, multiple nucleic acid samples from genetically unrelated members, multiple nucleic acid samples (matched) from a single individual such as a tumor sample and normal tissue sample, or genetic material from a single source that contains two distinct forms of genetic material such as maternal and fetal DNA obtained from a maternal subject, or the presence of contaminating bacteria DNA in a sample that contains plant or animal DNA. In some embodiments, the source of nucleic acid material can include nucleic acids obtained from a newborn, for example as typically procured as a blood sample for newborn screening.

The nucleic acid sample can include high molecular weight material such as genomic DNA or cDNA. The sample can include low molecular weight material such as nucleic acid molecules obtained from FFPE or archived DNA samples. In another embodiment, low molecular weight material includes enzymatically or mechanically sheared DNA. The sample can include cell-free circulating DNA such as material obtained from a maternal subject. In some embodiments, the sample can include nucleic acid molecules obtained from biopsies, tumors, scrapings, swabs, blood, mucus, urine, plasma, semen, hair, laser capture micro-dissections, surgical resections, and other clinical or laboratory obtained samples. In some embodiments, the sample can be an epidemiological, agricultural, forensic or pathogenic sample.

In some embodiments, the sample can include nucleic acid molecules obtained from an animal such as a human or mammalian source. In another embodiment, the sample can include nucleic acid molecules obtained from a non-mammalian source such as a plant, bacteria, virus or fungus. In some embodiments, the source of the nucleic acid molecules may be an archived or extinct sample or species.

In some embodiments, the disclosure relates generally to the selective amplification of at least one target sequence in a normal or diseased containing tissue, biopsy, core, tumor or other sample. In some embodiments, the disclosure generally relates to the selective amplification of at least one target sequence and the detection and/or identification of mutations in the diseased tissue, core, biopsy or tumor sample. In some embodiments, the diseased or normal sample can include whole genomic DNA, formalin-fixed paraffin-embedded tissue (FFPE), sheared or enzymatically treated DNA. In some embodiments, the disclosure is directed to the selective amplification of at least one target sequence and detection and/or identification of clinically actionable mutations. In some embodiments, the disclosure is directed to the detection and/or identification of mutations associated with drug resistance or drug susceptibility. In some embodiments, the disclosure is generally directed to the identification and/or quantitation of genetic markers associated with organ transplantation or organ rejection.

In some embodiments, the disclosure relates generally to the selective amplification of at least one target sequence in cell-free circulating DNA. In some embodiments, the selective amplification of at least one target sequence in a sample includes a mixture of different nucleic acid molecules. The selective amplification can optionally be accompanied by detection and/or identification of mutations observed in circulating DNA. In some embodiments, the selective amplification can optionally be accompanied by detection and/or identification of mutations associated with cancer or an inherited disease such as metabolic, neuromuscular, developmental, cardiovascular, autoimmune or other inherited disorder.

In some embodiments, the target-specific primers and primer pairs are target-specific sequences that can amplify specific regions of a nucleic acid molecule. In some embodiments, the target-specific primers can amplify genomic DNA or cDNA. In some embodiments, the target-specific primers can amplify mammalian DNA, such as human DNA. In some embodiments, the amount of DNA required for selective amplification can be from about 1 ng to 1 microgram. In some embodiments, the amount of DNA required for selective amplification of one or more target sequences can be about 1 ng, about 5 ng or about 10 ng. In some embodiments, the amount of DNA required for selective amplification of target sequence is about 10 ng to about 200 ng.

In some embodiments, selective amplification of at least one target sequence further includes nucleic acid sequencing of the amplified target sequence. Optionally, the method further includes detecting and/or identifying mutations present in the sample identified through nucleic acid sequencing of the amplified target sequence.

In some embodiments, target sequences or amplified target sequences are directed to mutations associated with cancer. In some embodiments, the target sequences or amplified target sequences are directed to mutations associated with one or more cancers selected from the group consisting of head and neck cancers, brain cancer, breast cancer, ovarian cancer, cervical cancer, colorectal cancer, endometrial cancer, gallbladder cancer, gastric cancer, bladder cancer, prostate cancer, testicular cancer, liver cancer, lung cancer, kidney (renal cell) cancer, esophageal cancer, pancreatic cancer, thyroid cancer, bile duct cancer, pituitary tumor, wilms tumor, kaposi sarcoma, osteosarcoma, thymus cancer, skin cancer, heart cancer, oral and larynx cancer, leukemia, neuroblastoma and non-hodgkin lymphoma. In one embodiment, the mutations can include substitutions, insertions, inversions, point mutations, deletions, mismatches and translocations. In one embodiment, the mutations can include variation in copy number. In one embodiment, the mutations can include germline or somatic mutations. In one embodiment, the mutations associated with cancer are located in at least one of the genes provided in Tables 1 or 4 (see U.S. Ser. No. 13/458,739, filed Apr. 27, 2012, hereby incorporated by reference in its entirety), or provided in Table 7 of U.S. Application No. 61/598,881 hereby incorporated by reference in its entirety. In some embodiments, the mutations can be any of the genomic coordinates provided in Table 18 (from U.S. Ser. No. 13/458,739, filed Apr. 27, 2012, hereby incorporated by reference in its entirety), or provided in Table 7 of US Application 61/598,881 hereby incorporated by reference in its entirety. In some embodiments, the target sequences directed to mutations associated with cancer can include any one or more of the mutations provided in Table 10 (from U.S. Ser. No. 13/458,739, filed Apr. 27, 2012, hereby incorporated by reference in its entirety). In some embodiments, the mutations can be found within any one or more of the genomic coordinates provided in Table 16 or Table 18 (both found in U.S. Ser. No. 13/458,739, filed Apr. 27, 2012, hereby incorporated by reference in its entirety).

In some embodiments, the mutations associated with cancer are located in at least one of the genes selected from ABI1; ABL1; ABL2; ACSL3; ACSL6; AFF1; AFF3; AFF4; AKAP9; AKT1; AKT2; ALK; APC; ARHGAP26; ARHGEF12; ARID1A; ARNT; ASPSCR1; ASXL1; ATF1; ATIC; ATM; AXIN2; BAP1; BARD1; BCAR3; BCL10; BCL11A; BCL11B; BCL2; BCL3; BCL6; BCL7A; BCL9; BCR; BIRC3; BLM; BMPR1A; BRAF; BRCA1; BRCA2; BRD3; BRD4; BRIP1; BUB1B; CARD11; CARS; CASC5; CBFA2T3; CBFB; CBL; CBLB; CBLC; CCDC6; CCNB1IP1; CCND1; CCND2; CD74; CD79A; CDC73; CDH1; CDH11; CDK4; CDK6; CDKN2A; CDKN2B; CDKN2C; CDX2; CEBPA; CEP110; CHEK1; CHEK2; CHIC2; CHN1; CIC; CIITA; CLP1; CLTC; CLTCL1; COL1A1; CREB1; CREB3L2; CREBBP; CRTC1; CRTC3; CSF1R; CTNNB1; CXCR7; CYLD; CYTSB; DCLK3; DDB2; DDIT3; DDR2; DDX10; DDX5; DDX6; DEK; DGKG; DICER1; DNMT3A; EGFR; EIF4A2; ELF4; ELL; ELN; EML4; EP300; EPS15; ERBB2; ERBB4; ERC1; ERCC2; ERCC3; ERCC4; ERCC5; ERG; ETV1; ETV4; ETV5; ETV6; EWSR1; EXT1; EXT2; EZH2; FAM123B; FANCA; FANCC; FANCD2; FANCE; FANCF; FANCG; FAS; FBXW7; FCRL4; FGFR1; FGFR1OP; FGFR2; FGFR3; FH; FIP1L1; FLCN; FLI1; FLT1; FLT3; FNBP1; FOXL2; FOXO1; FOXO3; FOXO4; FOXP1; FUS; GAS7; GATA1; GATA2; GATA3; GMPS; GNAQ; GNAS; GOLGA5; GOPC; GPC3; GPHNGPR124; HIP1; HIST1H4I; HLF; HNF1A; HNRNPA2B1; HOOK3; HOXA11; HOXA13; HOXA9; HOXC11; HOXC13; HOXD13; HRAS; HSP90AA1; HSP90AB1; IDH1; IDH2; IKZF1; IL2; IL21R; IL6ST; IRF4; ITGA10; ITGA9; ITK; JAK1; JAK2; JAK3; KDM5A; KDM5C; KDM6A; KDR; KDSR; KIAA1549; KIT; KLF6; KLK2; KRAS; KTN1; LASP1; LCK; LCP1; LHFP; LIFR; LMO2; LPP; MAF; MALT1; MAML2; MAP2K1; MAP2K4; MDM2; MDM4; MECOM; MEN1; MET; MITF; MKL1; MLH1; MLL; MLLT1; MLLT10; MLLT3; MLLT4; MLLT6; MN1; MPL; MRE11A; MSH2; MSH6; MSI2; MSN; MTCP1; MTOR; MUC1; MYB; MYC; MYCL1; MYCN; MYH11; MYH9; MYST3; MYST4; NACA; NBN; NCOA1; NCOA2; NCOA4; NEK9; NF1; NF2; NFE2L2; NFKB2; NIN; NKX2-1; NLRP1; NONO; NOTCH1; NOTCH2; NPM1; NR4A3; NRAS; NSD1; NTRK1; NTRK3; NUMA1; NUP214; NUP98; OLIG2; OMD; PAFAH1B2; PALB2; PATZ1; PAX3; PAX5; PAX7; PAX8; PBRM1; PBX1; PCM1; PDE4DIP; PDGFB; PDGFRA; PDGFRB; PER1; PHOX2B; PICALM; PIK3CA; PIK3R1; PIM1; PLAG1; PML; PMS1; PMS2; POU2AF1; POU5F1; PPARG; PPP2R1A; PRCC; PRDM16; PRF1; PRKAR1A; PRRX1; PSIP1; PTCH1; PTEN; PTPN11; RABEP1; RAD50; RAD51L1; RAF1; RANBP17; RAP1GDS1; RARA; RB1; RBM15; RECQL4; REL; RET; RHOH; RNF213; ROS1; RPN1; RPS6KA2; RUNX1; RUNX1T1; SBDS; SDHAF2; SDHB; SETD2; SFPQ; SFRS3; SH3GL1; SLC45A3; SMAD4; SMARCA4; SMARCB1; SMO; SOCS1; SRC; SRGAP3; SS18; SS18L1; STIL; STK11; STK36; SUFU; SYK; TAF15; TAF1L; TAL1; TAL2; TCF12; TCF3; TCL1A; TET1; TET2; TEX14; TFE3; TFEB; TFG; TFRC; THRAP3; TLX1; TLX3; TMPRSS2; TNFAIP3; TOP1; TP53; TPM3; TPM4; TPR; TRIM27; TRIM33; TRIP11; TSC1; TSC2; TSHR; USP6; VHL; WAS; WHSC1L1; WRN; WT1; XPA; XPC; ZBTB16; ZMYM2; ZNF331; ZNF384; and ZNF521.

In some embodiments, the mutations associated with cancer are located in at least one of the genes selected from ABL1; AKT1; ALK; APC; ATM; BRAF; CDH1; CDKN2A; CSF1R; CTNNB1; EGFR; ERBB2; ERBB4; FBXW7; FGFR1; FGFR2; FGFR3; FLT3; GNAS; HNF1A; HRAS; IDH1; JAK2; JAK3; KDR; KIT; KRAS; MET; MLH1; MPL; NOTCH1; NPM1; NRAS; PDGFRA; PIK3CA; PTEN; PTPN11; RB1; RET; SMAD4; SMARCB1; SMO; SRC; STK11; TP53; and VHL.

In some embodiments, the amplified target sequences are directed to any one of more of the genomic coordinates provided in Table 18 (from U.S. Ser. No. 13/458,739, filed Apr. 27, 2012, hereby incorporated by reference in its entirety). In some embodiments, any one or more of the cancer target-specific primers provided in Tables 2, 3 or 17 (all from U.S. Ser. No. 13/458,739, filed Apr. 27, 2012, hereby incorporated by reference in its entirety) can be used to amplify a target sequence present in a sample as disclosed by the methods described herein.

In some embodiments, the cancer target-specific primers from Tables 2, 3 or 17 (from U.S. Ser. No. 13/458,739, filed Apr. 27, 2012, hereby incorporated by reference in its entirety) can include 2, 3, 4, 5, 6, 7, 8, 9, 10, 20, 40, 60, 80, 100, 150, 200, 400, 500, 800, 1000, 2000, 3000, 4000, 5000, 6000, 7000, 8000, 9000, 10,000, 11,000, 12,000, 13,000 or more, target-specific primers. In some embodiments, the amplified target sequences can include any one or more of the amplified target sequences generated at the genomic coordinates (using amplicon ID target-specific primers) provided in Tables 10 or 18 (both found in U.S. Ser. No. 13/458,739, filed Apr. 27, 2012, hereby incorporated by reference in its entirety). In some embodiments, at least one of the target-specific primers associated with cancer is at least 90% identical to at least one nucleic acid sequence selected from SEQ ID NOs: 1-103,143. In some embodiments, at least one of the target-specific primers associated with cancer is complementary across its entire length to at least one target sequence in a sample. In some embodiments, at least one of the target-specific primers associated with cancer includes a non-cleavable nucleotide at the 3' end. In some embodiments, the non-cleavable nucleotide at the 3' end includes the terminal 3' nucleotide. In one embodiment, the amplified target sequences are directed to individual exons having a mutation associated with cancer. In some embodiments, the disclosure relates generally to the selective amplification of more than one target sequences in a sample and the detection and/or identification of mutations associated with cancer. In some embodiments, the amplified target sequences include two or more nucleotide sequences provided in Table 2 (from U.S. Ser. No. 13/458,739, filed Apr. 27, 2012, hereby incorporated by reference in its entirety). In some embodiments, the amplified target sequences can include any one or more the amplified target sequences generated at the genomic coordinates using the amplicon ID target-specific primers provided in Table 18 (found in U.S. Ser. No. 13/458,739, filed Apr. 27, 2012, hereby incorporated by reference in its entirety), or provided in Table 7 of US Application 61/598,881 hereby incorporated by reference in its entirety. In one embodiment, the amplified target sequences include 100, 200, 500, 1000, 2000, 3000, 6000, 8000, 10,000, 12,000, or more amplicons from Tables 1-5, or Tables 6 and 7 of US Application 61/598,881 hereby incorporated by reference in their entireties (also Tables 1-5, 6 and 7 found in U.S. Ser. No. 13/458,739, filed Apr. 27, 2012, hereby incorporated by reference in its entirety. In some embodiments, the disclosure relates generally to the detection and optionally, the identification of clinically actionable mutations. As defined herein, the term "clinically actionable mutations" includes mutations that are known or can be associated by one of ordinary skill in the art with, but not limited to, prognosis for the treatment of cancer. In one embodiment, prognosis for the treatment of cancer includes the identification of mutations associated with responsiveness or non-responsiveness of a cancer to a drug, drug combination, or treatment regime. In one embodiment, the disclosure relates generally to the amplification of a plurality of target sequences from a population of nucleic acid molecules linked to, or correlated with, the onset, progression or remission of cancer.

In some embodiments, target-specific primers are designed using the primer criteria disclosed herein. In some embodiments, target-specific primers are designed using the primer criteria disclosed herein and directed to one or more genes associated with breast cancer. In some embodiments, target-specific primers associated with breast cancer include at least one target-specific primer selected from one or more genes selected from the group consisting of AIM 1, AR, ATM, BARD1, BCAS1, BRIP1, CCND1, CCND2, CCNE1, CDH1, CDK3, CDK4, CDKN2A, CDKN2B, CAMK1D, CHEK2, DIRAS3, EGFR, ERBB2, EPHA3, ERBB4, ETV6, GNRH1, KCTD9, CDCA2, EBF2, EMSY, BNIP3L, PNMA2, DPYSL2, ADRA1A, STMN4, TRIM35, PAK1, AQP11, CLSN1A, RSF1, KCTD14, THRSP, NDUFC2, ALG8, KCTD21, USP35, GAB2, DNAH9, ZNF18, MYOCD, STK11, TP53, JAK1, JAK2, MET, PDGFRA, PML, PTEN, RET, TMPRSS2, WNK1, FGFR1, IGF1R, PPP1R12B, PTPRT, GSTM1, IP08, MYC, ZNF703, MDM1, MDM2, MDM4, MKK4, P14 KB, NCOR1, NBN, PALB2, RAD50, RAD51, PAK1, RSF1, INTS4, ZMIZ1, SEPHS1, FOXM1, SDCCAG1, IGF1R, TSHZ2, RPSK6K1, PPP2R2A, MTAP, MAP2K4, AURKB, BCL2, BUB1, CDCA3, CDCA4, CDC20, CDC45, CHEK1, FOXM1, HDAC2, IGF1R, KIF2C, KIFC1, KRAS, RB1, SMAD4, NCOR1, UTX, MTHDFD1L, RAD51AP1, TTK and UBE2C.

In some embodiments, the disclosure relates generally to the amplification of target sequences directed to mutations associated with a congenital or inherited disease. In some embodiments, the disclosure can include the amplification of target sequences directed to somatic or germline mutations. In some embodiments, the mutations can be autosomal dominant or autosomal recessive. In one embodiment, the mutations associated with a congenital or inherited disease are located in at least one of the genes or diseases provided in Table 4 (from U.S. Ser. No. 13/458,739, filed Apr. 27, 2012, hereby incorporated by reference in its entirety). In some embodiments, the disclosure relates to the amplification of target sequences in a sample associated with one or more inherited diseases selected from the group consisting of Adenosine Aminohydrolase Deficiency (ADA); Agammaglobulinemia, X-linked, Type 1; Alagille Syndrome; All Hypertrophic and Dilated Cardiomyopathy; Alopecia Universalis Congenita (ALUNC); Alpers Syndrome; Alpha-1-Antitrypsin Deficiency; Alpha-Thalassemia—Southeast Asia; Amyotrophic Lateral Sclerosis—Lou Gehrig's Disease; Androgen Insensitivity Syndrome; Aniridia; Ankylosing spondylitis; APC-Associated Polyposis Conditions; Argininosuccinate Lyase Deficiency; Arrhythmogenic Right Ventricular Dysplasia/Cardiomyopathy; Ataxia with Oculomotor Apraxia Type 2; Ataxia with Vitamin E Deficiency; Ataxia-Telangiectasia; Autoimmune Polyendocrine Syndrome; Beta-Hydroxyisobutyryl CoA Deacylase deficiency (HIBCH deficiency); Biotinidase Deficiency; Blepharophimosis-ptosis-epicanthus inversus; Bloom Syndrome; Brachydactyly; Brachydactyly—Hypertension Syndrome; Brachydactyly Type B1; Branchiootorenal Spectrum Disorders; BRCA1; Campomelic Dysplasia; Canavan; Cerebrotendinous Xanthomatosis; Ceroid-lipofuscinoses-Batton; Charcot-Marie-Tooth Disease Type 2B; Charcot-Marie-Tooth Neuropathy Type 1B; Charcot-Marie-Tooth Neuropathy Type 2A2; Charge Syndrome; Cherubism; Choroideremia; Citrin Deficiency; Citrullinemia Type I; Coffin-Lowry Syndrome; Cohen Syndrome; Collagen 4A5; Common Variable Immune Deficiency; Congenital Adrenal Hyperplasia; Congenital Cataracts, Facial Dysmorphism, and Neuropathy; Congenital Disorder of Glycosylation Type 1a; Congenital Myasthenic Syndromes; Cornelia de Lange Syndrome; Cystic fibrosis; Cystinosis; Darier Disease; Desmin Storage Myopathy; DFNA2 Nonsyndromic Hearing Loss; Diamond-Blackfan Anemia; Double Cortex Syndrome; Duane Syndrome; Duchenne/Becker muscular dystrophy; Dysferlinopathy; Dyskeratosis Congenita; Early-Onset Familial Alzheimer Disease; Early-Onset Primary Dystonia (DYT1); Ehlers Danlos; Ehlers-Danlos Syndrome, Classic Type; Ehlers-Danlos Syndrome, Hypermobility Type; Ehlers-Danlos Syndrome, Kyphoscoliotic Form; Emery-Dreifuss Muscular Dystrophy X linked; Epidermolysis Bullosa Simplex; Fabry Disease; Facioscapulohumeral Muscular Dystrophy; Familial Dysautonomia (HSAN III); Familial Hyperinsulinism (FHI); Familial Hypertrophic Cardiomyopathy; Familial Transthyretin Amyloidosis; Fanconi Anemia; Fragile X; Friedreich Ataxia; FRMD7-Related Infantile Nystagmus; Fryns Syndrome; Galactosemia; Gaucher Disease; Glycine Encephalopathy; Glycogen Storage Disease Type VI; Hemophagocytic Lymphohistiocytosis; Hemophilia A; Hemophilia B; Hepatic Veno-Occlusive Disease with Immunodeficiency; Hereditary Hemorrhagic Telangiectasia; Hereditary Neuropathy with Liability to Pressure Palsies; Hereditary Nonpolyposis Colon Cancer; Hexosaminidase A Deficiency; HFE-Associated Hereditary Hemochromatosis; Holt-Oram Syndrome; Huntington Disease; Hydroxymethylbilane Synthase (HMBS) Deficiency; Hypophosphatasia; Inclusion Body Myopathy 2; Incontinentia Pigmenti; Juvenile Polyposis Syndrome; Kallmann Syndrome; Leber Congenital Amaurosis; Leber congenital amaurosis 10; Li-Fraumeni Syndrome; Limb-Girdle Muscular Dystrophy Type 2A Calpainopathy; LIS1-Associated Lissencephaly; Long QT Syndrome; Lowe Syndrome; Malignant Hyperthermia Susceptibility; Maple Syrup Urine Disease; MAPT-Related Disorders; McKusick-Kaufman Syndrome; MECP2-Rett Syndrome; Menkes; Metachromatic Leukodystrophy; Methylmalonic Acidemia; Mucolipidosis II; Multiple Endocrine Neoplasia Type 1; Multiple Endocrine Neoplasia Type 2; Myotonia Congenita; Myotonic Dystrophy Type 1; Myotonic Dystrophy Type 2; Nail-Patella Syndrome; Nemaline Myopathy; Neurofibromatosis 1; Neurofibromatosis 2; Noonan Syndrome; Ocular Albinism, X-Linked; Oculocutaneous Albinism Type 1; Oculocutaneous Albinism Type 2; Oculopharyngeal Muscular Dystrophy; Optic Atrophy Type 1; Ornithine Transcarbamylase Deficiency; Osteogenesis Imperfecta; Parkinson Disease; Pendred Syndrome; Peroxisome Biogenesis, Zellweger; Phenylketonuria; Polycystic Kidney Disease; Pompe Disease—GSD II; Primary Ciliary Dyskinesia; Retinitis Pigmentosa; Retinoblastoma; Saethre-Chotzen Syndrome;

SCN9A-Related Inherited Erythromelalgia; SHOX-Related Haploinsufficiency; Sickle Cell Disease; Smith-Lemli-Opitz Syndrome; Smith-Magenis Syndrome; Sotos Syndrome; Spastic Paraplegia 3A; Spastic Paraplegia 7; Spastic Paraplegia 8; Spastic Paraplegia Type 1; Spastic Paraplegia Type 4; Spinal Muscular Atrophy; Spinocerebellar Ataxia 2; Spinocerebellar Ataxia 3; Spinocerebellar Ataxia 7; Spinocerebellar Ataxia Type 1; Stickler Syndrome; Thanatophoric Dysplasia; Thoracic Aortic Aneurysms and Aortic Dissections; Treacher Collins Syndrome; Trimethylaminuria; Tuberous Sclerosis Complex; Udd Distal Myopathy; Usher Syndrome type 1; Very Long Chain Acyl-Coenzyme A Dehydrogenase Deficiency; von Hippel-Lindau; Waardenburg Syndrome, Type 1; Werner Syndrome; Wilms Tumor; Wilson Disease; Wiskott-Aldrich; X-Linked Adrenal Hypoplasia Congenita; X-Linked Adrenoleukodystrophy; X-Linked Dystonia-Parkinsonism; X-linked Juvenile Retinoschisis; X-linked myotubular Myopathy; X-Linked SCIDS; and Zellweger Syndrome.

In one embodiment, the mutations associated with a congenital or inherited disease can include substitutions, insertions, inversions, point mutations, deletions, mismatches and translocations. In some embodiments, the mutations associated with an inherited or congenital disease includes copy number variation. In some embodiments, the disclosure relates generally to the selective amplification of at least one target sequence and the detection and/or identification of mutations associated with an inherited disease. In some embodiments, the mutations associated with a congenital or inherited disease can be located in one or more of the genes selected from the group consisting of ABCA4; ABCC8; ABCD1; ACADVL; ACTA2; ACTC; ACTC1; ACVRL1; ADA; AIPL1; AIRE; ALK1; ALPL; AMT; APC; APP; APTX; AR; ARL6; ARSA; ASL; ASPA; ASS; ASS1; ATL; ATM; ATP2A2; ATP7A; ATP7B; ATXN1; ATXN2; ATXN3; ATXN7; BBS6; BCKDHA; BCKDHB; BEST1; BMPR1A; BRCA1; BRCA2; BRIP1; BTD; BTK; C2orf25; CA4; CALR3; CAPN3; CAV3; CCDC39; CCDC40; CDH23; CEP290; CERKL; CFTR; CHAT; CHD7; CHEK2; CHM; CHRNA1; CHRNB1; CHRND; CHRNE; CLCN1; CNBP; CNGB1; COH1; COL11A1; COL11A2; COL1A1; COL1A2; COL2A1; COL3A1; COL4A5; COL5A1; COL5A2; COL7A1; COL9A1; CRB1; CRX; CTDP1; CTNS; CYP21A2; CYP27A1; DAX1; DBT; DCX; DES; DHCR7; DJ1; DKC1; DLD; DMD; DMPK; DNAAF1; DNAAF2; DNAH11; DNAH5; DNAI1; DNAI2; DNAL1; DNM2; DOK7; DSC2; DSG2; DSP; DYSF; DYT1; EMD; ENG; EYA1; EYS; F8; F9; FANCA; FANCC; FANCF; FANCG; FANCJ; FANDC2; FBN1; FBXO7; FGFR1; FGFR3; FMO3; FMR1; FOXL2; FRG1; FRMD7; FSCN2; FXN; GAA; GALT; GBA; GBE1; GCSH; GDF5; GJB2; GJB3; GJB6; GLA; GLDC; GNE; GNPTAB; GPC3; GPR143; GUCY2D; HBA1; HBA2; HBB; HD; HERG; HEXA; HFE; HHF; HIBCH; HLA-B27; HMBS; HPLH1; HPRP3; HR; HTNB; HTT; IKBKAP; IKBKG; IL2RG; IMPDH1; ITGB4; JAG1; JPH3; KCNE1; KCNE2; KCNH2; KCNQ1; KCNQ4; KIAA0196; KLHL7; KRAS; KRT14; KRT5; L1CAM; LAMB3; LAMP2; LDB3; LMNA; LMX18; LRAT; LRRK2; MAPT; MC1R; MECP2; MED12; MEN1; MERTK; MFN2; MKKS; MLH1; MMAA; MMAB; MMACHC; MMADHC; MPZ; MSH2; MTM1; MTND5; MTTG; MTTI; MTTK; MTTL1; MTTQ; MUT; MYBPC3; MYH11; MYH6; MYH7; MYL2; MYL3; MYLK2; MYO7A; ND5; ND6; NEMO; NF1; NF2; NIPBL; NROB1; NR2E3; NRAS; NSD1; OCA2; OCRL; OPA1; OTC; PABPN1; PAFAH1B1; PAH; PARK2; PARK7; PARKIN; PAX3; PAX6; PCDH15; PEX1; PEX2; PEX10; PEX13; PEX14; PEX19; PEX26; PEX3; PEX5; PINK1; PKD1; PKD2; PKD3; PKHD1; PKP2; PLEC1; PLOD1; PMM2; PMP22; POLG; PPT1; PRCD; PRKAG2; PRNP; PROM1; PRPF3; PRPF8; PRPH2; PRPN; PSEN1; PSEN2; PTCH1; PTPN11; RAB7A; RAF1; RAI1; RAPSN; RB1; RDH12; RDS; RECQL3; RET; RHO; ROR2; RP1; RP2; RP9; RPE65; RPGR; RPGRIP1; RPL11; RPL35A; RPS10; RPS17; RPS19; RPS24; RPS26; RPS6KA3; RPS7; RPSL5; RS1; RSPH4A; RSPH9; RYR1; RYR2; SALL4; SCA3; SCN5A; SCN9A; SEMA4A; SERPINAl; SERPINGi; SGCD; SH3BP2; SHOX; SIX1; SIX5; SLC25A13; SLC25A4; SLC26A4; SMAD4; SMN1; SNCA; SNRNP200; SOD1; SOS1; SOX9; SP110; SPAST; SPATA7; SPG3A; SPG4; SPG7; TAF1; TBX5; TCOF1; TGFBR1; TGFBR2; TNFRSC13C; TNNC1; TNNI3; TNNT1; TNNT2; TNXB; TOPORS; TOR1A; TP53; TPM1; TRNG; TRNI; TRNK; TRNL1; TRNQ; TSC1; TSC2; TTN; TTPA; TTR; TULP1; TWIST1; TXNDC3; TYR; USH1C; USH1H; USH2A; VCL; VHL; VPS13B; WAS; WRN; WT1; and ZNF9.

In some embodiments, target-specific primers directed to one or more inherited diseases or congenital disorders can be selected from any one or more of the target-specific primers provided in Table 15 (see U.S. Ser. No. 13/458,739, filed Apr. 27, 2012, hereby incorporated by reference in its entirety). In some embodiments, the target-specific primers from Table 15 (found in U.S. Ser. No. 13/458,739, filed Apr. 27, 2012, hereby incorporated by reference in its entirety) can include 2, 3, 4, 5, 6, 7, 8, 9, 10, 20, 40, 60, 80, 100, 150, 200, 400, 500, 800, 1000, 2000, 3000, 4000, 5000, 6000, 7000, 8000, 9000, 10,000, 11,000, 12,000, 13,000 or more target-specific primers. In some embodiments, the amplified target sequences can include any one or more of the amplified target sequences generated at the genomic coordinates (using amplicon ID target-specific primers) provided in Table 16 (see U.S. Ser. No. 13/458,739, filed Apr. 27, 2012, hereby incorporated by reference in its entirety). In some embodiments, at least one of the target-specific primers associated with a congenital disease or disorder is at least 90% identical to at least one nucleic acid sequence selected from SEQ ID NOs: 1-103,143. In some embodiments, at least one of the target-specific primers associated with a congenital disease or disorder is complementary across its entire length to at least one target sequence in a sample. In some embodiments, at least one of the target-specific primers associated with a congenital disease or disorder includes a non-cleavable nucleotide at the 3' end. In some embodiments, the non-cleavable nucleotide at the 3' end includes the terminal 3' nucleotide. In one embodiment, target sequences or resulting amplified target sequences are directed to individual exons having a mutation associated with an inherited disease. In some embodiments, congenital or inherited disease amplified target sequences can include two or more target-specific primers provided in Table 15 (from U.S. Ser. No. 13/458,739, filed Apr. 27, 2012, hereby incorporated by reference in its entirety) or Table 8 of US Application 61/598,881 hereby incorporated by reference in its entirety. In some embodiments, the amplified target sequences can include any one or more of the amplified target sequences generated at the genomic coordinates using the amplicon ID target-specific primers provided in Table 16 (from U.S. Ser. No. 13/458,739, filed Apr. 27, 2012, hereby incorporated by reference in its entirety) or Table 9 of US Application 61/598,881 hereby incorporated by reference in its entirety. In some embodiments, congenital or inherited disease amplified target sequences can include two or more target-specific primers provided in Table 15 (found in U.S.

Ser. No. 13/458,739, filed Apr. 27, 2012, hereby incorporated by reference in its entirety). In some embodiments, the amplified target sequences can include any one or more of the amplified target sequences generated at the genomic coordinates using the amplicon ID target-specific primers provided in Table 16 (found in U.S. Ser. No. 13/458,739, filed Apr. 27, 2012, hereby incorporated by reference in its entirety). In one embodiment, the congenital or inherited disease target-specific primers can include any one or more of the target-specific primers provided in Table 8 of US Application 61/598,881 hereby incorporated by reference in its entirety. In some embodiments, any one or more target-specific primers can be designed using the target-specific primer selection criteria outlined herein. In some embodiments, the disclosure relates generally to the selective amplification of more than one target sequence in a sample and the detection and/or identification of mutations associated with a congenital or inherited disease. In one embodiment, the disclosure relates generally to the amplification of a plurality of target sequences linked to, or correlated with a congenital or inherited disease.

In some embodiments, the target-specific primers are prepared to amplify regions or fragments of the human genome associated with a congenital or inherited disease. In some embodiments, the target-specific primers can be prepared to amplify regions of the human genome associated with heredity disorders, such as cystic fibrosis, Alagille syndrome, Alpers syndrome, Alpha-Thalassemia, Amyotrophic Lateral Sclerosis, Anklosing spondylitis, Ataxia-Telangiectasia, congenital Myasthenic syndromes, Darier disease, Diamond-Blackfan anemia, early onset familial Alzheimer disease, Ehlers-Danlos syndrome, Epidermolysis Bullosa Simplex, familial Hypertrophic Cardiomyopathy, Fanconi anemia, Glycine Encephalopathy, Hereditary Hemorrhagic Telangiectasia, Huntington Disease, Juvenile Polyposis syndrome, Leber Congential Amaurosis, Long QT syndrome, Maple Syrup Urine Disease, Marfan syndrome, Mitochondrial Encephalomyopathy, Methylmalonic Acidemia, Multiple Endocrine Neoplasia Type 2, Noonan syndrome, Parkinson disease, Peroxisome Biogenesis, Primary Cilary Dyskineasia, Retinitis Pigmentosa, Stickler syndrome, Thoracic Aortic Aneurysms and Aortic Dissections, Tuberous Sclerosis Complex, Usher syndrome, Werner syndrome, Wilson disease and Zellweger syndrome. In some embodiments, the target-specific primers can be prepared from any one or more of the genes provided in Table 4 (found in U.S. Ser. No. 13/458,739, filed Apr. 27, 2012, hereby incorporated by reference in its entirety).

In some embodiments, the disclosure relates generally to detecting the presence of a target sequence or amplified target sequence associated with one or more newborn disorders. In some embodiments, the disclosure relates generally to detecting the presence of an amplified target sequence obtained by amplifying a sample containing at least one target sequence associated with a newborn disorder with one or more target-specific primers disclosed herein. In some embodiments, the disclosure relates generally to detecting the presence of an amplified target sequence obtained by amplifying a sample containing at least one target sequence associated with a newborn disorder and a target-specific primer designed according to the primer criteria provided herein.

In some embodiments, the one or more newborn disorders can include 2-methyl-3-hydroxybutyric aciduria (2M3HBA); 2-methylbutyryl-CoA dehydrogenase (2MBG); 3-methylglutaconic aciduria (3MGA); argininemia (ARG); defects of biopterin cofactor biosynthesis (BIOPT-BS); defects of biopterin cofactor regeneration (BIOPT-REG); carnitine acylcarnitine translocase (CACT); methylmalonic acidemia (CBL-C,D); citrullinemia type II (CIT-II); carnitine palmitoyltransferase I (CPT-Ia); carnitine palmitoyltransferase II (CPT-II); Dienoyl-CoA reductase (De-Red); Glutaric acidemia type II (GA-II); galactose epimerase (GALE); galactokinase (GALK); benign hyperphenylalaninemia (H-PHE); isobutyryl-CoA dehydrogenase (IBG); medium/short chain L-3-hydroxy acyl-CoA dehydrogenase (M/SCHAD); malonic acidemia (MAL); medium chain ketoacyl-CoA thiolase (MCKAT); hypermethioninemia (MET); short chain acyl-CoA dehydrogenase (SCAD); Tyrosinemia type II (TYR-II); tyrosinemia type III (TYR-III); Biotinidase (BIO); Cystic fibrosis (CF); Transferase deficient galactosemia (GALT); Sickle—C disease (HB S/C); Congenital adrenal hyperplasia (CAH); Congenital hypothyroidism (CH); Sickle cell anemia (HB S/S); S-βeta thalassemia (HB S/A); (SCID) Severe Combined Immunodeficiency; 5-oxoprolinuria (pyroglutamic aciduria) (5-OXO); Glucose 6 phosphate dehydrogenase (G6PD); Nonketotic hyperglycinemia (NKH); Carbamoylphosphate synthetase (CPS); Hyperammonemia/ornithinemia/citrullinemia (Ornithine transporter defect) (HHH); Prolinemia (PRO); Ethylmalonic encephalopathy (EMA); Human immunodeficiency virus (HIV); Toxoplasmosis (TOXO); 3-Methylcrotonyl-CoA carboxylase (3-MCC); Carnitine uptake defect (CUD); Long-chain L-3-hydroxyacyl-CoA dehydrogenase (LCHAD); Phenylketonuria/Hyperphenylalaninemia (PKU); Argininosuccinate aciduria (ASA); Glutaric acidemia type 1 (GA-1); Medium-chain acyl-CoA dehydrogenase (MCAD); Propionic acidemia (Propionyl-CoA carboxylase) (PROP); Beta ketothiolase (mitochondrial acetoacetyl-CoA thiolase; short-chain ketoacyl thiolase; T2) (BKT); Homocystinuria (cystathionine beta synthase) (HCY); Multiple carboxylase (Holocarboxylase synthetase) (MCD); Trifunctional protein deficiency (TFP); Methylmalonic academia (Vitamin B12 Disorders) (CBL A,B); 3-Hydroxy 3-methylglutaric aciduria (3-Hydroxy 3-methylglutaryl-CoA lyase) (HMG); Maple syrup urine disease (branched-chain ketoacid dehydrogenase) (MSUD); Tyrosinemia Type 1 (TYR-1); Citrullinemia type I (Argininosuccinate synthetase) (CIT I); Isovaleric acidemia (Isovaleryl-CoA dehydrogenase) (IVA); Methylmalonic Acidemia (methylmalonyl-CoA mutase) (MUT); and very long-chain acyl-CoA dehydrogenase (VLCAD).

In some embodiments, the disclosure relates generally to target-specific primers for the detection of newborn screening disorders. In some embodiments, target-specific primers for newborn disorders including the disorders provided above can be prepared using the primer criteria disclosed herein. In some embodiments, the disclosure relates generally to detecting a newborn disorder by contacting a sample that may contain one or more target sequences for one or more newborn disorders and amplifying the one or more target sequences in the sample, thereby obtaining at least one amplified target sequence associated with at least one newborn disorder. In some embodiments, a plurality of target-specific primers can be designed to amplify a plurality of target sequences from a sample, thereby providing a means to detect a plurality of newborn disorders optionally, in a single method or procedure. In some embodiments, target-specific primers designed to amplify a plurality of amplified target sequences associated with one or more newborn disorders can be pooled and provided as a newborn screening panel.

In some embodiments, target sequences or amplified target sequences are directed to nucleic acids obtained from a forensic sample. In one embodiment, forensic samples can include nucleic acids obtained from a crime scene, nucleic acids obtained from a missing persons DNA database, nucleic acids obtained from a laboratory associated with a forensic investigation or include forensic samples obtained by law enforcement agencies, one or more military services or any such personnel. In some embodiments, target sequences can be present in one or more bodily fluids including but not limited to, blood, sputum, plasma, semen, urine and serum. In some embodiments, target sequences can be obtained from hair, skin, tissue samples, autopsy or remains of a victim. In some embodiments, nucleic acids including one or more target sequences can be obtained from a deceased animal or human. In some embodiments, target sequences can include nucleic acids obtained from non-human DNA such a microbial, plant or entomological DNA. In some embodiments, target sequences or amplified target sequences are directed to purposes of human identification. In some embodiments, the disclosure relates generally to methods for identifying a nucleic acid sample from an animal, including a human. In some embodiments, the disclosure relates generally to methods for identifying characteristics of a forensic sample. In some embodiments, the disclosure relates generally to human identification methods using one or more target-specific primers disclosed herein or one or more target-specific primers prepared using the primer criteria outlined herein.

In one embodiment, a forensic or human identification sample containing at least one target sequence can be amplified using any one or more of the target-specific primers disclosed herein or using the primer criteria outlined herein. In some embodiments, a forensic or human identification sample containing one or more target sequences can be identified by amplifying the at least one or more target sequences with any one or more target-specific primers provided in Tables 13 and 14 (both found in U.S. Ser. No. 13/458,739, filed Apr. 27, 2012, hereby incorporated by reference in its entirety). Table 13 (from U.S. Ser. No. 13/458,739, filed Apr. 27, 2012, hereby incorporated by reference in its entirety) provides a plurality of target-specific primers, provided as primer pairs, directed to single nucleotide polymorphisms (SNPs) associated with human identification. Table 14 (from U.S. Ser. No. 13/458,739, filed Apr. 27, 2012, hereby incorporated by reference in its entirety) provides a plurality of target-specific primers, provided as primer pairs, directed to short tandem repeats (STRs) associated with human identification. An individual inherits one copy of an STR from each parent, which may or may not have similar repeat sizes. The number of repeats in STR markers can be highly variable among individuals, which makes STRs effective for human identification purposes. In some embodiments, targets-specific primers such as those provided in Table 14 (from U.S. Ser. No. 13/458, 739, filed Apr. 27, 2012, hereby incorporated by reference in its entirety), or target-specific primers prepared as disclosed herein, that are directed to the gene amelogenin (AMG) can be used to determine the sex of the individual providing the sample. For example, primers to the amelogenin gene can be prepared using the criteria disclosed herein that are specific, for example, to intron 1. Once a sample is amplified using such target-specific primers, the amplification product from a male sample versus a female sample will generally result in amplification products (amplified target sequences) that differ by in length by several nucleotides and therefore provides a simple method by which to determine the sex of the individual providing the sample.

In one embodiment, a sample containing one or more target sequences can be amplified using any one or more of the target-specific primers disclosed herein. In another embodiment, amplified target sequences obtained using the methods (and associated compositions, systems, apparatuses and kits) disclosed herein, can be coupled to a downstream process, such as but not limited to, nucleic acid sequencing. For example, once the nucleic acid sequence of an amplified target sequence is known, the nucleic acid sequence can be compared to one or more reference samples such as Hg19 genome. The Hg19 genome is commonly used in the genomics field as a reference genome sample for humans. In some embodiments, a sample suspected of containing one or more SNPs and/or STRs can be identified by amplifying the sample suspected of containing the SNP or STR with any one or more of the target-specific primers provided in Tables 13 and 14 (both tables found in U.S. Ser. No. 13/458,739, filed Apr. 27, 2012, hereby incorporated by reference in its entirety). Consequently, the output from the amplification procedure can be optionally analyzed for example by nucleic acid sequencing to determine if the expected amplification product based on the target-specific primers is present in the amplification output. The identification of an appropriate SNP or STR amplification product can in some instances provide additional information regarding the source of the sample or it characteristics (e.g., a male or female sample or a sample of particular ancestral origin).

It is envisaged that one of ordinary skill in the art can readily prepare one or more target-specific primers using the primer criteria disclosed herein without undue experimentation. It is also envisaged that one of ordinary skill in the art can readily prepare one or more target-specific primers using the criteria disclosed herein, to identify at least one medically relevant polymorphism. In some instances, a medically relevant polymorphism can be used in forensic or human identification purposes. Generally, a medically relevant polymorphism includes a polymorphism that is associated with at least one disease state in multiple populations (e.g., a European Caucasian population). In some embodiments, a medically relevant polymorphism includes any one or more of the polymorphisms outlined below.

| Polymorphism | Caucasian MAF | Chromosome | Gene | Disease Associated with Polymorphism |
| --- | --- | --- | --- | --- |
| rs1137101 | 0.449 | 1p31 | LEPR | Obesity, Insulin Resistance, Non-Hodgkin's lymphoma |
| rs486907 | 0.408 | 1q25 | RNASEL | Prostate cancer |
| rs1042031 | 0.208 | 2p24 | APOB | Cardiovascular disease, Dislipidemia |
| rs231775 | 0.379 | 2q33 | CTLA4 | Multiple Sclerosis, Autoimmune Disease |
| rs5186 | 0.348 | 3q21 | AGTR1 | Metabolic syndrome, Aortic aneurism, Left-ventricular hypertrophy |
| rs6280 | 0.35 | 3q13.3 | DRD3 | Schizophrenia |
| rs1693482 | 0.477 | 4q21 | ADH1C | Alcohol dependence, Coronary heart disease |

-continued

| Polymorphism | Caucasian MAF | Chromosome | Gene | Disease Associated with Polymorphism |
|---|---|---|---|---|
| rs1799883 | 0.373 | 4q28 | FABP2 | Metabolic syndrome, Type 2 diabetes |
| rs4444903 | 0.392 | 4q25 | EGF | Cancer |
| rs4961 | 0.208 | 4p16.3 | ADD1 | Hypertension, Coronary artery disease |
| rs1042714 | 0.467 | 5q31 | ADRB2 | Obesity, COPD |
| rs351855 | 0.283 | 5q35.1 | FGFR4 | Cancer |
| rs5370 | 0.242 | 6p24 | EDN1 | Asthma, sleep apnea |
| rs6296 | 0.322 | 6q13 | HTR1B | Substance abuse |
| rs2227983 | 0.25 | 7p12.3 | EGFR | Cancer |
| rs213950 | 0.492 | 7q31.2 | CFTR | Cystic fibrosis |
| rs7493 | 0.237 | 7q21.3 | PON2 | Myocardial infarction |
| rs328 | 0.273 | 8p22 | LPL | Left ventricular hypertrophy |
| rs2383206 | 0.475 | 9p21 | | Coronary artery disease |
| rs1800861 | 0.25 | 10q11.2 | RET | Hirschsprung, disease, Thyroid cancer |
| rs1801253 | 0.283 | 10q24 | ADRB1 | Insulin Resistance |
| rs2227564 | 0.341 | 10q24 | PLAU | Alzheimer's disease, Asthma |
| rs1799750 | 0.433 | 11q22.3 | MMP1 | Endometriosis, Osteolysis, Rheumatoid arthritis |
| rs1063856 | 0.342 | 12p13.3 | VWF | Hypertension |
| rs6313 | 0.438 | 13q14 | HTR2A | Psychiatric disorders |
| rs2236225 | 0.396 | 14q24 | MTHFD1 | Neural tube defects |
| rs1800588 | 0.333 | 15q21 | LIPC | Coronary artery disease |
| rs243865 | 0.198 | 16q13 | MMP2 | Cancer |
| rs4673 | 0.342 | 16q24 | CYBA | Coronary artery disease |
| rs708272 | 0.478 | 16q21 | CETP | Coronary artery disease |
| rs1800012 | 0.188 | 17q21.3 | COL1A1 | Osteoporosis |
| rs4291 | 0.354 | 17q23 | ACE | Depression, Alzheimer's disease |
| rs4792311 | 0.331 | 17p11 | ELAC2 | Prostate cancer |
| rs16430 | 0.37 | 18p11.3 | ENOSF1/TYMS | Cancer |
| rs601338 | 0.391 | 19q13.3 | FUT2 | Infection susceptibility |
| rs688 | 0.45 | 19p13.2 | LDLR | Alzheimer's disease, Coronary artery disease |
| rs7121 | 0.458 | 20q13.3 | GNAS | Obesity, Cancer |
| rs234706 | 0.333 | 21q22 | CBS | Oral cleft defects |
| rs4680 | 0.483 | 22q11.21 | COMT | Schizophrenia, ADHD |
| AMG | 0.5 | Xp22.3 | AMG | Sex Marker |

In some embodiments, a medically relevant polymorphism can be present within a single exon of the corresponding disease associated gene. In some embodiments, the disclosure relates generally to the selective amplification of at least one target sequence in a sample and the detection and/or identification of a medically relevant polymorphism. In some embodiments, the disclosure relates generally to the selective amplification of at least one target sequence in a sample and the detection and/or identification of a SNP or STR. In some embodiments, amplified target sequences can be generated by amplifying a sample with one or more target-specific primers of Tables 13 or 14 (both tables found in U.S. Ser. No. 13/458,739, filed Apr. 27, 2012, hereby incorporated by reference in its entirety). In some embodiments, the amplified target sequences can include any one or more of the amplified target sequences generated at the genomic coordinates provided in the polymorphism table above. In one embodiment, an amplified target sequence can be prepared using one or more of the target-specific primers from Tables 13 or 14 (both from U.S. Ser. No. 13/458,739, filed Apr. 27, 2012, hereby incorporated by reference in its entirety). In some embodiments, any one or more target-specific primers corresponding to SEQ ID NOs: 50354-50451 can be used to selectively amplify at least one target sequence present in a sample. In some embodiments, at least one target-specific primer selected from SEQ ID NOs: 50354-50451 can be used to amplify a target sequence from a sample for the purposes of forensic or human identification.

In some embodiments, target-specific primers directed to human identification can be selected from any one or more of the target-specific primers provided in Tables 13 or 14 (from U.S. Ser. No. 13/458,739, filed Apr. 27, 2012, hereby incorporated by reference in its entirety). In some embodiments, the target-specific primers from Tables 13 or 14 (found in U.S. Ser. No. 13/458,739, filed Apr. 27, 2012, hereby incorporated by reference in its entirety) can include 1, 2, 3, 4, 5, 6, 7, 8, 9, 10, 15, 20, 22, 25, 27, 30, 35, 38, 40, 42, 45 or more target-specific primers. In some embodiments, at least one of the target-specific primers associated with human identification is at least 90% identical to at least one of the target-specific primers provided in Tables 13 or 14 (from U.S. Ser. No. 13/458,739, filed Apr. 27, 2012, hereby incorporated by reference in its entirety). In some embodiments, at least one of the target-specific primers associated with human identification is complementary across its entire length to at least one target sequence in a sample. In some embodiments, at least one of the target-specific primers associated with human identification includes a non-cleavable nucleotide at the 3' end. In some embodiments, the non-cleavable nucleotide at the 3' end includes the terminal 3' nucleotide.

In some embodiments, the disclosure relates generally to methods (and associated compositions, systems, apparatuses and kits) for reducing the formation of amplification artifacts in a multiplex PCR. In some embodiments, primer-dimers or non-specific amplification products are obtained in lower number or yield as compared to standard multiplex PCR of the prior art. In some embodiments, the reduction in amplification artifacts is in part, governed by the use of target-specific primer pairs in the multiplex PCR reaction. In one embodiment, the number of target-specific primer pairs in the multiplex PCR reaction can be greater than 1000, 3000, 5000, 10000, 12000, or more. In some embodiments, the disclosure relates generally to methods (and associated compositions, systems, apparatuses and kits) for performing multiplex PCR using target-specific primers that contain a cleavable group. In one embodiment, target-specific primers containing a cleavable group can include one or more cleavable moieties per primer of each primer pair. In some embodiments, a target-specific primer containing a cleavable group includes an nucleotide neither normally present in a non-diseased sample nor native to the population of nucleic acids undergoing multiplex PCR. For example, a target-specific primer can include one or more non-native nucleic acid molecules such as, but not limited to thymine dimers, 8-oxo-2'-deoxyguanosine, inosine, deoxyuridine, bromodeoxyuridine, apurinic nucleotides, and the like.

In some embodiments, the disclosed methods (and associated compositions, systems, etc.,) involve performing a primary amplification of target sequences from a population of nucleic acids, optionally using target-specific primers. In some embodiments, the disclosed methods involve amplifying target sequences using target-specific forward and reverse primer pairs. The target-specific forward and reverse primer pairs can optionally include one or more intron-specific and/or exon specific forward and reverse primer pairs. In some embodiments, each primer pair is directed to a single or discrete exon. In some embodiments, the disclosed methods involve amplifying target sequences using exon-specific forward and reverse primer pairs containing at least one cleavable group. In some embodiments, the target-specific forward and reverse primer pairs contain a uracil nucleotide as the one or more cleavable groups. In one embodiment, a target-specific primer pair can include a uracil nucleotide in each of the forward and reverse primers of each primer pair. In one embodiment, a target-specific forward or reverse primer contains one, two, three or more uracil nucleotides. In some embodiments, the disclosed methods involve amplifying at least 10, 50, 100, 200, 500, 1000, 2000, 3000, 5000, 6000, 8000, 10000, 12000 or more, target sequences from a population of nucleic acids having a plurality of target sequences using target-specific forward and reverse primer pairs containing at least two uracil nucleotides.

In some embodiments, target-specific primers (including but not limited to intron-specific and exon-specific primers, which can be forward and/or reverse primers) can be designed de novo using algorithms that generate oligonucleotide sequences according to specified design criteria. For example, the primers may be selected according to any one or more of criteria specified herein. In some embodiments, one or more of the target-specific primers are selected or designed to satisfy any one or more of the following criteria: (1) inclusion of two or more modified nucleotides within the primer sequence, at least one of which is included near or at the termini of the primer and at least one of which is included at, or about the center nucleotide position of the primer sequence; (2) primer length of about 15 to about 40 bases in length; (3) $T_m$ of from about 60° C. to about 70° C.; (4) low cross-reactivity with non-target sequences present in the target genome or sample of interest; (5) for each primer in a given reaction, the sequence of at least the first four nucleotides (going from 3' to 5' direction) are not complementary to any sequence within any other primer present in the same reaction; and (6) no amplicon includes any consecutive stretch of at least 5 nucleotides that is complementary to any sequence within any other amplicon.

In some embodiments, the target-specific primers include one or more primer pairs designed to amplify target sequences from the sample that are about 100 base pairs to about 500 base pairs in length. In some embodiments, the target-specific primers include a plurality of primer pairs designed to amplify target sequences, where the amplified target sequences are predicted to vary in length from each other by no more than 50%, typically no more than 25%, even more typically by no more than 10%, or 5%. For example, if one target-specific primer pair is selected or predicted to amplify a product that is 100 nucleotides in length, then other primer pairs are selected or predicted to amplify products that are between 50-150 nucleotides in length, typically between 75-125 nucleotides in length, even more typically between 90-110 nucleotides, or 95-105 nucleotides, or 99-101 nucleotides in length.

In some embodiments, at least one primer pair in the amplification reaction is not designed de novo according to any predetermined selection criteria. For example, at least one primer pair can be an oligonucleotide sequence selected or generated at random, or previously selected or generated for other applications. In one exemplary embodiment, the amplification reaction can include at least one primer pair selected from the TaqMan® probe reagents (Roche Molecular Systems). The TaqMan® reagents include labeled probes and can be useful, inter alia, for measuring the amount of target sequence present in the sample, optionally in real time. Some examples of TaqMan technology are disclosed in U.S. Pat. Nos. 5,210,015, 5,487,972, 5,804,375, 6,214,979, 7,141,377 and 7,445,900, hereby incorporated by reference in their entireties.

In some embodiments, at least one primer within the amplification reaction can be labeled, for example with an optically detectable label, to facilitate a particular application of interest. For example, labeling may facilitate quantification of target template and/or amplification product, isolation of the target template and/or amplification, product, and the like.

In some embodiments, one or more of the primers within the amplification reaction can be useful in genotyping of a nucleic acid sample.

In some embodiments, the target-specific primers can be provided as a set of target-specific primer pairs in a single amplification vessel. In some embodiments, the target-specific primers can be provided in one or more aliquots of target-specific primer pairs that can be pooled prior to performing the multiplex PCR reaction in a single amplification vessel or reaction chamber. In one embodiment, the target-specific primers can be provided as a pool of target-specific forward primers and a separate pool of target-specific reverse primers. In another embodiment, target-specific primer pairs can be pooled into subsets such as non-overlapping target-specific primer pairs. In some embodiments, the pool of target-specific primer pairs can be provided in a single reaction chamber or microwell, for example on a PCR plate to perform multiplex PCR using a thermocycler. In some embodiments, the target-specific forward and reverse primer pairs can be substantially complementary to the target sequences.

In some embodiments, the method of performing multiplex PCR amplification includes contacting a plurality of target-specific primer pairs having a forward and reverse primer, with a population of target sequences to form a plurality of template/primer duplexes; adding a DNA polymerase and a mixture of dNTPs to the plurality of template/primer duplexes for sufficient time and at sufficient temperature to extend either (or both) the forward or reverse primer in each target-specific primer pair via template-dependent synthesis thereby generating a plurality of extended primer product/template duplexes; denaturing the extended primer product/template duplexes; annealing to the extended primer product the complementary primer from the target-specific primer pair; and extending the annealed primer in the presence of a DNA polymerase and dNTPs to form a plurality of target-specific double-stranded nucleic acid molecules. In some embodiments, the steps of the amplification PCR method can be performed in any order. In some instances, the methods disclosed herein can be further optimized to remove one or more steps and still obtain sufficient amplified target sequences to be used in a variety of downstream processes. For example, the number of purification or clean-up steps can be modified to include more or less steps than disclose herein, providing the amplified target sequences are generated in sufficient yield.

In some embodiments, the target-specific primer pairs do not contain a common extension (tail) at the 3' or 5' end of the primer. In another embodiment, the target-specific primers do not contain a Tag or universal sequence. In some embodiments, the target-specific primer pairs are designed to eliminate or reduce interactions that promote the formation of non-specific amplification.

In one embodiment, the target-specific primer pairs comprise at least one cleavable group per forward and reverse target-specific primer. In one embodiment, the cleavable group can be a uracil nucleotide. In one embodiment, the target-specific primer pairs are partially or substantially removed after generation of the amplified target sequence. In one embodiment, the removal can include enzymatic, heat or alkali treatment of the target-specific primer pairs as part of the amplified target sequence. In some embodiments, the amplified target sequences are further treated to form blunt-ended amplification products, referred to herein as, blunt-ended amplified target sequences.

In some embodiments, any one or more of the target-specific primers disclosed in the methods, compositions, kits, systems and apparatuses may be designed using the following primer selection criteria.

There is a need for new methods, computer readable media, and systems for identifying or designing products or kits that use PCR to enrich one or more genomic regions of interest (which may be, for example, cumulative regions of 1 kb to 1 Mb) for subsequent sequencing.

There is a need for new methods, computer readable media, and systems for identifying or designing products or kits including primers or assays that maximize coverage of one or more genomic regions or targets of interest while minimizing one or more of off-target hybridization, a number of primers, and a number of primer pools.

In accordance with the teachings and principles embodied in this application, new methods, computer readable media, and systems are provided that identify or design products or kits that use PCR to enrich one or more genomic regions or targets of interest for subsequent sequencing and/or that include primers or assays that maximize coverage of one or more genomic regions or targets of interest while minimizing one or more of off-target hybridization, a number of primers, and a number of primer pools.

Figure 16:
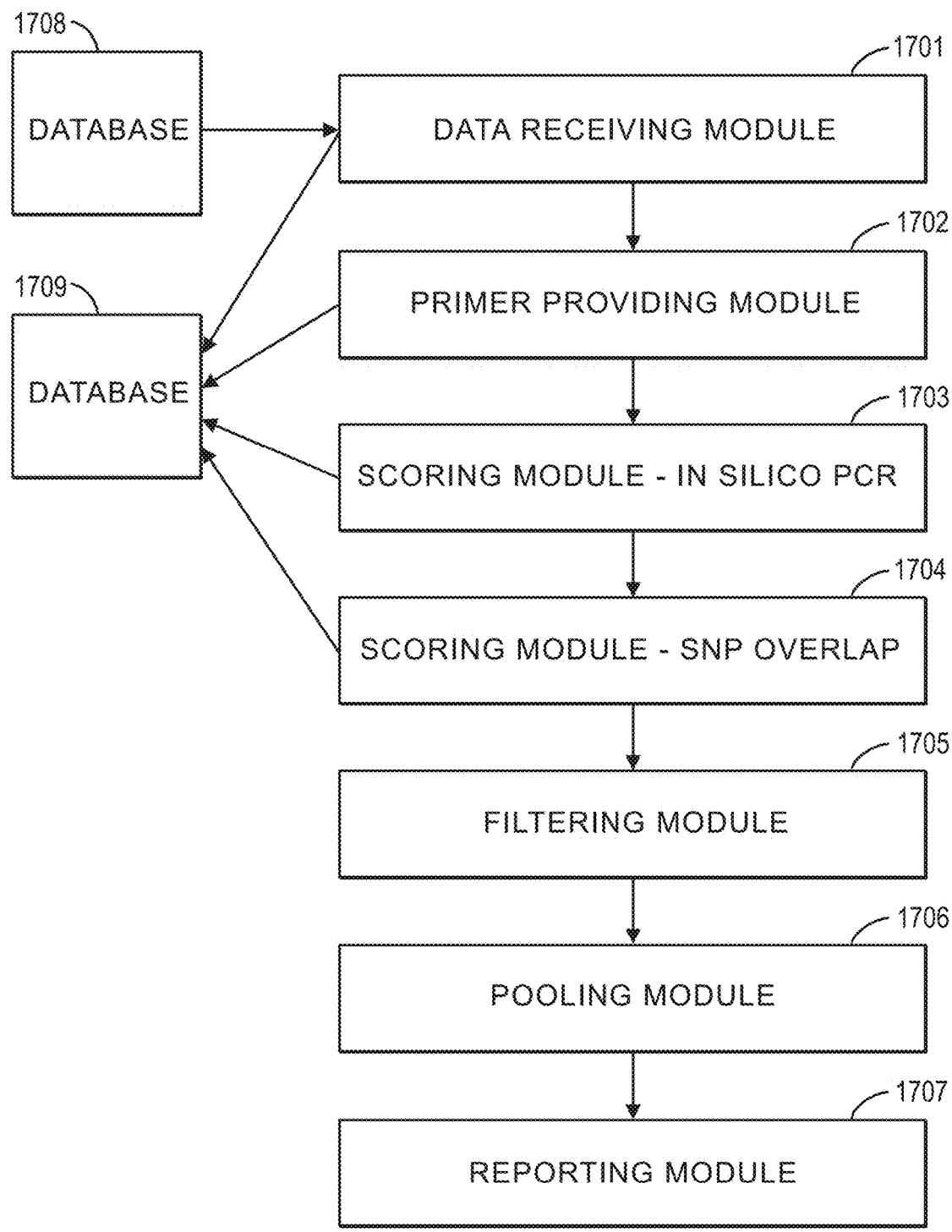
FIG. 16 illustrates a system for designing primers or assays according to an exemplary embodiment.

FIG. 16 illustrates a system for designing primers or assays according to an exemplary embodiment. The system includes a data receiving module 1701, a primer providing module 1702, a scoring (in silico PCR) module 1703, a scoring (SNP overlap) module 1704, a filtering module 1705, a pooling module 1706, and a reporting module 1707. The system also includes a database 1708, which may include data regarding genetic annotations, SNP-related data, or other genetic data such as identification of a repeat, chromosome, position, direction, etc., for example, or any other type of information that could be related to a genomic region or target of interest, and a database 1709, which may include primer-related data such as a melting temperature (Tm), a chromosome, a position, a direction, and SNP overlap information, etc., for example, or any other type of information that could be related to primers. The system may be implemented in or using one or more computers and/or servers using one or more software components, which may not be accessible or released to customers who may be ordering custom primers or assays that may be designed using such a system. Customers may order custom primers or assays at least in part through a web-accessible data portal by providing one or more genomic regions or targets of interest in any suitable format. In an exemplary embodiment, there is provided a method performing steps including the general steps associated with modules 1701-1707 and databases 1708 and 1709 (e.g., receiving data, providing primers, scoring primers and/or amplicons, filtering primers and/or amplicons, pooling primers and/or amplicons, reporting results, and querying databases).

Figure 17:
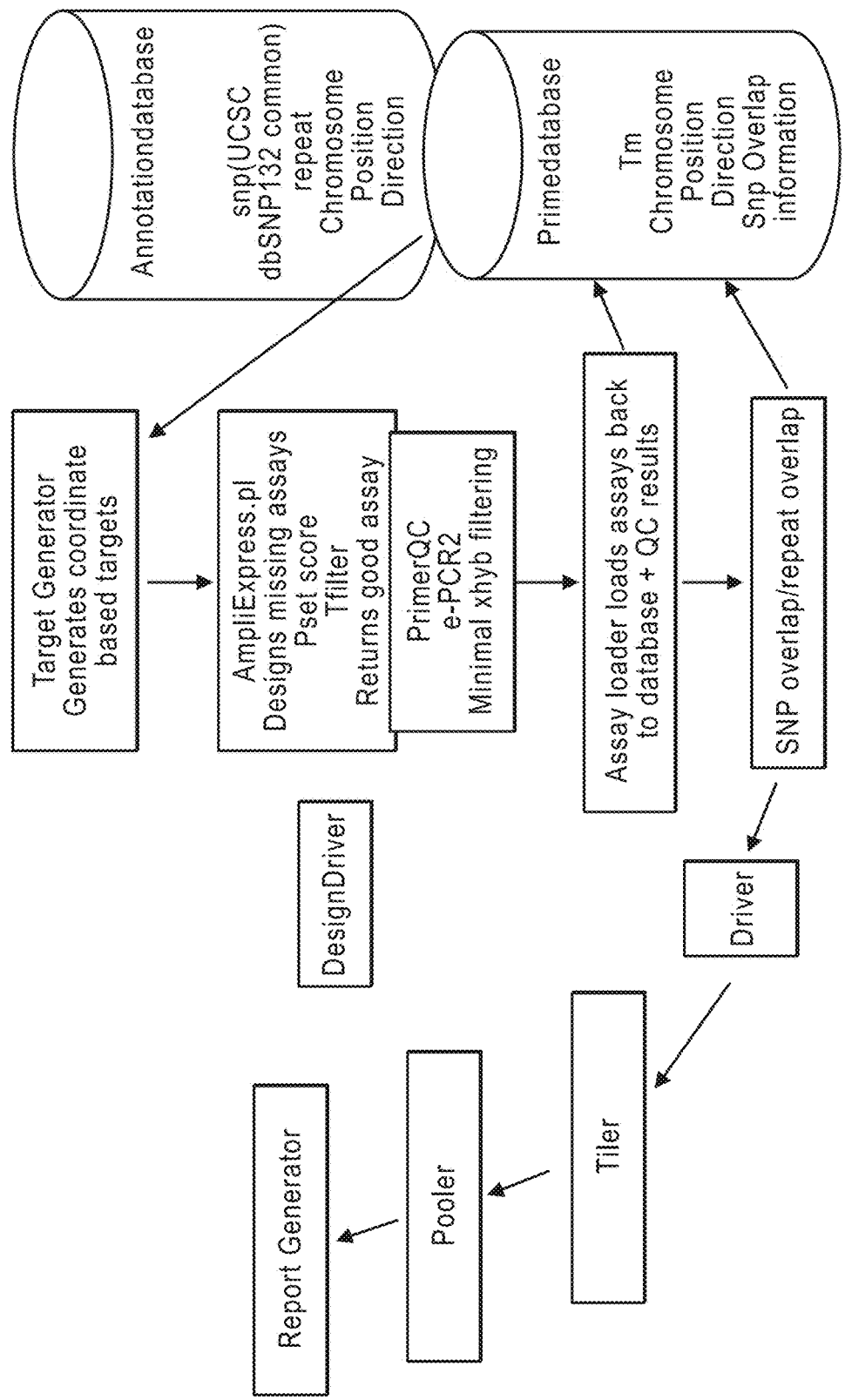
FIG. 17 illustrates a system for designing primers or assays according to an exemplary embodiment.

FIG. 17 illustrates a system for designing primers or assays according to an exemplary embodiment. The system includes a target generator module, which may generate one or more coordinate-based genomic regions or targets of interest and which may query and/or receive information from an annotation database (which may include data regarding genetic annotations, SNP-related data, or other genetic data such as identification of a repeat, chromosome, position, direction, etc., for example, as well as information regarding primers or any other type of information that could be related to a genomic region or target of interest); a designing module, which may design one or more primers or assays and determine and/or apply various scoring and filtering procedures for the primers or assays and which may perform various quality control procedures; a loader module, which may load the primers or assays and/or related information (such as quality control results, for example) to a primer database (which may be in communication with or comprised within the annotation database and which may include primer-related data such as a melting temperature (Tm), a chromosome, a position, a direction, and SNP overlap information, etc., for example, or any other type of information that could be related to primers); a SNP overlap/repeat overlap module; a driver module; a tiler module, which may determine a subset of amplicons or tiles maximizing a coverage of a genomic region or target of interest; a pooler module, which may determine a pooling of the amplicons or tiles into one or more pools of amplicons; and a report generator module. The system may be implemented in or using one or more computers and/or servers using one or more software components, which may not be accessible or released to customers who may be ordering custom primers or assays that may be designed using such a system. Customers may order custom primers or assays at least in part through a web-accessible data portal by providing one or more genomic regions or targets of interest in any suitable format. In an exemplary embodiment, there is provided a method performing steps including the general steps associated with these modules and databases.

Figure 18:
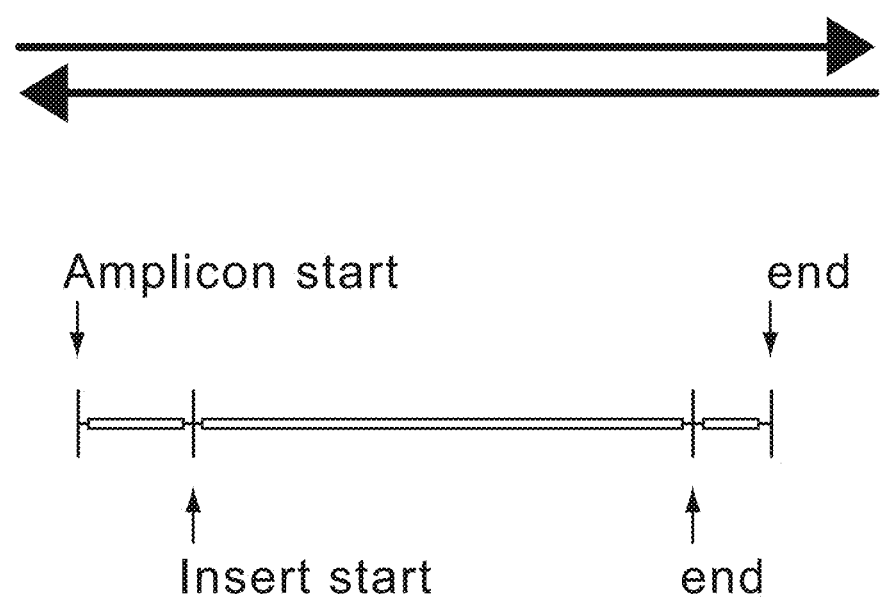
FIG. 18 illustrates an amplicon sequence including an insert sequence surrounded by a pair of primers designed according to an exemplary embodiment.

FIG. 18 illustrates an amplicon sequence including an insert sequence surrounded by a pair of primers designed according to an exemplary embodiment. The amplicon may include a forward primer and a reverse primer surrounding the insert sequence. The two primers may together form an assay, which may be customized and ordered. The primer component of an amplicon may be a copy of a spiked-in primer, rather than the underlying sample, and one or more inserts may be selected to cover the target.

Figure 19:
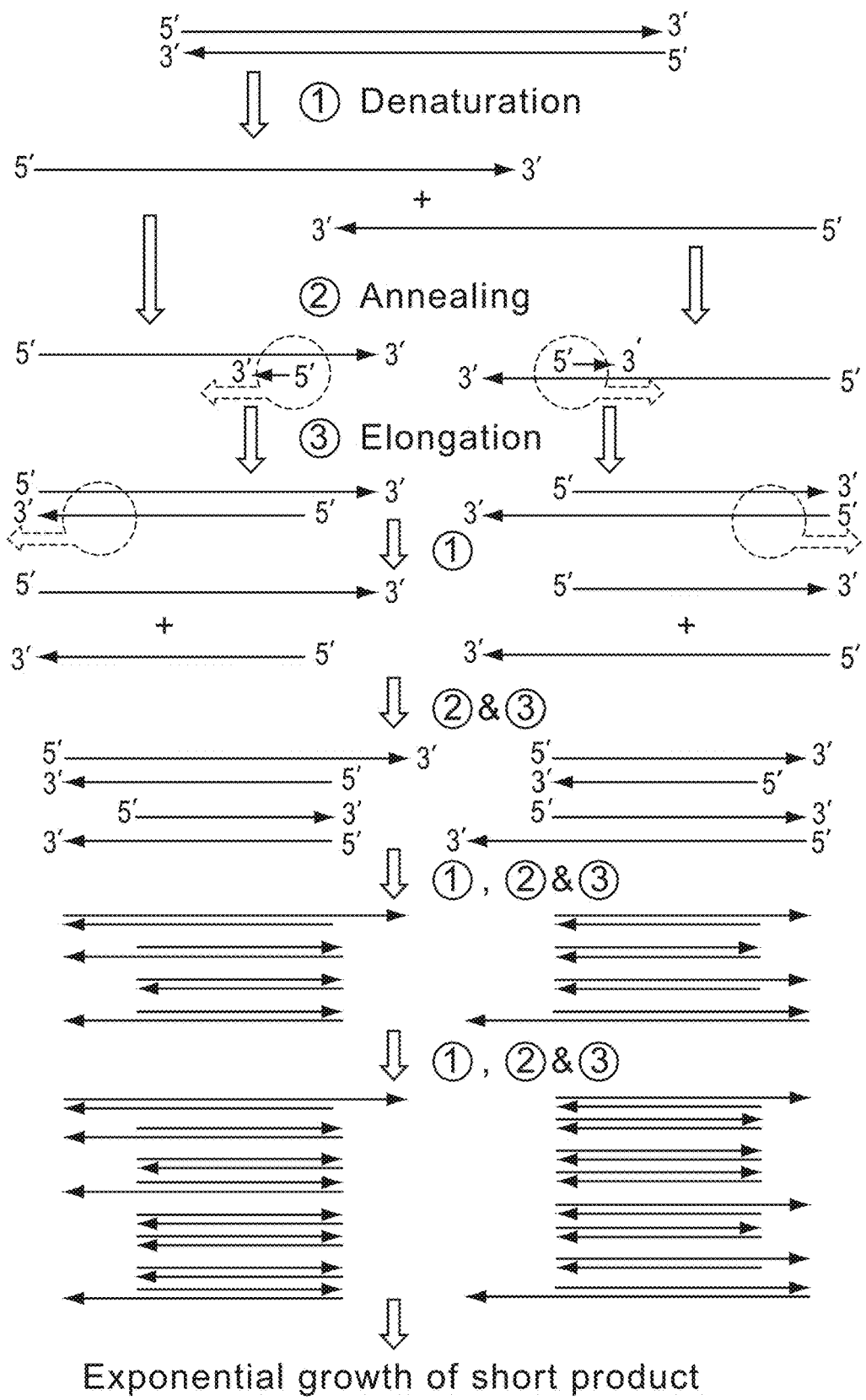
FIG. 19 illustrates PCR amplification of an amplicon sequence (which may be referred to as "tile" herein) including an insert surrounded by a pair of primers designed according to an exemplary embodiment.

FIG. 19 illustrates PCR amplification of an amplicon sequence (which may be referred to as "tile" herein) including an insert surrounded by a pair of primers designed according to an exemplary embodiment. Shown are denaturation, annealing, and elongation steps ultimately leading to exponential growth of the amplicon.

Figure 20A:
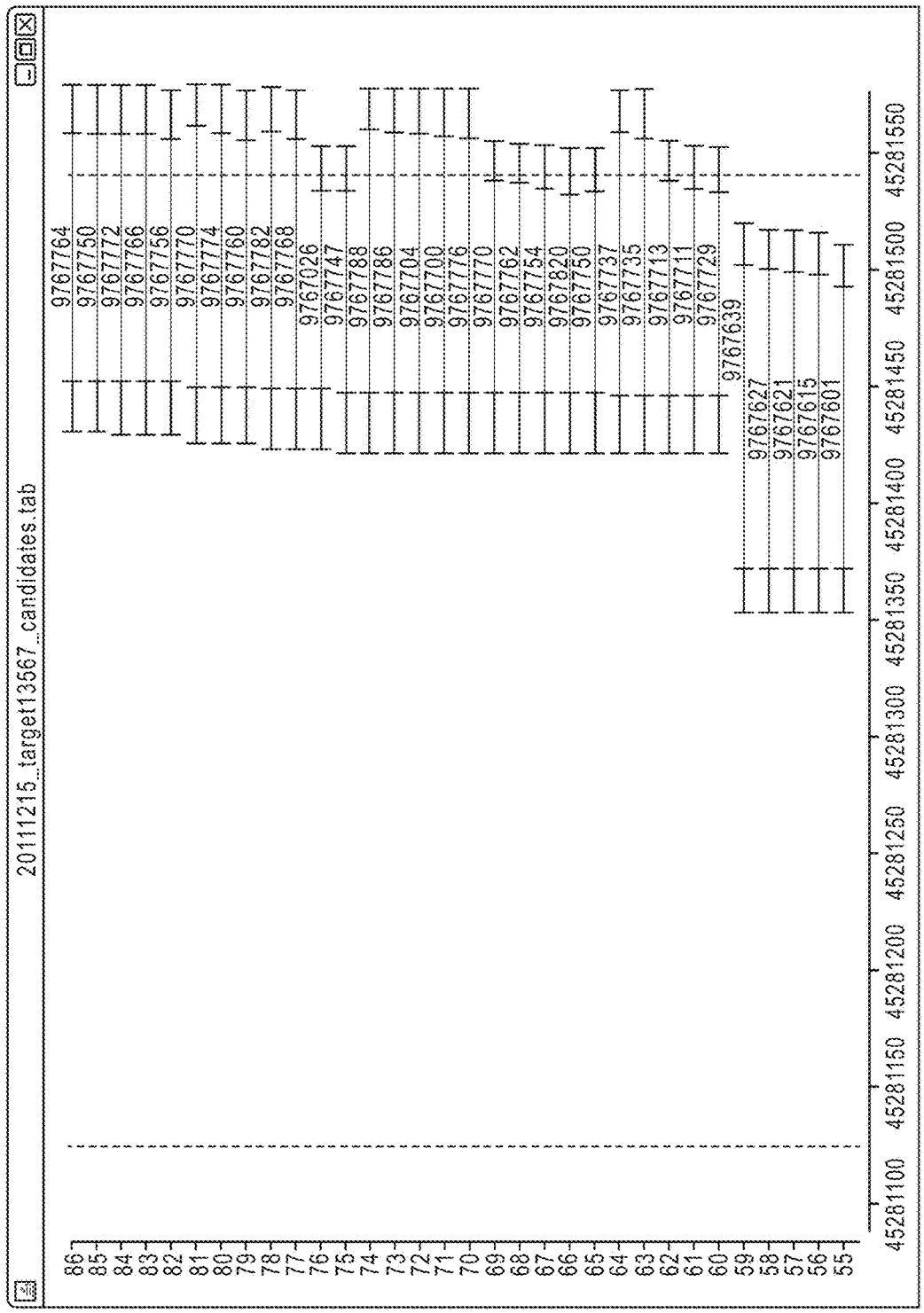
FIG. 20A-FIG. 20C illustrate a set of candidate amplicons for a given target region, each including an insert surrounded by a pair of primers, for tiling and pooling according to an exemplary embodiment.
Figure 20B:
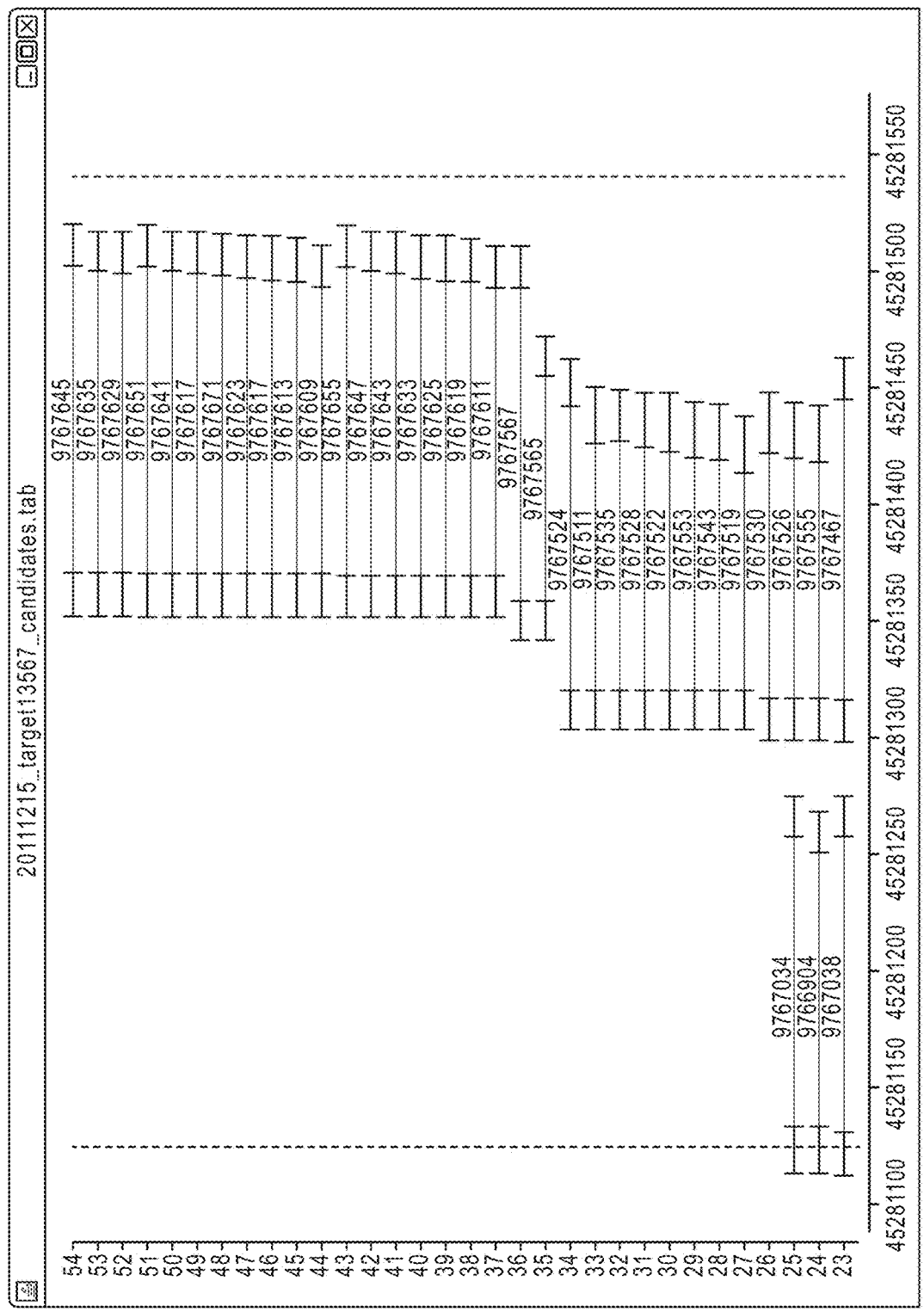
Figure 20C:
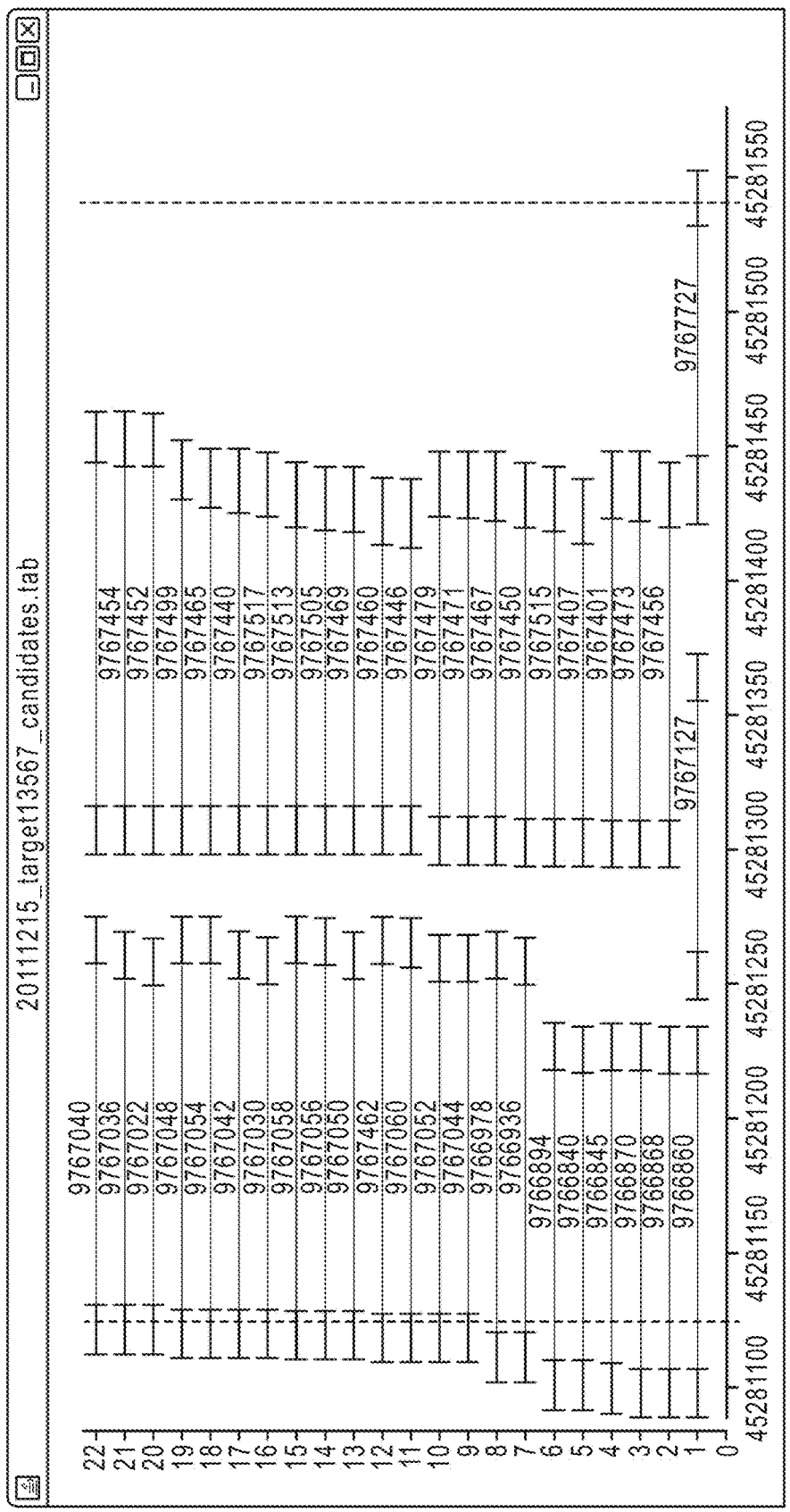

FIGS. 20A-20C illustrate a set of candidate amplicons for a given target region, each including an insert surrounded by a pair of primers, for tiling and pooling according to an exemplary embodiment. The dotted lines indicate the boundaries of a target region (on chromosome 19 in this example). There are 112 candidate amplicons for covering the target region in this example, but the number of candidate amplicons could of course be different, including much lower or much higher, and may be selected by taking into account computational resources, the length of the target region, and any other relevant factor.

According to various exemplary embodiments, there are provided methods for designing primers using a design pipeline that allows design of oligonucleotide primers across genomic areas of interest while incorporating various design criteria and considerations including amplicon size, primer composition, potential off-target hybridization, and SNP overlap of the primers. In an embodiment, the design pipeline includes several functional modules that may be sequentially executed as discussed next.

First, in an embodiment, a sequence retrieval module may be configured to retrieve sequences based on instructions of an operator regarding a final product desired by a customer. The operator may request a design of primer pairs for genomic regions which may be specified by chromosome and genome coordinates or by a gene symbol designator. In the latter case, the sequence retrieval module may retrieve the sequence based on the exon coordinates. The operator may also specify whether to include a 5' UTR sequence (untranslated sequence).

Second, in an embodiment, an assay design module may be configured to design primer pairs using a design engine, which may be a public tool such as Primer3 or another primer design software that can generate primer pairs across the entire sequence regions retrieved by the sequence retrieval module, for example. The primers pairs may be selected to tile densely across the nucleotide sequence. The primer design may be based on various parameters, including: (1) the melting temperature of the primer (which may be calculated using the nearest neighbor algorithm set forth in John SantaLucia, Jr., "A unified view of polymer, dumbbell, and oligonucleotide DNA nearest-neighbor thermodynamics," Proc. Natl. Acad. Sci. USA, vol. 95, 1460-1465 (1998), the contents of which is incorporated by reference herein in its entirety), (2) the primer composition (e.g., nucleotide composition such as GC content may be determined and filtered and penalized by the software, as may be primer hairpin formation, composition of the GC content in the 3' end of primer, and specific parameters that may be evaluated are stretches of homopolymeric nucleotides, hairpin formation, GC content, and amplicon size), (3) scores of forward primer, reverse primer and amplicon (the scores may be added up to obtain a probe set score, and the score may reflect how close the amplicon confirms with the intended parameters), and (4) conversion of some of the T's to U's (T's may be placed such that the predicted Tm of the T delimited fragments of a primer have a minimum average Tm.)

Third, in an embodiment, a primer mapping module may be configured to use a mapping software (e.g., e-PCR (NCBI), see Rotmistrovsky et al., "A web server for performing electronic PCR," Nucleic Acids Research, vol. 32, W108-W112 (2004), and Schuler, "Sequence Mapping by Electronic PCR," Genome Research, vol. 7, 541-550 (1997), which are both incorporated by reference herein in their entirety, or other similar software) to map primers to a genome. The primers mapping may be scored using a mismatch matrix. In an embodiment, a perfect match may receive a score of 0, and mismatched primers may receive a score of greater than 0. The mismatch matrix takes the position of the mismatch and the nature of the mismatch into account. For example, the mismatch matrix may assign a mismatch score to every combination of a particular motif (e.g., AA, AC, AG, CA, CC, CT, GA, GG, GT, TC, TG, TT, A-, C-, G-, T-, -A, -C, -G, and -T, where '-' denotes an ambiguous base or gap) with a particular position (e.g., base at 3' end, second base from 3' end, third base from 3' end, third base from 5' end, second base from 5' end, base at 5' end, and positions therebetween), which may be derived empirically and may be selected to reflect that mismatches closer to the 3'end tend to weaker PCR reactions more than mismatches closer to the 5' end and may therefore be generally larger. The mismatch scores for motifs with an ambiguous base or gap may be assigned an average of scores of other motifs consistent therewith (e.g., A- may be assigned an average of the scores of AA, AC, and AG). Based on the number of hits with a certain score threshold, an amplicon cost may be calculated.

Fourth, in an embodiment, a SNP module may be configured to determine underlying SNPs and repeat regions: SNPs may be mapped to the primers and based on the distance of a SNP from the 3' end, primers may be filtered as potential candidates. Similarly, if a primer overlaps to a certain percentage with a repeat region, the primer might be filtered.

Fifth, in an embodiment, a tiler module may be configured to use a function based on the amplicon cost (see primer mapping) and the number of primers necessary to select a set of primers covering the target while ensuring that selection of tiling primers for a target is independent of other targets that may be in a customer's request so that the same set of primers for a target will be selected whether the customer requested only that target or additional targets and whether amplicons are to help cover on that target or additional targets.

Sixth, in an embodiment, a pooler module may be configured to use a pooling algorithm that prevents amplicon overlaps, and ensures that the average number of primers in a pool does not deviate by more than a preset value.

Figure 21:
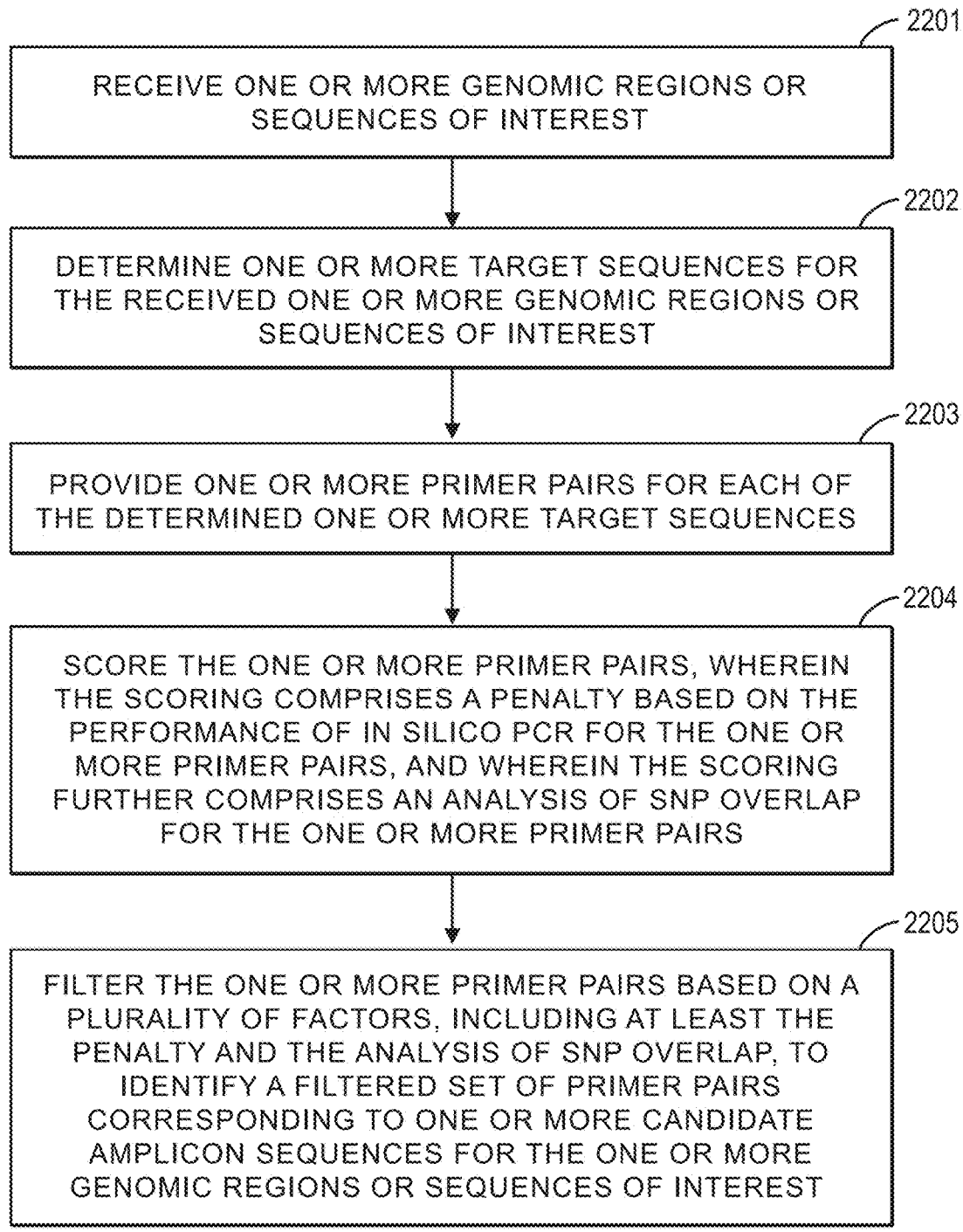
FIG. 21 illustrates a method according to an exemplary embodiment.

FIG. 21 illustrates a method according to an exemplary embodiment. In step 2201, a module or other hardware and/or software component receives one or more genomic regions or sequences of interest. In step 2202, a module or other hardware and/or software component determines one or more target sequences for the received one or more genomic regions or sequences of interest. In step 2203, a module or other hardware and/or software component provides one or more primer pairs for each of the determined one or more target sequences. In step 2204, a module or other hardware and/or software component scores the one or more primer pairs, wherein the scoring comprises a penalty based on the performance of in silico PCR for the one or more primer pairs, and wherein the scoring further comprises an analysis of SNP overlap for the one or more primer pairs. In step 2205, a module or other hardware and/or software component filters the one or more primer pairs based on a plurality of factors, including at least the penalty and the analysis of SNP overlap, to identify a filtered set of primer pairs corresponding to one or more candidate amplicon sequences for the one or more genomic regions or sequences of interest.

According to an exemplary embodiment, there is provided a method, comprising: (1) receiving one or more genomic regions or sequences of interest; (2) determining one or more target sequences for the received one or more genomic regions or sequences of interest; (3) providing one or more primer pairs for each of the determined one or more target sequences; (4) scoring the one or more primer pairs, wherein the scoring comprises a penalty based on the performance of in silico PCR for the one or more primer pairs, and wherein the scoring further comprises an analysis of SNP overlap for the one or more primer pairs; and (5) filtering the one or more primer pairs based on a plurality of factors, including at least the penalty and the analysis of SNP overlap, to identify a filtered set of primer pairs corresponding to one or more candidate amplicon sequences for the one or more genomic regions or sequences of interest.

In various embodiments, receiving one or more genomic regions or sequences of interest may comprise receiving a list of one or more gene symbols or identifiers. Receiving one or more genomic regions or sequences of interest may comprise receiving a list of one or more genomic coordinates or other genomic location identifiers. Receiving one or more genomic regions or sequences of interest may comprise receiving a list of one or more BED coordinates.

In various embodiments, determining one or more target sequences may comprise determining one or more exons or coding regions that correspond to each of the one or more genomic regions or sequences of interest. Determining one or more target sequences may comprise querying an amplicon or other genomic sequence database for a presence therein of the one or more genomic regions or sequences of interest and information related thereto.

In various embodiments, providing one or more primer pairs may comprise designing one or more primer pairs. Providing one or more primer pairs may comprise querying an amplicon or other genomic sequence database for a presence therein of the one or more genomic regions or sequences of interest or of the one or more primer pairs and information related thereto.

In various embodiments, the performance of in silico PCR may comprise performing in silico PCR against a reference or previously sequenced genome of any species. The performance of in silico PCR may comprise performing in silico PCR against an hg19 reference genome. The performance of in silico PCR against a reference genome may comprise determining a number of off-target hybridizations for each of the one or more primer pairs. The performance of in silico PCR against a reference genome may comprise determining a worst case attribute or score for each of the one or more primer pairs. The performance of in silico PCR may comprise determining one or more genomic coordinates for each of the one or more primer pairs. The performance of in silico PCR may comprise determining one or more predicted amplicon sequences for each of the one or more primer pairs. The performance of in silico PCR may comprise querying an amplicon or other genomic sequence database for a presence therein of the one or more genomic regions or sequences of interest or of in silico PCR results for the one or more primer pairs and information related thereto.

In various embodiments, the analysis of SNP overlap may comprise determining a SNP class for each of the one or more primer pairs. The analysis of SNP overlap may comprise querying an amplicon or other genomic sequence database for a presence therein of the one or more genomic regions or sequences of interest or of SNP overlap results for the one or more primer pairs and information related thereto.

In various embodiments, the plurality of factors may include one or more of an indication of forward SNP overlap, an indication of a reverse SNP overlap, an indication of a frequency of forward repeats, an indication of a frequency of reverse repeats, an indication of an off-target hybridization of each of the one or more primer pairs, and a composition of each of the one or more primer pairs. The plurality of factors may include one or more of a forward triplet factor, a reverse triplet factor, a forward A run factor, a reverse A run factor, a forward C run factor, a reverse C run factor, a forward G run factor, a reverse G run factor, a forward T run factor, and a reverse T run factor. The plurality of factors may include one or more of an indication of an extent to which each of the one or more primer pairs includes one or more homopolymers. The plurality of factors may include an indication of an extent to which each of the one or more primer pairs includes one or more repeating sequences. The plurality of factors may include a length of the one or more primer pairs, wherein a score for the one or more primer pairs decreases as the length gets shorter than a minimal length threshold and decreases as the length gets longer than a maximal length threshold. The plurality of factors may include a maximal number of a given base in the one or more primer pairs, wherein a score for the one or more primer pairs decreases as the number of instances of the given base exceeds a maximal base inclusion threshold. The plurality of factors may include a maximal number of contiguous instances of a given base, wherein a score for the one or more primer pairs decreases as the number of contiguous instances of the given base exceeds a maximal contiguous base inclusion threshold.

The plurality of factors may include a maximal percentage of a set of two given bases, wherein a score for the one or more primer pairs decreases as the percentage of the two given bases increases. The plurality of factors may include a maximal percentage of G and C bases, wherein a score for the one or more primer pairs decreases as the percentage of G and C bases increases. The plurality of factors may include a deviation of a predicted melting temperature for the one or more primer pairs relative to minimal and maximal melting temperature thresholds. The plurality of factors may include a number of primer-dimer inclusions for the one or more primer pairs. The plurality of factors may include a level of local complementarity for the one or more primer pairs. The plurality of factors may include an indication of a complexity level of each of the one or more primer pairs. The plurality of factors may include an indication of SNP overlap of each of the one or more primer.

In various embodiments, the method may comprise selecting a subset of the one or more candidate amplicon sequences that substantially covers the one or more genomic regions or sequences of interest while minimizing a cost function associated with the candidate amplicon sequences. Minimizing the cost function may include generating an overlap graph comprising a source vertex, one or more amplicon vertices, and a sink vertex.

In various embodiments, the method may comprise assembling the primer pairs in the filtered set of primer pairs that correspond with the selected subset of the one or more candidate amplicon sequences into a plurality of separate pools of primer pairs. Assembling the primer pairs may include limiting an inclusion of one or more primer pairs in the filtered set of primer pairs that correspond with the selected subset of the one or more candidate amplicon sequences into a given pool based at least on a minimal threshold distance between amplicon sequences in the given pool. The minimal threshold distance may be between about 5 base pairs and about 100 base pairs, or between about 15 base pairs and about 90 base pairs, or between about 25 base pairs and about 75 base pairs, or between about 40 base pairs and about 60 base pairs, for example. In some embodiments, the minimum threshold distance between amplicons may include any integer, including a negative one. For example, a value of 0 can mean that any two amplicons are allowed to "touch," and a value of −8 can mean that any two amplicons can overlap by up to 8 bases.

In various embodiments, assembling the filtered set of primer pairs into a plurality of separate pools of primer pairs may comprise splitting the primer pairs between tubes so as to prevent amplicon overlap within any given tube. Assembling the primer pairs may include limiting an inclusion of one or more primer pairs in the filtered set of primer pairs that correspond with the selected subset of the one or more candidate amplicon sequences into a given pool based at least on a pre-determined amplicon capacity of the given pool. Assembling the primer pairs may include limiting an inclusion of one or more primer pairs in the filtered set of primer pairs that correspond with the selected subset of the one or more candidate amplicon sequences into a given pool based at least on an inequality relating a size of the given pool with a product between a balance factor and a maximum value of the sizes of the separate pools.

In various embodiments, the method may comprise providing a report reporting on any one or more element of information of data used or generated by any one or more of the receiving, providing, scoring, filtering, selecting, and assembling steps.

According to an exemplary embodiment, there is provided a non-transitory machine-readable storage medium comprising instructions which, when executed by a processor, cause the processor to perform a method comprising: (1) receiving one or more genomic regions or sequences of interest; (2) determining one or more target sequences for the received one or more genomic regions or sequences of interest; (3) providing one or more primer pairs for each of the determined one or more target sequences; (4) scoring the one or more primer pairs, wherein the scoring comprises a penalty based on the performance of in silico PCR for the one or more primer pairs, and wherein the scoring further comprises an analysis of SNP overlap for the one or more primer pairs; and (5) filtering the one or more primer pairs based on a plurality of factors, including at least the penalty and the analysis of SNP overlap, to identify a filtered set of primer pairs corresponding to one or more candidate amplicon sequences for the one or more genomic regions or sequences of interest.

In various embodiments, such a non-transitory machine-readable storage medium may comprise instructions which, when executed by a processor, cause the processor to perform a method further comprising: (6) selecting a subset of the one or more candidate amplicon sequences that substantially covers the one or more genomic regions or sequences of interest while minimizing a cost function associated with the candidate amplicon sequences; and (7) assembling the primer pairs in the filtered set of primer pairs that correspond with the selected subset of the one or more candidate amplicon sequences into a plurality of separate pools of primer pairs.

According to an exemplary embodiment, there is provided a system, comprising: (1) a machine-readable memory; and (2) a processor configured to execute machine-readable instructions, which, when executed by the processor, cause the system to perform steps including: (a) receiving one or more genomic regions or sequences of interest; (b) determining one or more target sequences for the received one or more genomic regions or sequences of interest; (c) providing one or more primer pairs for each of the determined one or more target sequences; (d) scoring the one or more primer pairs, wherein the scoring comprises a penalty based on the performance of in silico PCR for the one or more primer pairs, and wherein the scoring further comprises an analysis of SNP overlap for the one or more primer pairs; and (e) filtering the one or more primer pairs based on a plurality of factors, including at least the penalty and the analysis of SNP overlap, to identify a filtered set of primer pairs corresponding to one or more candidate amplicon sequences for the one or more genomic regions or sequences of interest.

In various embodiments, the processor of such a system may further be configured to execute machine-readable instructions, which, when executed by the processor, cause the system to perform steps including: (f) selecting a subset of the one or more candidate amplicon sequences that substantially covers the one or more genomic regions or sequences of interest while minimizing a cost function associated with the candidate amplicon sequences; and (g) assembling the primer pairs in the filtered set of primer pairs that correspond with the selected subset of the one or more candidate amplicon sequences into a plurality of separate pools of primer pairs.

According to various exemplary embodiment, various parameters or criteria may be used to select primers and/or amplicons.

In an embodiment, a forward SNP score may be used and may be given a numerical attribute/score of 1 if there is no SNP within a given length of base pairs of the forward primer (such as 4, for example) or a numerical attribute of 0 if there is one or more SNPs within a length of 4 base pairs. In one embodiment, the forward SNP score may be given a numerical attribute/score of 1 if there is no SNP within a given length of base pairs from the 3' end of the forward primer. In some embodiments, a SNP can include one or more SNPs found on UCSC's Genome Browser Web Page including but not limited to, the SNP reference table referred to as "dbSNP132 common". An attribute/score of 1 may be a minimal attribute/score such that failure to achieve that attribute/score would result in disqualification. The base length threshold for the attribute/score determination could be lower or higher than 4, and could be 5, 6, 7, 8, 9, 10, 15, 20, for example, or more generally any positive integer larger than 4. The attribute/score could be other than binary and could be a more complex linear or non-linear function of the number of SNPs within the given length of base pairs.

In an embodiment, a reverse SNP score may be used and may be given a numerical attribute/score of 1 if there is no SNP within a given length of base pairs of the reverse primer (such as 4, for example) or a numerical attribute of 0 if there is one or more SNPs within a length of 4 base pairs. In one embodiment, the reverse SNP score may be given a numerical attribute/score of 1 if there is no SNP within a given length of base pairs from the 3' end of the reverse primer. In some embodiments, a SNP can include one or more SNPs found on UCSC's Genome Browser Web Page including but not limited to, the SNP reference table referred to as "dbSNP132 common". An attribute/score of 1 may be a minimal attribute/score such that failure to achieve that attribute/score would result in disqualification. The base length threshold for the attribute/score determination could be lower or higher than 4, and could be 5, 6, 7, 8, 9, 10, 15, 20, for example, or more generally any positive integer larger than 4. The attribute/score could be other than binary and could be a more complex linear or non-linear function of the number of SNPs within the given length of base pairs.

In an embodiment, a forward repeat score may be used and may be given a numerical attribute/score of 1 if there is no repeat within a given length of base pairs of the forward primer (such as 4, for example) or a numerical attribute of 0 if there is one or more repeats within a length of 4 base pairs. In one embodiment, the forward repeat score may be given a numerical attribute/score of 1 if there is less than 30% overlap of the forward primer with known repeats. In some embodiments, known repeats may include one or more repeats reported by UCSC's Genome Browser, for example repeat regions as provided by the repeat masked hg19 genome from UCSC. An attribute/score of 1 may be a minimal attribute/score such that failure to achieve that attribute/score would result in disqualification. The base length threshold for the attribute/score determination could be lower or higher than 4, and could be 5, 6, 7, 8, 9, 10, 15, 20, for example, or more generally any positive integer larger than 4. The attribute/score could be other than binary and could be a more complex linear or non-linear function of the number of repeats within the given length of base pairs.

In an embodiment, a reverse repeat score may be used and may be given a numerical attribute/score of 1 if there is no repeat within a given length of base pairs of the reverse primer (such as 4, for example) or a numerical attribute of 0 if there is one or more repeats within a length of 4 base pairs. In one embodiment, the reverse repeat score may be given a numerical attribute/score of 1 if there is less than 30% overlap of the reverse primer with known repeats. In some embodiments, known repeats may include one or more repeats reported by UCSC's Genome Browser, for example repeat regions as provided by the repeat masked hg19 genome from UCSC. An attribute/score of 1 may be a minimal attribute/score such that failure to achieve that attribute/score would result in disqualification. The base length threshold for the attribute/score determination could be lower or higher than 4, and could be 5, 6, 7, 8, 9, 10, 15, 20, for example, or more generally any positive integer larger than 4. The attribute/score could be other than binary and could be a more complex linear or non-linear function of the number of repeats within the given length of base pairs.

In various embodiments, one or more of a forward triplet score, a reverse triplet score, a forward A run score, a reverse A run score, a forward C run score, a reverse C run score, a forward G run score, a reverse G run score, a forward T run score, and a reverse T run score, may be used and may be given a numerical attribute/score equal to the number of forward triplets, reverse triplets, forward A runs, reverse A runs, forward C runs, reverse C runs, forward G runs, reverse G runs, forward T runs, and reverse T runs within the entire primer. An attribute/score of 3 may be a maximal attribute/score for the triplets such that failure to remain at or below that attribute/score would result in disqualification. An attribute/score of 5 may be a maximal attribute/score for the runs such that failure to remain at or below that attribute/score would result in disqualification. The attribute/score could be other than binary and could be a more complex linear or non-linear function of the number of triplets/runs.

In an embodiment, a length of the primers may be limited by a minimum primer length threshold and a maximum primer length, and a length score for the primers may be set so as to decrease as the length gets shorter than the minimum primer length threshold and to decrease as the length gets longer than the maximum primer length threshold. In an embodiment, the minimum primer length threshold may be 16. In other embodiments, the minimum primer length threshold may be 15, 14, 13, 12, 11, 10, 9, 8, 7, 6, or 5, for example, and may also be 17, 18, 19, 20, 21, 22, 23, and 24, for example. In an embodiment, the maximum primer length threshold may be 28. In other embodiments, the maximum primer length threshold may be 29, 30, 31, 32, 33, 34, 35, 36, 37, 38, 39, and 40, for example, and may also be 27, 26, 25, 24, 23, 22, 21, and 20, for example. In an embodiment, the primer length criterion may be given a score of 1.0 if the length thresholds are satisfied, for example, and that score may go down to 0.0 as the primer length diverges from the minimum or maximum length threshold. For example, if the maximum primer length threshold were set to 28, then the score could be set to 1.0 if the length does not exceed 28, to 0.7 if the length is 29, to 0.6 if the length is 30, to 0.5 if the length is 31, to 0.3 if the length is 32, to 0.1 if the length is 33, and to 0.0 if the length is 34 or more. The attribute/score could be scaled between values other than 0.0 and 1.0, of course, and the function defining how the score varies with an increase difference relative to the threshold could be any other or more complex linear or non-linear function that does not lead to increases in score for primer that further diverge from length thresholds.

In an embodiment, a number of G bases (or of A, C, or T bases) in the primers may be limited by a maximum threshold, and corresponding score for the primers may be set so as to decrease as the number of G bases (or of A, C, or T bases) exceeds the maximum threshold. In an embodiment, the maximum threshold may be 3. In other embodiments, the maximum threshold may be 2, 4, 5, 6, 7, 8, 9, and 10, for example. In an embodiment, the number of G bases (or of A, C, or T bases) criterion may be given a score of 1.0 if the maximum threshold is satisfied, for example, and that score may go down to 0.0 as the number of G bases (or of A, C, or T bases) diverges from the maximum threshold. For example, if the maximum threshold were set to 4, then the score could be set to 1.0 if the number of G bases (or of A, C, or T bases) does not exceed 4, to 0.9 if the number is 5, to 0.8 if the number is 6, to 0.6 if the number is 7, to 0.4 if the number is 8, to 0.2 if the number is 9, and to 0.0 if the number is 10 or more. The score could be scaled between values other than 0.0 and 1.0, of course, and the function defining how the score varies with an increased difference between the number of G bases (or of A, C, or T bases) and the maximum threshold could be any other or more complex linear or non-linear function that does not lead to increases in score for primer that further diverge from the maximum threshold.

In an embodiment, the numbers of contiguous and total matches in a loop (e.g., hairpin) in the primers may be limited by a maximum threshold, and corresponding scores for the primers may be set so as to decrease as the numbers of contiguous and total matches in a loop exceed the maximum threshold. In an embodiment, the maximum threshold for contiguous matches may be 3 and the maximum threshold for total matches may be 5. In other embodiments, the maximum threshold for contiguous matches may be 2, 4, 5, 6, 7, 8, 9, and 10, for example, and the maximum threshold for total matches may be 3, 4, 6, 7, 8, 9, 10, 11, 12, 13, 14, and 15, for example. In an embodiment, the numbers of contiguous and total matches in a loop criteria may be given a score of 1.0 if the maximum threshold is satisfied, for example, and that score may go down to 0.0 as the number of the numbers of contiguous and total matches in a loop diverge from the corresponding maximum threshold. For example, if the maximum threshold for contiguous matches were set to 3, then the score could be set to 1.0 if the number of contiguous matches does not exceed 3, to 0.9 if the number is 4, to 0.7 if the number is 5, to 0.4 if the number is 6, to 0.2 if the number is 7, to 0.1 if the number is 8, and to 0.0 if the number is 9 or more. For example, if the maximum threshold for total matches were set to 5, then the score could be set to 1.0 if the number of total matches does not exceed 5, to 0.9 if the number is 6, to 0.8 if the number is 7, to 0.6 if the number is 8, to 0.4 if the number is 9, to 0.2 if the number is 10, to 0.1 if the number is 11, and to 0.0 if the number is 12 or more. The scores could be scaled between values other than 0.0 and 1.0, of course, and the function defining how the scores vary with an increased difference between the number of contiguous/total matches and the corresponding maximum thresholds could be any other or more complex linear or non-linear function that does not lead to increases in score for primer that further diverge from the maximum threshold.

In an embodiment, a number of G and C bases (or any two of the A, C, G, and T bases) in the last five bases of the primers may be limited by a maximum threshold, and corresponding score for the primers may be set so as to decrease as the number of G and C bases (or any two of the A, C, G, and T bases) exceeds the maximum threshold. In an embodiment, the maximum threshold may be 2. In other embodiments, the maximum threshold may be 3, 4, and 5, for example. In an embodiment, the number of G and C bases (or any two of the A, C, G, and T bases) criterion may be given a score of 1.0 if the maximum threshold is satisfied, for example, and that score may go down to 0.0 as the number of G and C bases (or any two of the A, C, G, and T bases) diverges from the maximum threshold. For example, if the maximum threshold were set to 2, then the score could be set to 1.0 if the number of G and C bases (or any two of the A, C, G, and T bases) does not exceed 2, to 0.8 if the number is 3, to 0.4 if the number is 4, and to 0.1 if the number is 5. The score could be scaled between values other than 0.0 and 1.0, of course, and the function defining how the score varies with an increased difference between the number of G and C bases (or any two of the A, C, G, and T bases) and the maximum threshold could be any other or more complex linear or non-linear function that does not lead to increases in score for primer that further diverge from the maximum threshold. In other embodiments, this criterion could consider the number of G and C bases (or any two of the A, C, G, and T bases) in a larger window of bases, such as in the last six bases, the last seven bases, the last eight bases, etc., for example.

In an embodiment, a percentage of G and C bases (or any two of the A, C, G, and T bases) in the primers may be limited by minimum and maximum thresholds, and corresponding score for the primers may be set so as to decrease as the percentage of G and C bases (or any two of the A, C, G, and T bases) diverges from the minimum or maximum threshold. In an embodiment, the minimum threshold may be 0.2 (20%) and the maximum threshold may be 0.8 (80%). In other embodiments, the minimum threshold may be any percentage between about 0.2 (20%) and about 0.5 (50%) and the maximum threshold may be any percentage between about 0.8 (80%) and 0.5 (50%), for example. In an embodiment, the percentage of G and C bases (or any two of the A, C, G, and T bases) criterion may be given a score of 1.0 if the minimum and maximum thresholds are satisfied, for example, and that score may go down to 0.0 if either of the thresholds is not satisfied. The score could be scaled between values other than 0.0 and 1.0, of course, and the function defining how the score varies with an increased difference between the percentage of G and C bases (or any two of the A, C, G, and T bases) and the minimum or maximum threshold could be any other or more complex linear or non-linear function that does not lead to increases in score for primer that further diverge from the minimum or maximum threshold.

In an embodiment, a melting temperature (Tm) of the primers may be limited by minimum and maximum thresholds, and corresponding score for the primers may be set so as to decrease as the melting temperature diverges from the minimum or maximum threshold. In an embodiment, the minimum threshold may be 60 and the maximum threshold may be 67 with a target melting temperature of 62. In other embodiments, the minimum threshold may be a value between about 55 and about 65 and the maximum threshold may be a value between about 62 and about 72, for example. In an embodiment, the melting temperature criterion may be given a score of 1.0 if the minimum and maximum thresholds are satisfied, for example, and that score may go down to 0.0 if either of the thresholds is not satisfied. The score could be scaled between values other than 0.0 and 1.0, of course, and the function defining how the score varies with an increased difference between the melting temperature and the minimum or maximum threshold could be any other or more complex linear or non-linear function that does not lead to increases in score for primer that further diverge from the minimum or maximum threshold. The melting temperature of a primer may be calculated using the teachings set forth in John SantaLucia, Jr., "A unified view of polymer, dumbbell, and oligonucleotide DNA nearest-neighbor thermodynamics," Proc. Natl. Acad. Sci. USA, vol. 95, 1460-1465 (1998), the contents of which is incorporated by reference herein in its entirety.

In an embodiment, a primer-dimer propensity in the primers may be limited by a maximum threshold of contiguous primer-dimers at the 3' end and a maximum threshold of total contiguous matches over the full length, and corresponding score for the primers may be set so as to decrease as the primer-dimer propensity diverges from the maximum thresholds. In an embodiment, the maximum threshold of contiguous primer-dimers at the 3' end may be 4 and the maximum threshold of total contiguous matches over the full length may be 8. In other embodiments, the maximum threshold of contiguous primer-dimers at the 3' end may be a value between about 2 and about 6 and the maximum threshold of total contiguous matches over the full length may be a value between about 4 and 10, for example. In an embodiment, the primer-dimer propensity criteria may be given a score of 1.0 if the threshold is satisfied, for example, and that score may go down to 0.0 if the threshold is not satisfied. The score could be scaled between values other than 0.0 and 1.0, of course, and the function defining how the score varies with an increased difference between the primer-dimer propensity and the maximum threshold could be any other or more complex linear or non-linear function that does not lead to increases in score for primer that further diverge from the maximum threshold.

In an embodiment, a percentage of G and C bases (or any two of the A, C, G, and T bases) in an amplicon sequence may be limited by minimum and maximum thresholds, and corresponding score for the amplicons may be set so as to decrease as the percentage of G and C bases (or any two of the A, C, G, and T bases) diverges from the minimum or maximum threshold. In an embodiment, the minimum threshold may be 0.0 (0%) and the maximum threshold may be 1.0 (100%). In other embodiments, the minimum threshold may be any percentage between about 0.1 (10%) and about 0.25 (25%) and the maximum threshold may be any percentage between about 0.75 (75%) and 0.9 (90%), for example. In an embodiment, the percentage of G and C bases (or any two of the A, C, G, and T bases) criterion may be given a score of 1.0 if the minimum and maximum thresholds are satisfied, for example, and that score may go down to 0.0 if either of the thresholds is not satisfied. The score could be scaled between values other than 0.0 and 1.0, of course, and the function defining how the score varies with an increased difference between the percentage of G and C bases (or any two of the A, C, G, and T bases) and the minimum or maximum threshold could be any other or more complex linear or non-linear function that does not lead to increases in score for amplicons that further diverge from the minimum or maximum threshold.

In an embodiment, a length of the amplicons may be limited by a minimum amplicon length threshold and a maximum amplicon length, and a length score for the amplicons may be set so as to decrease as the length gets shorter than the minimum amplicon length threshold and to decrease as the length gets longer than the maximum amplicon length threshold. In an embodiment, the minimum amplicon length threshold may be 110. In other embodiments, the minimum primer length threshold may be a value between about 80 and about 140, for example. In an embodiment, the maximum amplicon length threshold may be 240. In other embodiments, the maximum amplicon length threshold may be a value between about 200 and about 280, for example. In an embodiment, the amplicon length criterion may be given a score of 1.0 if the length thresholds are satisfied and of 0.0 if either is not satisfied. In another embodiment, that score may go down to 0.0 as the amplicon length diverges from the minimum or maximum length threshold. For example, if the maximum amplicon length threshold were set to 240, then the score could be set to 1.0 if the length does not exceed 240, to 0.8 if the length is at least 250, to 0.6 if the length is at least 260, to 0.4 if the length is at least 270, to 0.1 if the length is at least 280, and to 0.0 if the length is at least 290. The attribute/score could be scaled between values other than 0.0 and 1.0, of course, and the function defining how the score varies with an increase difference relative to the threshold could be any other or more complex linear or non-linear function that does not lead to increases in score for amplicons that further diverge from length thresholds.

According to an exemplary embodiment, there is provided a method for selecting a subset (which may be referred to as "tiling" herein) of amplicons (which may be referred to as "tiles" herein) from a plurality of candidate amplicons for covering one or more specific desired (e.g., customized) genomic regions or targets using one or more pools of amplicons. The method may include receiving as input a set of one or more targets and a set of candidate amplicons, and may include outputting as output a subset of the candidate amplicons and an assignment of each of the amplicons in the subset to a pool in which that amplicon can be multiplexed. Amplicons of any suitable sizes may be used. In an embodiment, an assay or primer design may accommodate 200 bp amplicons and 150 bp amplicons, for example, which may be especially useful for certain challenging samples such as FFPE, for example. In an embodiment, an assay or primer design may be adapted to be compatible with one or more specific library kits, such as, for example, the Ion AmpliSeq™ Library Kit 2.0.

According to an exemplary embodiment, there is provided a method for tiling and pooling, comprising (1) selecting a subset of amplicons (which may be referred to as "tiling" herein) from a set of input amplicons such that the subset of amplicons (i) covers as much of each target as do the amplicons in the set of input amplicons, (ii) has many fewer amplicons than the set of input amplicons, and (iii) maximizes a quality of the amplicons; and (2) assigns each amplicon or tile in the subset of amplicons or tiling to a pool so as to allow each pool to be multiplexed.

Figure 22:
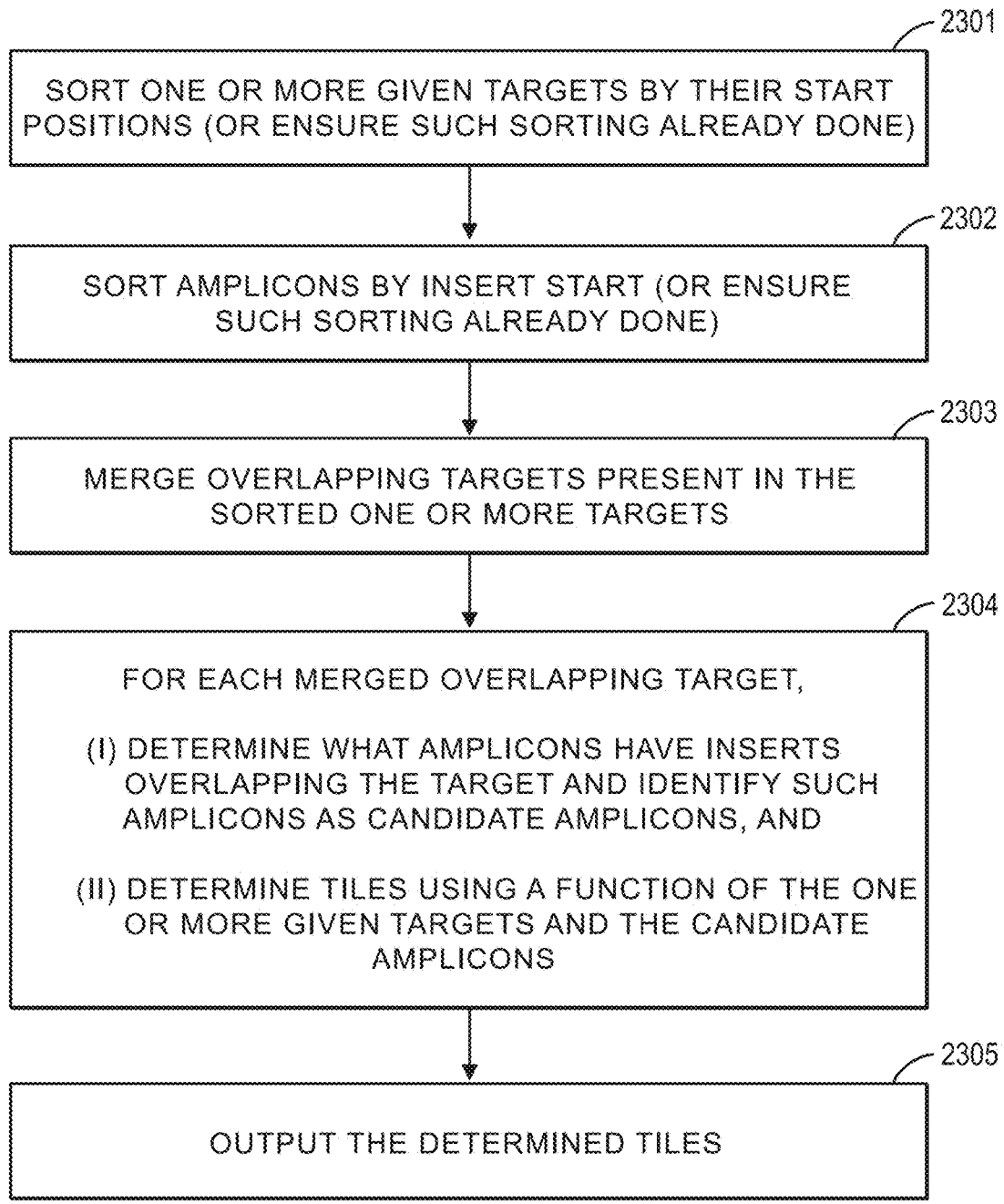
FIG. 22 illustrates a method for tiling a plurality of amplicons for one or more given targets according to an exemplary embodiment.

FIG. 22 illustrates a method for tiling a plurality of amplicons for one or more given targets according to an exemplary embodiment. In step 2301, a module or other hardware and/or software component sorts the one or more given targets by their start positions (or ensures that the given targets were already pre-sorted in such a manner when provided as input). In step 2302, a module or other hardware and/or software component sorts the amplicons by insert start (or ensures that the amplicons were already pre-sorted in such a manner when provided as input). In step 2303, a module or other hardware and/or software component merges overlapping targets present in the sorted one or more targets. In step 2304, for each merged overlapping target, a module or other hardware and/or software component (i) determines what amplicons have inserts overlapping the target and identifies such amplicons as candidate amplicons, and (ii) determines tiles using a function of the one or more given targets and the candidate amplicons. In step 2305, a module or other hardware and/or software component outputs the determined tiles. In some embodiments, targets may or may not be merged ahead of gathering any target amplicons, amplicons may be gathered for unmerged targets, and, if two targets share at least one amplicon, such two targets may be merged together (and one of the two targets may already represent a set of merged input amplicons).

According to an exemplary embodiment, there is provided a method for tiling a plurality of amplicons for one or more given targets, comprising: (1) sorting the one or more given targets by their start positions or ensuring that the given targets were already pre-sorted in such a manner when provided as input; (2) sorting the amplicons by insert start or ensuring that the amplicons were already pre-sorted in such a manner when provided as input; (3) merging overlapping targets present in the sorted one or more targets; (4) for each merged overlapping target, (i) determining what amplicons have inserts overlapping the target and identifying such amplicons as candidate amplicons and (ii) determining the tiles using a function of the one or more given targets and the candidate amplicons; and (5) outputting the tiles.

Figure 23:
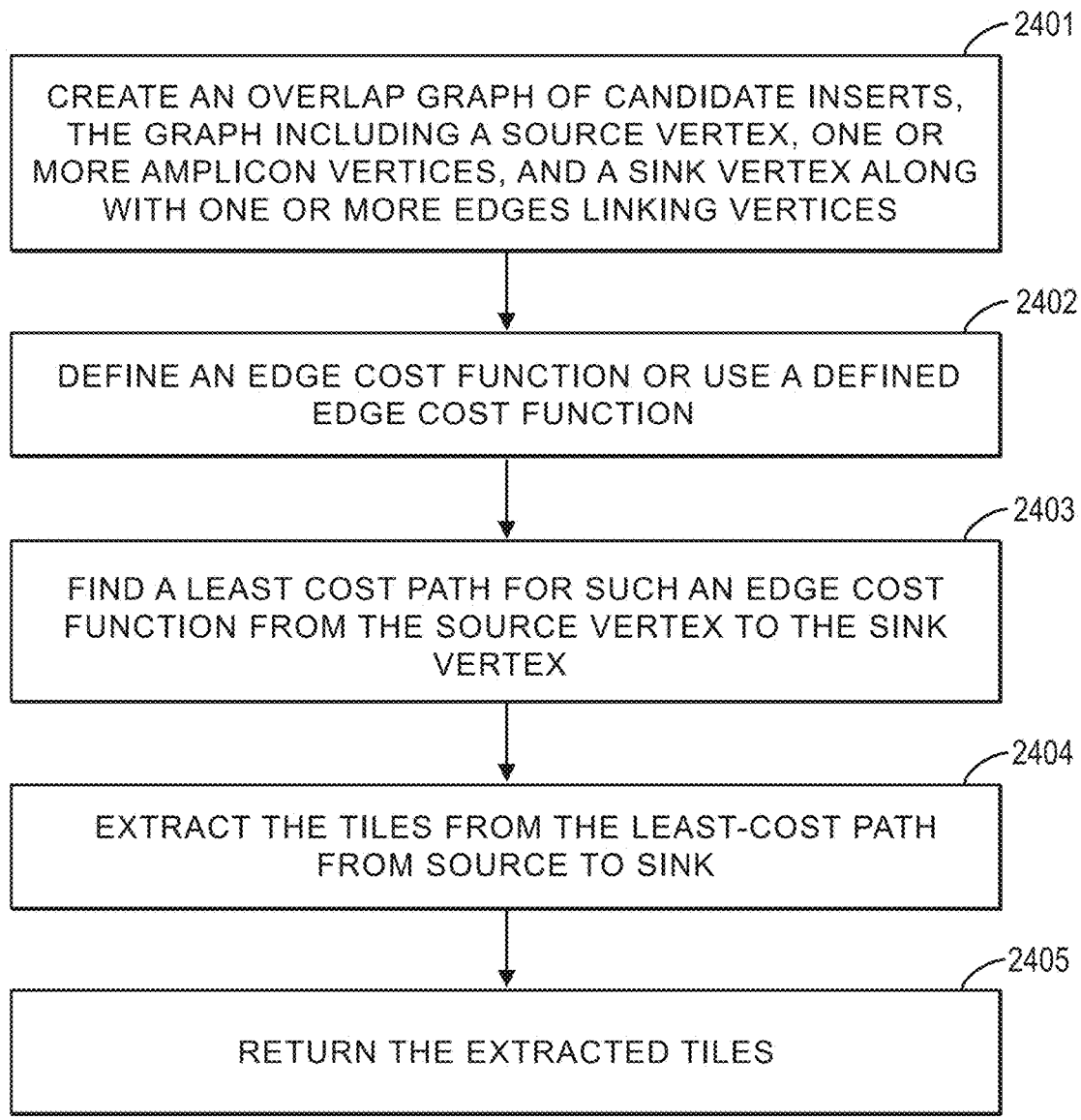
FIG. 23 illustrates a method for determining tiles for one or more given targets and candidate amplicons according to an exemplary embodiment.

FIG. 23 illustrates a method for determining tiles for one or more given targets and candidate amplicons according to an exemplary embodiment. In step 2401, a module or other hardware and/or software component creates an overlap graph of candidate inserts, the graph including a source vertex, one or more amplicon vertices, and a sink vertex along with one or more edges linking vertices. In step 2402, a module or other hardware and/or software component defines an edge cost function or uses a defined edge cost function. In step 2403, a module or other hardware and/or software component finds a least cost path for such an edge cost function from the source vertex to the sink vertex. In step 2404, a module or other hardware and/or software component extracts the tiles from the least-cost path from source to sink. In step 2405, a module or other hardware and/or software component returns the extracted tiles.

According to an exemplary embodiment, there is provided a method for determining tiles for one or more given targets and candidate amplicons, comprising: (1) creating an overlap graph of candidate inserts, the overlap graph comprising a set of vertices V and a set of edges E (e.g., a graph G=(V,E)), such creating including (i) letting V equal the union of the set of candidate amplicons (each of which being assigned a corresponding vertex) and the set consisting of a source element and a sink element (e.g., V={amplicons}∪{source,sink}), (ii) connecting the source vertex to all initial vertices and the sink vertex to all terminal vertices, (iii) connecting each amplicon vertex to all subsequent, proper, overlaps, and (iv) connecting rightmost vertices on the left of a gap to leftmost vertices on the right of that gap; (2) defining an edge cost function or using a defined edge cost function; (3) finding a least cost path for such an edge cost function from the source vertex to each vertex; (4) extracting the tiles from the least-cost path from source to sink; and (5) returning the extracted tiles.

Figure 24A:
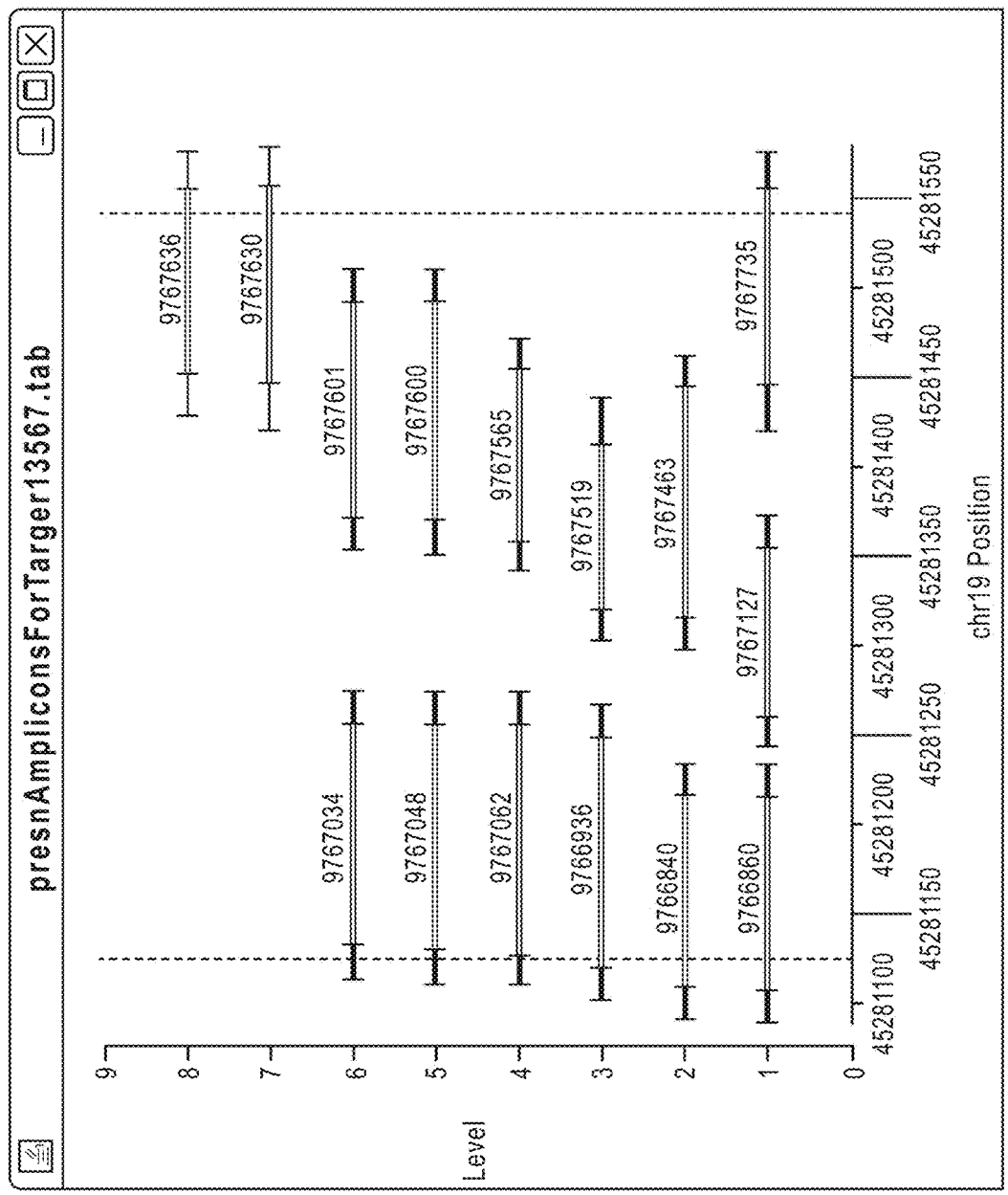
FIG. 24A illustrates a set of candidate amplicons for covering a given target region, each including an insert surrounded by a pair of primers, for tiling and pooling according to an exemplary embodiment.

FIG. 24A illustrates a set of candidate amplicons for covering a given target region, each including an insert surrounded by a pair of primers, for tiling and pooling according to an exemplary embodiment. The dotted lines indicate the boundaries of the target region (on chromosome 19 in this example).

Figure 24B:
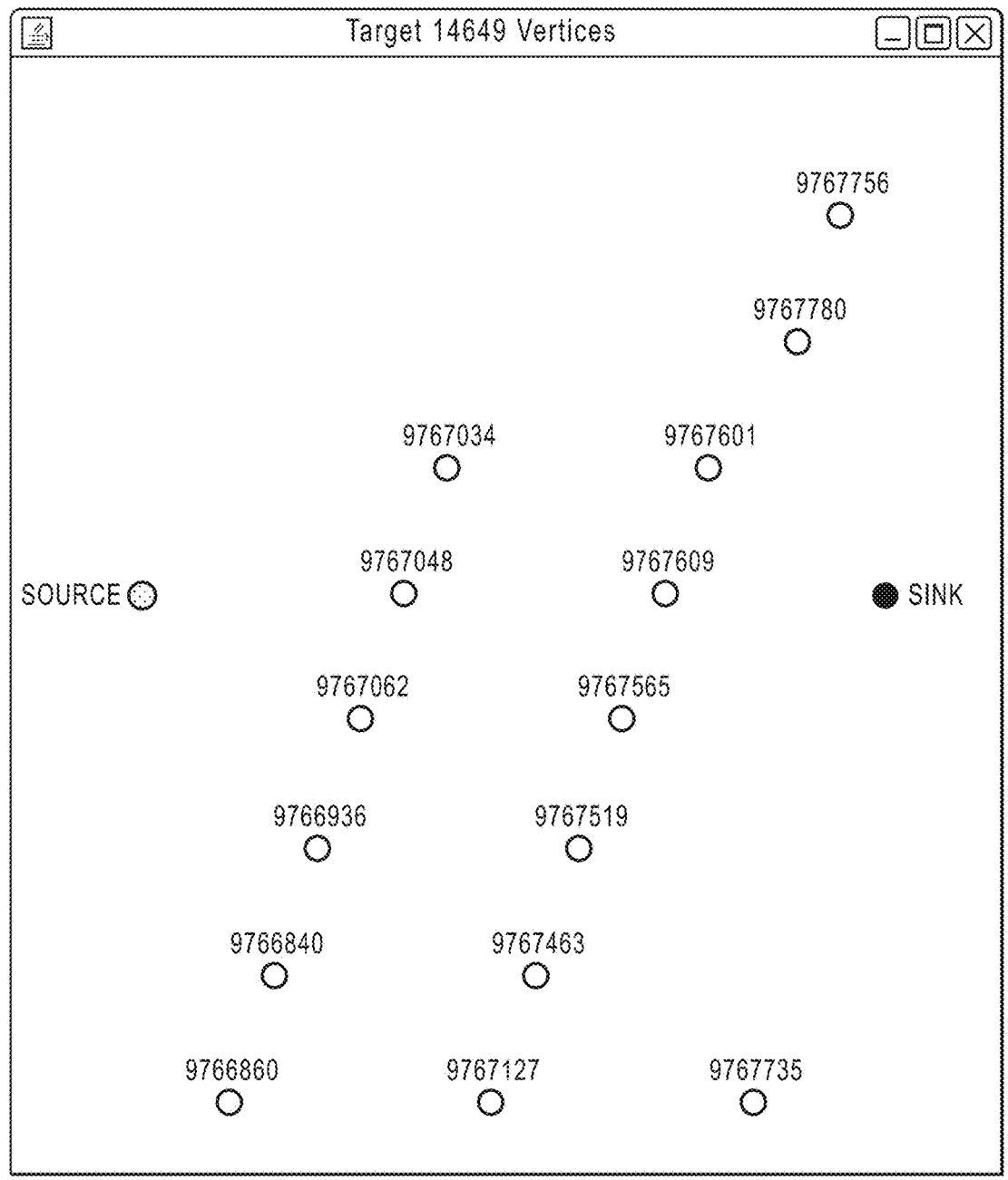
FIG. 24B illustrates a set of vertices for generating a graph according to an exemplary embodiment.
Figure 25A:
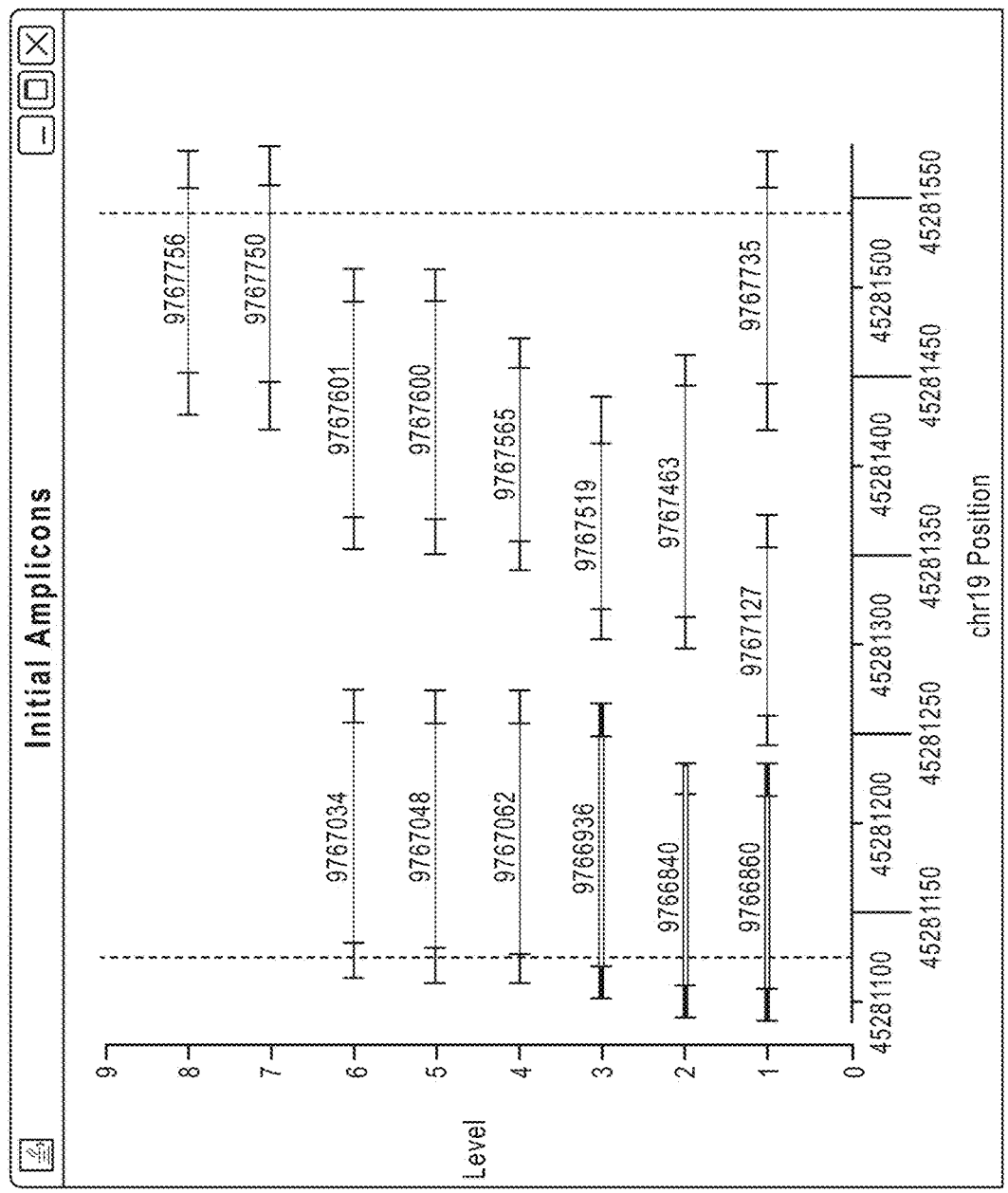
FIG. 25A illustrates the 15 candidate amplicons of FIG. 24A, except that three "initial" amplicons having at least some overlap between their insert and the beginning of the target region are highlighted.

FIG. 24B illustrates a set of vertices for generating a graph. The vertices V includes 15 amplicon vertices (white) corresponding to the 15 candidate amplicons illustrated in FIG. 24A together with a source vertex (light gray or green, left) and a sink vertex (dark grey or red, right). FIG. 25A illustrates the 15 candidate amplicons of FIG. 24A, except that three "initial" amplicons having at least some overlap between their insert and the beginning of the target region are highlighted.

Figure 25B:
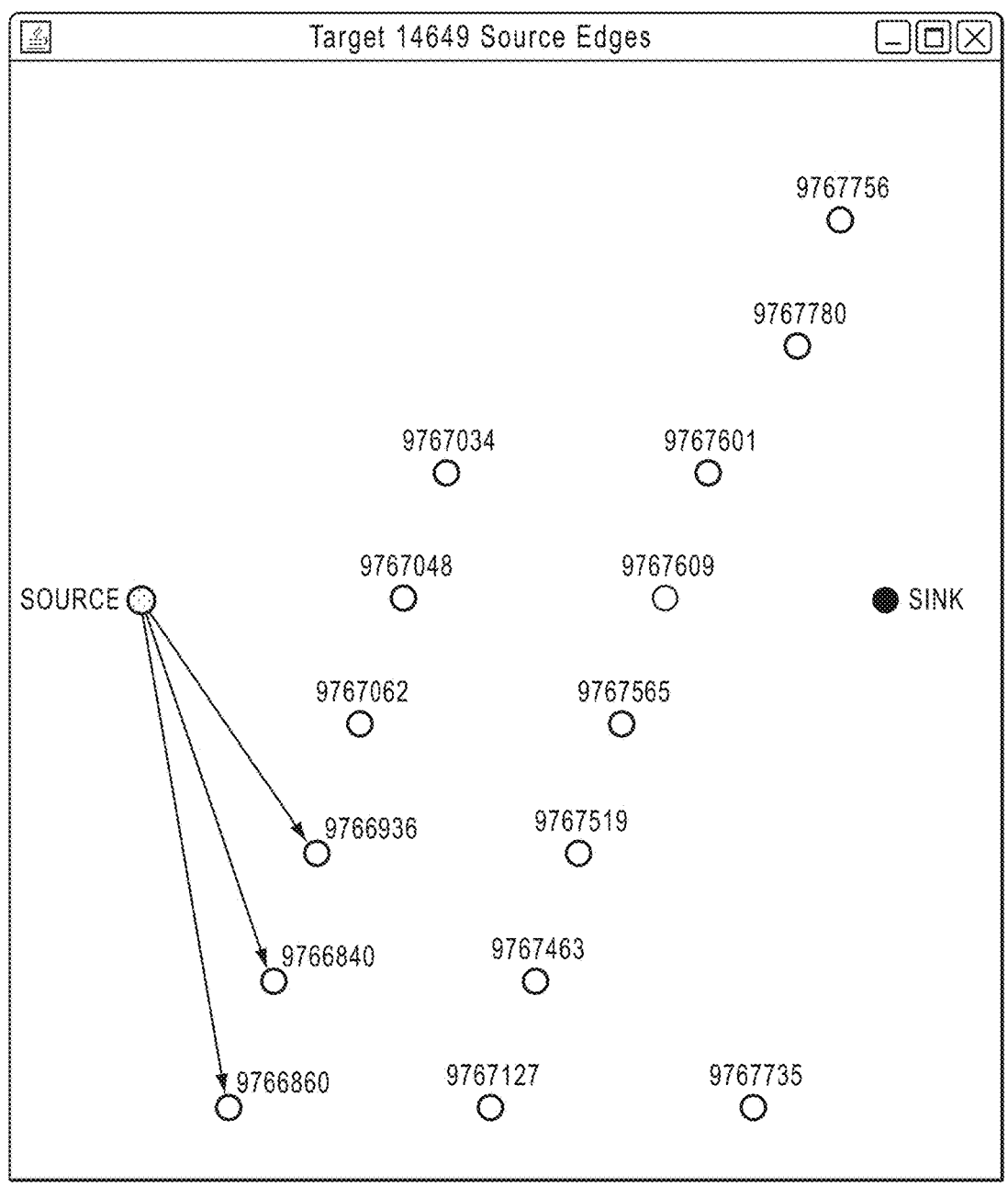
FIG. 25B illustrates the connection of a source vertex to three vertices corresponding to the initial amplicons of FIG. 25A with edges.

FIG. 25B illustrates the connection of a source vertex to three vertices corresponding to the initial amplicons of FIG. 25A with edges.

Figure 26A:
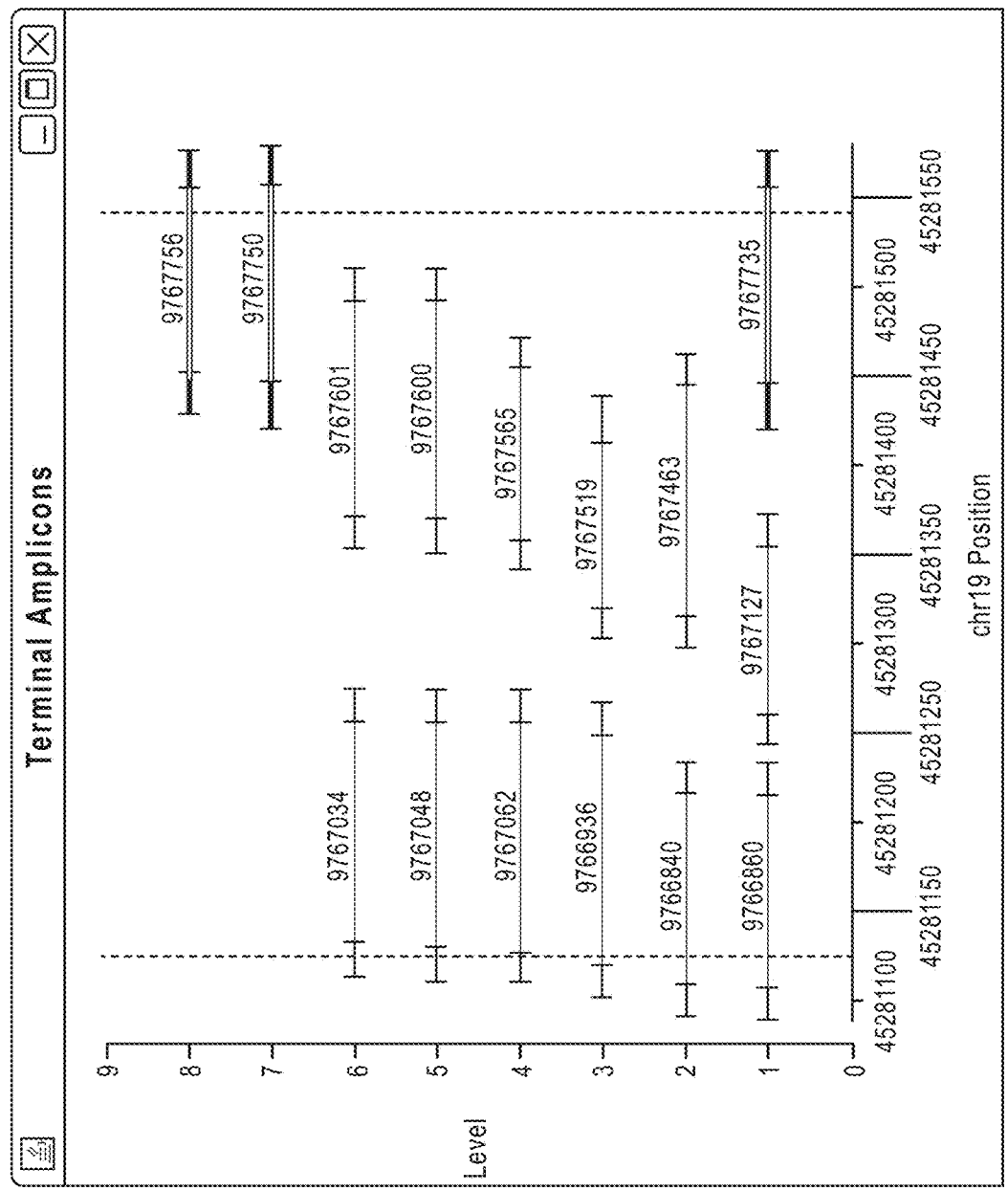
FIG. 26A illustrates the 15 candidate amplicons of FIG. 24A, except that three "terminal" amplicons having at least some overlap between their insert and the end of the target region are highlighted.

FIG. 26A illustrates the 15 candidate amplicons of FIG. 24A, except that three "terminal" amplicons having at least some overlap between their insert and the end of the target region are highlighted.

Figure 26B:
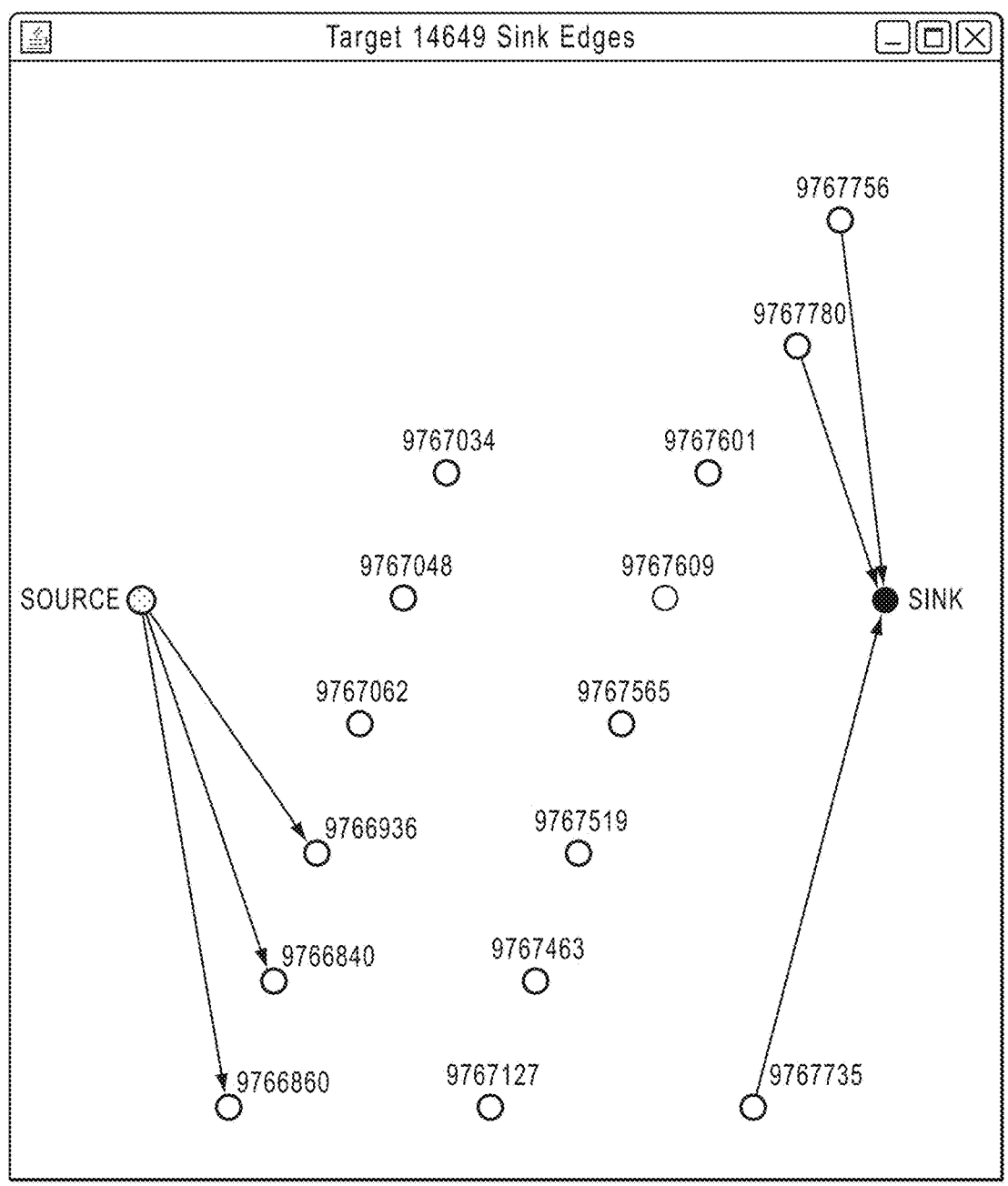
FIG. 26B illustrates the connection of a sink vertex to three vertices corresponding to the terminal amplicons of FIG. 26A with edges.

FIG. 26B illustrates the connection of a sink vertex to three vertices corresponding to the terminal amplicons of FIG. 26A with edges.

Figure 27A:
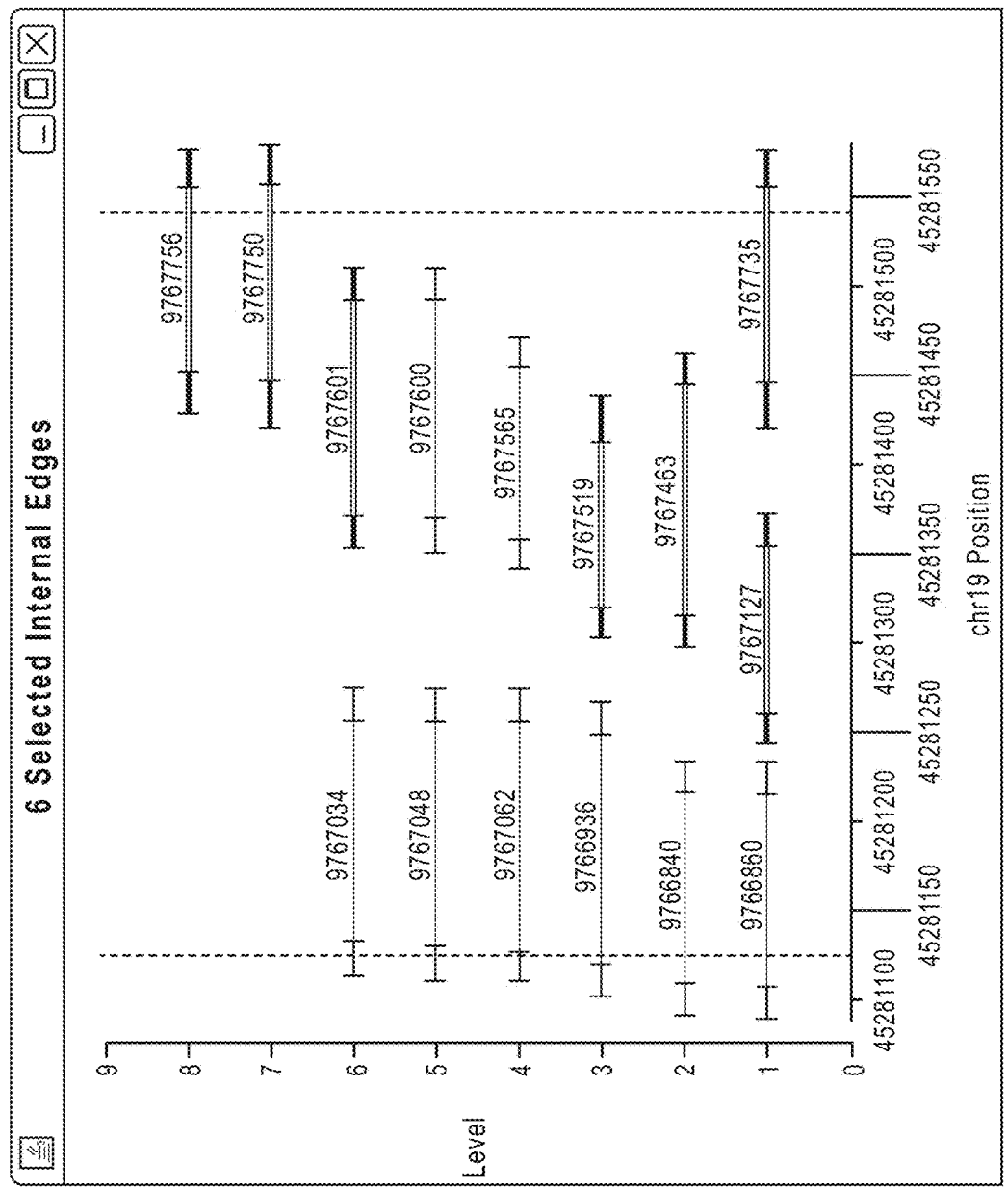
FIG. 27A illustrates the 15 candidate amplicons of FIG. 24A, except that various amplicons for building internal edges are highlighted.

FIG. 27A illustrates the 15 candidate amplicons of FIG. 24A, except that various amplicons for building internal edges are highlighted.

Figure 27B:
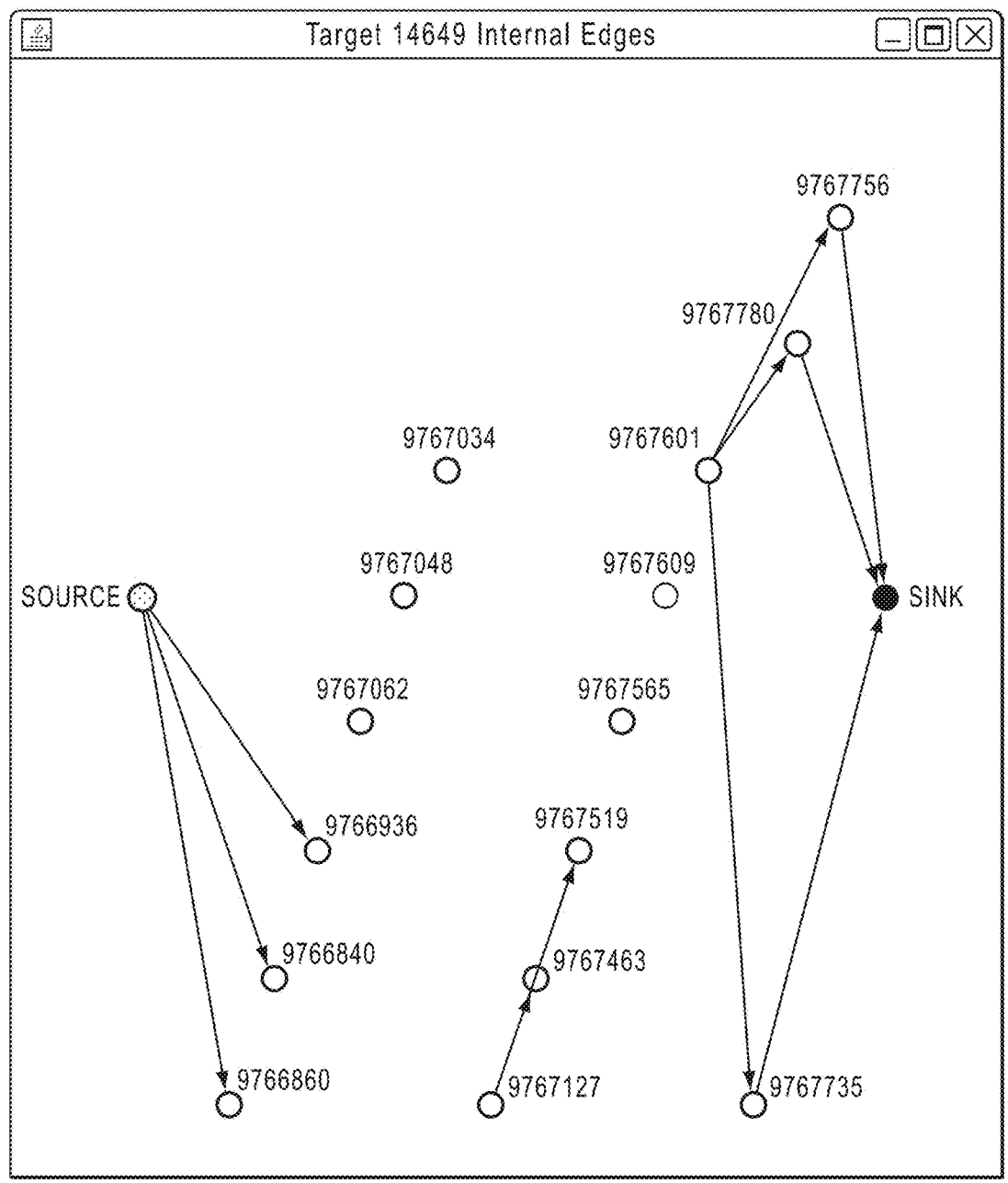
FIG. 27B illustrates the connection of some amplicon insert vertices to subsequent, proper, overlaps according to an exemplary embodiment.

FIG. 27B illustrates the connection of some amplicon insert vertices to subsequent, proper, overlaps according to an exemplary embodiment. Shown are arrows linking the 9767127 amplicon vertex to the 9767463 and 9767519 amplicon vertices (whose inserts overlap the insert of the 9767127 amplicon vertex) and arrows linking the 9767610 amplicon vertex to the 9767780 and 9767756 amplicon vertices (whose inserts overlap the insert of the 9767610 amplicon vertex).

Figure 28A:
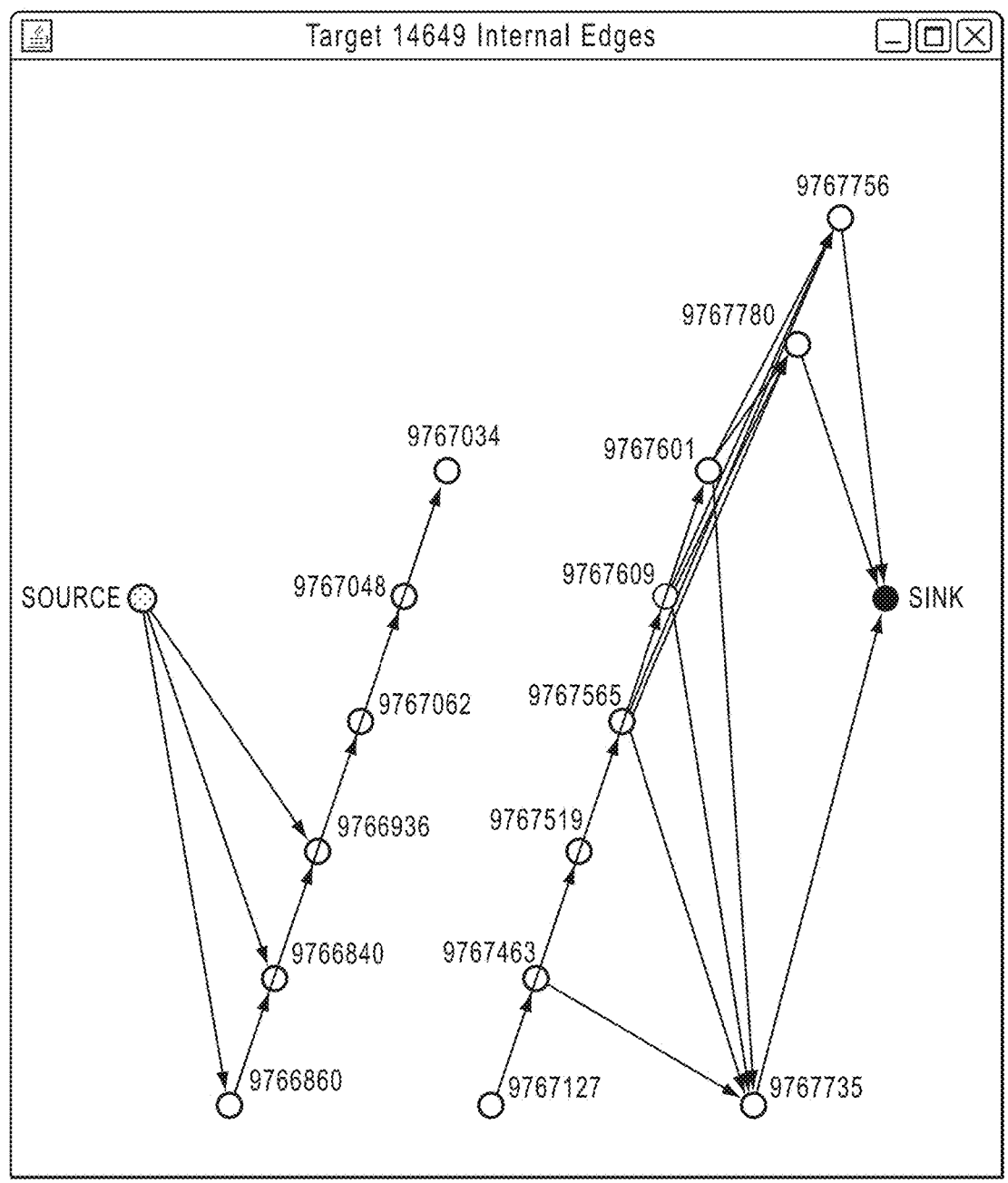
FIG. 28A illustrates the connection of additional amplicon insert vertices to subsequent, proper, overlaps according to an exemplary embodiment.

FIG. 28A illustrates the connection of additional amplicon insert vertices to subsequent, proper, overlaps according to an exemplary embodiment. Also shown is a disconnect or gap that may arise if the candidate amplicons do not fully cover the target.

Figure 28B:
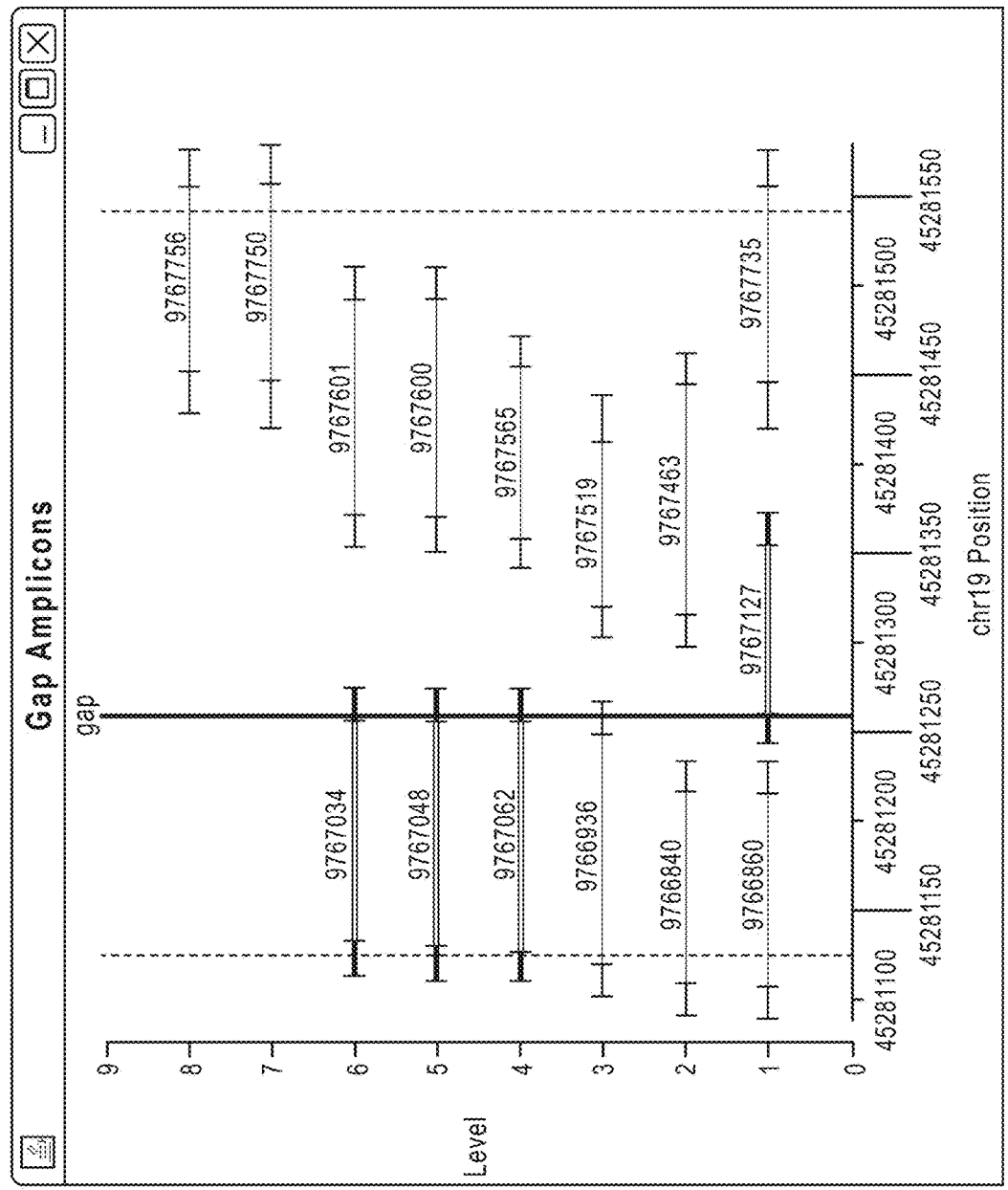
FIG. 28B illustrates the 15 candidate amplicons of FIG. 24A, along with the basis for the gap shown in FIG. 28A according to an exemplary embodiment.

FIG. 28B illustrates the 15 candidate amplicons of FIG. 24A, along with the basis for the gap shown in FIG. 28A according to an exemplary embodiment.

Figure 29A:
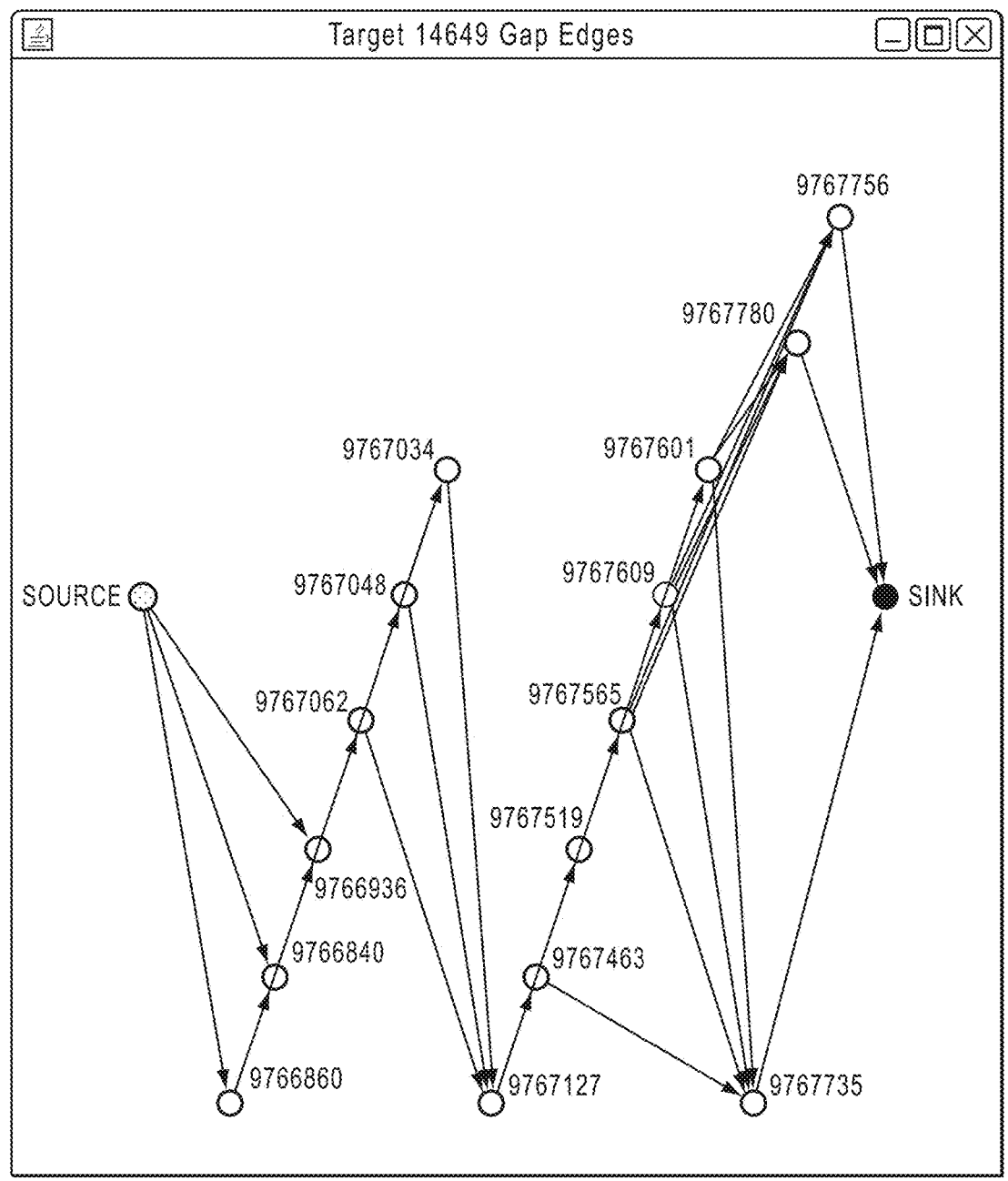
FIG. 29A illustrates three possible additional edges that could be used from source to sink to tile the target in this example according to an exemplary embodiment.

FIG. 29A illustrates three possible additional edges that could be used from source to ink to tile the target in this example according to an exemplary embodiment. In an embodiment, of the possible paths the one with a least cost may be selected.

Figure 29B:
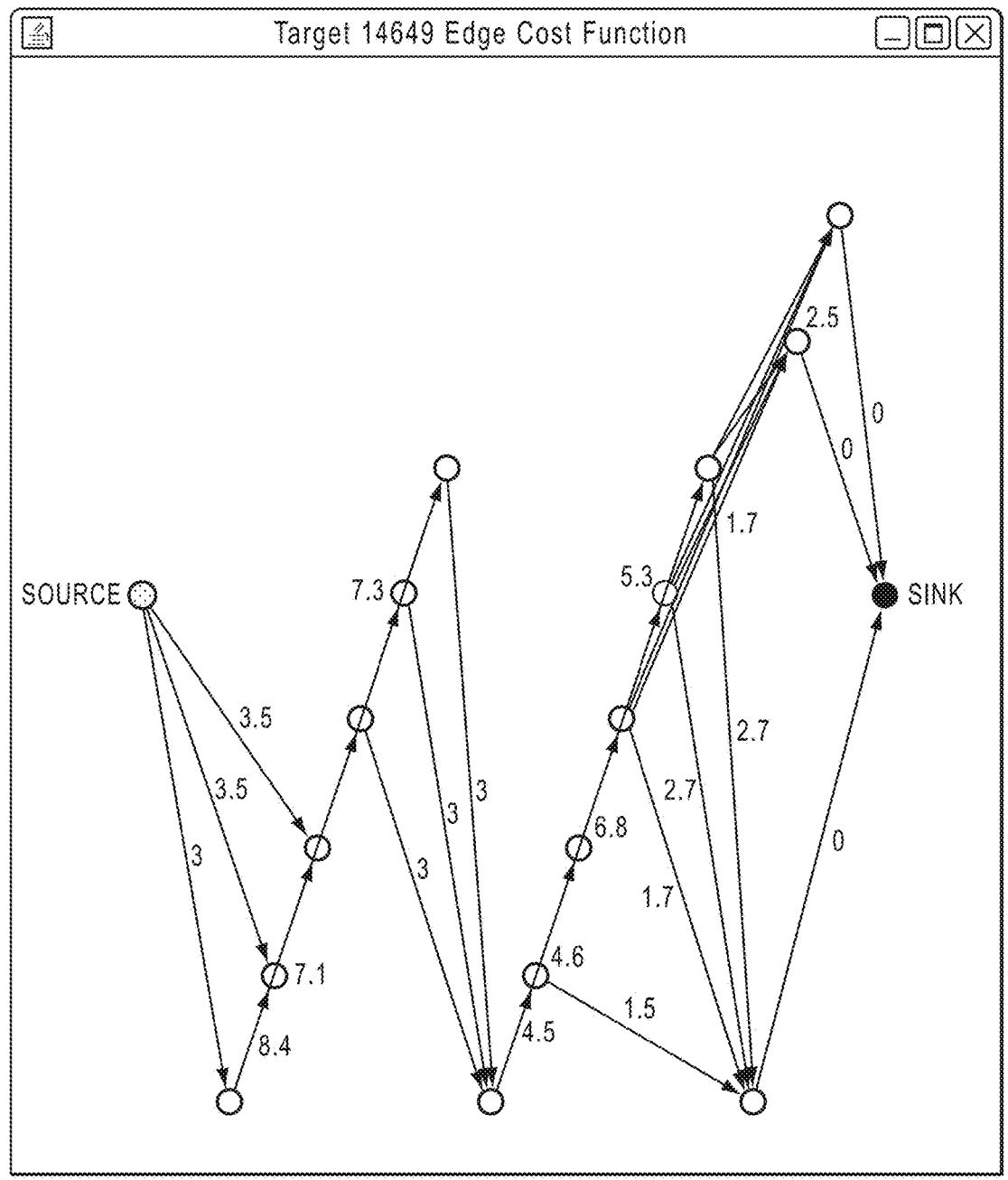
FIG. 29B illustrates an exemplary definition of an edge cost function assigning a cost to each one of the graph's edges linking amplicon vertices according to an exemplary embodiment.

FIG. 29B illustrates an exemplary definition of an edge cost function assigning a cost to each one of the graph's edges linking amplicon vertices according to an exemplary embodiment.

Figure 29C:
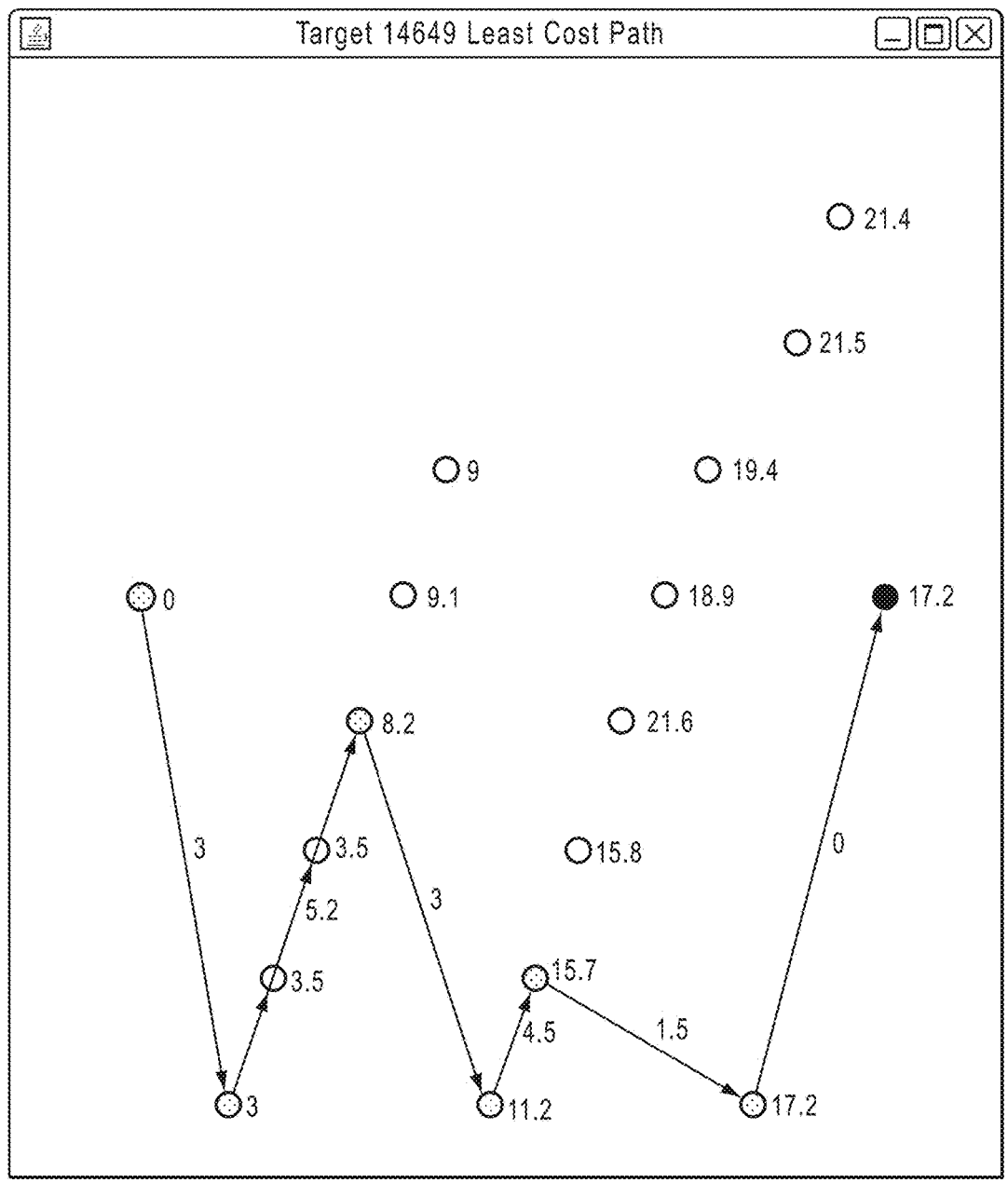
FIG. 29C illustrates the least-cost path from source to sink in the example of FIG. 29B according to an exemplary embodiment.

FIG. 29C illustrates the least-cost path from source to ink in the example of FIG. 29B according to an exemplary embodiment.

Figure 30:
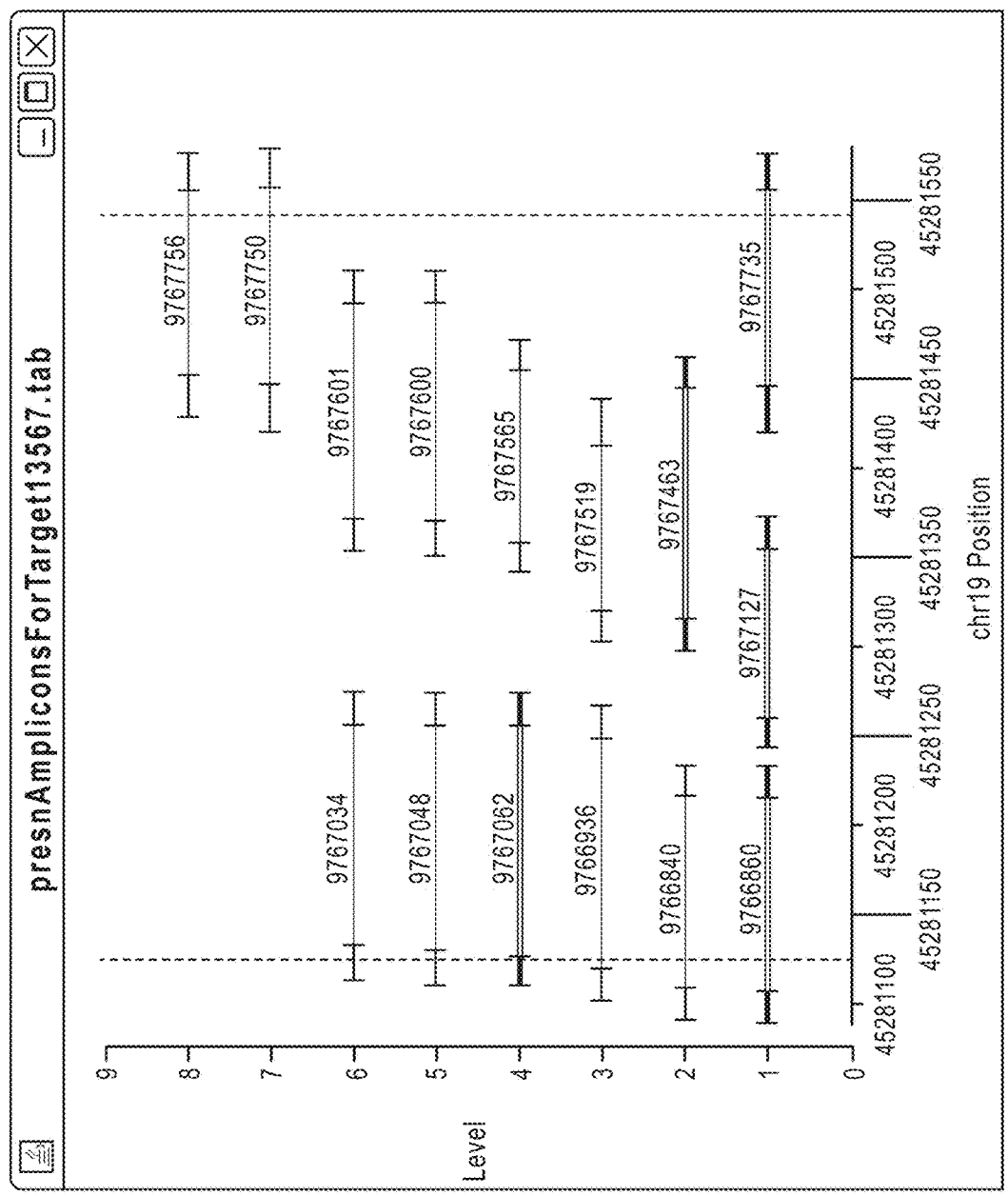
FIG. 30 illustrates the 15 candidate amplicons of FIG. 24A, except that the five amplicons corresponding to the vertices forming the least-cost path shown in FIG. 29C are highlighted.

FIG. 30 illustrates the 15 candidate amplicons of FIG. 24A, except that the five amplicons corresponding to the vertices forming the least-cost path shown in FIG. 29C are highlighted.

According to an exemplary embodiment, the least-cost path may be determined using an O(|V|+|E|) algorithm. The least-cost path may be determined as follows: (1) for each vertex v, (i) initialize D[v] to infinity (the least cost so far in the process) from the source vertex to v and initialize D[source] to zero, and (ii) initialize Pred[v] to null (the predecessor of v in the least-cost path from the source vertex to v); and (2) for each vertex u in topological order, for each vertex v in adj[u], if D[u]+cost(u,v)<D[v], then let D[v]=D[u]+cost(u,v) and Pred[v]=u. More information regarding algorithms for constructing paths on graphs may be found in Dijkstra, "A Note on Two Problems in Connexion with Graphs," Numerische Mathematik, vol. 1, 269-271 (1959), and Sniedovich, "Dijkstra's algorithm revisited: the dynamic programming connexion," Control and Cybernetics, vol. 35, 599-620 (2006), which are both incorporated by reference herein in their entirety.

According to an exemplary embodiment, the cost of a path (e.g., amplicon plus "union" redundancy) may be the sum of the edges forming the path. In an embodiment, the cost of a path may be determined using Equation 1 below:

$$\text{cost(path)} = \sum_{(u,v) \in path} \text{cost}(u, v) \qquad \text{Equation 1}$$

According to an exemplary embodiment, the cost of an edge forming a path may be a sum of an amplicon cost and an overlap cost weighed using a factor α selected to blend the two costs, e.g., 0≤α≤1. In an embodiment, the cost of an edge forming the path may be determined using Equation 2 below:

$$\text{cost}(u,v) = \alpha\text{cost}(v.\text{amplicon}) + (1-\alpha)\text{cost}(\text{overlap}(u,v)) \qquad \text{Equation 2}$$

According to an exemplary embodiment, there is provided a method for determining a cost associated with a tiling or subset of amplicons. In an embodiment, the cost of a tiling may be the sum of a cost of each amplicon in the tiling plus a cost of any one or more insert overlaps. The cost of an amplicon may be assigned any suitable value in any suitable predetermined range of values such that a low value imparts a low cost and a high value imparts a high cost so as to penalize various undesirable characteristics such as, for example, off-target amplification, primer-dimer propensity, etc. For example, the cost of an amplicon may be assigned a value from 1 to 10 such that a higher/lower cost is associated with a higher/lower level of undesirable characteristics (using any appropriate relationships, which may be linear/proportional or non-linear, for example). The cost of an insert overlap may also similarly be assigned any suitable value in any suitable predetermined range of values, for example, such that a low value imparts a low cost and a high value imparts a high cost so as to penalize various undesirable characteristics such as, for example, the redundancy introduced by overlapping inserts. For example, the cost of an insert overlap may also be assigned a value from 1 to 10. In an embodiment, one may opt to select a least-cost tiling from a set of candidate amplicons. In an embodiment, the cost of an insert overlap may be determined based on the redundancy introduced by overlapping inserts using Equation 3 below:

$$\text{redundancy}(\text{overlap}(u, v)) = \frac{\text{numBP}(\text{overlap}(u, v))}{\text{numBP}(\text{union}(u, v))} \quad \text{Equation 3}$$

According to an exemplary embodiment, the costs for amplicon and specificity may be used by a tiling hardware or software component of tiler to calculate the cost of an edge. In an embodiment, a cost system may be used that allows a scaled cost calculation for a vertex in the tiler. The cost of an amplicon may be a composite of the amplicon cost and the specificity cost. The amplicon cost may reflect the quality of PCR amplification and the specificity cost may reflect the propensity of the amplicon to amplify off-target nucleotides.

In an embodiment, the cost of an amplicon may be determined as follows: Initially, a threshold may be used to filter primers that allow potential off-target amplification. The filter may be based on a program such as e-PCR2 (NCBI), see Rotmistrovsky et al., "A web server for performing electronic PCR," Nucleic Acids Research, vol. 32, W108-W112 (2004), and Schuler, "Sequence Mapping by Electronic PCR," Genome Research, vol. 7, 541-550 (1997), which are both incorporated by reference herein in their entirety, or other similar programs capable of being used for filtering primers. Various scoring strategies may be used for filtering. In various embodiments, the assays may be filtered that have a sum of score of forward and reverve primer less than a certain minimal score threshold (e.g., 150) or show more than 50 hits with a score less than some threshold (e.g., 200). Of course, numerical cut-offs may differ and will vary according to software used. In various embodiments, scores used for filtering may be converted to a cost using a conversion table such as illustrated below:

| 0-19 | 170+ | 10 |
| 20-39 | 150-169 | 9 |
| 40-59 | 130-149 | 8 |
| 60-79 | 110-129 | 7 |
| 80-99 | 90-109 | 6 |
| 100-119 | 70-89 | 5 |
| 120-149 | 50-69 | 4 |
| 150-179 | 30-49 | 3 |
| 180-210 | 10-29 | 2 |
| 210+ | 0-9 | 1 |

In this exemplary table, the first column represents sp_score, which is a specificity score; the second column represents sp_hits, which is the number of matches for the forward and reverse primers facing each other; and the third column is a corresponding cost. The first perfect match is free, since it is the self match. In an embodiment, Acost is the cost based on binning the sp_score values, Bcost is the cost based on sp_hits values, and the amplicon cost may be calculated using the formula:

AmpliconCost=0.9*$A$cost+0.1*$B$cost.

Figure 31:
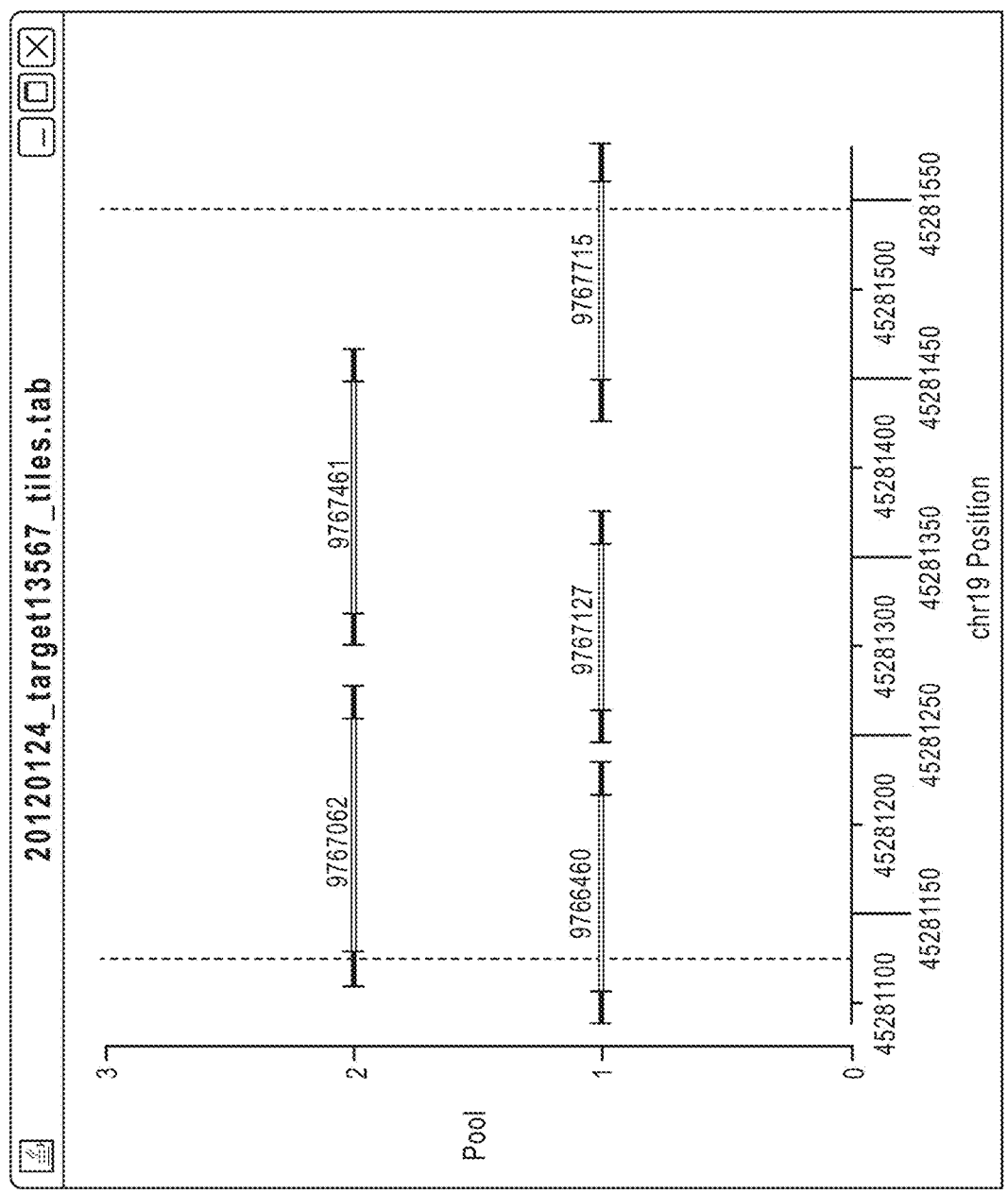
FIG. 31 illustrates three amplicons assigned to a first pool and two amplicons assigned to a second pool according to an exemplary embodiment.

FIG. 31 illustrates three amplicons assigned to a first pool and two amplicons assigned to a second pool according to an exemplary embodiment. The dotted lines indicate the boundaries of a target region (on chromosome 19 in this example). As illustrated, the amplicons in the first and second pools substantially cover the target regions, with the exception of the gaps.

According to an exemplary embodiment, there is provided a method for pooling amplicons into one or more pools of amplicons. In an embodiment, the method may pool the amplicons using one or more pooling criteria, which may related at least in part to pool sizes. In an embodiment, a number of pools may be limited to a pre-determined maximum number of pools, which may be 10 pools, for example, or which may be 50, 40, 30, 20, 9, 8, 7, 6, 5, 4, 3, 2, or 1, for example, or any other positive integer. In an embodiment, a capacity of each pool (e.g., a maximal size of a pool) may also be limited to a pre-determined maximal value, which may be any fixed number of amplicons, and which may be about 10,000, about 7,500, about 5,000, about 2,500, about 2,000, about 1,500, about 1,000, and about 500, or any value between those examples, for example, and which may be a maximum of 768 or 1,536 amplicons, for example. In an embodiment, a balance factor may be used, which may be a percentage between about 60% and 100%, or between about 65% and 95%, or between about 70% and 90%, or about 90%, for example. In an embodiment, the size of a pool p may be constrained by the inequality set forth in Equation 4 below:

$$\text{size}(p) \geq \left\lfloor \text{balanceFactor} \times \max_{q \in \text{pools}} \{\text{size}(q)\} \right\rfloor \quad \text{Equation 4}$$

According to an exemplary embodiment, an intra pool distance may be limited by a minimal threshold distance, which may be, for example, an integer number of base pairs (e.g., 50 base pairs, or 5, 10, 15, 20, etc., or any predetermined number of base pairs).

Figure 32A:
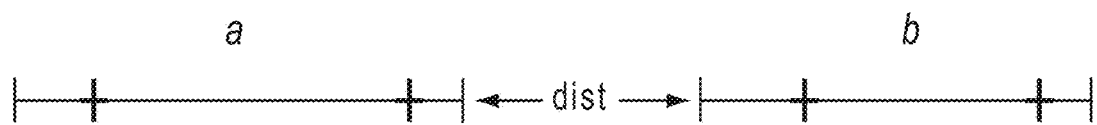
FIG. 32A illustrates a minimal distance between amplicons according to an exemplary embodiment.
Figure 32B:
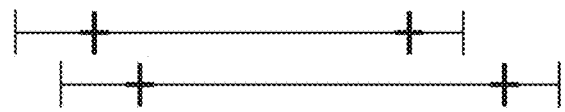
FIG. 32B-D illustrate several problems, including primer "race condition," preferential amplification of sub amplicons, and super amplicons that may be ameliorated by using a minimal distance as illustrated in FIG. 32A.
Figure 32C:
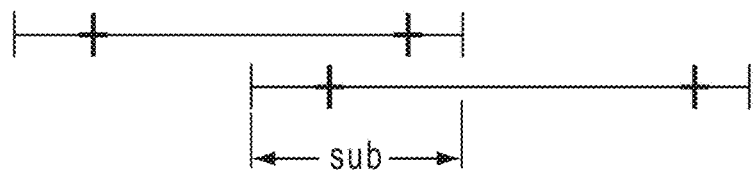
Figure 32D:
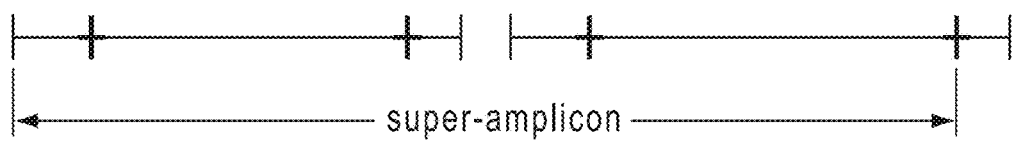

FIG. 32A illustrates a minimal distance between amplicons according to an exemplary embodiment. FIGS. 32B-D illustrate several problems, including primer "race condition" (see FIG. 32B), preferential amplification of sub amplicons (see FIG. 32C), and super amplicons (see FIG. 32D) that may be ameliorated by using a minimal distance as illustrated in FIG. 32A. In an embodiment, the distance may be determined using equation 5, for example. Such an approach may prevent or reduces "race condition," preferential amplification of sub amplicons, and super amplicons.

dist($a$,$b$)=max($a$.start,$b$.start)−min($a$.end,$b$.end)−1   Equation 5

According to an exemplary embodiment, amplicons may be disqualified from being added to a pool in certain circumstances. For example, an amplicon amp may not be added to a pool p if one or more of the following criteria are met: (1) the size of the pool p equals or exceeds the pool capacity limit; (2) the size of the pool p equals the size of the largest pool (e.g., size(p)=size(largest pool)) and the size of the smallest pool is less than a floor (rounded down) value of the product of (i) the size of the pool p plus 1 and (ii) a balance factor (e.g., size(smallest pool)<floor((size(p)+1) balanceFactor)); and (3) the distance between amp and any other amplicon already in the pool is less than a minimum amplicon separation threshold (e.g., which distance may be determined using Equation 5, for example).

Figure 33:
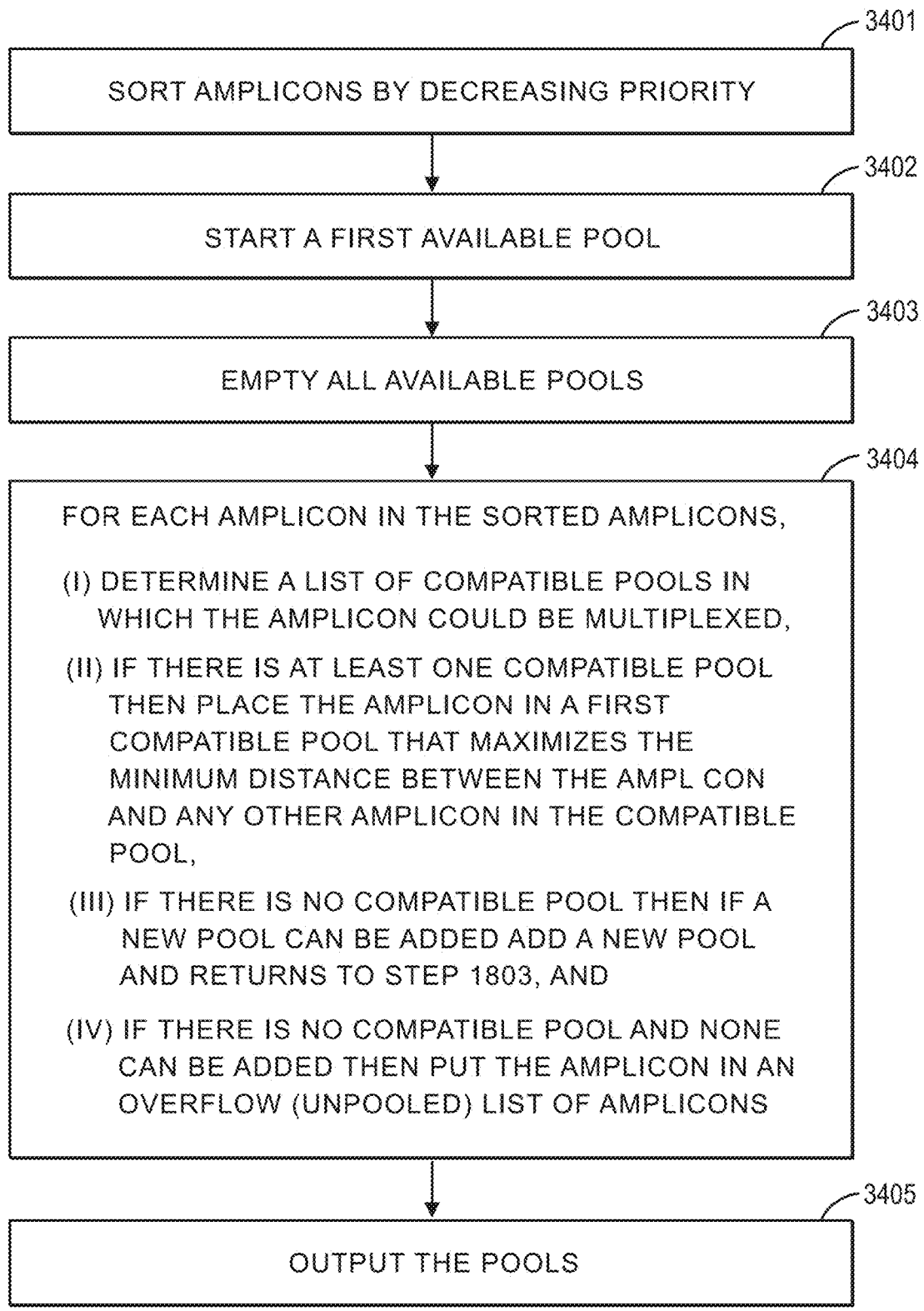
FIG. 33 illustrates a method for pooling amplicons across a plurality of pools according to an exemplary embodiment.

FIG. 33 illustrates a method for pooling amplicons across a plurality of pools according to an exemplary embodiment. In step 3401, a module or other hardware and/or software component sorts the amplicons by decreasing priority. In step 3402, a module or other hardware and/or software component starts a first available pool. In step 3403, a module or other hardware and/or software component empties all available pools. In step 3404, for each amplicon in the sorted amplicons, a module or other hardware and/or software component, (i) determines a list of compatible pools in which the amplicon could be multiplexed, (ii) if there is at least one compatible pool then places the amplicon in a first compatible pool that maximizes the minimum distance between the amplicon and any other amplicon in the compatible pool, (iii) if there is no compatible pool then if a new pool can be added adds a new pool and returns to step 3403, and (iv) if there is no compatible pool and none can be added then puts the amplicon in an overflow (unpooled) list of amplicons. In step 3405, a module or other hardware and/or software component outputs the pools.

According to an exemplary embodiment, a method for pooling amplicons across a plurality of pools comprises: (1) sorting the amplicons by decreasing priority; (2) starting a first available pool; (3) emptying all available pools; (4) for each amplicon in the sorted amplicons, (i) determining a list of compatible pools in which the amplicon could be multiplexed, (ii) if there is at least one compatible pool then placing the amplicon in a first compatible pool that maximizes the minimum distance between the amplicon and any other amplicon in the compatible pool, (iii) if there is no compatible pool then if a new pool can be added add a new pool and return to step (3), and (iv) if there is no compatible pool and none can be added then put the amplicon in an overflow (unpooled) list of amplicons. The method may further comprise outputting the amplicon pools.

Such a method may help ensure that the PCR pools cover as much of the targets as do the candidate amplicons supplied as input. It may generate a small number of PCR pools (e.g., 2, 4, etc.). The primers in a pool will not interact, which may help avoid undesired preferential amplification, "race condition" competition for primer hybridization, and super-amplicons. Further, such a method may run very quickly and using only a reasonable amount of memory.

Figure 34:
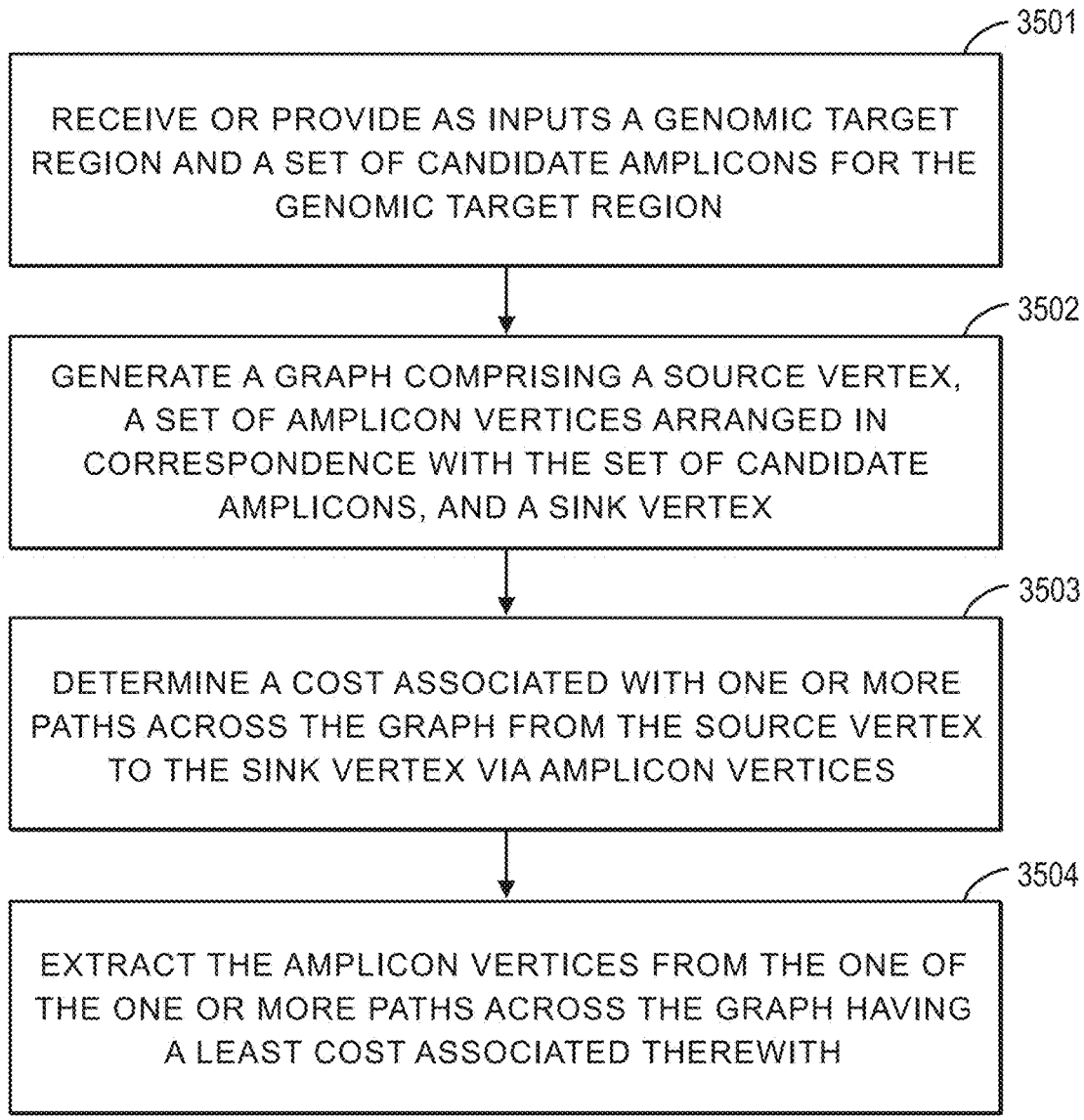
FIG. 34 illustrates a method according to an exemplary embodiment.

FIG. 34 illustrates a method for tiling according to an exemplary embodiment. In step 3501, a module or other hardware and/or software component receives or provides as inputs a genomic target region and a set of candidate amplicons for the genomic target region. In step 3502, a module or other hardware and/or software component generates a graph comprising a source vertex, a set of amplicon vertices arranged in correspondence with the set of candidate amplicons, and a sink vertex. In step 3503, a module or other hardware and/or software component determines a cost associated with one or more paths across the graph from the source vertex to the sink vertex via amplicon vertices. In step 3504, a module or other hardware and/or software component extracts the amplicon vertices from the one of the one or more paths across the graph having a least cost associated therewith. In some embodiments, such a method may be extended to a method for pooling amplicons across a plurality of pools by using as input the amplicons corresponding to the extracted vertices. For example, various steps such as described in FIG. 33 may be performed on amplicons corresponding to the extracted vertices to pool the amplicons.

According to an exemplary embodiment, there is provided a method comprising: (1) receiving or providing as inputs a genomic target region and a set of candidate amplicons for the genomic target region; (2) generating a graph comprising a source vertex, a set of amplicon vertices arranged in correspondence with the set of candidate amplicons, and a sink vertex; (3) determining a cost associated with one or more paths across the graph from the source vertex to the sink vertex via amplicon vertices; and (4) extracting the amplicon vertices from the one of the one or more paths across the graph having a least cost associated therewith.

In various embodiments, the one or more paths may comprise a sequence of amplicons wherein an ending portion of an insert of a first amplicon in the sequence of amplicons overlaps a beginning portion of an insert of a second amplicon in the sequence of amplicons. An ending portion of an insert of the second amplicon in the sequence of amplicons may overlap a beginning portion of an insert of a third amplicon in the sequence of amplicons. An ending portion of an insert of the third amplicon in the sequence of amplicons may overlap a beginning portion of an insert of a fourth amplicon in the sequence of amplicons.

In various embodiments, the one or more paths may comprise a sequence of N amplicons, N being a positive integer, wherein an ending portion of an insert of an amplicon amp in the sequence of amplicons overlaps a beginning portion of an insert of an amplicon amp+1 in the sequence of amplicons, wherein amp is an integer taking values 1, . . . , N−1. The one or more paths may comprise a sequence of L=N+M amplicons, N and M being positive integers, wherein an ending portion of an insert of an amplicon amp in the sequence of amplicons overlaps (which may include merely touching) a beginning portion of an insert of an amplicon amp+1 in the sequence of amplicons where amp is an integer taking values 1, . . . , N−1; wherein an ending portion of an insert of an amplicon amp in the sequence of amplicons overlaps (which may include merely touching) a beginning portion of an insert of an amplicon amp+1 in the sequence of amplicons where amp is an integer taking values N+1, . . . , N+M−1; and wherein there is a gap between an ending portion of an insert of amplicon amp=N and a beginning portion of an insert of amplicon amp=N+1.

In various embodiments, the cost associated with each of the one or more paths may be a sum of the cost of every edge of the path linking two amplicon vertices. The cost associated with every edge of the path linking two amplicon vertices may be a sum of a first term related to the cost of the edge's destination amplicon vertex and a second term related to the cost of an overlap between an insert of the edge's destination amplicon and an insert of the edge's origin amplicon. The first term and the second term may be weighed by a blending factor such that the first term is multiplied by the blending factor or a function thereof and the second term is multiplied by one minus the blending factor or a function thereof. The cost of an amplicon vertex may be a numerical value along a scale between a first value representing a lower level of one or more undesirable characteristics selected from a group comprising at least a level of off-target amplification and a level of primer-dimer propensity and a second value representing a higher level of the one or more undesirable characteristics. The cost of an overlap between an insert of the edge's destination amplicon and an insert of the edge's origin amplicon may be determined based on a redundancy introduced by overlapping inserts. The cost of an overlap between an insert of the edge's destination amplicon and an insert of the edge's origin amplicon may be a function of a quotient between a number of base pairs in an overlap between the insert of the edge's destination amplicon and the insert of the edge's origin amplicon and a number of base pairs in a union of the insert of the edge's destination amplicon and the insert of the edge's origin amplicon.

In various embodiments, such a method may further comprise determining a pooling of amplicons corresponding to the extracted amplicons into one or more pools of amplicons. Determining a pooling of amplicons may comprise limiting a number of amplicon pools and a capacity of each amplicon pool. Determining a pooling of amplicons may comprise limiting the number of amplicon pools to a threshold number between about 2 and about 5 and limiting the capacity of each amplicon pool to a threshold capacity between about 500 amplicons and about 2,500 amplicons, for example. Determining a pooling of amplicons may comprise limiting a size of any of the one or more pools based on a maximum size of other pools.

In various embodiments, determining a pooling of amplicons may comprise limiting an inclusion of one or more into a given pool based at least on a minimal threshold distance between amplicon sequences in the given pool. The minimal threshold distance may be between about 5 base pairs and about 100 base pairs, for example.

According to an exemplary embodiment, there is provided a non-transitory machine-readable storage medium comprising instructions which, when executed by a processor, cause the processor to perform a method comprising: (1) receiving or providing as inputs a genomic target region and a set of candidate amplicons for the genomic target region; (2) generating a graph comprising a source vertex, a set of amplicon vertices arranged in correspondence with the set of candidate amplicons, and a sink vertex; (3) determining a cost associated with one or more paths across the graph from the source vertex to the sink vertex via amplicon vertices; and (4) extracting the amplicon vertices from the one of the one or more paths across the graph having a least cost associated therewith. In some embodiments, such a method may be extended to a method for pooling amplicons across a plurality of pools by using as input the amplicons corresponding to the extracted vertices. For example, various steps such as described in FIG. 33 may be performed on amplicons corresponding to the extracted vertices to pool the amplicons.

In various embodiments, such a non-transitory machine-readable storage medium may comprise instructions which, when executed by a processor, cause the processor to perform a method further comprising determining a pooling of amplicons corresponding to the extracted amplicons into one or more pools of amplicons.

According to an exemplary embodiment, there is provided a system, comprising: (1) a machine-readable memory; and (2) a processor configured to execute machine-readable instructions, which, when executed by the processor, cause the system to perform steps including: (a) receiving or providing as inputs a genomic target region and a set of candidate amplicons for the genomic target region; (b) generating a graph comprising a source vertex, a set of amplicon vertices arranged in correspondence with the set of candidate amplicons, and a sink vertex; (c) determining a cost associated with one or more paths across the graph from the source vertex to the sink vertex via amplicon vertices; and (d) extracting the amplicon vertices from the one of the one or more paths across the graph having a least cost associated therewith. In some embodiments, such a system may be extended to a system for pooling amplicons across a plurality of pools by using as input the amplicons corresponding to the extracted vertices. For example, various steps such as described in FIG. 33 may be performed on amplicons corresponding to the extracted vertices to pool the amplicons.

In various embodiments, the processor of such a system may further be configured to execute machine-readable instructions, which, when executed by the processor, cause the system to perform steps including determining a pooling of amplicons corresponding to the extracted amplicons into one or more pools of amplicons.

According to various exemplary embodiments, one or more features of any one or more of the above-discussed teachings and/or exemplary embodiments may be performed or implemented using appropriately configured and/or programmed hardware and/or software elements. Determining whether an embodiment is implemented using hardware and/or software elements may be based on any number of factors, such as desired computational rate, power levels, heat tolerances, processing cycle budget, input data rates, output data rates, memory resources, data bus speeds, etc., and other design or performance constraints.

Examples of hardware elements may include processors, microprocessors, input(s) and/or output(s) (I/O) device(s) (or peripherals) that are communicatively coupled via a local interface circuit, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. The local interface may include, for example, one or more buses or other wired or wireless connections, controllers, buffers (caches), drivers, repeaters and receivers, etc., to allow appropriate communications between hardware components. A processor is a hardware device for executing software, particularly software stored in memory. The processor can be any custom made or commercially available processor, a central processing unit (CPU), an auxiliary processor among several processors associated with the computer, a semiconductor based microprocessor (e.g., in the form of a microchip or chip set), a macroprocessor, or generally any device for executing software instructions. A processor can also represent a distributed processing architecture. The I/O devices can include input devices, for example, a keyboard, a mouse, a scanner, a microphone, a touch screen, an interface for various medical devices and/or laboratory instruments, a bar code reader, a stylus, a laser reader, a radio-frequency device reader, etc. Furthermore, the I/O devices also can include output devices, for example, a printer, a bar code printer, a display, etc. Finally, the I/O devices further can include devices that communicate as both inputs and outputs, for example, a modulator/demodulator (modem; for accessing another device, system, or network), a radio frequency (RF) or other transceiver, a telephonic interface, a bridge, a router, etc.

Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. A software in memory may include one or more separate programs, which may include ordered listings of executable instructions for implementing logical functions. The software in memory may include a system for identifying data streams in accordance with the present teachings and any suitable custom made or commercially available operating system (O/S), which may control the execution of other computer programs such as the system, and provides scheduling, input-output control, file and data management, memory management, communication control, etc.

According to various exemplary embodiments, one or more features of any one or more of the above-discussed teachings and/or exemplary embodiments may be performed or implemented using appropriately configured and/or programmed non-transitory machine-readable medium or article that may store an instruction or a set of instructions that, if executed by a machine, may cause the machine to perform a method and/or operations in accordance with the exemplary embodiments. Such a machine may include, for example, any suitable processing platform, computing platform, computing device, processing device, computing system, processing system, computer, processor, scientific or laboratory instrument, etc., and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, read-only memory compact disc (CD-ROM), recordable compact disc (CD-R), rewriteable compact disc (CD-RW), optical disk, magnetic media, magneto-optical media, removable memory cards or disks, various types of Digital Versatile Disc (DVD), a tape, a cassette, etc., including any medium suitable for use in a computer. Memory can include any one or a combination of volatile memory elements (e.g., random access memory (RAM, such as DRAM, SRAM, SDRAM, etc.)) and non-volatile memory elements (e.g., ROM, EPROM, EEROM, Flash memory, hard drive, tape, CDROM, etc.). Moreover, memory can incorporate electronic, magnetic, optical, and/or other types of storage media. Memory can have a distributed architecture where various components are situated remote from one another, but are still accessed by the processor. The instructions may include any suitable type of code, such as source code, compiled code, interpreted code, executable code, static code, dynamic code, encrypted code, etc., implemented using any suitable high-level, low-level, object-oriented, visual, compiled and/or interpreted programming language.

According to various exemplary embodiments, one or more features of any one or more of the above-discussed teachings and/or exemplary embodiments may be performed or implemented at least partly using a distributed, clustered, remote, or cloud computing resource.

According to various exemplary embodiments, one or more features of any one or more of the above-discussed teachings and/or exemplary embodiments may be performed or implemented using a source program, executable program (object code), script, or any other entity comprising a set of instructions to be performed. When a source program, the program can be translated via a compiler, assembler, interpreter, etc., which may or may not be included within the memory, so as to operate properly in connection with the O/S. The instructions may be written using (a) an object oriented programming language, which has classes of data and methods, or (b) a procedural programming language, which has routines, subroutines, and/or functions, which may include, for example, C, C++, Pascal, Basic, Fortran, Cobol, Perl, Java, and Ada.

According to various exemplary embodiments, one or more of the above-discussed exemplary embodiments may include transmitting, displaying, storing, printing or outputting to a user interface device, a computer readable storage medium, a local computer system or a remote computer system, information related to any information, signal, data, and/or intermediate or final results that may have been generated, accessed, or used by such exemplary embodiments. Such transmitted, displayed, stored, printed or outputted information can take the form of searchable and/or filterable lists of runs and reports, pictures, tables, charts, graphs, spreadsheets, correlations, sequences, and combinations thereof, for example.

Various additional exemplary embodiments may be derived by repeating, adding, or substituting any generically or specifically described features and/or components and/or substances and/or steps and/or operating conditions set forth in one or more of the above-described exemplary embodiments. Further, it should be understood that an order of steps or order for performing certain actions is immaterial so long as the objective of the steps or action remains achievable, unless specifically stated otherwise. Furthermore, two or more steps or actions can be conducted simultaneously so long as the objective of the steps or action remains achievable, unless specifically stated otherwise. Moreover, any one or more feature, component, aspect, step, or other characteristic mentioned in one of the above-discussed exemplary embodiments may be considered to be a potential optional feature, component, aspect, step, or other characteristic of any other of the above-discussed exemplary embodiments so long as the objective of such any other of the above-discussed exemplary embodiments remains achievable, unless specifically stated otherwise.

Various additional exemplary embodiments may be derived by incorporating in the above described exemplary embodiments one or more of the features described in U.S. Pat. Appl. Publ. No. 2008/0228589 A1, published Sep. 18, 2008, and U.S. Pat. Appl. Publ. No. 2004/0175733 A1, published Sep. 9, 2004, the contents of both of which are incorporated by reference herein in their entireties.

In some embodiments, the amplified target sequences generated by the methods disclosed herein represent at least 60%, 70%, 80%, 90%, or more, of one or more exons amplified from the plurality of target sequences. In one embodiment, amplified target sequences of the present invention are about 90 to about 140 base pairs in length, about 100 to about 200 base pairs in length, about 100 to about 300 base pairs in length, or about 100 to about 400 base pairs in length. In one embodiment, the amplified target sequence includes the length of the forward primer and the length of the complementary reverse primer for each primer pair. In another embodiment, the amplified target sequence length includes the length of the reverse primer and the length of the complementary forward primer. In some embodiments, the length of the amplified target sequence minus the forward and reverse primer lengths is about 40 base pairs to about 350 base pairs. In some embodiments, the length of the amplified target sequences generated in the multiplex PCR reaction is substantially the same. As defined herein, "substantially the same" with respect to length of amplified target sequences generated via the methods disclosed herein refers to no more than 30% deviation in nucleotide length across the total number of amplified target sequences. In one embodiment, the percent GC content of an amplicon is less than 85%, less than 75%, less than 65%, less than 60%, or less than 50%. In one embodiment, substantially all amplified target sequences within a reaction contain between 30% and less than 85% GC content. In one embodiment, where the nucleic acid molecules are obtained from an archived or FFPE DNA sample, the length of the amplified target sequence is typically about 100 to about 200 base pairs in length. In one embodiment, if the nucleic acid sample is derived or obtained from genomic DNA, the length of the amplified target sequence can be about 100 to about 500 base pairs in length.

In some embodiments, the amplified target sequences of the disclosed methods can be used in various downstream analysis or assays with, or without, further purification or manipulation. For example, the amplified target sequences can be clonally amplified by techniques known in the art, such a bridge amplification or emPCR to generate a template library that can be used in next generation sequencing. In some embodiments, the amplified target sequences of the disclosed methods or the resulting template libraries can be used for single nucleotide polymorphism (SNP) analysis, genotyping or epigenetic analysis, copy number variation analysis, gene expression analysis, analysis of gene mutations including but not limited to detection, prognosis and/or diagnosis, detection and analysis of rare or low frequency allele mutations, nucleic acid sequencing including but not limited to de novo sequencing, targeted resequencing and synthetic assembly analysis. In one embodiment, amplified target sequences can be used to detect mutations at less than 5% allele frequency. In some embodiments, the methods disclosed herein can be used to detect mutations in a population of nucleic acids at less than 4%, 3%, 2% or at about 1% allele frequency. In another embodiment, amplified target sequences prepared as described herein can be sequenced to detect and/or identify germline or somatic mutations from a population of nucleic acid molecules.

In some embodiments, the forward and/or reverse target-specific primers in the target-specific primer pairs can be "complementary" or "substantially complementary" to the population of nucleic acid molecules. As termed herein "substantially complementary to the population of nucleic acid molecules" refers to percentage complementarity between the primer and the nucleic acid molecule to which the primer will hybridize. Generally, the term "substantially complementary" as used herein refers to at least 70% complementarity. Therefore, substantially complementary refers to a range of complementarity of at least 70% but less than 100% complementarity between the primer and the nucleic acid molecule. A complementary primer is one that possesses 100% complementarity to the nucleic acid molecule. In one embodiment, each target-specific primer pair is designed to minimize cross-hybridization to another primer (or primer pair) in the same multiple PCR reaction (i.e., reduce the prevalence of primer-dimers). In another embodiment, each target-specific primer pair is designed to minimize cross-hybridization to non-specific nucleic acid sequences in the population of nucleic acid molecules (i.e., minimize off-target hybridization). In one embodiment, each target-specific primer is designed to minimize self-complementarity, formation of hairpin structures or other secondary structures.

In some embodiments, the amplified target sequences are formed via polymerase chain reaction. Extension of target-specific primers can be accomplished using one or more DNA polymerases. In one embodiment, the polymerase can be any Family A DNA polymerase (also known as pol I family) or any Family B DNA polymerase. In some embodiments, the DNA polymerase can be a recombinant form capable of extending target-specific primers with superior accuracy and yield as compared to a non-recombinant DNA polymerase. For example, the polymerase can include a high-fidelity polymerase or thermostable polymerase. In some embodiments, conditions for extension of target-specific primers can include 'Hot Start' conditions, for example Hot Start polymerases, such as Amplitaq Gold® DNA polymerase (Applied Biosciences), Platinum® Taq DNA Polymerase High Fidelity (Invitrogen) or KOD Hot Start DNA polymerase (EMD Biosciences). Generally, a 'Hot Start' polymerase includes a thermostable polymerase and one or more antibodies that inhibit DNA polymerase and 3'-5' exonuclease activities at ambient temperature. In some instances, 'Hot Start' conditions can include an aptamer.

In some embodiments, the polymerase can be an enzyme such as Taq polymerase (from *Thermus aquaticus*), Tfi polymerase (from *Thermus filiformis*), Bst polymerase (from *Bacillus stearothermnophilus*), Pfu polymerase (from *Pyrococcus furiosus*), Tth polymerase (from *Thermus thermophilus*), Pow polymerase (from *Pyrococcus woesei*), Tli polymerase (from *Thermococcus litoralis*), Ultima polymerase (from *Thermotoga maritima*), KOD polymerase (from *Thermococcus kodakaraensis*), Pol I and II polymerases (from *Pyrococcus abyssi*) and Pab (from *Pyrococcus abyssi*). In some embodiments, the DNA polymerase can include at least one polymerase such as Amplitaq Gold® DNA polymerase (Applied Biosciences), Stoffel fragment of Amplitaq® DNA Polymerase (Roche), KOD polymerase (EMD Biosciences), KOD Hot Start polymerase (EMD Biosciences), Deep Vent™ DNA polymerase (New England Biolabs), Phusion polymerase (New England Biolabs), Klentaql polymerase (DNA Polymerase Technology, Inc), Klentaq Long Accuracy polymerase (DNA Polymerase Technology, Inc), Omni KlenTaq™ DNA polymerase (DNA Polymerase Technology, Inc), Omni KlenTaq™ LA DNA polymerase (DNA Polymerase Technology, Inc), Platinum® Taq DNA Polymerase (Invitrogen), Hemo Klentaq™ (New England Biolabs), Platinum® Taq DNA Polymerase High Fidelity (Invitrogen), Platinum® Pfx (Invitrogen), Accuprime™ Pfx (Invitrogen), or Accuprime™ Taq DNA Polymerase High Fidelity (Invitrogen).

In some embodiments, the DNA polymerase can be a thermostable DNA polymerase. In some embodiments, the mixture of dNTPs can be applied concurrently, or sequentially, in a random or defined order. In some embodiments, the amount of DNA polymerase present in the multiplex reaction is significantly higher than the amount of DNA polymerase used in a corresponding single plex PCR reaction. As defined herein, the term "significantly higher" refers to an at least 3-fold greater concentration of DNA polymerase present in the multiplex PCR reaction as compared to a corresponding single plex PCR reaction.

In some embodiments, the amplification reaction does not include a circularization of amplification product, for example as disclosed by rolling circle amplification.

In some embodiments, the methods of the disclosure include selectively amplifying target sequences in a sample containing a plurality of nucleic acid molecules and ligating the amplified target sequences to at least one Adaptersadapters and/or barcode. Adapters and barcodes for use in molecular biology library preparation techniques are well known to those of skill in the art. The definitions of adapters and barcodes as used herein are consistent with the terms used in the art. For example, the use of barcodes allows for the detection and analysis of multiple samples, sources, tissues or populations of nucleic acid molecules per multiplex reaction. A barcoded and amplified target sequence contains a unique nucleic acid sequence, typically a short 6-15 nucleotide sequence, that identifies and distinguishes one amplified nucleic acid molecule from another amplified nucleic acid molecule, even when both nucleic acid molecules minus the barcode contain the same nucleic acid sequence. The use of adapters allows for the amplification of each amplified nucleic acid molecule in a uniformed manner and helps reduce strand bias. Adapters can include universal adapters or propriety adapters both of which can be used downstream to perform one or more distinct functions. For example, amplified target sequences prepared by the methods disclosed herein can be ligated to an adapter that may be used downstream as a platform for clonal amplification. The adapter can function as a template strand for subsequent amplification using a second set of primers and therefore allows universal amplification of the adapter-ligated amplified target sequence. In some embodiments, selective amplification of target nucleic acids to generate a pool of amplicons can further comprise ligating one or more barcodes and/or adapters to an amplified target sequence. The ability to incorporate barcodes enhances sample throughput and allows for analysis of multiple samples or sources of material concurrently. In one example, amplified target nucleic acid molecules prepared by the disclosed methods can be ligated to Ion Torrent™ Sequencing AdaptersAdapters (A and P1 Adaptersadapters, sold as a component of the Ion Fragment Library Kit, Life Technologies, Part No. 4466464) or Ion Torrent™ DNA Barcodes (Life Technologies, Part No. 4468654).

The methods disclosed herein are directed to the amplification of multiple target sequences via polymerase chain reaction (PCR). In some embodiments the multiplex PCR comprises hybridizing one or more target-specific primer pairs to a nucleic acid molecule, extending the primers of the target-specific primer pairs via template dependent synthesis in the presence of a DNA polymerase and dNTPs; repeating the hybridization and extension steps for sufficient time and sufficient temperature there generating a plurality of amplified target sequences. In some embodiments, the steps of the multiplex amplification reaction method can be performed in any order.

The amount of nucleic acid material required for successful multiplex amplification can be about 1 ng. In some embodiments, the amount of nucleic acid material can be about 10 ng to about 50 ng, about 10 ng to about 100 ng, or about 1 ng to about 200 ng of nucleic acid material. Higher amounts of input material can be used, however one aspect of the disclosure is to selectively amplify a plurality of target sequence from a low (ng) about of starting material.

The multiplex PCR amplification reactions disclosed herein can include a plurality of "cycles" typically performed on a thermocycler. Generally, each cycle includes at least one annealing step and at least one extension step. In one embodiment, a multiplex PCR amplification reaction is performed wherein target-specific primer pairs are hybridized to a target sequence; the hybridized primers are extended generating an extended primer product/nucleic acid duplex; the extended primer product/nucleic acid duplex is denatured allowing the complementary primer to hybridize to the extended primer product, wherein the complementary primer is extended to generate a plurality of amplified target sequences. In one embodiment, the methods disclosed herein have about 5 to about 18 cycles per preamplification reaction. The annealing temperature and/or annealing duration per cycle can be identical; can include incremental increases or decreases, or a combination of both. The extension temperature and/or extension duration per cycle can be identical; can include incremental increases or decreases, or a combination of both. For example, the annealing temperature or extension temperature can remain constant per cycle. In some embodiments, the annealing temperature can remain constant each cycle and the extension duration can incrementally increase per cycle. In some embodiments, increases or decreases in duration can occur in 15 second, 30 second, 1 minute, 2 minute or 4 minute increments. In some embodiments, increases or decrease in temperature can occur as 0.5, 1, 2, 3, or 4 Celsius deviations. In some embodiments, the amplification reaction can be conducted using hot-start PCR techniques. These techniques include the use of a heating step (>60° C.) before polymerization begins to reduce the formation of undesired PCR products. Other techniques such as the reversible inactivation or physical separation of one or more critical reagents of the reaction, for example the magnesium or DNA polymerase can be sequestered in a wax bead, which melts as the reaction is heated during the denaturation step, releasing the reagent only at higher temperatures. The DNA polymerase can also be kept in an active state by binding to an aptamer or an antibody. This binding is disrupted at higher temperatures, releasing the functional DNA polymerase that can proceed with the PCR unhindered.

In some embodiments, the disclosed methods can optionally include destroying one or more primer-containing amplification artifacts, e.g., primer-dimers, dimer-dimers or superamplicons. In some embodiments, the destroying can optionally include treating the primer and/or amplification product so as to cleave specific cleavable groups present in the primer and/or amplification product. In some embodiments, the treating can include partial or complete digestion of one or more target-specific primers. In one embodiment, the treating can include removing at least 40% of the target specific primer from the amplification product. The cleavble treatment can include enzymatic, acid, alkali, thermal, photo or chemical activity. The cleavable treatment can result in the cleavage or other destruction of the linkages between one or more nucleotides of the primer, or between one or more nucleotides of the amplification product. The primer and/or the amplification product can optionally include one or more modified nucleotides or nucleobases. In some embodiments, the cleavage can selectively occur at these sites, or adjacent to the modified nucleotides or nucleobases. In some embodiments, the cleavage or treatment of the amplified target sequence can result in the formation of a phosphorylated amplified target sequence. In some embodiments, the amplified target sequence is phosphorylated at the 5' terminus.

In some embodiments, the template, primer and/or amplification product includes nucleotides or nucleobases that can be recognized by specific enzymes. In some embodiments, the nucleotides or nucleobases can be bound by specific enzymes. Optionally, the specific enzymes can also cleave the template, primer and/or amplification product at one or more sites. In some embodiments, such cleavage can occur at specific nucleotides within the template, primer and/or amplification product. For example, the template, primer and/or amplification product can include one or more nucleotides or nucleobases including uracil, which can be recognized and/or cleaved by enzymes such as uracil DNA glycosylase (UDG, also referred to as UNG) or formamidopyrimidine DNA glycosylase (Fpg). The template, primer and/or amplification product can include one or more nucleotides or nucleobases including RNA-specific bases, which can be recognized and/or cleaved by enzymes such as RNAseH. In some embodiments, the template, primer and/or amplification product can include one or more abasic sites, which can be recognized and/or cleaved using various proofreading polymerases or apyrase treatments. In some embodiments, the template, primer and/or amplification product can include 7,8-dihydro-8-oxoguanine (8-oxoG) nucleobases, which can be recognized or cleaved by enzymes such as Fpg. In some embodiments, one or more amplified target sequences can be partially digested by a FuPa reagent.

In some embodiments, the primer and/or amplification product includes one or more modified nucleotides including bases that bind, e.g., base pair, with other nucleotides, for example nucleotides in a complementary nucleic acid strand, via chemical linkages. In some embodiments, the chemical linkages are subject to specific chemical attack that selectively cleaves the modified nucleotides (or selectively cleaves one or more covalent linkages between the modified nucleotides and adjacent nucleotides within the primer and/or amplification product) but leaves the other nucleotides unaffected. For example, in some embodiments modified nucleotides can form disulfite linkages with other nucleotides in a complementary strand. Such disulfite linkages can be oxidized via suitable treatments. Similarly, certain modified nucleotides can base pair with other nucleotides in a complementary nucleic acid strand through linkages that can be selectively disrupted via alkali treatment. In some embodiments, the primer and/or amplification product includes one or more modified nucleotides that bind, e.g., base pair, with other nucleotides in a complementary nucleic acid strand through linkages exhibiting decreased thermal stability relative to typical base pairing linkages formed between natural bases. Such reduced-thermal stability linkages can be selectively disrupted through exposure of the primer and/or amplification product to elevated temperatures following amplification.

An exemplary embodiment is depicted in FIG. 1, which depicts a schematic of degradable amplification primers. The amplification primers are bisulfite in design, with either a 5' universal forward amplification sequence linked to a 3' target-specific forward primer, or a 5' universal reverse amplification sequence linked to a 3' target-specific reverse primer. Both primers contain modified nucleotides.

In some embodiments, primers are synthesized that are complementary to, and can hybridize with, discrete segments of a nucleic acid template strand, including: a primer that can hybridize to the 5' region of the template, which encompasses a sequence that is complementary to either the forward or reverse amplification primer. In some embodiments, the forward primers, reverse primers, or both, share no common nucleic acid sequence, such that they hybridize to distinct nucleic acid sequences. For example, target-specific forward and reverse primers can be prepared that do not compete with other primer pairs within the primer pool to amplify the same nucleic acid sequence. In this example, primer pairs that do not compete with other primer pairs in the primer pool assist in the reduction of non-specific or spurious amplification products. In some embodiments, the forward and reverse primers of each primer pair are unique, in that the nucleotide sequence for each primer is non-complementary and non-identical to the other primer in the primer pair. In some embodiments, the primer pair can differ by at least 10%, at least 20%, at least 30%, at least 40%, at least 50%, at least 60%, at least 70%, at least 75%, at least 80%, at least 85%, or at least 90% nucleotide identity. In some embodiments, the forward and reverse primers in each primer pair are non-complementary or non-identical to other primer pairs in the primer pool or multiplex reaction. For example, the primer pairs within a primer pool or multiplex reaction can differ by at least 5%, at least 10%, at least 20%, at least 30%, at least 40%, at least 50%, at least 60%, or at least 70% nucleotide identity to other primer pairs within the primer pool or multiplex reaction. Generally, primers are designed to minimize the formation of primer-dimers, dimer-dimers or other non-specific amplification products. Typically, primers are optimized to reduce GC bias and low melting temperatures ($T_m$) during the amplification reaction. In some embodiments, the primers are designed to possess a $T_m$ of about 55° C. to about 72° C. In some embodiments, the primers of a primer pool can possess a $T_m$ of about 59° C. to about 70° C., 60° C. to about 68° C., or 60° C. to about 65° C. In some embodiments, the primer pool can possess a $T_m$ that does not deviate by more than 5° C.

In some embodiments, the target-specific primers do not contain a carbon-spacer or terminal linker. In some embodiments, the target-specific primers or amplified target sequences do not contain an enzymatic, magnetic, optical or fluorescent label.

The template can include a 3' region that contains the sequence for either the upstream or downstream regions surrounding a particular gene or region of interest, such that the region of interest is bracketed by a forward amplification/upstream gene-specific fusion, and a reverse amplification/downstream region of interest fusion primer. In some embodiments, an internal separator sequence can separate the template regions that can hybridize to the amplification and gene-specific primers, and this may act as a key or barcode for subsequent downstream applications such as sequencing, etc. In some embodiments, a barcode or key can be incorporated into each of the amplification products to assist with data analysis and for example, cataloging. In some embodiments, the barcodes can be Ion Torrent™ DNA barcodes (Life Technologies).

In some embodiments, the primer includes a sufficient number of modified nucleotides to allow functionally complete degradation of the primer by the cleavage treatment, but not so many as to interfere with the primer's specificity or functionality prior to such cleavage treatment, for example in the amplification reaction. In some embodiments, the primer includes at least one modified nucleotide, but no greater than 75% of nucleotides of the primer are modified.

In some embodiments, multiple different primers including at least one modified nucleotide can be used in a single amplification reaction. For example, multiplexed primers including modified nucleotides can be added to the amplification reaction mixture, where each primer (or set of primers) selectively hybridizes to, and promotes amplification of different target nucleic acid molecules within the nucleic acid population. In some embodiments, different primer combinations can be added to the amplification reaction at plexy of at least about 24, 96, 384, 768, 1000, 2000, 3000, 6000 or 10000, or more (where "plexy" indicates the total number of different targets that can theoretically be amplified in a sequence-specific manner in the amplification reaction). In some embodiments, the modified primers contain at least one modified nucleotide near or at the termini of the primer. In some embodiments, the modified primers contain two or more modified nucleotides within the primer sequence. In an exemplary embodiment, the primer sequence contains a uracil near, or at, the termini of the primer sequence. For the purposes of this disclosure "near" or "at the termini" of the primer sequences refers up to 10 nucleotides from the termini of the primer sequence. In some embodiments, the primer sequence contains a uracil located at, or about, the center nucleotide position of the primer sequence. For the purposes of this disclosure "at, or about the center nucleotide position of the primer sequence" refers to the incorporation of a uracil moiety at the center nucleotide of the primer sequence or within eight nucleotides, in either a 3' or 5' direction flanking the center nucleotide. In one embodiment, the target-specific primer sequence can contain a modified nucleobase at or about the center nucleotide position and contain a modified nucleobase at the 3' and/or 5' terminus. In some embodiments, the length of the forward or reverse primer sequence can be about 15 to about 40 bases in length. In some embodiments, the $T_m$ of the primer sequence used in the multiplex reaction can be about 55° C. to about 72° C. In some embodiments, the primer pairs are designed to amplify sequences from the target nucleic acid molecules or amplicons that are about 100 base pairs to about 500 base pairs in length.

In some embodiments, the amplification reactions are conducted in parallel within a single reaction phase (for example, within the same amplification reaction mixture within a single tube). In some instances, an amplification reaction can generate a mixture of products including both the intended amplicon product as well as unintended, unwanted, nonspecific amplification artifacts such as primer-dimers. Post amplification, the reactions are then treated with any suitable agent that will selectively cleave or otherwise selectively destroy the nucleotide linkages of the modified nucleotides within the excess unincorporated primers and the amplification artifacts without cleaving or destroying the specification amplification products. For example, the primers can include uracil-containing nucleobases that can be selectively cleaved using UNG/UDG (optionally with heat and/or alkali). In some embodiments, the primers can include uracil-containing nucleotides that can be selectively cleaved using UNG and Fpg. In some embodiments, the cleavage treatment includes exposure to oxidizing conditions for selective cleavage of dithiols, treatment with RNAseH for selective cleavage of modified nucleotides including RNA-specific moieties (e.g., ribose sugars, etc.), and the like. This cleavage treatment can effectively fragment the original amplification primers and non-specific amplification products into small nucleic acid fragments that include relatively few nucleotides each. Such fragments are typically incapable of promoting further amplification at elevated temperatures. Such fragments can also be removed relatively easily from the reaction pool through the various post-amplification cleanup procedures known in the art (e.g., spin columns, NaEtOH precipitation, etc).

In some embodiments, amplification products following cleavage or other selective destruction of the nucleotide linkages of the modified nucleotides are optionally treated to generate amplification products that possess a phosphate at the 5' termini. In some embodiments, the phosphorylation treatment includes enzymatic manipulation to produce 5' phosphorylated amplification products. In one embodiment, enzymes such as polymerases can be used to generate 5' phosphorylated amplification products. For example, T4 polymerase can be used to prepare 5' phosphorylated amplicon products. Klenow can be used in conjunction with one or more other enzymes to produce amplification products with a 5' phosphate. In some embodiments, other enzymes known in the art can be used to prepare amplification products with a 5' phosphate group. For example, incubation of uracil nucleotide containing amplification products with the enzyme UDG, Fpg and T4 polymerase can be used to generate amplification products with a phosphate at the 5' termini. It will be apparent to one of skill in the art that other techniques, other than those specifically described herein, can be applied to generate phosphorylated amplicons. It is understood that such variations and modifications that are applied to practice the methods, systems, kits, compositions and apparatuses disclosed herein, without resorting to undue experimentation are considered within the scope of the disclosure.

In some embodiments, primers that are incorporated in the intended (specific) amplification products, these primers are similarly cleaved or destroyed, resulting in the formation of "sticky ends" (e.g., 5' or 3' overhangs) within the specific amplification products. Such "sticky ends" can be addressed in several ways. For example, if the specific amplification products are to be cloned, the overhang regions can be designed to complement overhangs introduced into the cloning vector, thereby enabling sticky ended ligations that are more rapid and efficient than blunt ended ligations. Alternatively, the overhangs may need to be repaired (as with several next-generation sequencing methods). Such repair can be accomplished either through secondary amplification reactions using only forward and reverse amplification primers (in the embodiment shown in FIG. 1, this corresponds to A and P1 primers) comprised of only natural bases. In this manner, subsequent rounds of amplification rebuild the double-stranded templates, with nascent copies of the amplicon possessing the complete sequence of the original strands prior to primer destruction. Alternatively, the sticky ends can be removed using some forms of fill-in and ligation processing, wherein the forward and reverse primers are annealed to the templates. A polymerase can then be employed to extend the primers, and then a ligase, optionally a thermostable ligase, can be utilized to connect the resulting nucleic acid strands. This could obviously be also accomplished through various other reaction pathways, such as cyclical extend-ligation, etc. In some embodiments, the ligation step can be performed using one or more DNA ligases.

The amplification reaction can include any reaction that increases the copy number of a nucleic acid molecule, optionally in a cyclical fashion, and can include without limitation isothermal amplification (for example, rolling circle amplification or isothermal amplification as described in U.S. Provisional Application Nos. 61/424,599, 61/445,324 and 61/451,919, hereby incorporated by reference in their entireties), amplification using thermocycling, and the like.

In some embodiments, the disclosure generally relates to methods for single-tube multiplex PCR. In some embodiments, the method for single-tube multiplex PCR can include target-specific or exon-specific primers. In some embodiments, the exon-specific or target-specific primers can include at least one uracil nucleotide. In some embodiments, single-tube multiplex PCR can include selective amplification of at least 1000, 2000, 3000, 4000, 5000, 6000 or more target nucleic acid molecules using target-specific or exon-specific uracil based primers.

In some embodiments, the disclosure relates generally to methods for generating a target-specific or exon-specific amplicon library. In some embodiments, the amplicon library generated using target-specific or exon-specific primers can be associated with mutations of human cancers. In some embodiments, the mutations can be in the KRAS, BRAF and/or EGFR genes. In some embodiments, the amplicon library can be generated from genomic DNA or formalin-fixed, paraffin-embedded (FFPE) tissue. In some embodiments, the amplicons of the amplicon library prepared using the methods disclosed herein can be about 100 to about 300 base pairs in length, about 100 to about 250 base pairs in length, about 120 to about 220 base pairs in length or about 135 to about 205 base pairs in length. In some embodiments, the amplicon library can be prepared using primer pairs that are targeted to cancer specific mutations. In some embodiments, the primer pairs can be directed to non-cancer related mutations, such as inherited diseases, e.g., cystic fibrosis and the like. In some embodiments, the primer pairs can be used to generate amplicons that once sequenced by any sequencing platform, including semiconductor sequencing technology can be used to detect genetic mutations such as inversion, deletions, point mutations and variations in copy number.

In some embodiments, the primer pairs used to produce an amplicon library can result in the amplification of target-specific nucleic acid molecules possessing one or more of the following metrics: greater than 97% target coverage at 20× if normalized to 100× average coverage depth; greater than 97% of bases with greater than 0.2× mean; greater than 90% base without strand bias; greater than 95% of all reads on target; greater than 99% of bases with greater than 0.01× mean; and greater than 99.5% per base accuracy.

In some embodiments, the amplicon library can be used to detect and/or identify known mutations or de novo mutations in a sample.

In some embodiments, the amplicon library prepared using target-specific primer pairs can be used in downstream enrichment applications such as emulsion PCR or bridge PCR. In some embodiments, the amplicon library can be used in an enrichment application and a sequencing application. For example, an amplicon library can be sequenced using any suitable DNA sequencing platform. In some embodiments, an amplicon library can be sequenced using an Ion Torrent PGM Sequencer (Life Technologies). In some embodiments, a PGM sequencer can be coupled to server that applies parameters or software to determine the sequence of the amplified target nucleic acid molecules. In some embodiments, the amplicon library can be prepared, enriched and sequenced in less than 24 hours. In some embodiments, the amplicon library can be prepared, enriched and sequenced in approximately 9 hours. In some embodiments, an amplicon library can be a paired library, that is, a library that contains amplicons from a tumor sample and amplicons from a non-diseased sample. Each pair can be aligned, to detect and/or identify mutations present in the target nucleic acid molecules.

In some embodiments, methods for generating an amplicon library can include: amplifying genomic DNA targets using exon-specific or target-specific primers to generate amplicons; purifying the amplicons from the input DNA and primers; phosphorylating the amplicons; ligating Adaptersadapters to the phosphorylated amplicons; purifying the ligated amplicons; nick-translating the amplified amplicons; and purifying the nick-translated amplicons to generate the amplicon library. In some embodiments, additional amplicon library manipulations can be conducted following the step of amplification of genomic DNA targets to generate the amplicons. In some embodiments, any combination of additional reactions can be conducted in any order, and can include: purifying; phosphorylating; ligating Adaptersadapters; nick-translating; amplification and/or sequencing. In some embodiments, any of these reactions can be omitted or can be repeated. It will be readily apparent to one of skill in the art that the method can repeat or omit any one or more of the above steps. It will also be apparent to one of skill in the art that the order and combination of steps may be modified to generate the required amplicon library, and is not therefore limited to the exemplary methods provided.

A phosphorylated amplicon can be joined to an adapter to conduct a nick translation reaction, subsequent downstream amplification (e.g., template preparation), or for attachment to particles (e.g., beads), or both. For example, an adapter that is joined to a phosphorylated amplicon can anneal to an oligonucleotide capture primer which is attached to a particle, and a primer extension reaction can be conducted to generate a complementary copy of the amplicon attached to the particle or surface, thereby attaching an amplicon to a surface or particle. AdaptersAdapters can have one or more amplification primer hybridization sites, sequencing primer hybridization sites, barcode sequences, and combinations thereof. In some embodiments, amplicons prepared by the methods disclosed herein can be joined to one or more Ion Torrent™ compatible Adaptersadapters to construct an amplicon library. Amplicons generated by such methods can be joined to one or more Adaptersadapters for library construction to be compatible with a next generation sequencing platform. For example, the amplicons produced by the teachings of the present disclosure can be attached to Adaptersadapters provided in the Ion Fragment Library Kit (Life Technologies, Catalog No. 4466464).

In some embodiments, amplification of genomic DNA targets (such as high molecular weight DNA) or FFPE samples can be conducted using a 2× AmpliSeq Hi Fi Master Mix. In some embodiments, the AmpliSeq Hi Fi Master Mix can include glycerol, dNTPs, and a DNA polymerase, such as Platinum® Taq DNA polymerase High Fidelity. In some embodiments, the 2× AmpliSeq Hi Fi Master Mix can further include at least one of the following: a preservative, magnesium sulfate, tris-sulfate and/or ammonium sulfate.

In some embodiments, amplification of genomic DNA targets (such as high molecular weight DNA) or FFPE samples can be conducted using a 5× Ion AmpliSeq Hi Fi Master Mix. In some embodiments, the 5× Ion AmpliSeq Hi Fi Master Mix can include glycerol, dNTPs, and a DNA polymerase such as Platinum® Taq DNA polymerase High Fidelity. In some embodiments, the 5× Ion AmpliSeq Hi Fi Master Mix can further include at least one of the following: a preservative, magnesium chloride, magnesium sulfate, tris-sulfate and/or ammonium sulfate.

In some embodiments, phosphorylation of the amplicons can be conducted using a FuP reagent. In some embodiments, the FuP reagent can include a DNA polymerase, a DNA ligase, at least one uracil cleaving or modifying enzyme, and/or a storage buffer. In some embodiments, the FuP reagent can further include at least one of the following: a preservative and/or a detergent.

In some embodiments, phosphorylation of the amplicons can be conducted using a FuPa reagent. In some embodiments, the FuPa reagent can include a DNA polymerase, at least one uracil cleaving or modifying enzyme, an antibody and/or a storage buffer. In some embodiments, the FuPa reagent can further include at least one of the following: a preservative and/or a detergent. In some embodiments, the antibody is provided to inhibit the DNA polymerase and 3'-5' exonuclease activities at ambient temperature.

In some embodiments, the amplicon library produced by the teachings of the present disclosure are sufficient in yield to be used in a variety of downstream applications including the Ion Xpress™ Template Kit using an Ion Torrent™ PGM system (e.g., PCR-mediated addition of the nucleic acid fragment library onto Ion Sphere™ Particles) (Life Technologies, Part No. 4467389). For example, instructions to prepare a template library from the amplicon library can be found in the Ion Xpress Template Kit User Guide (Life Technologies, Part No. 4465884). Instructions for loading the subsequent template library onto the Ion Torrent™ Chip for nucleic acid sequencing are described in the Ion Sequencing User Guide (Part No. 4467391). In some embodiments, the amplicon library produced by the teachings of the present disclosure can be used in paired end sequencing (e.g., paired-end sequencing on the Ion Torrent™ PGM system (Life Technologies, Part No. MAN0006191).

It will be apparent to one of ordinary skill in the art that numerous other techniques, platforms or methods for clonal amplification such as wildfire PCR and bridge amplification can be used in conjunction with the amplified target sequences of the present disclosure. It is also envisaged that one of ordinary skill in art upon further refinement or optimization of the conditions provided herein can proceed directly to nucleic acid sequencing (for example using the Ion Torrent PGM™ or Proton™ sequencers, Life Technologies) without performing a clonal amplification step.

In some embodiments, at least one of the amplified targets sequences to be clonally amplified can be attached to a support or particle. The support can be comprised of any suitable material and have any suitable shape, including, for example, planar, spheroid or particulate. In some embodiments, the support is a scaffolded polymer particle as described in U.S. Published App. No. 20100304982, hereby incorporated by reference in its entirety.

In some embodiments, nucleic acid sequencing of the amplified target sequences produced by the teachings of this disclosure include de novo sequencing or targeted resequencing. In some embodiments, nucleic acid sequencing further includes comparing the nucleic acid sequencing results of the amplified target sequences against a reference nucleic acid sample. In some embodiments, the reference sample can be normal tissue or well documented tumor sample. In some embodiments, nucleic acid sequencing of the amplified target sequences further includes determining the presence or absence of a mutation within the nucleic acid sequence. In some embodiments, the method further includes correlating the presence of a mutation with drug susceptibly, prognosis of treatment and/or organ rejection. In some embodiments, nucleic acid sequencing includes the identification of genetic markers associated with cancer and/or inherited diseases. In some embodiments, nucleic acid sequencing includes the identification of copy number variation in a sample under investigation.

In some embodiments, a kit is provided for amplifying multiple target sequences from a population of nucleic acid molecules in a single reaction. In some embodiments, the kit includes a plurality of target-specific primer pairs containing one or more cleavable groups, one or more DNA polymerases, a mixture of dNTPs and at least one cleaving reagent. In one embodiment, the cleavable group can be 8-oxo-deoxyguanosine, deoxyuridine or bromodeoxyuridine. In some embodiments, the at least one cleaving reagent includes RNaseH, uracil DNA glycosylase, Fpg or alkali. In one embodiment, the cleaving reagent can be uracil DNA glycosylase. In some embodiments, the kit is provided to perform multiplex PCR in a single reaction chamber or vessel. In some embodiments, the kit includes at least one DNA polymerase, which can be a thermostable DNA polymerase. In some embodiments, the concentration of the one or more DNA polymerases is present in a 3-fold excess as compared to a single PCR reaction. In some embodiments, the final concentration of each target-specific primer pair is present at about 25 nM to about 50 nM. In one embodiment, the final concentration of each target-specific primer pair can be present at a concentration that is 50% lower than conventional single plex PCR reactions. In some embodiments, the kit provides amplification of at least 100, 500, 1000, 3000, 6000, 10000, 12000, or more, target sequences from a population of nucleic acid molecules in a single reaction chamber.

In some embodiments, the kit further comprises one or more adapters, barcodes, and/or antibodies.

The following description of various exemplary embodiments is exemplary and explanatory only and is not to be construed as limiting or restrictive in any way. Other embodiments, features, objects, and advantages of the present teachings will be apparent from the description and accompanying drawings, and from the claims.

Although the present description described in detail certain exemplary embodiments, other embodiments are also possible and within the scope of the present invention. Variations and modifications will be apparent to those skilled in the art from consideration of the specification and figures and practice of the teachings described in the specification and figures, and the claims.

EXAMPLES

Example 1

Library Preparation

PCR Amplify Genomic DNA Targets

Figure 5:
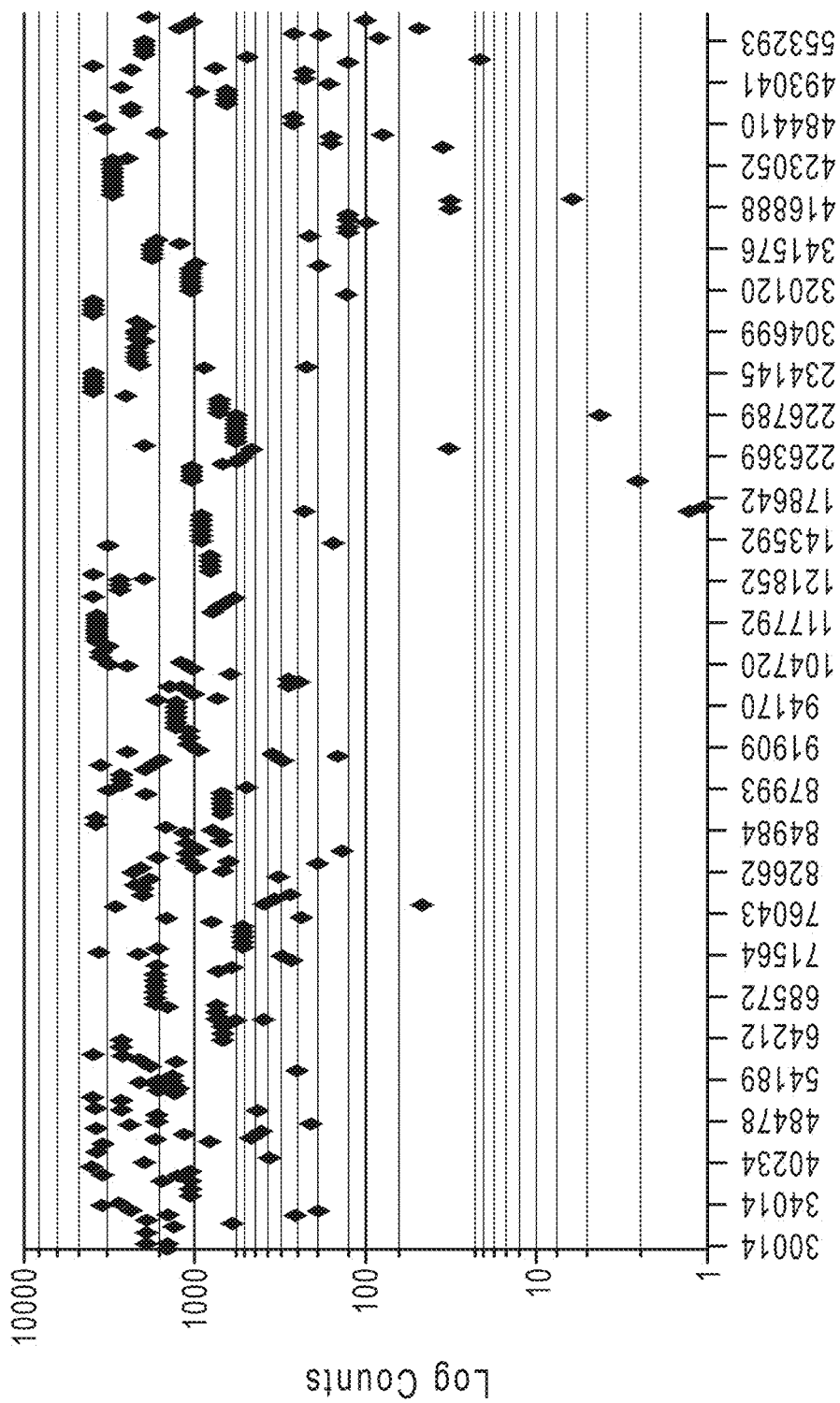
FIG. 5 shows quantification of the abundance and reproducibility of an exemplary multiplex reaction on genomic DNA using primer set HSMv12. The data is averaged across individual 3 runs performed on an Ion Torrent PGM™ Sequencer (Life Technologies). The level of coverage per amplicon is provided as Log of Counts.

A multiplex polymerase chain reaction was performed to amplify 384 individual amplicons across a genomic DNA sample. A pool of greater than 32,000 primers was originally developed covering more than 300 genes. A representative list of genes that were incorporated for investigation while synthesizing the initial primer pool is provided in Table 1 (found in U.S. Ser. No. 13/458,739, filed Apr. 27, 2012, hereby incorporated by reference in its entirety). A sub-set of the primer pool known as "HSMv12" was used to generate the data presented in FIG. 5 (primers from HSMv12 are presented in Table 2 (found in U.S. Ser. No. 13/458,739, filed Apr. 27, 2012, hereby incorporated by reference in its entirety)). Each primer pair in the primer pool was designed to contain at least one uracil nucleotide near the terminus of each forward and reverse primer. Each primer pair was also designed to selectively hybridize to, and promote amplification of a specific gene or gene fragment of the genomic DNA sample.

To a single well of a 96-well PCR plate was added 5 microliters of HSMv12 Primer Pool containing 384 primer pairs at a concentration of 15 µM in TE, 10-50 ng genomic DNA and 10 microliters of an amplification reaction mixture (2× AmpliSeq HiFi Master Mix) that can include glycerol, dNTPs, and Platinum® Taq High Fidelity DNA Polymerase (Invitrogen, Catalog No. 11304) to a final volume of 20 microliters with DNase/RNase Free Water (Life Technologies, CA, Part No. 600004).

The PCR plate was sealed and loaded into a thermal cycler (GeneAmp® PCR system 9700 Dual 96-well thermal cycler (Life Technologies, CA, Part No. N8050200 and 4314445)) and run on the following temperate profile to generate the preamplified amplicon library.

An initial holding stage was performed at 98° C. for 2 minutes, followed by 16 cycles of denaturing at 98° C. for 15 seconds and an annealing and extending stage at 60° C. for 4 minutes. After cycling, the preamplified amplicon library was held at 4° C. until proceeding to the purification step outlined below. A schematic of an exemplary library amplification process is shown in FIG. 2.

Purify the Amplicons from Input DNA and Primers

Two rounds of Agencourt® AMPure® XP Reagent (Beckman Coulter, CA) binding, wash, and elution at 0.6× and 1.2× volume ratios were found to remove genomic DNA and unbound or excess primers. The amplification and purification step outlined herein produces amplicons of about 100 bp to about 600 bp in length.

In a 1.5 ml LoBind tube (Eppendorf, Part No. 022431021), the preamplified amplicon library (20 microliters) was combined with 12 microliters (0.6× volumes) of Agencourt® AMPure® XP reagent (Beckman Coulter, CA). The bead suspension was pipetted up and down to thoroughly mix the bead suspension with the preamplified amplicon library. The sample was then pulse-spin and incubated for 5 minutes at room temperature.

The tube containing the sample was placed on a magnetic rack such as a DynaMag™-2 spin magnet (Life Technologies, CA, Part No. 123-21D) for 2 minutes to capture the beads. Once the solution cleared, the supernatant was transferred to a new tube, where 24 microliters (1.2× volume) of AgenCourt® AMPure® XP beads (Beckman Coulter, CA) were added to the supernatant. The mixture was pipetted to ensure the bead suspension mixed with the preamplified amplicon library. The sample was then pulse-spin and incubated at room temperature for 5 minutes. The tube containing the sample was placed on the magnetic rack for 2 minutes to capture the beads. Once the solution cleared, the supernatant was carefully discarded without disturbing the bead pellet. The desired preamplified amplicon library was now bound to the beads. Without removing the tube from the magnetic rack, 200 microliters of freshly prepared 70% ethanol was introduced into the sample. The sample was incubated for 30 seconds while gently rotating the tube on the magnetic rack. After the solution cleared, the supernatant was discarded without disturbing the pellet. A second ethanol wash was performed and the supernatant discarded. Any remaining ethanol was removed by pulse-spinning the tube and carefully removing residual ethanol while not disturbing the pellet. The pellet was air-dried for about 5 minutes at room temperature.

Once the tube was dry, the tube was removed from the magnetic rack and 20 microliters of DNase/RNase Free Water was added (Life Technologies, CA, Part No. 600004). The tube was vortexed and pipetted to ensure the sample was mixed thoroughly. The sample was pulse-spin and placed on the magnetic rack for two minutes. After the solution cleared, the supernatant containing the eluted DNA was transferred to a new tube.

Phosphorylate the Amplicons

To the eluted DNA (~20 microliters), 3 microliters of DNA ligase buffer (Invitrogen, Catalog No. 15224041), 2 microliters dNTP mix, and 2 microliters of FuP reagent were added. The reaction mixture was mixed thoroughly to ensure uniformity and incubated at 37° C. for 10 minutes.

Ligate Adpaters to the Amplicons and Purify the Ligated Amplicons

After incubation, the reaction mixture proceeded directly to a ligation step. Here, the reaction mixture now containing the phosphorylated amplicon library was combined with 1 microliter of A/P1 Adaptersadapters (20 μm each) (sold as a component of the Ion Fragment Library Kit, Life Technologies, Part No. 4466464) and 1 microliter of DNA ligase (sold as a component of the Ion Fragment Library Kit, Life Technologies, Part No. 4466464), and incubated at room temperature for 30 minutes.

After the incubation step, 52 microliters (1.8× sample volume) of AgenCourt® AMPure® Reagent (Beckman Coulter, CA) was added to the ligated DNA. The mixture was pipetted thoroughly to mix the bead suspension with the ligated DNA. The mixture was pulse-spin and incubated at room temperature for 5 minutes. The samples underwent another pulse-spin and were placed on a magnetic rack such as a DynaMag™-2 spin magnet (Life Technologies, CA, Part No. 123-21D) for two minutes. After the solution had cleared, the supernatant was discarded. Without removing the tube from the magnetic rack, 200 microliters of freshly prepared 70% ethanol was introduced into the sample. The sample was incubated for 30 seconds while gently rotating the tube on the magnetic rack. After the solution cleared, the supernatant was discarded without disturbing the pellet. A second ethanol wash was performed and the supernatant discarded. Any remaining ethanol was removed by pulse-spinning the tube and carefully removing residual ethanol while not disturbing the pellet. The pellet was air-dried for about 5 minutes at room temperature.

The pellet was resuspended in 20 microliters of DNase/RNase Free Water (Life Technologies, CA, Part No. 600004) and vortexed to ensure the sample was mixed thoroughly. The sample was pulse-spin and placed on the magnetic rack for two minutes. After the solution cleared, the supernatant containing the ligated DNA was transferred to a new Lobind tube (Eppendorf, Part No. 022431021).

Nick Translate and Amplify the Amplicon Library and Purify the Library

The ligated DNA (~20 microliters) was combined with 76 microliters of Platinum® PCR SuperMix High Fidelity (Life Technologies, CA, Part No. 12532-016, sold as a component of the Ion Fragment Library Kit, Life Technologies, Part No. 4466464) and 4 microliters of Library Amplification Primer Mix (5 μM each) (Life Technologies, CA, Part No. 602-1068-01, sold as a component of the Ion Fragment Library Kit, Life Technologies, Part No. 4466464), the mixture was pipetted thoroughly to ensure a uniformed solution. The solution was applied to a single well of a 96-well PCR plate and sealed. The plate was loaded into a thermal cycler (GeneAmp® PCR system 9700 Dual 96-well thermal cycler (Life Technologies, CA, Part No. N8050200 and 4314445)) and run on the following temperate profile to generate the final amplicon library.

A nick-translation was performed at 72° C. for 1 minute, followed by an enzyme activation stage at 98° C. for 2 minutes, followed by 5-10 cycles of denaturing at 98° C. for 15 seconds and an annealing and extending stage at 60° C. for 1 minute. After cycling, the final amplicon library was held at 4° C. until proceeding to the final purification step outlined below.

In a 1.5 ml LoBind tube (Eppendorf, Part No. 022431021), the final amplicon library (~100 microliters) was combined with 180 microliters (1.8× sample volume) of Agencourt® AMPure® XP reagent (Beckman Coulter, CA). The bead suspension was pipetted up and down to thoroughly mix the bead suspension with the final amplicon library. The sample was then pulse-spin and incubated for 5 minutes at room temperature.

The tube containing the final amplicon library was placed on a magnetic rack such as a DynaMag™-2 spin magnet (Life Technologies, CA, Part No. 123-21D) for 2 minutes to capture the beads. Once the solution cleared, the supernatant was carefully discarded without disturbing the bead pellet. Without removing the tube from the magnetic rack, 400 microliters of freshly prepared 70% ethanol was introduced into the sample. The sample was incubated for 30 seconds while gently rotating the tube on the magnetic rack. After the solution cleared, the supernatant was discarded without disturbing the pellet. A second ethanol wash was performed and the supernatant discarded. Any remaining ethanol was removed by pulse-spinning the tube and carefully removing residual ethanol while not disturbing the pellet. The pellet was air-dried for about 5 minutes at room temperature.

Once the tube was dry, the tube was removed from the magnetic rack and 20 microliters of Low TE was added (Life Technologies, CA, Part No. 602-1066-01). The tube was pipetted and vortexed to ensure the sample was mixed thoroughly. The sample was pulse-spin and placed on the magnetic rack for two minutes. After the solution cleared, the supernatant containing the final amplicon library was transferred to a new Lobind tube (Eppendorf, Part No. 022431021).

Assess the Library Size Distribution and Determine the Template Dilution Factor

The final amplicon library was quantitated to determine the library dilution (Template Dilution Factor) that results in a concentration within the optimized target range for Template Preparation (e.g., PCR-mediated addition of library molecules onto Ion Sphere™ Particles). The final amplicon library is typically quantitated for downstream Template Preparation procedure using an Ion Library Quantitation Kit (qPCR) (Life Technologies, Part No. 4468802) and/or a Bioanalyzer™ (Agilent Technologies, Agilent 2100 Bioanalyzer) to determine the molar concentration of the amplicon library, from which the Template Dilution Factor is calculated. For example, instructions to determine the Template Dilution Factor by quantitative real-time PCR (qPCR) can be found in the Ion Library Quantitation Kit User Guide (Life Technologies, Part No. 4468986).

In this example, 1 microliter of the final amplicon library preparation was analyzed on the 2100 Bioanalyzer™ with an Agilent High Sensitivity DNA Kit (Agilent Technologies, Part No. 5067-4626) to generate peaks in the 135-205 bp size range and at a concentration of about $5 \times 10^9$ copies per microliter.

Proceed to Template Preparation

An aliquot of the final library was used to prepare DNA templates that were clonally amplified on Ion Sphere™ Particles using emulsion PCR (emPCR). The preparation of template in the instant example was prepared according to the manufacturer's instructions using an Ion Xpress Template Kit (Life Technologies, Part No. 4466457). Once template-positive Ion Sphere Particles were enriched, an aliquot of the Ion Spheres were loaded onto an Ion 314™ Chip (Life Technologies, Part No. 4462923) as described in the Ion Sequencing User Guide (Part No. 4467391), and subjected to analysis and sequencing as described in the Ion Torrent PGM Sequencer User Guide (Life Technologies, Part No. 4462917). The data obtained from this example is provided in FIG. 5.

Example 2

Optimizing Multiplex Reactions to Minimize GC Bias

This example demonstrates that optimizing multiplex PCR reactions performed under the guidance of the exemplary library amplification process described in Example 1 help to minimize GC bias.

In this example, a low-plex sample containing 94 primer pairs of target-specific primers and a high-plex sample containing 380 primer pairs of target-specific primers were prepared from across the human genome. Each low-plex and high plex sample was subjected to library amplification as described in Example 1. The melting temperature of amplicon products was observed to correlate with GC content of the amplicon assay (FIG. 4A-4H). The high multiplex (384-plex) sample with high GC content (i.e., 80%) was observed to have a higher melting temperature than the corresponding 94-plex sample (FIG. 4A-4H). Additionally, high-plex samples with highest GC content (75% and 80%) were observed to possess a single predominant peak, the amplicon product (connected to X-axis via dotted line), in contrast to other non-specific amplification products (observed as additional peaks and noise across the X-axis). The low-plex samples containing highest GC content (75% and 80%) were found to form multiple peaks along the X-axis suggesting the formation of a substantial amount of non-specific amplification products in addition to the desired amplicons. This example demonstrates that high-multiplex PCR reactions (394-plex) can be successfully optimized, for example through primer design, to increase the melting temperature of the desired amplicon product, increase the amount of amplicon specific product generated, and decrease the formation of amplification artifacts.

Example 3

Optimizing Primer Design to Reduce Non-specific Amplification

Figure 3A:
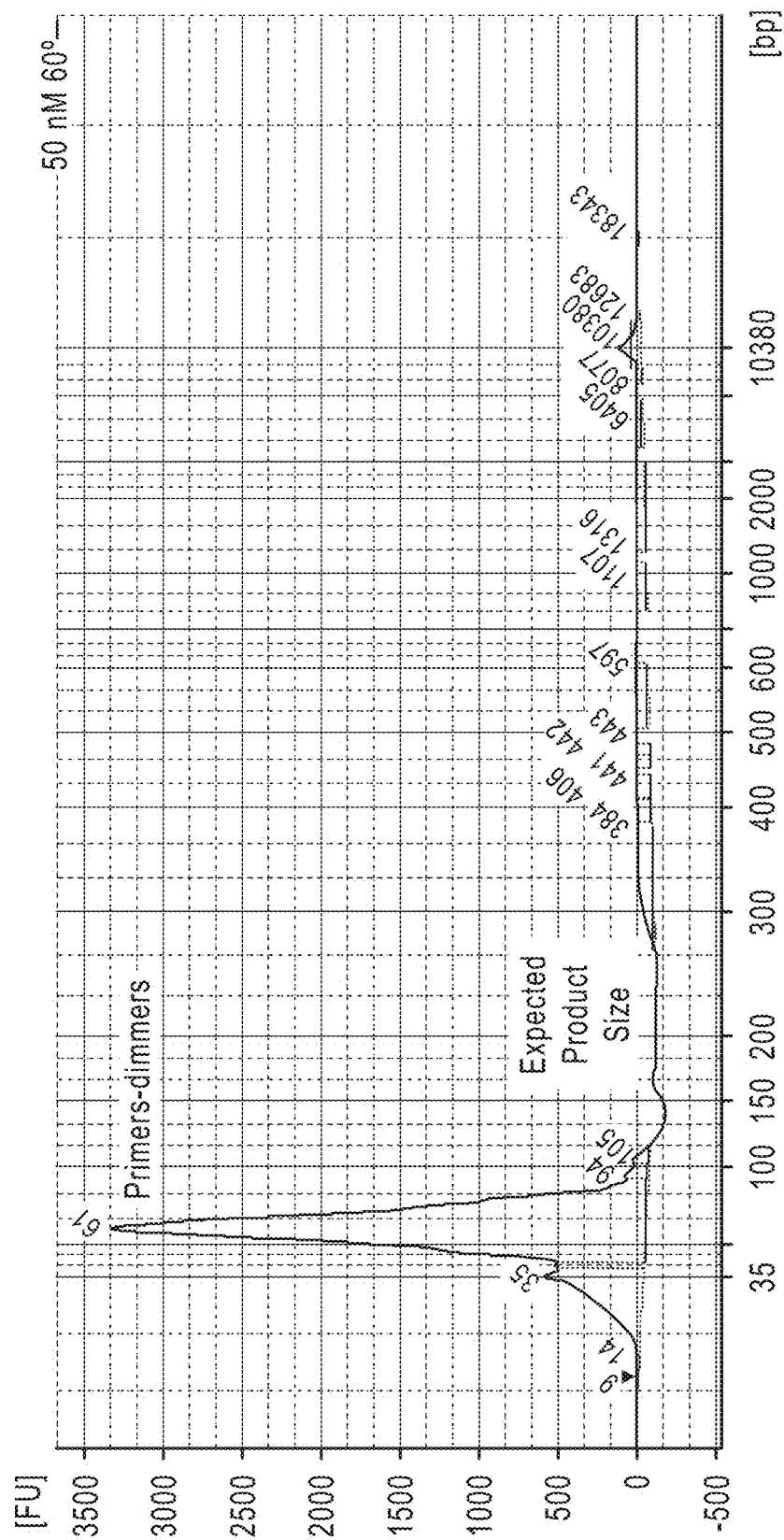
FIG. 3A-FIG. 3B show examples of elution profiles for exemplary unmodified and modified primer pools.
Figure 3B:
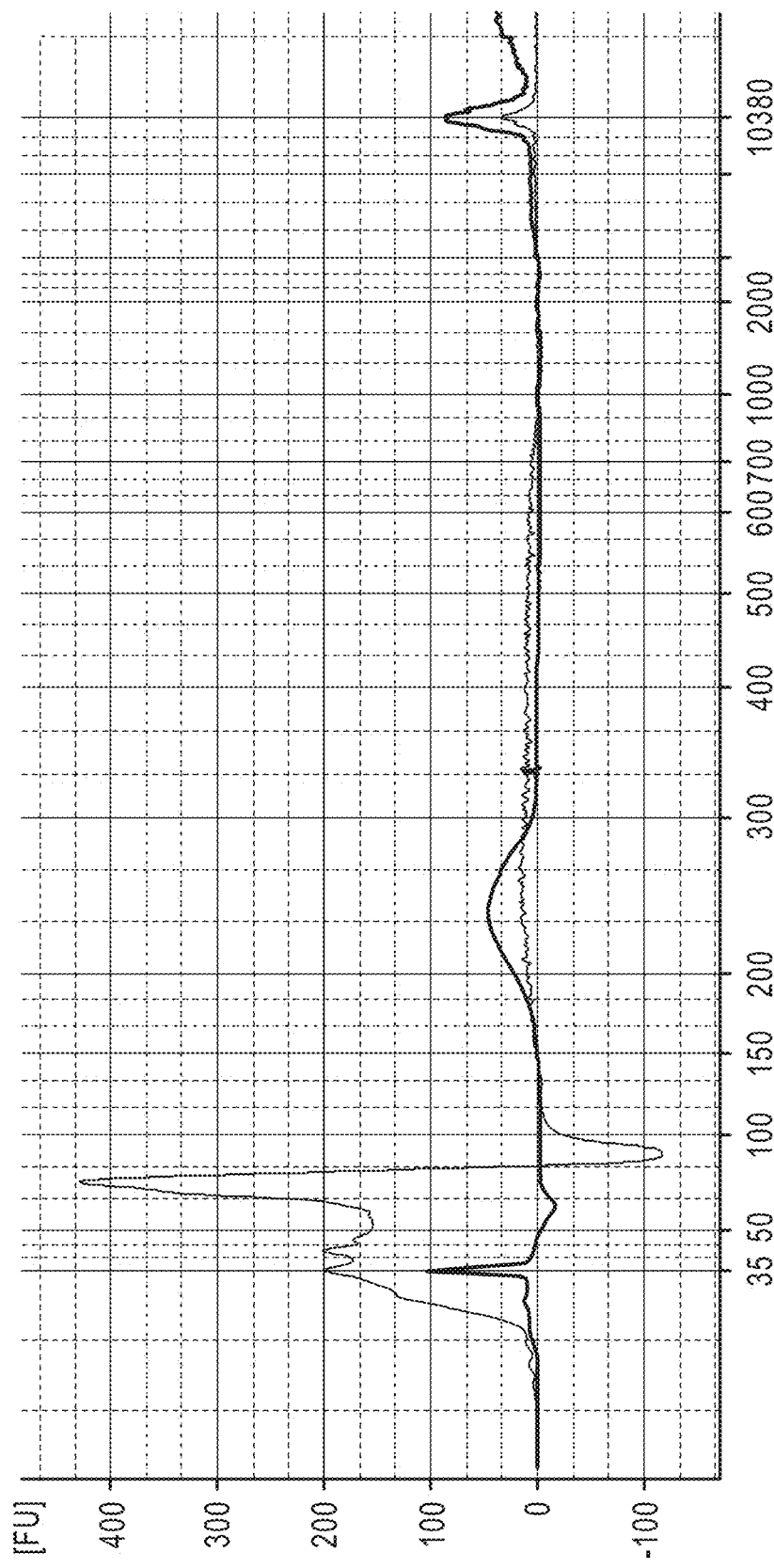
Figures 4A, 4B:
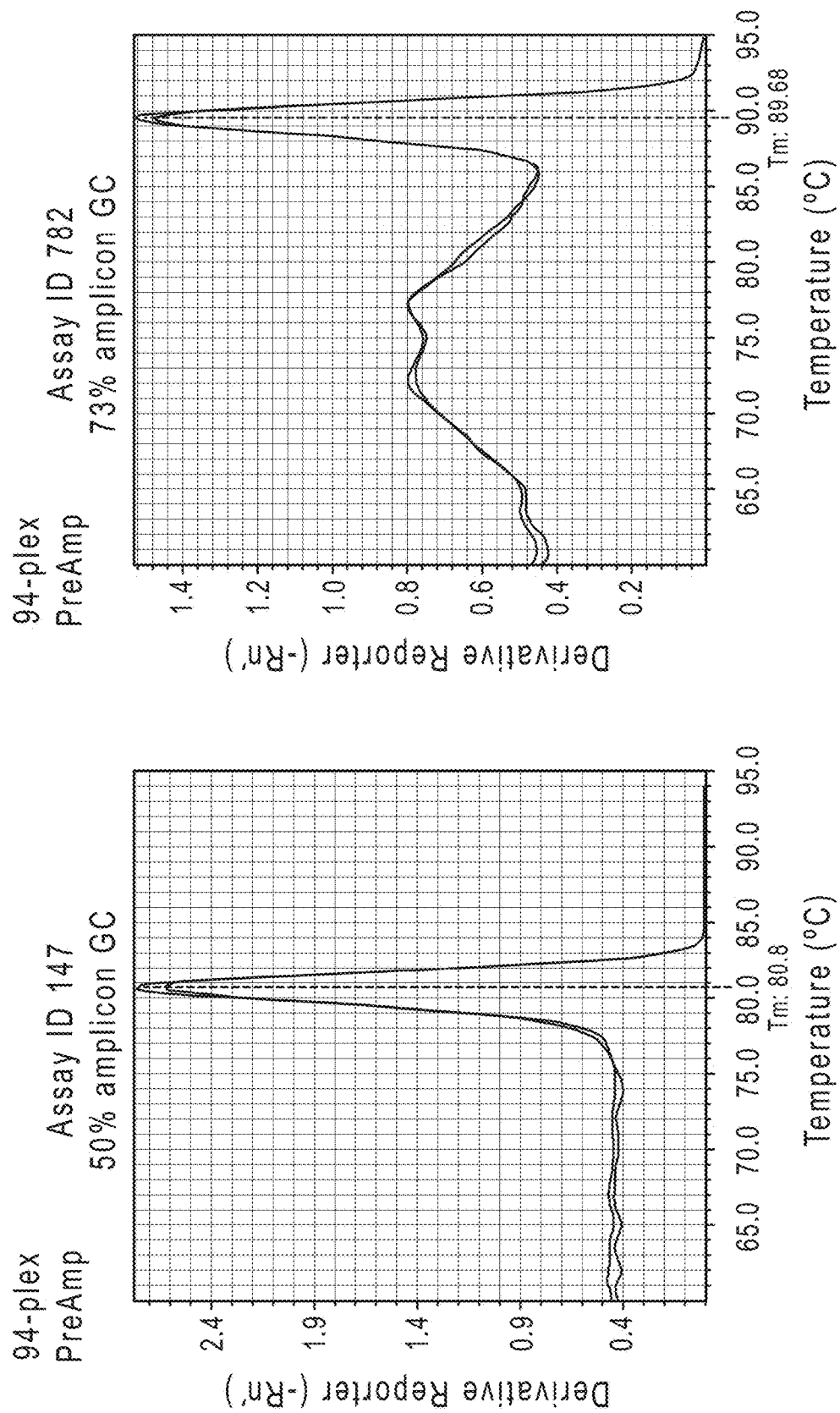
FIG. 4A-FIG. 4H show the effect of increasing amplicon GC content in both an exemplary 94-plex and an exemplary 380-plex reaction.
Figures 4C, 4D:
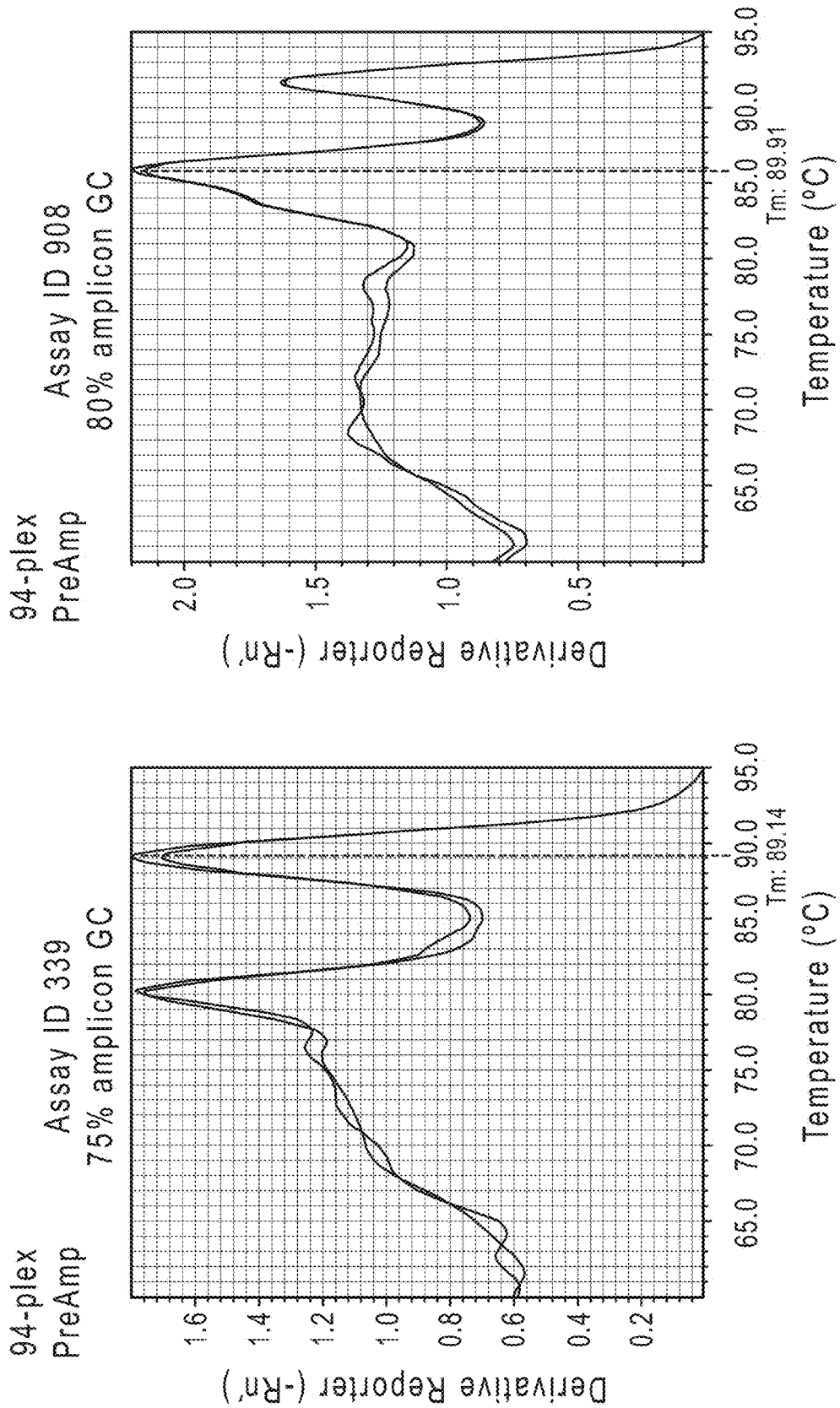
Figure 4F:
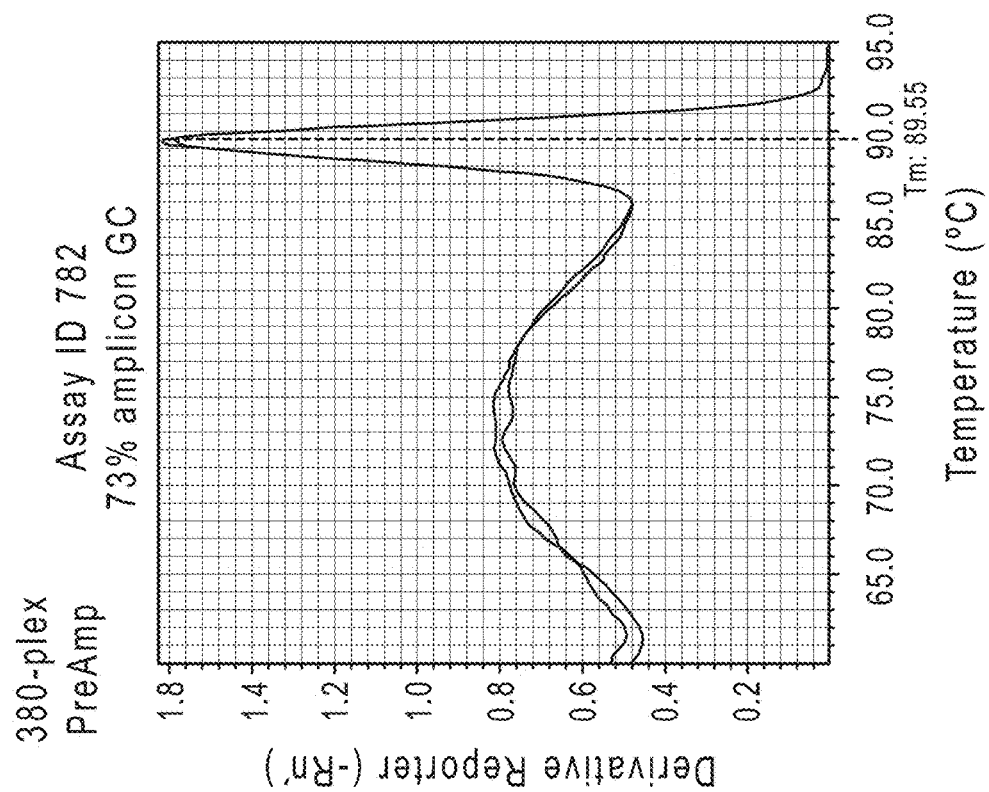
Figure 4E:
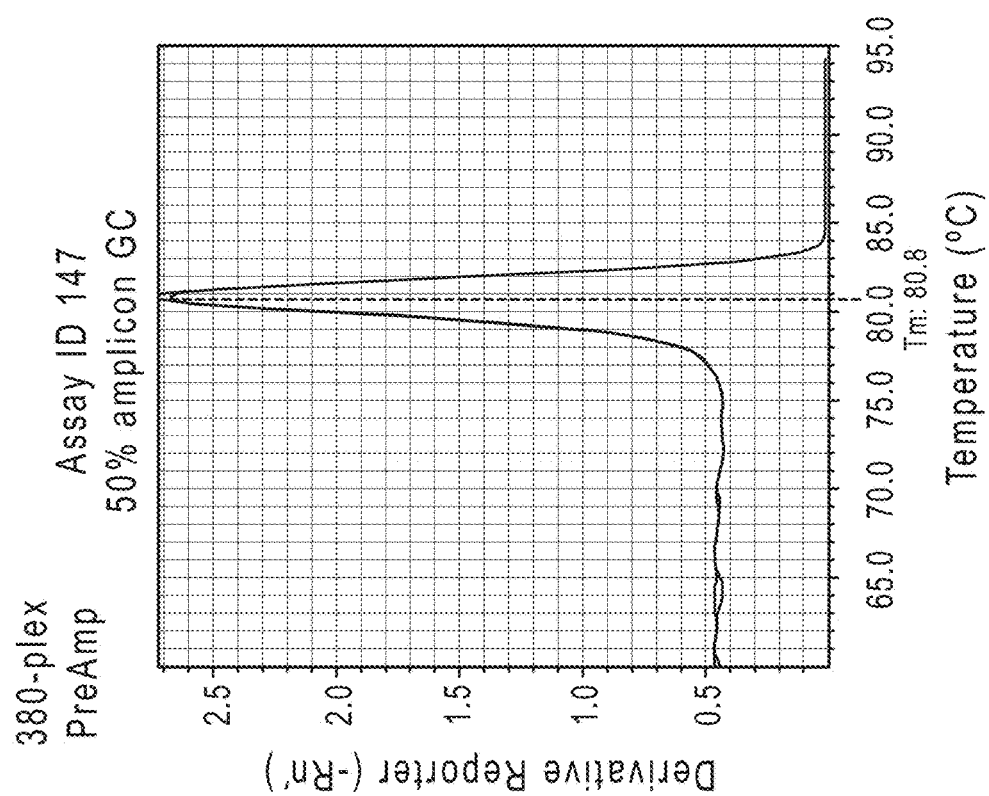
Figure 4H:
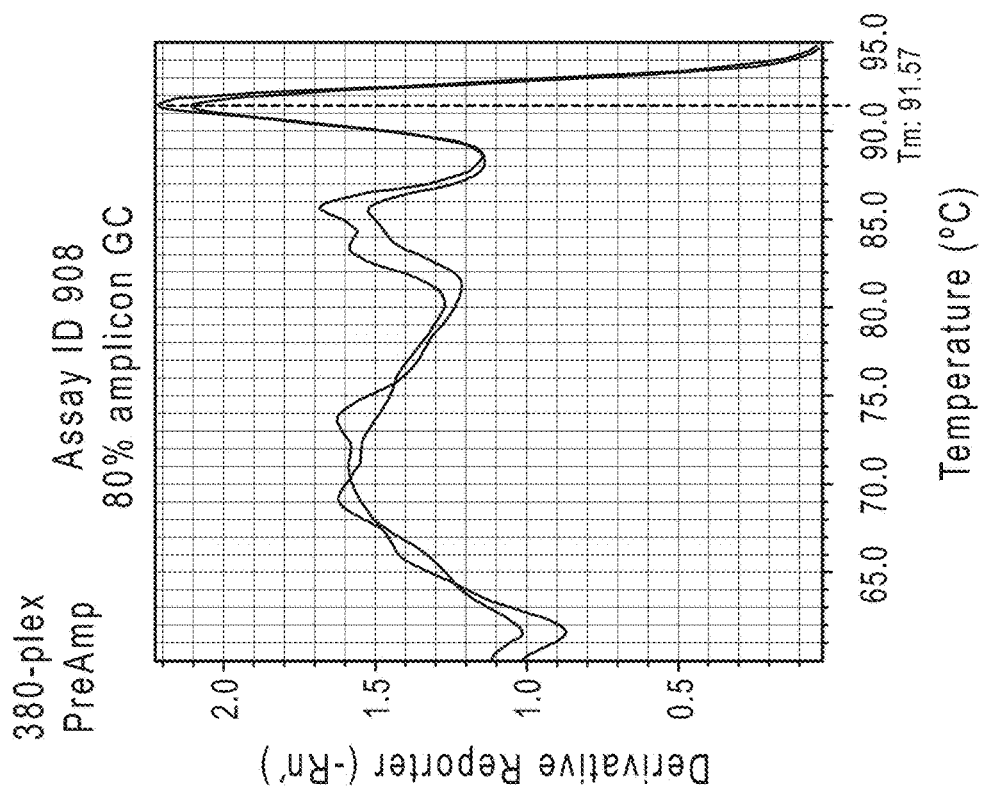
Figure 4G:
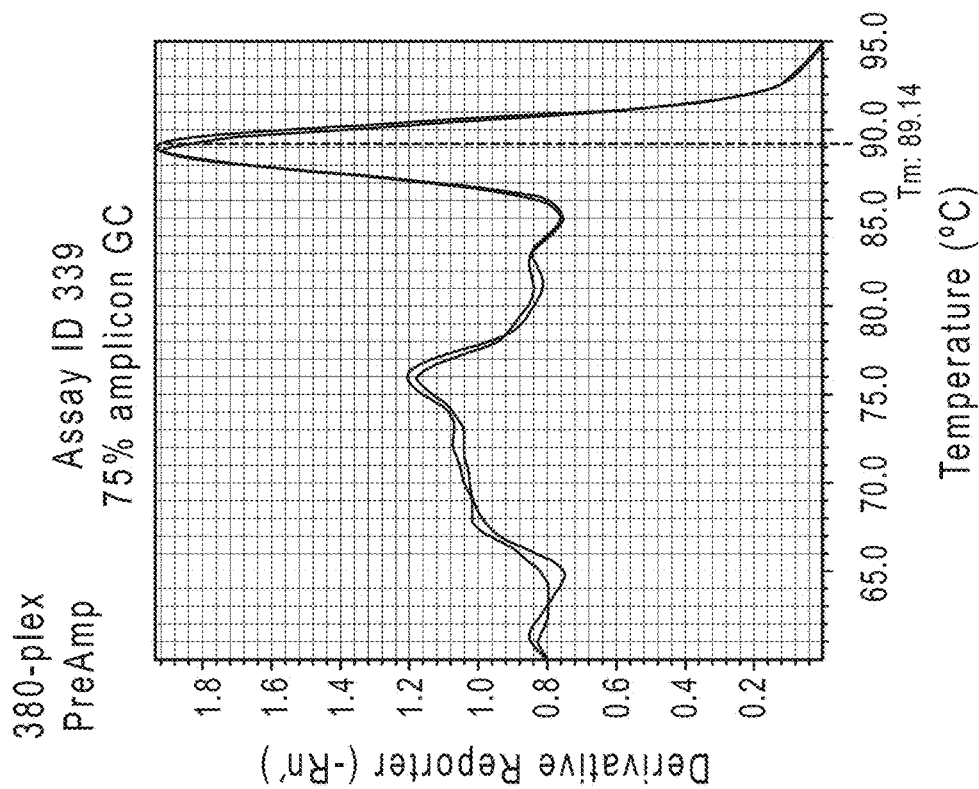

This example demonstrates that target-specific primers containing modified nucleotides generated substantially fewer primer-dimers than a corresponding non-modified primer pool. In this example, a population of non-modified primer pairs were prepared using conventional methods and subjected to the library amplification process as described in Example 1. A corresponding primer set containing modified nucleotides were prepared and amplified as described in Example 1. The amount of amplicon product and non-specific amplification product generated for each primer pool was compared. The amount of primer-dimers observed in the non-modified primer pool was found to greatly exceed the amount of primer-dimers in the corresponding modified primer pool (FIGS. 3A and 3B). The production of amplification artifacts can cause significant, if not permanent, amplification issues in downstream amplification events such as those commonly used in next-generating sequencing assays. The use of modified primers as disclosed herein can be used to alleviate these issues and decrease the output of amplification artifacts per multiplex reaction.

Example 4

Generation of a 384-plex (Multiplex) PCR Reaction

In this example, a multiplex polymerase chain reaction was performed to amplify 384 amplicons across genomic DNA. A primer pool containing modified forward and reverse primer pairs was cycled with genomic DNA and subjected to library amplification as described in Example 1. The data obtained from 3 individual runs on an Ion Torrent PGM™ Sequencer was averaged and is presented in FIG. 5. The data shows an average read rate of 1000 per amplicon.

Example 5

Figure 6B:
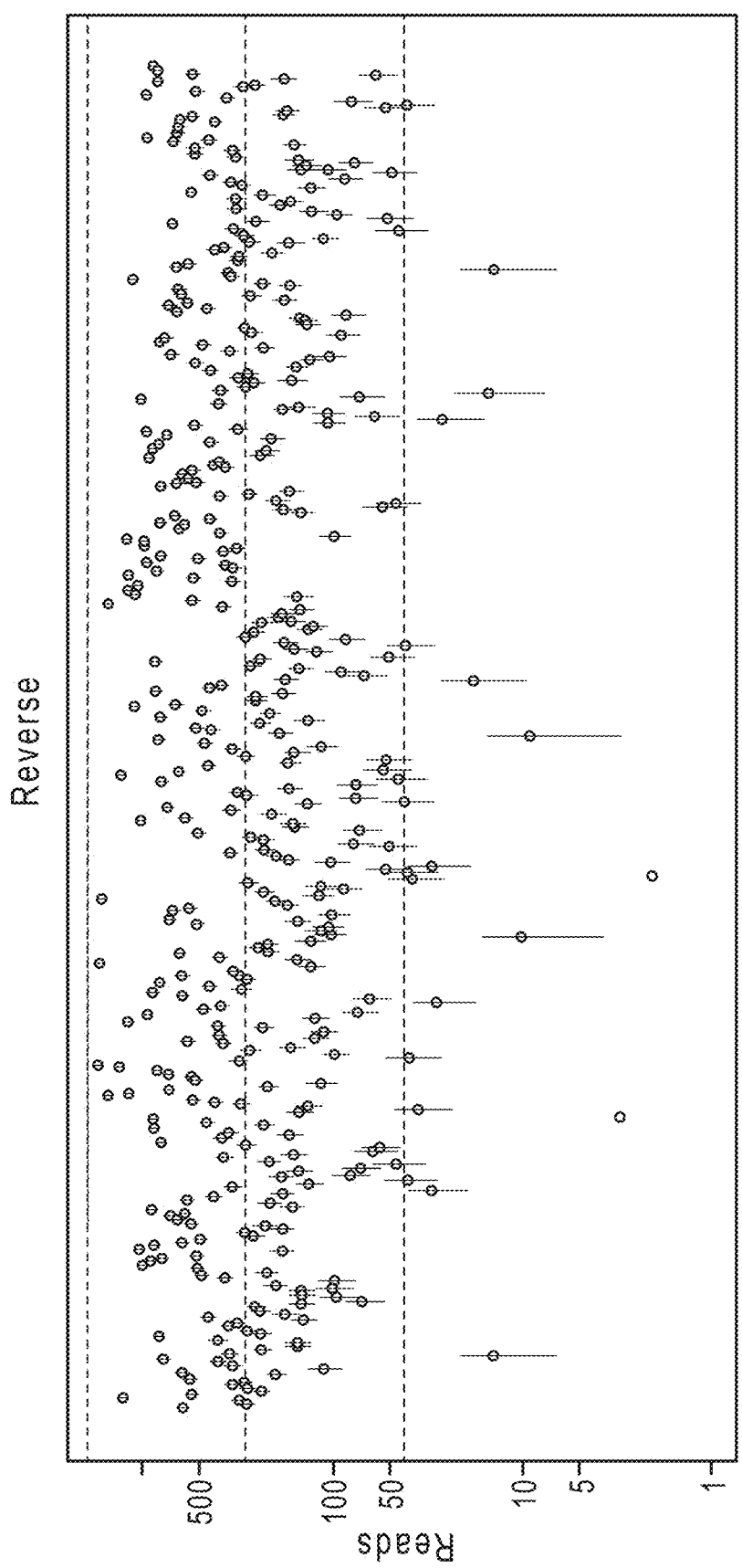

Effect of Forward and Reverse Primers on the Coverage of a 384-plex Multiplex PCR Reaction In this example, a multiplex polymerase chain reaction was performed to amplify 411 amplicons across genomic DNA. The primer pool for the amplification reaction contained modified forward and reverse primers and was subjected to library amplification as described in Example 1. The data obtained from a single run on an Ion Torrent PGM™ Sequencer shows the average read rate of about 400 for both the reverse and forward modified primers (FIGS. 6A and 6B).

Example 6

Reproducibility of 384-multiplex Reactions

Figure 7:
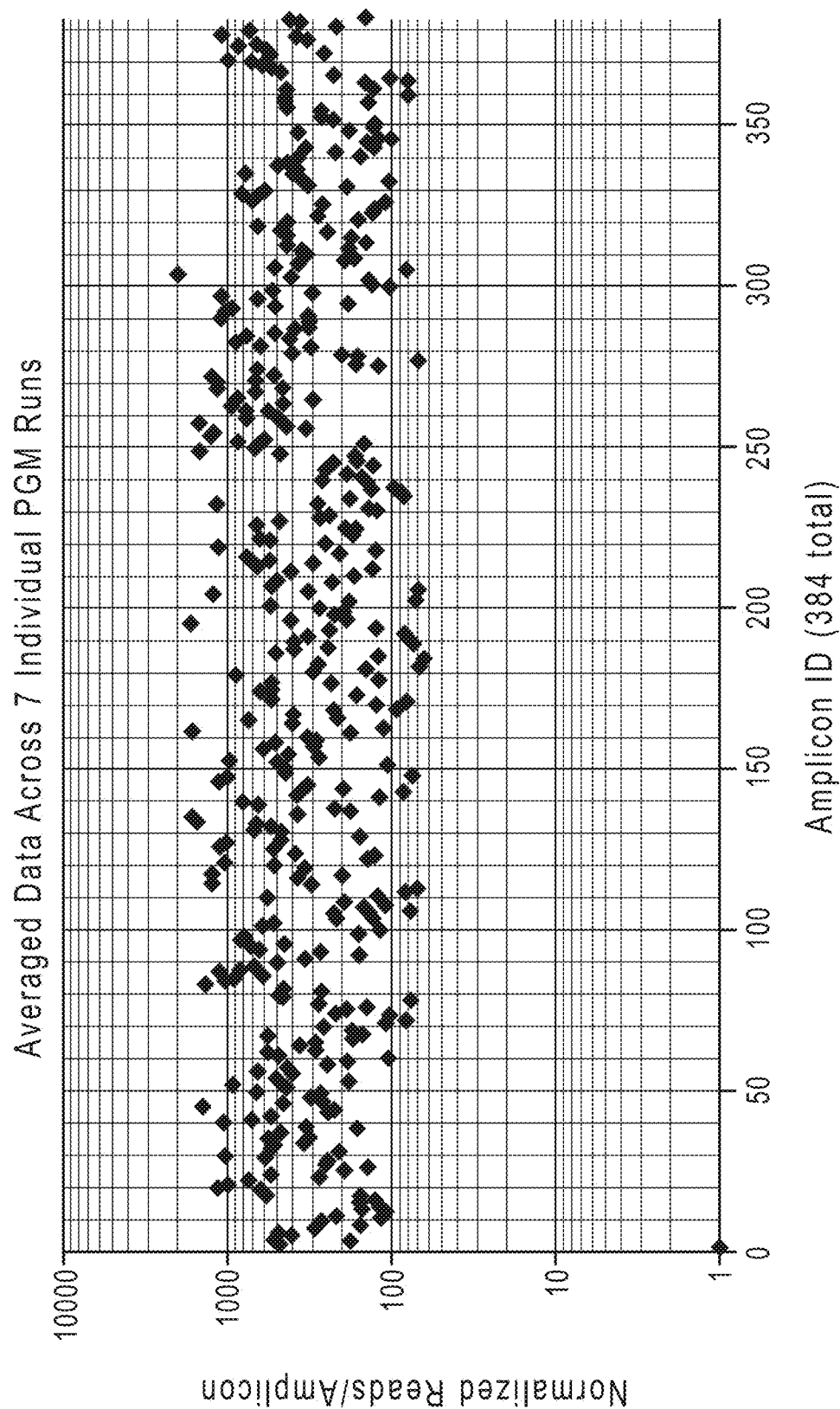
FIG. 7 shows quantification of the abundance and reproducibility of an exemplary 384-plex reaction on a genomic DNA sample across 7 individual runs on an Ion Torrent PGM™ Sequencer (Life Technologies). The average number of reads per amplicon is 400.

In this example, a multiplex polymerase chain reaction was performed to amplify 384 amplicons across genomic DNA. The primer pool contained modified forward and reverse primer pairs and was subjected to library amplification as described in Example 1. The data obtained from 7 individual runs on the Ion Torrent PGM™ Sequencer was averaged and is presented in FIG. 7. The data shows an average read rate of about 400 per amplicon.

Example 7

Reproducibility of 411-multiplex Reactions

Figure 8:
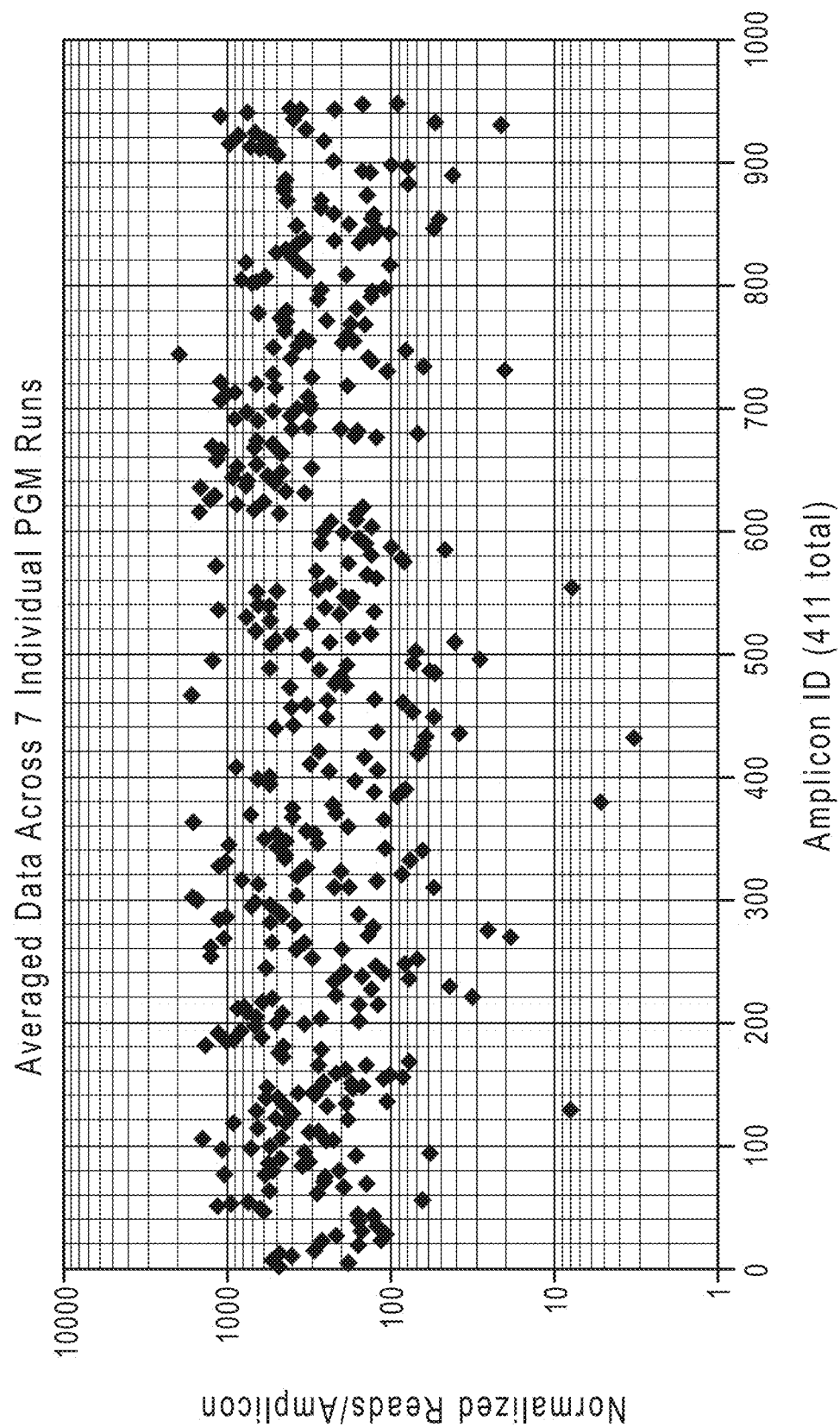
FIG. 8 shows quantification of the abundance and reproducibility of an exemplary 411-plex PCR of genomic DNA across 7 individual runs on an Ion Torrent PGM™ Sequencer (Life Technologies). The average number of reads per amplicon is 400.

In this example, a multiplex polymerase chain reaction was performed to amplify 411 amplicons across genomic DNA. The primer pool contained modified forward and reverse primer pairs and was subjected to library amplification as described in Example 1. The data obtained from 7 individual runs on the Ion Torrent PGM™ Sequencer was averaged and is presented in FIG. 8. The data shows an average read rate of about 400 per amplicon.

Example 8

FFPE Samples as Amendable Substrates for Low Multiplex PCR

Figure 9:
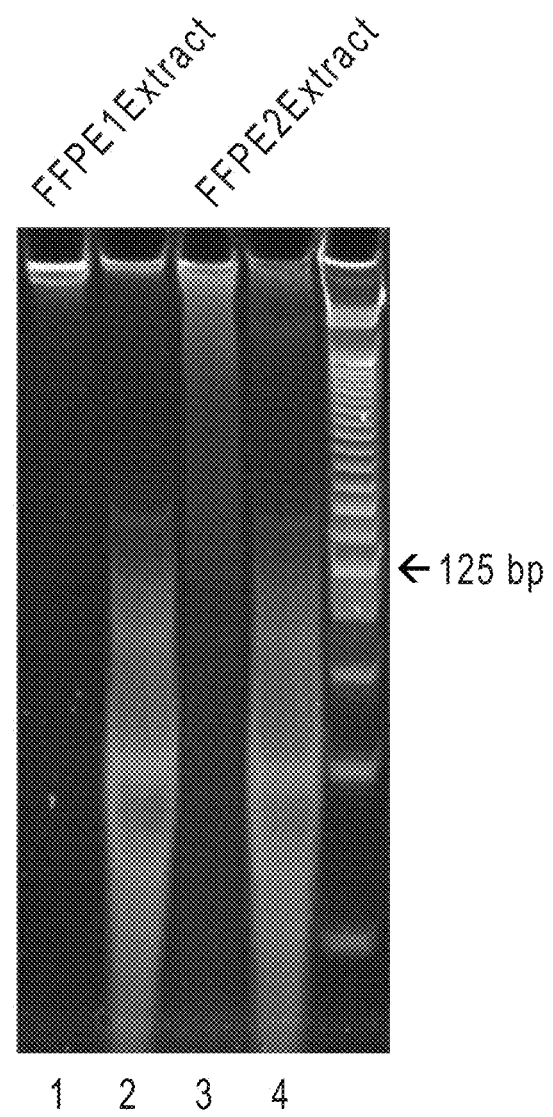
FIG. 9 shows an image of agarose gel electrophoresis visualizing exemplary amplification products (lanes 2 and 4) after performing a multiplex PCR and library amplification on an FFPE sample according to an exemplary embodiment.

In this example, a multiplex polymerase chain reaction was performed to amplify 96 amplicons from a Fresh-Frozen Paraffin-Embedded (FFPE) sample. Fresh-Frozen and FFPE samples are often problematic for amplification processes due to the small amount of DNA that can be extracted from such samples. Additionally, because of the harsh chemical treatment required to preserve these samples, the quality of DNA extracted from such a sample is generally very poor. DNA was extracted from a FFPE sample and loaded onto an agarose gel for visualization (lanes 1 and 3) or subjected to multiplex PCR and library amplification as described in Example 1 and then loaded onto the agarose gel for visualization (lanes 2 and 4). A 96-plex PCR reaction and library amplification was performed on 10 ng of FFPE DNA as described in Example 1. FIG. 9 shows a photograph of the agarose electrophoresis gel including FFPE DNA prior to and after library amplification as described in Example 1.

Example 9

FFPE Samples as Amenable Substrates for High Multiplex PCR

Figure 10:
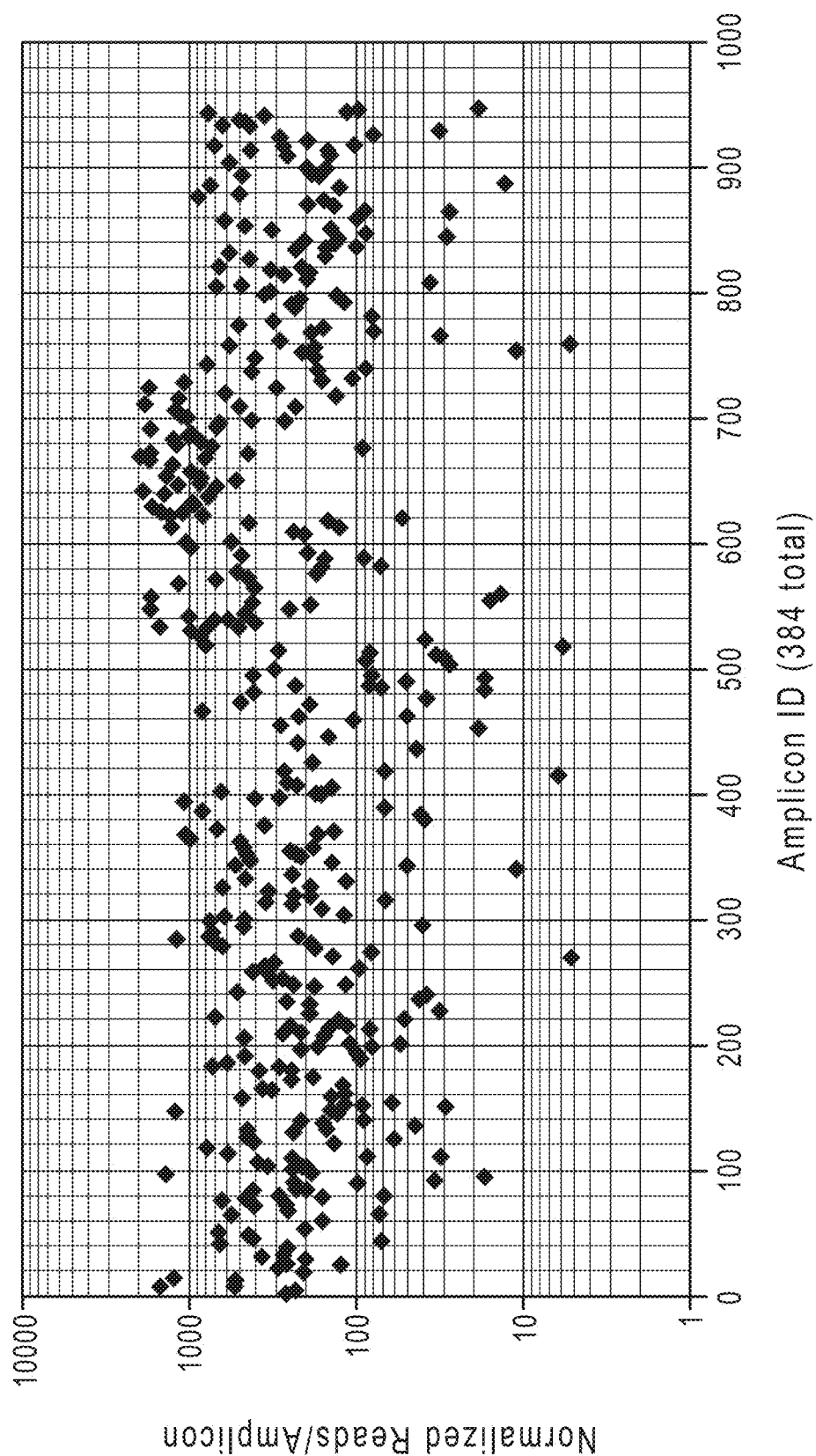
FIG. 10 shows quantification of the abundance and reproducibility of data obtained from an FFPE DNA sample (10 ng) in an exemplary 384-plex PCR obtained using an Ion Torrent PGM™ Sequencer (Life Technologies). The average number of reads per amplicon is 400.
Figure 11A:
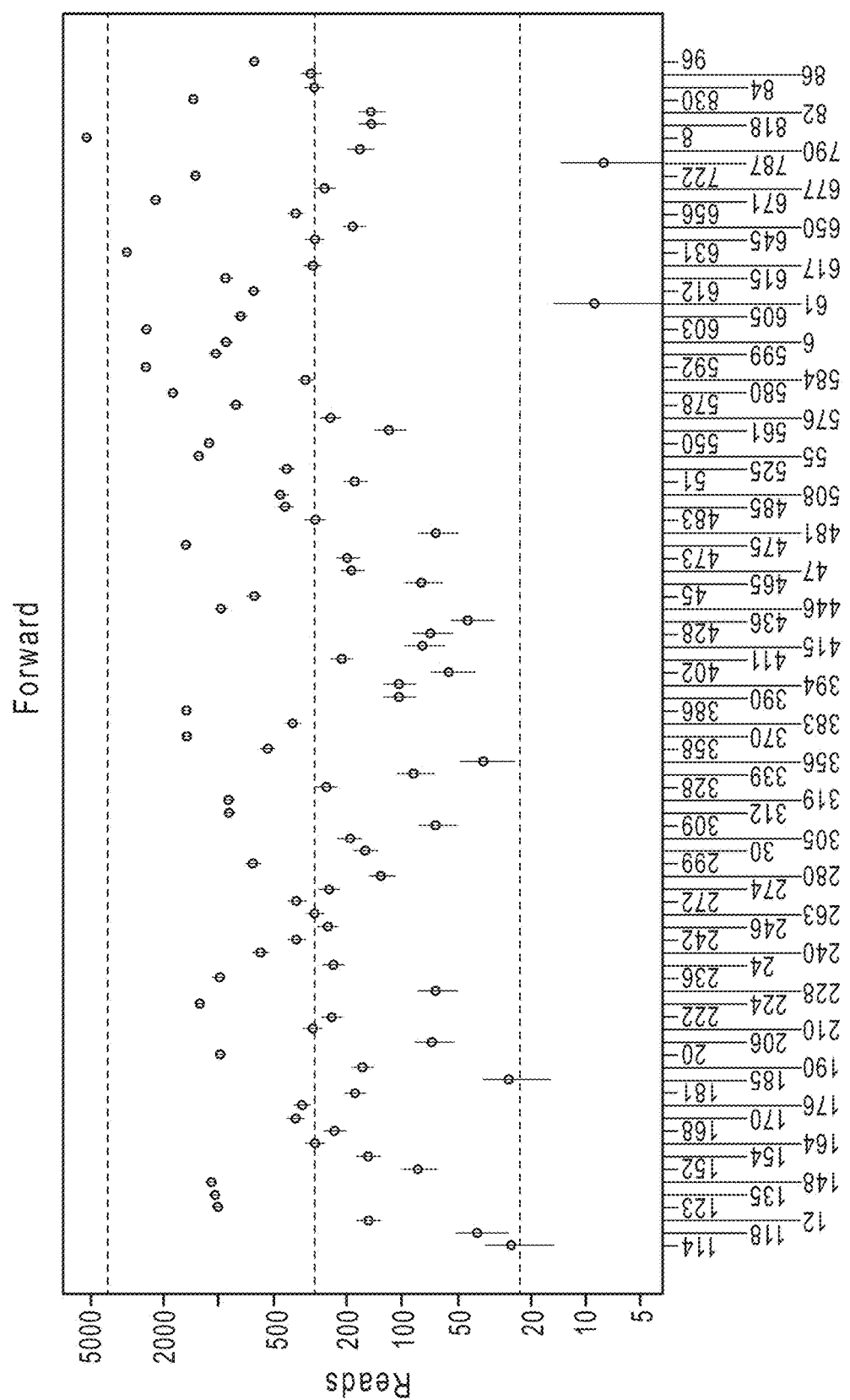
FIG. 11A-11B show quantification of the abundance and reproducibility of data obtained from a FFIPE DNA sample (10 ng) after an exemplary 94-plex reaction. The data shows the number of reads per amplicon for both the forward (FIG. 11A) and reverse primers (FIG. 11B) in the primer pool.
Figure 11B:
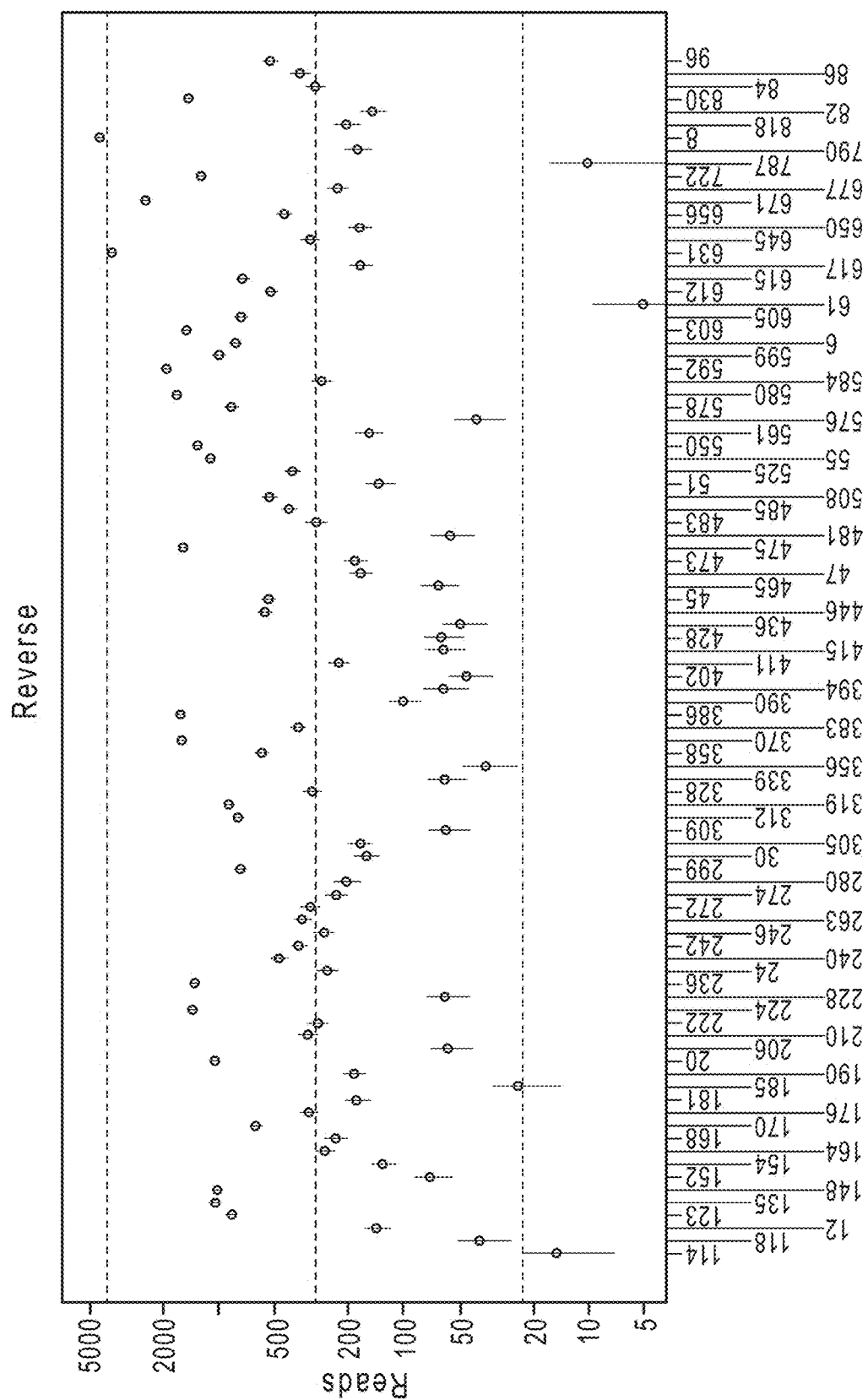

In this example, a multiplex polymerase chain reaction was performed to amplify 384 amplicons from a Fresh-Frozen Paraffin-Embedded (FFPE) sample. As discussed in Example 8, Fresh-Frozen and FFPE samples are often problematic for amplification due to low extracted DNA quantity and quality. In this example, 10 ng of DNA was extracted from a FFPE sample and subjected to a 384-plex PCR reaction and library amplification as described by Example 1. The data obtained from the Ion Torrent PGM™ Sequencer was averaged and is presented in FIG. 10. The data shows an average read rate of about 400 per amplicon. Further analysis of the read rate for some of the modified forward and reverse primer pairs used in the 384-plex reaction is presented in FIGS. 11A and 11B.

Example 10

Detection of Variants in Control Mix of KRAS Codon 12 and Codon 13 Mutants

Figure 12:
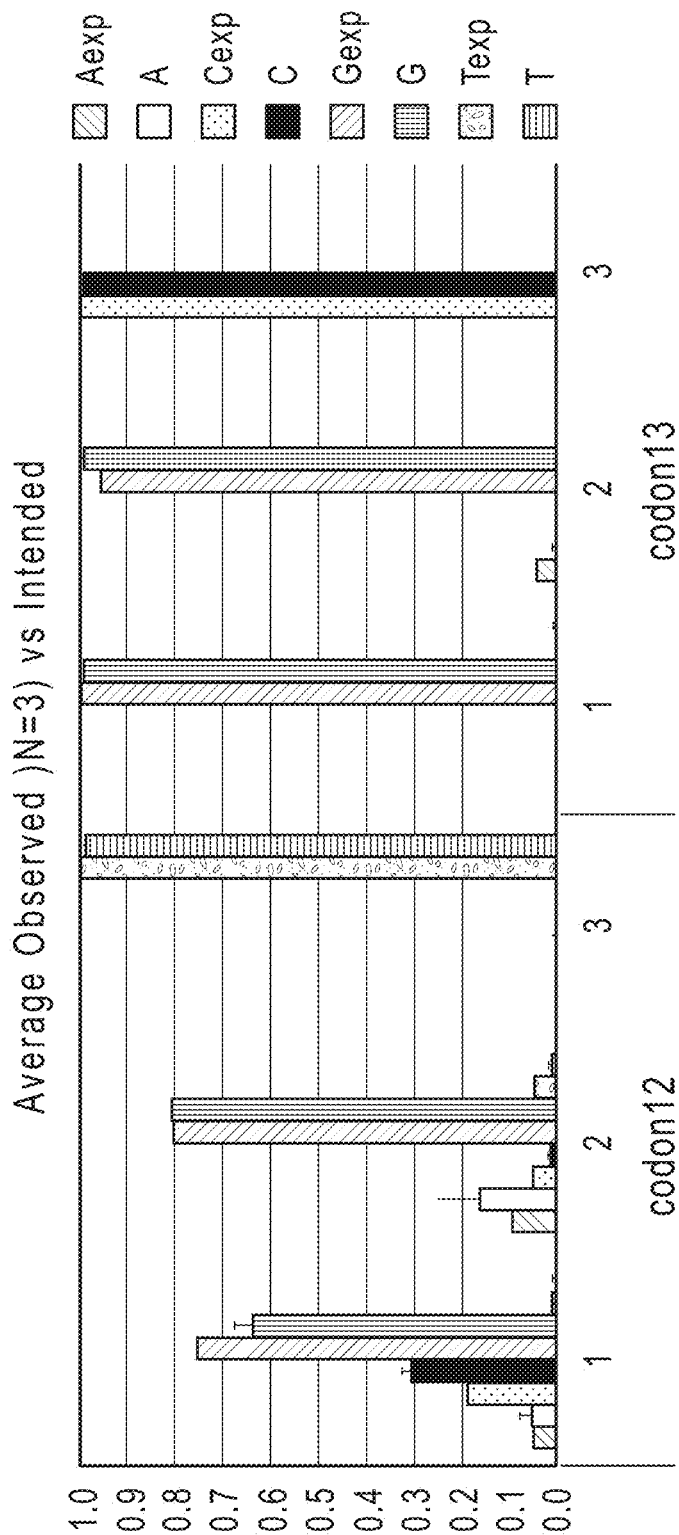
FIG. 12 shows a graph reporting the detection of mutations in codon 12 and codon 13 of the KRAS gene obtained by performing multiplex PCR and library amplification of control DNA and sequencing on an Ion Torrent PGM™ Sequencer (life Technologies).

In this example, a sample of DNA containing spiked amounts of mutations of the KRAS gene at codon 12 and codon 13 were provided as a blind test sample. The sample was amplified using target-specific modified primer pairs developed for the KRAS gene. The primer pool and samples were amplified as described in Example 1. The amplified library was prepared as a template and enriched. The enriched template was applied to an Ion 314™ Chip and analyzed using an Ion Torrent PGM™ Sequencer as described in Example 1. The data from 3 individual runs was averaged and is provided as FIG. 12. The amplicon products generated during the library amplification process correspond to the expected level of mutations present in the control DNA sample for the KRAS gene at codon 12 and codon 13.

Example 11

Resequencing the Cystic Fibrosis Transmembrane Conductance Regulator (CFTR) Gene Coding Region The CFTR protein is encoded by the CFTR gene which is approximately 200 kbp, spanning 27 exons. CFTR is an ABC transporter-class ion channel that transports chloride and thiocyanate ions across epithelial cell membranes. Mutations of the CFTR gene affect functioning of the chloride ion channels in these cell membranes, leading to cystic fibrosis and congenital absence of the vas deferens. As a consequence, a male carrier of the mutation in the CFTR gene can be infertile so the detection of the defect is key in IVD considerations.

In this example, genomic DNA (gDNA) was obtained containing mutations of the CFTR gene. The gDNA was prepared for library amplification, template preparation and applied to Ion Torrent 314™ Chip as described in Example 1. Over 8947 bases were amplified during the multiplex PCR reaction. The resulting amplicon library contained 34 amplicons with an average amplicon length of 104 bp. Sequence analysis of the amplicon library was conducted against the CFTR gene sequence reference: NCBI gi|287325315|ref|NG_016465.1|, 195703 bp.

The generated amplicon library was used to evaluate detection of the CFTR gene mutations in the sample. It was found that the library amplification process detected and identified 5 point mutations and 1 insertion/deletion at low coverage (4,001 reads) (FIGS. 13A-13E). The naming system for the 6 mutations is as follows:

Naming system: CFMD (UMD)
    c.869+11C>T (1001+11C/T)
    c.1408A>G (M470V)
    c.2562T>G (2694T/G)

c.4389G>A (4521G/A)

c.1-8G>C (125G/C)

c.1521_1523delCTT (ΔF508).

Most resequencing assays are based on amplicons that are greater than 100 bp. This example demonstrates the applicability and amenability of the library amplification process exemplified in Example 1, to generate amplicons of a length necessary for resequencing assays. The example also shows the accuracy of the Ion Torrent PGM™ Sequencer to correctly identify point mutations and insertions/deletion mutations in a given sample.

Example 12

Generation of Target-specific Primers

Table 2 (see in U.S. Ser. No. 13/458,739, filed Apr. 27, 2012, hereby incorporated by reference in its entirety) provides a list of target-specific forward and reverse uracil containing primers that were used in the above examples to amplify target-specific regions of gDNA or DNA extracted from samples, such as FFPE samples. Table 2 (from U.S. Ser. No. 13/458,739, filed Apr. 27, 2012, hereby incorporated by reference in its entirety) provides the chromosome location of each primer pair, the nucleotide sequence of each forward and reverse primer in each primer pair. Table 2 (from U.S. Ser. No. 13/458,739, filed Apr. 27, 2012, hereby incorporated by reference in its entirety) also provides the coordinates of the 5' end of the upstream/forward primer, the length of each amplicon, the corresponding amplicon nucleotide sequence, the length of each forward and reverse primer, and the $T_m$ for each forward or reverse primer. Tables 3a-3d (found in U.S. Ser. No. 13/458,739, filed Apr. 27, 2012, hereby incorporated by reference in its entirety) also provide a list of distinct target-specific forward and reverse primer pairs that were used in example 13 to amplify target-specific regions of gDNA or DNA extracted from FFPE samples from the genes of Table 1 (from U.S. Ser. No. 13/458,739, filed Apr. 27, 2012, hereby incorporated by reference in its entirety) that are associated with cancer. The following primer pair was also included for coverage of a mutation in the AKT1 gene (c.49G>A). Forward primer: GCCGCCAGGUCTTGATGUA and reverse primer: GCACAUCTGTCCUGGCACA.

Example 13

Alternate Library Protocol

PCR Amplify Genomic DNA Targets

In this example, a multiplex polymerase chain reaction was performed to amplify multiple individual amplicons across a genomic DNA sample or FFPE sample. A representative list of genes associated with cancers that were incorporated for investigation while synthesizing the primer pool is provided in Table 1 (found in U.S. Ser. No. 13/458, 739, filed Apr. 27, 2012, hereby incorporated by reference in its entirety). Each primer pair in the primer pool was designed to contain at least one uracil nucleotide in each of the forward and reverse primer (Tables 3a-3d found in U.S. Ser. No. 13/458,739, filed Apr. 27, 2012, hereby incorporated by reference in its entirety). Each primer pair was also designed to selectively hybridize to, and promote amplification of a specific gene or gene fragment of the genomic DNA sample to reduce formation of non-specific amplification products.

To a single well of a 96-well PCR plate was added 4 microliters of 5× Primer Pool (containing the primer pairs) at a concentration of 250 nm each in TE, 10 ng of genomic DNA and 10 microliters of an amplification reaction mixture (2× Stoffel HiFi Master Mix) that can include glycerol, dNTPs and Stoffel fragment of Amplitaq® DNA Polymerase (Invitrogen, Catalog No. N8080038) to a final volume of 20 microliters with nuclease free water (Life Technologies, CA, Part No. 600004).

The PCR plate was sealed and loaded into a thermal cycler (GeneAmp® PCR system 9700 Dual 96-well thermal cycler (Life Technologies, CA, Part No. N8050200 and 4314445)) and run on the following temperature profile to generate the preamplified amplicon library. Variation to the number of cycles was performed based on the total plexy of the reaction mixture under investigation. For example, a plexy of 48-96 was run for 17 cycles; a plexy of 97-192 was run for 16 cycles; a plexy of 193-384 was run for 15 cycles; a plexy of 385-768 was run for 14 cycles; a plexy of 769-1536 was run for 13 cycles. Additionally, for reaction mixtures containing barcodes or pooled reaction mixtures the number of cycles was lowered by one or more additional cycles. For example, 2-3 barcodes per sample were subtracted by one cycle; 4-8 barcodes per sample were subtracted by 2 cycles, and 9-16 barcodes were subtracted by 3 cycles. An initial holding stage was performed at 99° C. for 2 minutes, followed by X cycles (as determined above) of denaturing at 99° C. for 15 seconds and an annealing and extending stage at 60° C. for 4 minutes. After cycling, the preamplified amplicon library was held at 4° C. until proceeding to the digestion and phosphorylation step outlined below.

Digest/Phosphorylate/Heat Kill the Amplicons

To the preamplified library (~20 microliters), 2 microliters of FuPa reagent was added. Typically, the FuPa reagent comprises one or more uracil degradable enzymes such as UDG, FPG and the like, a DNA polymerase such as Pol I, T4PNK, Klenow and the like, and an antibody such as an anti-Taq antibody. In this example, the relative amount of each enzymatic component in the FuPa reagent was 1:1:1:1 but can be varied according to the number of required cycles, variations to the temperature profile, etc., as can be determined by one of ordinary skill in the art. The PCR plate was sealed and loaded into a thermal cycler (GeneAmp® PCR system 9700 Dual 96-well thermal cycler (Life Technologies, CA, Part No. N8050200 and 4314445)) and run on the following temperature profile. An initial holding stage was performed at 37° C. for 5 minutes, followed by 55° C. for 10 minutes and then 60° C. for 20 minutes. After cycling, the preamplified amplicon library was held at 4° C. until proceeding to the ligation/nick translation step outlined below.

Ligate Adpaters to the Amplicons and Nick Translate

After phosphorylation, the amplicon preamplification library (~22 µl) proceeded directly to a ligation step. In this example, the preamplification library now containing the phosphorylated amplicon library was combined with 1 microliter of A/P1 Adaptersadapters (20 µm each) (sold as a component of the Ion Fragment Library Kit, Life Technologies, Part No. 4466464), 2 microliters of 10× ligation buffer and 1 microliter of DNA ligase (sold as components of the Ion Fragment Library Kit, Life Technologies, Part No. 4466464). The PCR plate was sealed and loaded into a thermal cycler (GeneAmp® PCR system 9700 Dual 96-well thermal cycler (Life Technologies, CA, Part No. N8050200 and 4314445)) and run on the following temperature profile. An initial holding stage was performed at 22° C. for 30 minutes, followed by 65° C. for 10 minutes and then held at 4° C. until proceeding to the next step.

If the amplicon library is to contain barcodes (for example Ion DNA Barcoding 1-16 kit, Life Technologies, Part No. 4468654, incorporated herein in its entirety), the barcodes can be added at this step to the PCR plate essentially according to the manufacturer's instructions prior to proceeding to the next step.

1.8×AMPure XP Purification 1.8× sample volume of AgenCourt® AMPure® Reagent (Beckman Coulter, CA) was added to the ligated DNA. The mixture was mixed and incubated at room temperature for 5 minutes. After the solution had cleared, the supernatant was discarded. An ethanol wash was performed and the supernatant discarded. Any remaining ethanol was removed and the pellet was air-dried for about 5 minutes at room temperature. The pellet was resuspended in 20 microliters of DNase/RNase Free Water (Life Technologies, CA, Part No. 600004). In some instances, an optional library amplification step can be performed on the amplicon library, as outlined below.

Nick Translate and Amplify the Amplicon Library and Purify the Library

The ligated DNA (~20 microliters) was combined with 78 microliters of Platinum® PCR SuperMix High Fidelity (Life Technologies, CA, Part No. 12532-016, sold as a component of the Ion Fragment Library Kit, Life Technologies, Part No. 4466464) and 4 microliters of Library Amplification Primer Mix (5 µM each) (Life Technologies, CA, Part No. 602-1068-01, sold as a component of the Ion Fragment Library Kit, Life Technologies, Part No. 4466464). The solution was applied to a single well of a 96-well PCR plate and sealed. The plate was loaded into a thermal cycler (GeneAmp® PCR system 9700 Dual 96-well thermal cycler (Life Technologies, CA, Part No. N8050200 and 4314445)) and run on the following temperate profile to generate the final amplicon library.

A nick-translation was performed at 72° C. for 1 minute, followed by an enzyme activation stage at 98° C. for 2 minutes, followed by 7 cycles of denaturing at 98° C. for 15 seconds and an annealing and extending stage at 60° C. for 1 minute. After cycling, the final amplicon library was held at 4° C. until proceeding to the final purification step outlined below.

The final amplicon library (~100 microliters) was combined with 1.8× sample volume of Agencourt® AMPure® XP reagent (Beckman Coulter, CA). The mixture was then incubated for 5 minutes at room temperature. The PCR plate containing the final amplicon library was washed with 70% ethanol and the supernatant discarded. Any remaining ethanol was removed and air-dried for about 5 minutes at room temperature. Once dry, the library was resuspended in 20 microliters of Low TE (Life Technologies, CA, Part No. 602-1066-01).

Assess the Library Size Distribution and Determine the Template Dilution Factor

The final amplicon library was quantitated to determine the library dilution (Template Dilution Factor) that results in a concentration within the optimized target range for Template Preparation (e.g., PCR-mediated addition of library molecules onto Ion Sphere™ Particles). The final amplicon library is typically quantitated for downstream Template Preparation procedure using an Ion Library Quantitation Kit (qPCR) (Life Technologies, Part No. 4468802) and/or a Bioanalyzer™ (Agilent Technologies, Agilent 2100 Bioanalyzer) to determine the molar concentration of the amplicon library, from which the Template Dilution Factor is calculated. For example, instructions to determine the Template Dilution Factor by quantitative real-time PCR (qPCR) can be found in the Ion Library Quantitation Kit User Guide (Life Technologies, Part No. 4468986).

In this example, 1 microliter of the final amplicon library preparation was analyzed on the 2100 Bioanalyzer™ with an Agilent High Sensitivity DNA Kit (Agilent Technologies, Part No. 5067-4626) to generate peaks in the 135-205 bp size range and at a concentration of about $5 \times 10^9$ copies per microliter.

Proceed to Template Preparation

An aliquot of the final library was used to prepare DNA templates that were clonally amplified on Ion Sphere™ Particles using emulsion PCR (emPCR). The preparation of template in the instant example was prepared according to the manufacturer's instructions using an Ion Xpress Template Kit (Life Technologies, Part No. 4466457). Once template-positive Ion Sphere Particles were enriched, an aliquot of the Ion Spheres were loaded onto an Ion 314™ Chip (Life Technologies, Part No. 4462923) as described in the Ion Sequencing User Guide (Part No. 4467391), and subjected to analysis and sequencing as described in the Ion Torrent PGM Sequencer User Guide (Life Technologies, Part No. 4462917).

Example 14

Alternate Library Protocol

PCR Amplify Genomic DNA Targets

In this example, a multiplex polymerase chain reaction was performed to amplify multiple individual amplicons across a genomic DNA sample. A representative list of genes associated with cancers that were incorporated for investigation while synthesizing the primer pool is provided in Table 1 (found in U.S. Ser. No. 13/458,739, filed Apr. 27, 2012, hereby incorporated by reference in its entirety). Each primer pair in the primer pool was designed to contain at least one uracil nucleotide in each of the forward and reverse primer (Table 2—see U.S. Ser. No. 13/458,739, filed Apr. 27, 2012, hereby incorporated by reference in its entirety). Each primer pair was also designed to selectively hybridize to, and promote amplification of a specific gene or gene fragment of the genomic DNA sample to reduce formation of non-specific amplification products.

To a single well of a 96-well PCR plate was added 5 microliters of 4×HSM Primer Pool (containing the primer pairs of Table 2 (see U.S. Ser. No. 13/458,739, filed Apr. 27, 2012, hereby incorporated by reference in its entirety)) at a concentration of 250 nm each in TE, 50 ng of genomic DNA and 10 microliters of an amplification reaction mixture (2× PreAmp HiFi Master Mix) that can include glycerol, dNTPs and a DNA Polymerase (such as Taq DNA Polymerase, Invitrogen, Catalog No. N8080038) to a final volume of 20 microliters with nuclease free water (Life Technologies, CA, Part No. 600004).

The PCR plate was sealed and loaded into a thermal cycler (GeneAmp® PCR system 9700 Dual 96-well thermal cycler (Life Technologies, CA, Part No. N8050200 and 4314445)) and run on the following temperature profile to generate the preamplified amplicon library. An initial holding stage was performed at 98° C. for 2 minutes, followed by 16 cycles of denaturing at 98° C. for 15 seconds and an annealing and extending stage at 60° C. for 4 minutes. After cycling, the preamplified amplicon library was held at 4° C. until proceeding to the purification step outlined below.

Purify the Amplicons from Input DNA and Primers

Two rounds of Agencourt® AMPure® XP Reagent (Beckman Coulter, CA) binding, wash, and elution at 0.6× and 1.2× volume ratios were found to remove genomic DNA and unbound or excess primers. In a 1.5 ml LoBind tube (Eppendorf, Part No. 022431021), the preamplified amplicon library (20 microliters) was combined with 12 microliters (0.6× volumes) of Agencourt® AMPure® XP reagent (Beckman Coulter, CA). The bead suspension was pipetted up and down to thoroughly mix the bead suspension with the preamplified amplicon library. The sample was then pulse-spin and incubated for 5 minutes at room temperature.

The tube containing the sample was placed on a magnetic rack such as a DynaMag™-2 spin magnet (Life Technologies, CA, Part No. 123-21D) for 2 minutes to capture the beads. Once the solution cleared, the supernatant was transferred to a new tube, where 24 microliters (1.2× volume) of AgenCourt® AMPure® XP beads (Beckman Coulter, CA) were added to the supernatant. The mixture was pipetted to ensure the bead suspension mixed with the preamplified amplicon library. The sample was then pulse-spin and incubated at room temperature for 5 minutes. The tube containing the sample was placed on the magnetic rack for 2 minutes to capture the beads. Once the solution cleared, the supernatant was carefully discarded without disturbing the bead pellet. The desired preamplified amplicon library was now bound to the beads. Without removing the tube from the magnetic rack, 200 microliters of freshly prepared 70% ethanol was introduced into the sample. The sample was incubated for 30 seconds while gently rotating the tube on the magnetic rack. After the solution cleared, the supernatant was discarded without disturbing the pellet. A second ethanol wash was performed and the supernatant discarded. Any remaining ethanol was removed by pulse-spinning the tube and carefully removing residual ethanol while not disturbing the pellet. The pellet was air-dried for about 5 minutes at room temperature.

Once the tube was dry, the tube was removed from the magnetic rack and 20 microliters of DNase/RNase Free Water was added (Life Technologies, CA, Part No. 600004). The tube was vortexed and pipetted to ensure the sample was mixed thoroughly. The sample was pulse-spin and placed on the magnetic rack for two minutes. After the solution cleared, the supernatant containing the eluted DNA was transferred to a new tube.

Phosphorylate the Amplicons

To the eluted DNA (~20 microliters), 3 microliters of DNA ligase buffer (Invitrogen, Catalog No. 15224041), 2 microliters dNTP mix (10 mm), and 2 microliters of FuP reagent were added. The reaction mixture was mixed thoroughly to ensure uniformity and incubated at 37° C. for 10 minutes.

Ligate Adpaters to the Amplicons and Purify the Ligated Amplicons

After incubation, the reaction mixture proceeded directly to a ligation step. Here, the reaction mixture now containing the phosphorylated amplicon library was combined with 1 microliter of A/P1 adapters (20 μm each) (sold as a component of the Ion Fragment Library Kit, Life Technologies, Part No. 4466464) and 1 microliter of DNA ligase (sold as a component of the Ion Fragment Library Kit, Life Technologies, Part No. 4466464), and incubated at room temperature for 30 minutes.

After the incubation step, 52 microliters (1.8× sample volume) of AgenCourt® AMPure® Reagent (Beckman Coulter, CA) was added to the ligated DNA. The mixture was pipetted thoroughly to mix the bead suspension with the ligated DNA. The mixture was pulse-spin and incubated at room temperature for 5 minutes. The samples underwent another pulse-spin and were placed on a magnetic rack such as a DynaMag™-2 spin magnet (Life Technologies, CA, Part No. 123-21D) for two minutes. After the solution had cleared, the supernatant was discarded. Without removing the tube from the magnetic rack, 200 microliters of freshly prepared 70% ethanol was introduced into the sample. The sample was incubated for 30 seconds while gently rotating the tube on the magnetic rack. After the solution cleared, the supernatant was discarded without disturbing the pellet. A second ethanol wash was performed and the supernatant discarded. Any remaining ethanol was removed by pulse-spinning the tube and carefully removing residual ethanol while not disturbing the pellet. The pellet was air-dried for about 5 minutes at room temperature.

The pellet was resuspended in 20 microliters of DNase/RNase Free Water (Life Technologies, CA, Part No. 600004) and vortexed to ensure the sample was mixed thoroughly. The sample was pulse-spin and placed on the magnetic rack for two minutes. After the solution cleared, the supernatant containing the ligated DNA was transferred to a new Lobind tube (Eppendorf, Part No. 022431021).

Nick Translate and Amplify the Amplicon Library and Purify the Library

The ligated DNA (~20 microliters) was combined with 76 microliters of Platinum® PCR SuperMix High Fidelity (Life Technologies, CA, Part No. 12532-016, sold as a component of the Ion Fragment Library Kit, Life Technologies, Part No. 4466464) and 4 microliters of Library Amplification Primer Mix (5 μM each) (Life Technologies, CA, Part No. 602-1068-01, sold as a component of the Ion Fragment Library Kit, Life Technologies, Part No. 4466464), the mixture was pipetted thoroughly to ensure a uniformed solution. The solution was applied to a single well of a 96-well PCR plate and sealed. The plate was loaded into a thermal cycler (GeneAmp® PCR system 9700 Dual 96-well thermal cycler (Life Technologies, CA, Part No. N8050200 and 4314445)) and run on the following temperate profile to generate the final amplicon library.

A nick-translation was performed at 72° C. for 1 minute, followed by an enzyme activation stage at 98° C. for 2 minutes, followed by 6 cycles of denaturing at 98° C. for 15 seconds and an annealing and extending stage at 60° C. for 1 minute. After cycling, the final amplicon library was held at 4° C. until proceeding to the final purification step outlined below.

In a 1.5 ml LoBind tube (Eppendorf, Part No. 022431021), the final amplicon library (~100 microliters) was combined with 180 microliters (1.8× sample volume) of Agencourt® AMPure® XP reagent (Beckman Coulter, CA). The bead suspension was pipetted up and down to thoroughly mix the bead suspension with the final amplicon library. The sample was then pulse-spin and incubated for 5 minutes at room temperature.

The tube containing the final amplicon library was placed on a magnetic rack such as a DynaMag™-2 spin magnet (Life Technologies, CA, Part No. 123-21D) for 2 minutes to capture the beads. Once the solution cleared, the supernatant was carefully discarded without disturbing the bead pellet. Without removing the tube from the magnetic rack, 400 microliters of freshly prepared 70% ethanol was introduced into the sample. The sample was incubated for 30 seconds while gently rotating the tube on the magnetic rack. After the solution cleared, the supernatant was discarded without disturbing the pellet. A second ethanol wash was performed and the supernatant discarded. Any remaining ethanol was removed by pulse-spinning the tube and carefully removing residual ethanol while not disturbing the pellet. The pellet was air-dried for about 5 minutes at room temperature.

Once the tube was dry, the tube was removed from the magnetic rack and 20 microliters of Low TE was added (Life Technologies, CA, Part No. 602-1066-01). The tube was pipetted and vortexed to ensure the sample was mixed thoroughly. The sample was pulse-spin and placed on the magnetic rack for two minutes. After the solution cleared, the supernatant containing the final amplicon library was transferred to a new Lobind tube (Eppendorf, Part No. 022431021).

Assess the Library Size Distribution and Determine the Template Dilution Factor

The final amplicon library was quantitated to determine the library dilution (Template Dilution Factor) that results in a concentration within the optimized target range for Template Preparation (e.g., PCR-mediated addition of library molecules onto Ion Sphere™ Particles). The final amplicon library is typically quantitated for downstream Template Preparation procedure using an Ion Library Quantitation Kit (qPCR) (Life Technologies, Part No. 4468802) and/or a Bioanalyzer™ (Agilent Technologies, Agilent 2100 Bioanalyzer) to determine the molar concentration of the amplicon library, from which the Template Dilution Factor is calculated. For example, instructions to determine the Template Dilution Factor by quantitative real-time PCR (qPCR) can be found in the Ion Library Quantitation Kit User Guide (Life Technologies, Part No. 4468986).

In this example, 1 microliter of the final amplicon library preparation was analyzed on the 2100 Bioanalyzer™ with an Agilent High Sensitivity DNA Kit (Agilent Technologies, Part No. 5067-4626).

Proceed to Template Preparation

An aliquot of the final library was used to prepare DNA templates that were clonally amplified on Ion Sphere™ Particles using emulsion PCR (emPCR). The preparation of template in the instant example was prepared according to the manufacturer's instructions using an Ion Xpress Template Kit (Life Technologies, Part No. 4466457). Once template-positive Ion Sphere Particles were enriched, an aliquot of the Ion Spheres were loaded onto an Ion 314™ Chip (Life Technologies, Part No. 4462923) as described in the Ion Sequencing User Guide (Part No. 4467391), and subjected to analysis and sequencing as described in the Ion Torrent PGM Sequencer User Guide (Life Technologies, Part No. 4462917).

Example 15

Alternate Library Protocol

PCR Amplify Genomic DNA Targets

In this example, a multiplex polymerase chain reaction was performed to amplify multiple individual amplicons across a genomic DNA sample. A representative list of genes associated with cancers that were incorporated for investigation while synthesizing the primer pool is provided in Table 1 (see U.S. Ser. No. 13/458,739, filed Apr. 27, 2012, hereby incorporated by reference in its entirety). Each primer pair in the primer pool was designed to contain at least one uracil nucleotide in each of the forward and reverse primer (Table 2—see U.S. Ser. No. 13/458,739, filed Apr. 27, 2012, hereby incorporated by reference in its entirety). Each primer pair was also designed to selectively hybridize to, and promote amplification of a specific gene or gene fragment of the genomic DNA sample to reduce formation of non-specific amplification products.

To a single well of a 96-well PCR plate was added 10 microliters of 2× Primer Pool (containing the primer pairs of Table 2 (found in U.S. Ser. No. 13/458,739, filed Apr. 27, 2012, hereby incorporated by reference in its entirety)) at a concentration of 250 nm each, 10 ng of genomic DNA and 4 microliters of an amplification reaction mixture (5× Ion Ampliseq Master Mix) that can include glycerol, dNTPs and a DNA polymerase (for example, Stoffel fragment of Amplitaq® DNA Polymerase (Invitrogen Catalog No. N8080038)) to a final volume of 20 microliters with nuclease free water (Life Technologies, CA, Part No. 600004).

The PCR plate was sealed and loaded into a thermal cycler (GeneAmp® PCR system 9700 Dual 96-well thermal cycler (Life Technologies, CA, Part No. N8050200 and 4314445)) and run on the following temperature profile to generate the preamplified amplicon library. Variation to the number of cycles was performed based on the total plexy of the reaction mixture under investigation. For example, a plexy of 48-96 was run for 17 cycles; a plexy of 97-192 was run for 16 cycles; a plexy of 193-384 was run for 15 cycles; a plexy of 385-768 was run for 14 cycles; a plexy of 769-1536 was run for 13 cycles. Additionally, for reaction mixtures containing barcodes or pooled reaction mixtures the number of cycles was lowered by one or more additional cycles. For example, 2-3 barcodes per sample were subtracted by one cycle; 4-8 barcodes per sample were subtracted by 2 cycles, and 9-16 barcodes were subtracted by 3 cycles. For samples that contain fragmented DNA, e.g., enzymatically digested DNA, the number of cycles can be increased for up to 3 cycles. For selective amplification of one or more DNA samples using a starting input of 1 ng or less DNA, the number of cycles was increased by an additional 3 cycles. An initial holding stage was performed at 99° C. for 2 minutes, followed by X cycles (as determined above) of denaturing at 99° C. for 15 seconds and an annealing and extending stage at 60° C. for 4 minutes. After cycling, the preamplified amplicon library was held at 4° C. until proceeding to the purification step outlined below.

Digest/Phosphorylate/Heat Kill the Amplicons

To the preamplified library (~20 microliters), 2 microliters of FuPa reagent was added. Typically, the FuPa reagent comprises one or more uracil degradable enzymes such as UDG, FPG and the like, a DNA polymerase such as Klenow fragment, and an antibody such as an anti-Taq antibody. In this example, the relative amount of each enzymatic component in the FuPa reagent was 1:1:1:2 but can be varied according to the number of required cycles, variations to the temperature profile, etc., as can be determined by one of ordinary skill in the art. The PCR plate was sealed and loaded into a thermal cycler (GeneAmp® PCR system 9700 Dual 96-well thermal cycler (Life Technologies, CA, Part No. N8050200 and 4314445)) and run on the following temperature profile. An initial holding stage was performed at 37° C. for 10 minutes, followed by 55° C. for 10 minutes and then 60° C. for 20 minutes. After cycling, the preamplified amplicon library was held at 4° C. until proceeding to the ligation/nick translation step outlined below.

Ligate Adpaters to the Amplicons and Nick Translate

After phosphorylation, the amplicon preamplification library (~22 µl) proceeded directly to a ligation step. In this example, the preamplification library now containing the phosphorylated amplicon library was combined with 2 microliters of A/P1 Adaptersadapters (5 µm each) (sold as a component of the Ion Fragment Library Kit, Life Technologies, Part No. 4466464), 4 microliters of 7.5× ligation buffer and 2 microliters of T4 DNA ligase (5 u/µl). The PCR plate was sealed and loaded into a thermal cycler (GeneAmp®

PCR system 9700 Dual 96-well thermal cycler (Life Technologies, CA, Part No. N8050200 and 4314445)) and run on the following temperature profile. An initial holding stage was performed at 22° C. for 30 minutes, followed by 60° C. for 5 minutes and then held at 4° C. until proceeding to the next step.

If the amplicon library is to contain barcodes (for example Ion DNA Barcoding 1-16 kit, Life Technologies, Part No. 4468654, incorporated herein in its entirety), the barcodes are added at this step to the PCR plate essentially according to the manufacturer's instructions prior to proceeding to the next step. Optionally, all the samples or barcodes can be pooled into a single tube at this step.

1.6×AMPure XP Purification 1.6× sample volume of AgenCourt® AMPure® Reagent (Beckman Coulter, CA) was added to the ligated DNA. The mixture was mixed and incubated at room temperature for 5 minutes. An ethanol wash was performed and the supernatant discarded. Any remaining ethanol was removed and air-dried for about 5 minutes at room temperature. The dry tube containing the library was resuspended in 20 microliters of Nuclease Free Water (Life Technologies, CA, Part No. 600004). In some instances, an optional nick translation/library amplification step can be performed on the amplicon library, as outlined below.

Nick Translate and Amplify the Amplicon Library and Purify the Library

The ligated DNA (~20 microliters) was combined with 78 microliters of Platinum® PCR SuperMix High Fidelity (Life Technologies, CA, Part No. 12532-016, sold as a component of the Ion Fragment Library Kit, Life Technologies, Part No. 4466464) and 4 microliters of Library Amplification Primer Mix (5 µM each) (Life Technologies, CA, Part No. 602-1068-01, sold as a component of the Ion Fragment Library Kit, Life Technologies, Part No. 4466464). The solution was applied to a single well of a 96-well PCR plate and sealed. The plate was loaded into a thermal cycler (GeneAmp® PCR system 9700 Dual 96-well thermal cycler (Life Technologies, CA, Part No. N8050200 and 4314445)) and run on the following temperate profile to generate the final amplicon library.

A nick-translation was performed at 72° C. for 1 minute, followed by an enzyme activation stage at 98° C. for 2 minutes, followed by 7 cycles of denaturing at 98° C. for 15 seconds and an annealing and extending stage at 60° C. for 1 minute. After cycling, the final amplicon library was held at 4° C. until proceeding to the final purification step outlined below.

The final amplicon library (~100 microliters) was combined with 1.8× sample volume of Agencourt® AMPure® XP reagent (Beckman Coulter, CA). The mixture was then incubated for 5 minutes at room temperature. The final amplicon library was washed with 70% ethanol and the supernatant discarded. Any remaining ethanol was removed and air-dried for about 5 minutes at room temperature. Once dry, the library was resuspended in 20 microliters of Low TE (Life Technologies, CA, Part No. 602-1066-01). In this example, 1 microliter of the final amplicon library preparation was analyzed on the 2100 Bioanalyzer™ with an Agilent High Sensitivity DNA Kit (Agilent Technologies, Part No. 5067-4626).

Example 16

In this example, an amplicon library was prepared using 2946 target-specific primer pairs. The primer pairs were prepared from the list of genes in Tables 1 and 18 (both found in U.S. Ser. No. 13/458,739, filed Apr. 27, 2012, hereby incorporated by reference in its entirety). Each primer pair was designed to selectively hybridize and promote amplification of the selected targeted region. The libraries were prepared according to Example 14 except that the primer pool was pooled into a single PCR tube, evaporated and resuspended in low TE and supplemented with 0.25 mM magnesium chloride prior to incubating with DNA and the amplification reaction mixture. In this example, both high molecular weight DNA or mechanically sheared DNA were applied as input DNA (10 ng input). The results from this sequencing experiment are provided in the Table below and demonstrated approximately 91-98% of all reads were on target, greater than 99% target coverage at 1× when normalized to 100×, and greater than 98% base accuracy.

| | 2946 Sheared | 2946 HMW |
|---|---|---|
| Plexity of PreAmp | | |
| Target DNA | | |
| Percent greater than 0.01 mean reads per base | 99.40% | 99.29% |
| Percent greater than 0.1 mean reads per base | 96.33% | 95.16% |
| Percent greater than 0.2 mean reads per base | 92.26% | 89.40% |
| Percent no strand bias of all Amps | 71.15% | 72.98% |
| Percent no strand bias of all Amps >100 reads | 73.31% | 77.12% |
| Percent end to end read of on target reads | −1.00% | −1.00% |
| Per base accuracy | 98.34% | 98.59% |
| Percent of total reads mapped ontarget | 99.10% | 99.14% |
| Percent wells with read | 35.94% | 31.23% |
| Number of total reads | 2277968 | 1979529 |
| Number of mapped reads | 2257427 | 1962501 |
| Number of targets | 2946 | 2946 |
| Number of reads on target | 2094328 | 1941916 |
| Percent all reads on target | 91.94% | 98.10% |
| Percent mapped reads on target | 92.78% | 98.95% |
| Percent reads off target | 7.16% | 1.04% |
| Percent reads unmapped | 0.90% | 0.86% |
| Bases in targeted reference | 327815 | 327815 |
| Bases covered (at least 1x) | 326642 | 326656 |
| Total base reads on target | 220235195 | 206585756 |
| Average base coverage depth | 671.83 | 630.19 |
| Maximum base read depth | 3070 | 2520 |
| Average base read depth | 674.23 | 632.43 |
| Std. Dev base read depth | 431.42 | 466.91 |
| Target coverage at 1x | 99.64% | 99.65% |
| Target coverage at 10x | 99.23% | 99.12% |
| Target coverage at 20x | 98.77% | 98.42% |
| Target coverage at 1x - norm 100 | 99.40% | 99.29% |
| Target coverage at 10x - norm 100 | 96.33% | 95.16% |
| Target coverage at 20x - norm 100 | 92.26% | 89.40% |
| Percent end to end read of on target reads | −1.00% | −1.00% |
| Percent forward end to end read of on target reads | −1.00% | −1.00% |
| Percent reverse end to end read of on target reads | −1.00% | −1.00% |
| Coverage needed for 99 percentile base with at least 1x coverage | 52.2 | 48.96 |
| Coverage needed for 98 percentile base with at least 10x coverage | 207.65 | 247.24 |
| Coverage needed for 95 percentile base with at least 20x coverage | 145.33 | 203.58 |

Example 17

In this example, an amplicon library was prepared using 6110 target-specific primer pairs. The library corresponds to approximately 450 cancer genes. The primer pairs were prepared from the list of genes in Tables 1 and 18 (both found in U.S. Ser. No. 13/458,739, filed Apr. 27, 2012, hereby incorporated by reference in its entirety). Each primer pair was designed to selectively hybridize and promote amplification of the selected targeted region using the target-specific selection criteria outline herein. The libraries were prepared according to Example 14 except that the primer pools were prepared as two tubes (3188-plex and 2946-plex) and supplemented with 0.5 mM magnesium chloride. The PCR preamplification cycling steps were also modified to increase the denaturing temperature to 99° C., included an extending step of 72° C. for 5 minutes, after the 60° C. annealing step, which was also extended to 10 minutes. After cycling, each tube containing the amplicon library was combined into a single emulsion for emulsion PCR enrichment. The amplicon library was used to prepare DNA templates that were clonally amplified on Ion Sphere™ Particles using emulsion PCR (emPCR). The preparation of template in the instant example was prepared according to the manufacturer's instructions using an Ion Xpress Template Kit (Life Technologies, Part No. 4466457). Once template-positive Ion Sphere Particles were enriched, an aliquot of the Ion Spheres were loaded onto an Ion 316™ Chip (Life Technologies, Part No. 4466616) as described in the Ion Sequencing User Guide (Part No. 4467391), and subjected to analysis and sequencing as described in the Ion Torrent PGM Sequencer User Guide (Life Technologies, Part No. 4462917).

In this example, high molecular weight DNA was applied as the input DNA (10 ng). The results from this experiment are provided in the Table below and demonstrated approximately 95% of all reads were on target, approximately 95% of all reads (greater than 100 reads) showed no strand bias, and greater than 97% base accuracy.

| | |
|---|---:|
| Percent greater than 0.01 mean reads per base | 81.58% |
| Percent greater than 0.1 mean reads per base | 75.40% |
| Percent greater than 0.2 mean reads per base | 69.73% |
| Percent no strand bias of all bases | 92.16% |
| Percent no strand bias of all Amps | 72.16% |
| Percent no strand bias of all Amps >100 reads | 95.06% |
| Percent end to end read of on target reads | −1.00% |
| Per base accuracy | 97.78% |
| Percent of total reads mapped to hg19 | 98.05% |
| Percent wells with read | 34.51% |
| Number of total reads | 2190638 |
| Number of mapped reads | 2147835 |
| Number of targets | 6110 |
| Number of reads on target | 2098176 |
| Percent all reads on target | 95.78% |
| Percent mapped reads on target | 97.69% |
| Percent reads off target | 2.27% |
| Percent reads unmapped | 1.95% |
| Bases in targeted reference | 677270 |
| Bases covered (at least 1x) | 556880 |
| Total base reads on target | 243058082 |
| Average base coverage depth | 358.88 |
| Maximum base read depth | 2402 |
| Average base read depth | 436.45 |
| Std. Dev base read depth | 371.45 |
| Target coverage at 1x | 82.22% |
| Target coverage at 10x | 80.45% |
| Target coverage at 20x | 78.41% |
| Target coverage at 100x | 66.15% |
| Target coverage at 500x | 29.11% |
| Target coverage at 1x - norm 100 | 81.58% |
| Target coverage at 10x - norm 100 | 75.40% |
| Target coverage at 20x - norm 100 | 69.73% |
| Target coverage at 100x - norm 100 | 40.40% |
| Target coverage at 500x - norm 100 | 0.34% |
| Percent end to end read of on target reads | −1.00% |
| Percent forward end to end read of on target reads | −1.00% |
| Percent reverse end to end read of on target reads | −1.00% |
| Coverage needed for 99 percentile base with at least 1x coverage | 865.36 |
| Coverage needed for 98 percentile base with at least 20x coverage | 8653.57 |
| Coverage needed for 95 percentile base with at least 350x coverage | 60574.98 |
| Percent priority 1 design covered | 0 |
| Percent priority 9 design covered | 0 |

Example 18

In this example, an amplicon library was prepared using approximately 1500 target-specific primer pairs. The primer pairs were prepared from genes in Table 1 (see U.S. Ser. No. 13/458,739, filed Apr. 27, 2012, hereby incorporated by reference in its entirety). Each primer pair was designed to selectively hybridize and promote amplification of the selected targeted region using the target-specific primer selection criteria outlined herein. The libraries were prepared according to Example 15 except that the number of preamplification PCR cycles was amended as follows: Plexy: 12–24=18 cycles; 25–48=17 cycles; 48–96=16 cycles; 97–192=15 cycles; 193–384=14 cycles; 385–768=13 cycles; 769–1536=12 cycles; 1537–3072=11 cycles. When using fragmented DNA, up to 2 additional cycles were added to the preamplification PCR process. Additionally, the annealing temperature (60° C.) can be increased from 4 minutes to 8 minutes when using 1537+plexy.

During the nick translation and library amplification step, the number of PCR cycles can be increased, for example to about 10, when necessary.

The amplicon library was used to prepare DNA templates that were clonally amplified on Ion Sphere™ Particles using emulsion PCR (emPCR). The preparation of template in the instant example was prepared according to the manufacturer's instructions using an Ion Xpress Template Kit (Life Technologies, Part No. 4466457). Once template-positive Ion Sphere Particles were enriched, an aliquot of the Ion Spheres were loaded onto an Ion 316™ Chip (Life Technologies, Part No. 4466616) as described in the Ion Sequencing User Guide (Part No. 4467391), and subjected to analysis and sequencing as described in the Ion Torrent PGM Sequencer User Guide (Life Technologies, Part No. 4462917).

In this example, 10 ng FFPE DNA was applied as the input DNA. The results from this experiment are provided in the Table below and demonstrated approximately 94% showed base without strand bias, greater than 98% per base accuracy, and 99% of bases with greater than 20× coverage when average coverage normalized to 100×.

| | |
|---|---:|
| Number of targets | 1459 |
| Per Base Accuracy | 98.70% |
| Percent bases >0.2x mean | 99.20% |
| Target coverage at 20x if normalized to 100x average coverage depth | 99.20% |
| Base without Strand Bias | 94.12% |
| Percent of reads on target | 80.54% |
| Coverage needed for 98 percentile base with at least 20x coverage | 65.07 |
| Percent bases >0.01x mean | 99.77% |

Example 19

Multiplex PCR with 12,500 Target Specific Primers

In this example, several amplicon libraries were prepared using approximately 12,000 target-specific primer pairs in a single reaction. The target-specific primer pairs were prepared from genes associated with cancers, provided in Table 18 (found in U.S. Ser. No. 13/458,739, filed Apr. 27, 2012, hereby incorporated by reference in its entirety). The target-specific primers were designed using the primer selection criteria outlined herein. In this example, primers from Table 6 of US Application 61/598,881 hereby incorporated by reference in its entirety were used as target-specific primers in the reaction. Each target-specific primer pair was designed to promote amplification of the intended target sequence outlined in Table 18 (from U.S. Ser. No. 13/458, 739, filed Apr. 27, 2012, hereby incorporated by reference in its entirety). Each amplicon library was prepared according to the section of Example 13 titled PCR amplify genomic DNA targets, except that the concentration of target-specific primers in the primer pool was amended to 25 nM and the number of target-specific primers was about 12,000. Additionally, the preamplification PCR cycles was amended as follows: An initial holding stage was performed at 99° C. for 2 minutes, followed by 11 cycles of denaturing at 99° C. for 15 seconds; a first annealing stage at 60° C. for 10 minutes; a second annealing stage at 63° C. for 5 minutes; a third annealing stage at 66° C. for 5 minutes; a fourth annealing stage at 69° C. for 5 minutes; and an extending stage at 72° C. for 5 minutes; followed by 5 cycles of denaturing at 99° C. for 15 seconds; a first annealing stage at 60° C. for 10 minutes; a second annealing stage at 63° C. for 6 minutes; a third annealing stage at 66° C. for 6 minutes; a fourth annealing stage at 69° C. for 6 minutes; and an extending stage at 72° C. for 6 minutes. After cycling, the preamplified amplicon library was held at 4° C. until proceeding to the next step as outlined below.

Purify the Amplicons from Input DNA and Primers

One round of Agencourt® AMPure® XP Reagent (Beckman Coulter, CA) binding, wash, and elution at 1.2× volume ratio was found to remove genomic DNA and unbound or excess primers.

In a 1.5 ml LoBind tube (Eppendorf, Part No. 022431021), the preamplified amplicon library (20 microliters) was combined with 24 microliters (1.2× volume) of Agencourt® AMPure® XP reagent (Beckman Coulter, CA). The bead suspension was pipetted up and down to thoroughly mix the bead suspension with the preamplified amplicon library. The sample was then pulse-spin and incubated for 5 minutes at room temperature.

The tube containing the sample was placed on a magnetic rack such as a DynaMag™-2 spin magnet (Life Technologies, CA, Part No. 123-21D) for 2 minutes to capture the beads. Once the solution cleared, the supernatant was transferred to a new tube, where 13.3 ul of nuclease free water was added. Then, 48 microliters of AgenCourt® AMPure® XP beads (Beckman Coulter, CA) were added to the diluted supernatant. The mixture was pipetted to ensure the bead suspension mixed with the preamplified amplicon library. The sample was then pulse-spin and incubated at room temperature for 5 minutes. The tube containing the sample was placed on the magnetic rack for 2 minutes to capture the beads. Once the solution cleared, the supernatant was carefully discarded without disturbing the bead pellet. The desired preamplified amplicon library was now bound to the beads. Without removing the tube from the magnetic rack, 200 microliters of freshly prepared 70% ethanol was introduced into the sample. The sample was incubated for 30 seconds while gently rotating the tube on the magnetic rack. After the solution cleared, the supernatant was discarded without disturbing the pellet. A second ethanol wash was performed and the supernatant discarded. Any remaining ethanol was removed by pulse-spinning the tube and carefully removing residual ethanol while not disturbing the pellet. The pellet was air-dried for about 5 minutes at room temperature.

Once the tube was dry, the tube was removed from the magnetic rack and 20 microliters of DNase/RNase Free Water was added (Life Technologies, CA, Part No. 600004). The tube was vortexed and pipetted to ensure the sample was mixed thoroughly. The sample was pulse-spin and placed on the magnetic rack for two minutes. After the solution cleared, the supernatant containing the eluted DNA was transferred to a new tube.

Phosphorylate the Amplicons

To the eluted DNA (~20 microliters), 3 microliters of DNA ligase buffer (Invitrogen, Catalog No. 15224041), 2 microliters dNTP mix, and 2 microliters of FuP reagent were added. The reaction mixture was mixed thoroughly to ensure uniformity and incubated at 37° C. for 13 minutes.

Ligate Adpaters to the Amplicons and Purify the Ligated Amplicons

After incubation, the reaction mixture proceeded directly to a ligation step. Here, the reaction mixture now containing the phosphorylated amplicon library was combined with 1.5 microliter of A/P1 adapters (20 μm each) (sold as a component of the Ion Fragment Library Kit, Life Technologies, Part No. 4466464) and 1 microliter of DNA ligase (sold as a component of the Ion Fragment Library Kit, Life Technologies, Part No. 4466464), and incubated at room temperature for 30 minutes.

After the incubation step, 52 microliters (1.8× sample volume) of AgenCourt® AMPure® Reagent (Beckman Coulter, CA) was added to the ligated DNA. The mixture was pipetted thoroughly to mix the bead suspension with the ligated DNA. The mixture was pulse-spin and incubated at room temperature for 5 minutes. The samples underwent another pulse-spin and were placed on a magnetic rack such as a DynaMag™-2 spin magnet (Life Technologies, CA, Part No. 123-21D) for two minutes. After the solution had cleared, the supernatant was discarded. Without removing the tube from the magnetic rack, 200 microliters of freshly prepared 70% ethanol was introduced into the sample. The sample was incubated for 30 seconds while gently rotating the tube on the magnetic rack. After the solution cleared, the supernatant was discarded without disturbing the pellet. A second ethanol wash was performed and the supernatant discarded. Any remaining ethanol was removed by pulse-spinning the tube and carefully removing residual ethanol while not disturbing the pellet. The pellet was air-dried for about 5 minutes at room temperature.

The pellet was resuspended in 20 microliters of DNase/RNase Free Water (Life Technologies, CA, Part No. 600004) and vortexed to ensure the sample was mixed thoroughly. The sample was pulse-spin and placed on the magnetic rack for two minutes. After the solution cleared, the supernatant containing the ligated DNA was transferred to a new Lobind tube (Eppendorf, Part No. 022431021).

Nick Translate and Amplify the Amplicon Library and Purify the Library

The ligated DNA (~20 microliters) was combined with 76 microliters of Platinum® PCR SuperMix High Fidelity (Life Technologies, CA, Part No. 12532-016, sold as a component of the Ion Fragment Library Kit, Life Technologies, Part No. 4466464) and 4 microliters of Library Amplification Primer Mix (5 μM each) (Life Technologies, CA, Part No. 602-1068-01, sold as a component of the Ion Fragment Library Kit, Life Technologies, Part No. 4466464), the mixture was pipetted thoroughly to ensure a uniformed solution. The solution was applied to a single well of a 96-well PCR plate and sealed. The plate was loaded into a thermal cycler (GeneAmp® PCR system 9700 Dual 96-well thermal cycler (Life Technologies, CA, Part No. N8050200 and 4314445)) and run on the following temperate profile to generate the final amplicon library.

A nick-translation was performed at 72° C. for 1 minute, followed by an enzyme activation stage at 98° C. for 2 minutes, followed by 6 cycles of denaturing at 98° C. for 15 seconds and an annealing and extending stage at 60° C. for 1 minute. After cycling, the final amplicon library was held at 4° C. until proceeding to the final purification step outlined below.

In a 1.5 ml LoBind tube (Eppendorf, Part No. 022431021), the final amplicon library (~100 microliters) was combined with 180 microliters (1.8× sample volume) of Agencourt® AMPure® XP reagent (Beckman Coulter, CA). The bead suspension was pipetted up and down to thoroughly mix the bead suspension with the final amplicon library. The sample was then pulse-spin and incubated for 5 minutes at room temperature.

The tube containing the final amplicon library was placed on a magnetic rack such as a DynaMag™-2 spin magnet (Life Technologies, CA, Part No. 123-21D) for 2 minutes to capture the beads. Once the solution cleared, the supernatant was carefully discarded without disturbing the bead pellet. Without removing the tube from the magnetic rack, 400 microliters of freshly prepared 70% ethanol was introduced into the sample. The sample was incubated for 30 seconds while gently rotating the tube on the magnetic rack. After the solution cleared, the supernatant was discarded without disturbing the pellet. A second ethanol wash was performed and the supernatant discarded. Any remaining ethanol was removed by pulse-spinning the tube and carefully removing residual ethanol while not disturbing the pellet. The pellet was air-dried for about 5 minutes at room temperature.

Once the tube was dry, the tube was removed from the magnetic rack and 20 microliters of Low TE was added (Life Technologies, CA, Part No. 602-1066-01). The tube was pipetted and vortexed to ensure the sample was mixed thoroughly. The sample was pulse-spin and placed on the magnetic rack for two minutes. After the solution cleared, the supernatant containing the final amplicon library was transferred to a new Lobind tube (Eppendorf, Part No. 022431021).

Assess the Library Size Distribution and Determine the Template Dilution Factor

The final amplicon library was quantitated to determine the library dilution (Template Dilution Factor) that results in a concentration within the optimized target range for Template Preparation (e.g., PCR-mediated addition of library molecules onto Ion Sphere™ Particles). The final amplicon library is typically quantitated for downstream Template Preparation procedure using an Ion Library Quantitation Kit (qPCR) (Life Technologies, Part No. 4468802) and/or a Bioanalyzer™ (Agilent Technologies, Agilent 2100 Bioanalyzer) to determine the molar concentration of the amplicon library, from which the Template Dilution Factor is calculated. For example, instructions to determine the Template Dilution Factor by quantitative real-time PCR (qPCR) can be found in the Ion Library Quantitation Kit User Guide (Life Technologies, Part No. 4468986).

In this example, 1 microliter of the final amplicon library preparation was analyzed on the 2100 Bioanalyzer™ with an Agilent High Sensitivity DNA Kit (Agilent Technologies, Part No. 5067-4626) to generate peaks in the 135-205 bp size range and at a concentration of about $5 \times 10^9$ copies per microliter.

Proceed to Template Preparation

An aliquot of the final library was used to prepare DNA templates that were clonally amplified on Ion Sphere™ Particles using emulsion PCR (emPCR). The preparation of template in the instant example was prepared according to the manufacturer's instructions using an Ion Xpress Template Kit (Life Technologies, Part No. 4466457). Once template-positive Ion Sphere Particles were enriched, an aliquot of the Ion Spheres were loaded onto an Ion 314™ Chip (Life Technologies, Part No. 4462923) as described in the Ion Sequencing User Guide (Part No. 4467391), and subjected to analysis and sequencing as described in the Ion Torrent PGM Sequencer User Guide (Life Technologies, Part No. 4462917). The data obtained from this example is provided in the Table below.

| Ampliseq 1.0 work flow mod | | | | |
|---|---|---|---|---|
| Sample (50 ng NA12878) | | | | enrich unbound |
| Plexity | 6,000 | 12,000 | 12,000 | 12,000 |
| C450 oligo pool | pool 1 + 3 | pool 1 + 2 + 3 + 4 | pool 1 + 2 + 3 + 4 | pool 1 + 2 + 3 + 4 |
| PreAmp cycle (6 hr = PA1, 9 hr = PA2) | 6 hr | 6 hr | 9 hr | 9 hr |
| PA enzyme/load % | Taq/69% | Taq/82% | Stoffel/35% | Stoffel/43% |
| Percent greater than 0.01 mean reads per base | 97.72% | 79.15% | 82.08% | 78.42% |
| Percent greater than 0.1 mean reads per base | 84.32% | 54.28% | 82.08% | 54.22% |
| Percent greater than 0.2 mean reads per base | 73.79% | 44.86% | 68.80% | 45.45% |
| Percent no strand bias of all bases | 80.42% | 68.48% | 45.19% | 66.01% |
| Percent no strand bias of all Amps | 81.23% | 62.87% | 32.58% | 54.80% |
| Percent no strand bias of all Amps >100 reads | 139.07% | 229.75% | 8126.00% | 334.62% |
| Percent end to end read of on target reads | 71.40% | 69.05% | 53.32% | 77.87% |
| Per bass accuracy | 97.38% | 97.47% | 97.18% | 98.87% |
| Percent of total reads mapped to hg19 | 98.17% | 97.86% | 97.85% | 97.10% |
| Percent wells with read | 25.93% | 30.24% | 1.62% | 12.97% |
| Number of total reads | 1643486 | 1916570 | 102466 | 821799 |
| Number of mapped reads | 1613458 | 1875619 | 100261 | 797953 |
| Number of targets | 6249 | 12469 | 12469 | 12469 |
| Number of reads on target | 1634973 | 1793835 | 93560 | 763982 |
| Percent all reads on target | 93.40% | 93.60% | 91.31% | 92.96% |
| Percent mapped reads on target | 95.14% | 95.64% | 93.32% | 95.74% |
| Percent reads off target | 4.78% | 4.27% | 6.54% | 4.13% |
| Percent reads unmapped | 1.83% | 2.14% | 2.15% | 2.90% |
| Bases in targeted reference | 668162 | 1249178 | 1249178 | 1249178 |
| Bases covered (at least 1x) | 661416 | 1076079 | 1025284 | 979564 |
| Total base reads on target | 156995237 | 189835759 | 9789500 | 80845870 |
| Average base coverage depth | 234.97 | 151.97 | 7.84 | 64.72 |
| Maximum base read depth | 2391 | 4284 | 339 | 3921 |

| Ampliseq 1.0 work flow mod | | | | |
|---|---|---|---|---|
| Sample (50 ng NA12878) | | | | enrich unbound |
| Plexity | 6,000 | 12,000 | 12,000 | 12,000 |
| C450 oligo pool | pool 1 + 3 | pool 1 + 2 + 3 + 4 | pool 1 + 2 + 3 + 4 | pool 1 + 2 + 3 + 4 |
| PreAmp cycle (6 hr = PA1, 9 hr = PA2) | 6 hr | 6 hr | 9 hr | 9 hr |
| PA enzyme/load % | Taq/69% | Taq/82% | Stoffel/35% | Stoffel/43% |
| Average base read depth | 237.32 | 176.23 | 9.52 | 82.46 |
| Std. Dev base read depth | 277.21 | 351.91 | 16.09 | 157.73 |
| Target coverage at 1x | 98.99% | 86.14% | 82.08% | 78.42% |
| Target coverage at 10x | 93.38% | 60.43% | 22.25% | 49.45% |
| Target coverage at 20x | 86.73% | 51.08% | 9.49% | 39.12% |
| Target coverage at 100x | 57.38% | 28.52% | 0.44% | 17.75% |
| Target coverage at 500x | 14.24% | 9.07% | 0.00% | 2.34% |
| Target coverage at 1x - norm 100 | 97.72% | 79.15% | 82.08% | 78.42% |
| Target coverage at 10x -norm 100 | 84.32% | 54.28% | 82.08% | 54.22% |
| Target coverage at 20x - norm 100 | 73.79% | 44.86% | 68.80% | 45.45% |
| Target coverage at 100x - norm 100 | 33.67% | 23.15% | 27.66% | 23.26% |
| Target coverage at 500x - norm 100 | 1.20% | 5.22% | 3.24% | 5.22% |
| Percent end to end read of on target reads | 71.40% | 69.05% | 53.32% | 77.87% |
| Percent forward end to end read of on target reads | 36.45% | 35.07% | 26.64% | 39.40% |
| Percent reverse end to end read of on target reads | 34.95% | 33.98% | 26.67% | 38.47% |
| Coverage needed for 99 percentile base with at least 1x coverage | 156.65 | 475.51 | 215.63 | 274.86 |

Example 20

Assessment of Relative Copy Number Variation (CNV)

In this example, several DNA samples were amplified using 3000 target-specific primer pairs. The target-specific primers were designed using the target-specific primer selection criteria outlined herein. The sequences of the selected target-specific primers used in this experiment can be found in Table 17 (see U.S. Ser. No. 13/458,739, filed Apr. 27, 2012, hereby incorporated by reference in its entirety) (or Table 6 of U.S. Application 61/598,881 hereby incorporated by reference in its entirety). The DNA samples were barcoded during the library amplification process (as outlined in Example 13). In this example, the DNA samples were obtained from a commercial source (Coriell DNA) and contained known variations in copy number to demonstrate that the multiplex amplification methods disclosed herein can be used to assess copy number variation.

Four DNA samples were purchased from Coriell DNA that contained a 3 Mb deletion on chromosome 22 that was associated with DiGeorge Syndrome. An additional DNA sample was purchased from Coriell DNA that contained a 16 Mb deletion on chromosome 7 associated with Grieg Cephalopolysyndactyly Syndrome (GCPS). An amplicon library was prepared for each DNA sample including a barcode for the purposes of distinguishing one DNA sample from another. Each amplicon library was prepared according to the method outlined in Example 15, except in this example, 3000 target-specific primer pairs were used in a single preamplification reaction. The target-specific primer pairs were prepared from the genes in Table 18 (see U.S. Ser. No. 13/458,739, filed Apr. 27, 2012, hereby incorporated by reference in its entirety). Each amplicon library was prepared using 10 ng of DNA from the starting material. The libraries were prepared according to Example 15 except that the number of preamplification PCR cycles was amended as follows: Plexy: 12–24=18 cycles; 25–48=17 cycles; 48–96=16 cycles; 97–192=15 cycles; 193–384=14 cycles; 385–768=13 cycles; 769–1536=12 cycles; 1537–3072=11 cycles. When using fragmented DNA (e.g., FFPE DNA samples), up to 2 additional cycles can be added to the preamplification PCR process. Additionally, the annealing temperature (60° C.) can be increased from 4 minutes to 8 minutes when using 1537+plexy, if a higher yield is necessary.

If required, the number of PCR cycles can be increased during the nick translation and library amplification step, for example to about 10 cycles.

The amplicon library was used to prepare DNA templates that were clonally amplified on Ion Sphere™ Particles using emulsion PCR (emPCR). The preparation of template in the instant example was prepared according to the manufacturer's instructions using an Ion Xpress Template Kit (Life Technologies, Part No. 4466457). Once template-positive Ion Sphere Particles were enriched, an aliquot of the Ion Spheres were loaded onto an Ion 316™ Chip (Life Technologies, Part No. 4466616) as described in the Ion Sequencing User Guide (Part No. 4467391), and subjected to analysis and sequencing as described in the Ion Torrent PGM Sequencer User Guide (Life Technologies, Part No. 4462917).

In this example, 10 ng DNA was applied as the input DNA. The results from this experiment are provided in FIGS. 14-15.

Figure 14:
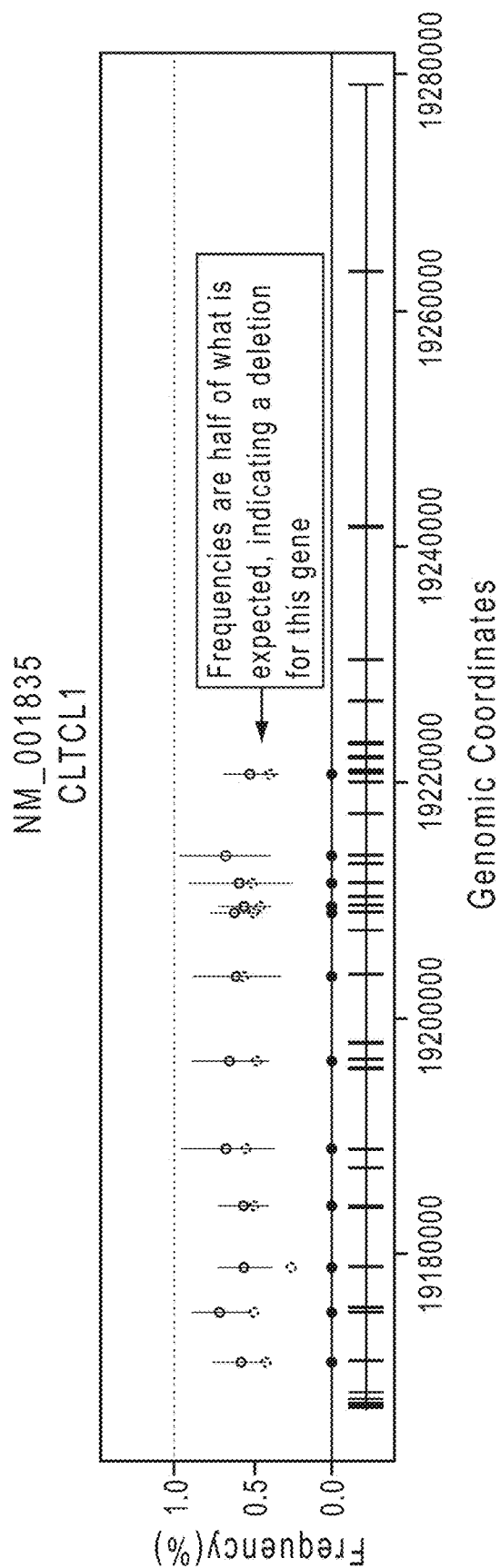
FIG. 14 shows the frequencies of twelve different amplicons obtained for a region of the CLTCL1 gene in several DNA samples containing known copy number variation. The amplicons were obtained according to exemplary embodiments of the disclosure.

FIG. 14 shows that the multiplex PCR amplification methods disclosed herein can be used to assess copy number variation. FIG. 14 shows the amplicon frequency data for 12 amplicons spanning part of the critical region of the gene CLTCL1 associated with DiGeorge Syndrome. The circles plotted at frequency 0 represent each amplicon of CLTCL1 amplified by the multiplex amplification method. The (solo) circles are data points from a single DiGeorge Syndrome DNA sample obtained from Coriell DNA. Four DiGeorge Syndrome DNA samples were tested in this experiment and an average ratio of percent total reads filtered for DiGeorge samples compared to controls are plotted as circles with error bars. The dotted line at frequency 1.0 is the frequency expected for a normal sample (i.e., a sample not containing a variation in copy number). As is shown in FIG. 14, the frequencies of the tested DiGeorge Syndrome samples are about 0.5, indicating that a deletion within the CLTCL1 gene has occurred and can be observed and detected using the amplification methods disclosed herein.

Figure 15:
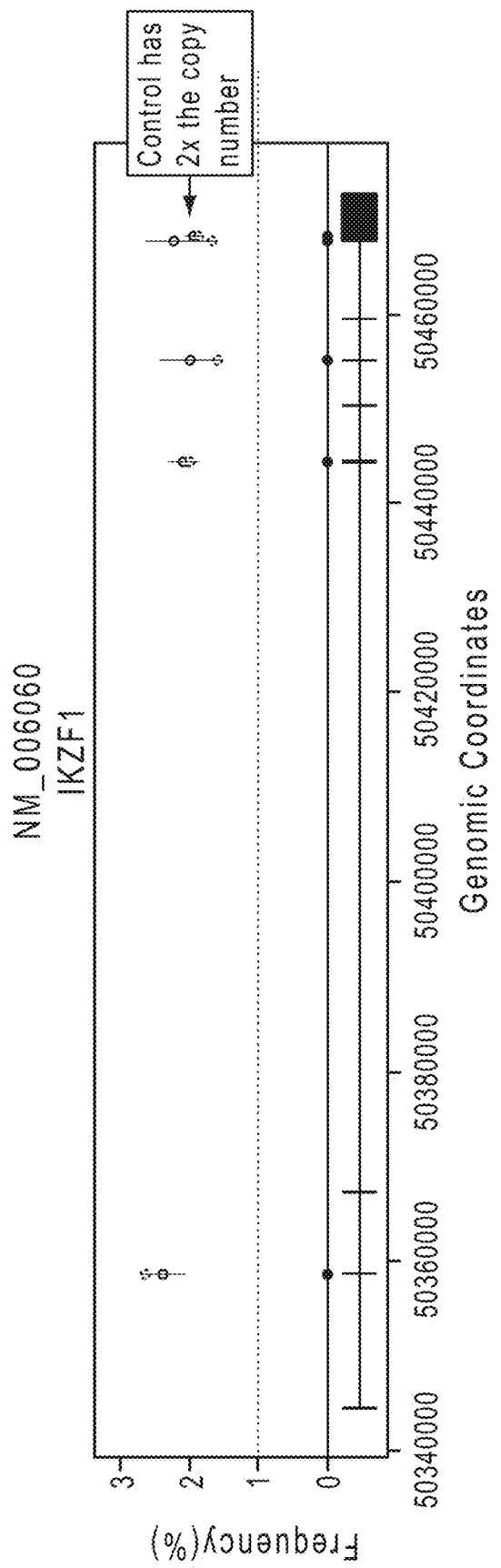
FIG. 15 shows the frequencies of four different amplicons obtained for a region of the IKZF1 gene in several DNA samples containing known copy number variation. The amplicons were obtained according to exemplary embodiments of the multiplex PCR methods disclosed herein.

FIG. 15 shows that the multiplex amplification methods disclosed herein can be used to assess copy number variation in a different chromosome. FIG. 15 shows the amplicon frequency data for 4 amplicons spanning part of the gene IKZF1, associated with Greig Cephalopolysyndactyly Syndrome (GCPS). The circles plotted at frequency 0 represent each of the four amplicons of IKZF1 that were amplified by the multiplex PCR amplification method outlined in this example. Ratios were obtained for a single GCPS sample as compared to four control samples and their frequencies are plotted in FIG. 15. GCPS DNA has only one copy of the GCPS gene, whereas normal (or control) DNA samples contain two copies of the gene. As noted in FIG. 15, the control samples show 2× for copy number as compared to the expected frequency (dotted line). As is demonstrated by FIG. 15, variation in copy number can be determined using the multiplex PCR amplification method disclosed herein.

Example 21

Multiplex Amplification with an Inosine Cleavable Group

In this example, target-specific primers containing one or more cleavable groups denoted as an inosine were prepared according to the primer selection criteria disclosed herein. After an initial in silico evaluation of the primer pairs to proposed target sequences, the evaluated target-specific primers (disclosed in Table 19—see U.S. Ser. No. 13/458,739, filed Apr. 27, 2012, hereby incorporated by reference in its entirety) were ordered from Integrated DNA Technologies (IDT) (Coravilla, Iowa). The inosine containing primers were received from IDT and subjected to multiplex amplification, performed according to the method of Example 15 with the following exceptions. The 2× Primer Pool (containing primer from Table 2—see U.S. Ser. No. 13/458,739, filed Apr. 27, 2012, hereby incorporated by reference in its entirety) was replaced with the Inosine containing primers (disclosed on Table 19 (see U.S. Ser. No. 13/458,739, filed Apr. 27, 2012, hereby incorporated by reference in its entirety), corresponding to SEQ ID NOs: 103122-103143). Additionally, after performing PCR amplification of genomic DNA targets, the samples was subjected to digestion with EndoV and FuPa.

In this example, an aliquot of the final library was used to prepare DNA templates that were clonally amplified on Ion Sphere™ Particles using emulsion PCR (emPCR). The preparation of template in the instant example was prepared according to the manufacturer's instructions using an Ion Xpress Template Kit (Life Technologies, Part No. 4466457). Once template-positive Ion Sphere Particles were enriched, an aliquot of the Ion Spheres were loaded onto an Ion 314™ Chip (Life Technologies, Part No. 4462923) as described in the Ion Sequencing User Guide (Part No. 4467391), and subjected to analysis and sequencing as described in the Ion Torrent PGM Sequencer User Guide (Life Technologies, Part No. 4462917). The data obtained from this example included a per base accuracy percentage of 97.17% and percent of reads on target were observed as 96.83%.

Example 22

Alternative Multiplex PCR Protocol

In this example, various alternative embodiments are presented over one or more of the prior multiplex PCR methods.

PCR Amplify Genomic DNA Targets

In this example, a multiplex polymerase chain reaction was performed to amplify multiple individual amplicons (target sequences) across a genomic DNA sample and an FFPE sample. A representative list of genes associated with cancers and inherited diseases that were incorporated for investigation while synthesizing the primer pool is provided in at least Tables 1 and 4 (both found in U.S. Ser. No. 13/458,739, filed Apr. 27, 2012, hereby incorporated by reference in its entirety). Each primer pair in the primer pool was designed to contain at least one uracil nucleotide in each of the forward and reverse primer (Table 2—see U.S. Ser. No. 13/458,739, filed Apr. 27, 2012, hereby incorporated by reference in its entirety) or designed to contain at least one inosine residue in each of the forward and reverse primer (Table 19—see U.S. Ser. No. 13/458,739, filed Apr. 27, 2012, hereby incorporated by reference in its entirety). Each primer pair was also designed to selectively hybridize to, and promote amplification of a specific gene or gene fragment of the genomic DNA or FFPE sample to reduce formation of non-specific amplification products.

To a single well of a 96-well PCR plate was added 10 microliters of 2× Primer Pool (containing the primer pairs of Table 2-found in U.S. Ser. No. 13/458,739, filed Apr. 27, 2012, hereby incorporated by reference in its entirety), 4 microliters of 5× Cancer Primer pool (containing the primer pairs of Table 17-found in U.S. Ser. No. 13/458,739, filed Apr. 27, 2012, hereby incorporated by reference in its entirety), 4 microliters of 5×IDP Primer pool (containing the primer pairs of Table 15-found in U.S. Ser. No. 13/458,739, filed Apr. 27, 2012, hereby incorporated by reference in its entirety) or 10 microliters of 2×HID Primer Pool (containing the primer pairs of Tables 13 and 14-both found in U.S. Ser. No. 13/458,739, filed Apr. 27, 2012, hereby incorporated by reference in its entirety), at a concentration of 200 nm each for plexy under 96, or at a concentration of 50 nm for plexy above 96. 10 ng of genomic DNA or FFPE DNA and 4 microliters of an amplification reaction mixture (5× Ion Ampliseq HiFi Master Mix) was added to a final volume of 20 microliters with nuclease free water (Life Technologies, CA, Part No. 600004).

The PCR plate was sealed and loaded into a thermal cycler (GeneAmp® PCR system 9700 Dual 96-well thermal cycler (Life Technologies, CA, Part No. N8050200 and 4314445)) and run on the following temperature profile to generate the preamplified amplicon library. Variation to the number of cycles was performed based on the total plexy of the reaction mixture under investigation. For example, a plexy of 12-24 was run for 20 cycles; a plexy of 25-48 was run for 19 cycles; a plexy of 48-96 was run for 18 cycles; a plexy of 97-192 was run for 17 cycles; a plexy of 193-384 was run for 16 cycles; a plexy of 385-768 was run for 15 cycles; a plexy of 769-1536 was run for 14 cycles; a plexy of 1537-3072 was run for 13 cycles; a plexy of 3073-6144 was run for 12 cycles. Additionally, for reaction mixtures containing barcodes or pooled reaction mixtures the number of cycles was lowered by one or more additional cycles. For example, 2-3 barcodes per sample were subtracted by one cycle; 4-8 barcodes per sample were subtracted by 2 cycles, and 9-16 barcodes were subtracted by 3 cycles. For samples that contain fragmented DNA, e.g., FFPE or enzymatically digested DNA, the number of cycles can be increased for up to 3 cycles.

An initial holding stage was performed at 99° C. for 2 minutes, followed by X cycles (as determined above) of denaturing at 99° C. for 15 seconds and an annealing and extending stage at 60° C. for 4 minutes. For plexy above 1536, the annealing and extending stage was increase to 8 minutes at 60° C. After cycling, the preamplified amplicon library was held at 10° C. until proceeding to the purification step outlined below.

Digest/Phosphorylate/Heat Kill the Amplicons

To the preamplified library (~20 microliters), 2 microliters of FuPa reagent was added. The PCR plate was sealed and loaded into a thermal cycler (GeneAmp® PCR system 9700 Dual 96-well thermal cycler (Life Technologies, CA, Part No. N8050200 and 4314445)) and run on the following temperature profile. An initial holding stage was performed at 50° C. for 10 minutes, followed by 55° C. for 10 minutes and then 65° C. for 20 minutes. After cycling, the preamplified amplicon library was held at 10° C. until proceeding to the ligation/nick translation step outlined below.

Ligate Adpaters to the Amplicons and Nick Translate

After phosphorylation, the amplicon preamplification library (~22 µl) proceeded directly to a ligation step. In this example, the preamplification library now containing the phosphorylated amplicon library was combined with 2 microliters of A/P1 Adapter (5 µm each) (sold as a component of the Ion Fragment Library Kit, Life Technologies, Part No. 4466464), 4 microliters of Switch Solution and 2 microliters of DNA ligase (5 u/µl). The PCR plate was sealed and loaded into a thermal cycler (GeneAmp® PCR system 9700 Dual 96-well thermal cycler (Life Technologies, CA, Part No. N8050200 and 4314445)) and run on the following temperature profile. An initial holding stage was performed at 22° C. for 30 minutes, followed by 72° C. for 10 minutes and then held at 10° C. until proceeding to the next step.

If the amplicon library is to contain barcodes (for example Ion DNA Barcoding 1-16 kit, Life Technologies, Part No. 4468654, incorporated herein in its entirety), the barcodes are added at this step to the PCR plate essentially according to the manufacturer's instructions prior to proceeding to the next step. Optionally, all the samples or barcodes can be pooled into a single tube at this step.

1.5×AMPure XP Purification 1.5× sample volume (45 microliters) of AgenCourt® AMPure® Reagent (Beckman Coulter, CA) was added to the ligated DNA. The mixture was mixed and incubated at room temperature for 5 minutes and then transferred to a magnet plate. Sample was incubated on the magnet plate for 2 minutes, and the supernatant discarded. An ethanol wash was performed and the supernatant discarded. Any remaining ethanol was removed and air-dried for about 5 minutes at room temperature. The dry tube containing the library was resuspended in 20 microliters of Nuclease Free Water (Life Technologies, CA, Part No. 600004) or low Tris-EDTA buffer. In some instances, an optional nick translation/library amplification step can be performed on the amplicon library, as outlined below.

Nick Translate and Amplify the Amplicon Library and Purify the Library

The ligated DNA (~20 microliters) was combined with 50 microliters of Platinum® PCR SuperMix High Fidelity (Life Technologies, CA, Part No. 12532-016, sold as a component of the Ion Fragment Library Kit, Life Technologies, Part No. 4466464) and placed on a magnet plate for 2 minutes. 48 ul of the eluted amplicons in the PCR supermix were transferred to a new well of a 96-well plate to which was added 2 microliters of Library Amplification Primer Mix (Life Technologies, CA, Part No. 602-1068-01, sold as a component of the Ion Fragment Library Kit, Life Technologies, Part No. 4466464). The PCR plate was sealed and loaded into a thermal cycler (GeneAmp® PCR system 9700 Dual 96-well thermal cycler (Life Technologies, CA, Part No. N8050200 and 4314445)) and run on the following temperate profile to generate the final amplicon library.

An enzyme activation stage at 98° C. for 2 minutes, followed by 5 cycles of denaturing at 98° C. for 15 seconds and an annealing and extending stage at 60° C. for 1 minute. After cycling, the final amplicon library was held at 4° C. until proceeding to the final purification step outlined below.

The final amplicon library (~100 microliters) was combined with 0.5× sample volume of Agencourt® AMPure® XP reagent (Beckman Coulter, CA). The mixture was then incubated for 5 minutes at room temperature. The sample was transferred to a magnet plate for 2 minutes and the supernatant (~75 microliters) removed to a new well. 1.2× volume of Agencourt® AMPure® XP reagent (Beckman Coulter, CA) was added and incubated at room temperature for 5 minutes. The sample was then placed on a magnet plate for 2 minutes and the supernatant discarded. The final amplicon library was washed with 70% ethanol and the supernatant discarded. Any remaining ethanol was removed and air-dried for about 5 minutes at room temperature. Once dry, the library was resuspended in 20 microliters of Low TE (Life Technologies, CA, Part No. 602-1066-01). In this example, 1 microliter of the final amplicon library preparation was analyzed on a 2100 Bioanalyzer™ with an Agilent High Sensitivity DNA Kit (Agilent Technologies, Part No. 5067-4626) or analyzed on a Qubit machine using the DSDNA HS Assay Kit (Part number Q32851).

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10017811B2). An electronic copy of the "Sequence Listing" will also be available from the USPTO upon request and payment of the fee set forth in 37 CFR 1.19(b)(3).

We claim:

1. An in vitro cell free composition comprising at least 50 target-specific in vitro amplified primer products each having at least one cleavable group, a polymerase, a cleaving reagent capable of cleaving the at least one cleavable group from a plurality of the at least 50 target-specific in vitro amplified primer products, a ligase capable of blunt-ended ligation, and a plurality of target molecules; wherein the composition is prepared directly from a sample and not from a portion of the sample pre-enriched for target molecules;

wherein each of the target specific primer regions of the primer products have the following criteria:

(1) includes two or more modified nucleotides within the primer sequence, at least one of which is included near or at the termini of the primer and at least one of which is included at, or about the center nucleotide position of the primer sequence;
(2) length is about 15 to about 40 bases in length;
(3) $T_m$ is from about 60° C. to about 70° C.;
(4) has low cross-reactivity with non-target sequences present in the sample; (5) at least the first four nucleotides (going from 3' to 5' direction) are non-complementary to any sequence within any other primer present in the reaction; and
(6) are non-complementary to any consecutive stretch of at least 5 nucleotides within any other produced amplified target sequence.

2. The composition of claim 1, wherein the plurality of target molecules is between 1-10 ng of genomic DNA or cDNA.

3. The composition of claim 1, wherein the ligase capable of blunt-ended ligation is an isothermal ligase.

4. The composition of claim 1, wherein the ligase capable of blunt-ended ligation is not a thermostable ligase.

5. The composition of claim 1, wherein the ligase capable of blunt-ended ligation is an ATP dependent ligase.

6. The composition of claim 1, further comprising dNTPs.

7. The composition of claim 1, further comprising a plurality of adapters.

8. The composition of claim 7, further comprising a plurality of double-stranded adapters.

9. The composition of claim 7, wherein at least one of the plurality of adapters further includes a barcode, a tag, or universal priming sequence.

10. The composition of claim 8, wherein the plurality of double-stranded adapters do not include a nucleic acid sequence that is complementary to the terminal 10 nucleotides at the 5' end of the at least 50 target-specific extended primer products or a nucleic acid sequence that is complementary to the terminal 10 nucleotides at the 3' end of the at least 50 target-specific extended primer products.

11. The composition of claim 7, wherein the plurality of adapters do not include a phosphorylated adapter.

12. The composition of claim 1, further comprising one or more DNA polymerase antibodies capable of recognizing a DNA polymerase.

13. The composition of claim 1, wherein the polymerase includes a proofreading activity.

14. The composition of claim 1, wherein the plurality of target molecules are present in an amount from 1 ng to 200 ng.

15. The composition of claim 1, wherein the plurality of target molecules are present in an amount from 10 ng to 50 ng.

16. The composition of claim 1, wherein the plurality of target molecules are present in an amount less than 1 ng.

17. The composition of claim 1, wherein the plurality of target molecules are isolated from a single cell.

18. The composition of claim 1, wherein a portion of the at least 50 target-specific amplified primer products having at least one cleavable group are complementary to a portion of at least one gene selected from the group consisting of EGFR, FLT3, KRAS, BRAS, NRAS and TP53.

19. The composition of claim 1, wherein a portion of the at least 50 target-specific amplified primer products having at least one cleavable group are complementary to a portion of at least one gene selected from the group consisting of FLT3, BRCA1, BRCA2, ALK, ROS1, RET or CFTR.

20. The composition of claim 1, wherein at least one amplified primer product is obtained using a primer pair, wherein the primer pair includes a forward primer and a reverse primer, wherein the forward primer hybridizes to a first intron and the reverse primer hybridizes to a second intron, and wherein the primer pair amplifies an exon between the first and second intron.

* * * * *